US009358250B2

(12) United States Patent
Ashkenazi et al.

(10) Patent No.: US 9,358,250 B2
(45) Date of Patent: Jun. 7, 2016

(54) METHODS OF USING SCD1 ANTAGONISTS

(71) Applicant: Genentech, Inc., South San Francisco, CA (US)

(72) Inventors: Avi Ashkenazi, San Mateo, CA (US); Xiangnan Du, Fremont, CA (US); Jing Qing, San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 13/651,226

(22) Filed: Oct. 12, 2012

(65) Prior Publication Data

US 2013/0096181 A1 Apr. 18, 2013

Related U.S. Application Data

(60) Provisional application No. 61/547,706, filed on Oct. 15, 2011, provisional application No. 61/704,397, filed on Sep. 21, 2012.

(51) Int. Cl.

| | | |
|---|---|---|
| A61K 31/497 | (2006.01) | |
| A61K 31/501 | (2006.01) | |
| A61K 31/506 | (2006.01) | |
| A61K 31/713 | (2006.01) | |
| A61K 31/445 | (2006.01) | |
| A61K 31/513 | (2006.01) | |
| A61K 45/06 | (2006.01) | |
| A61K 31/4355 | (2006.01) | |
| A61K 31/496 | (2006.01) | |
| G01N 33/50 | (2006.01) | |
| G01N 33/574 | (2006.01) | |

(52) U.S. Cl.
CPC ........... *A61K 31/713* (2013.01); *A61K 31/4355* (2013.01); *A61K 31/445* (2013.01); *A61K 31/496* (2013.01); *A61K 31/501* (2013.01); *A61K 31/506* (2013.01); *A61K 31/513* (2013.01); *A61K 45/06* (2013.01); *G01N 33/5011* (2013.01); *G01N 33/57407* (2013.01); *G01N 2510/00* (2013.01); *G01N 2800/52* (2013.01)

(58) Field of Classification Search
CPC .. A61K 31/497; A61K 31/501; A61K 31/506
USPC .......................... 514/44, 252.03, 252.14, 327
See application file for complete search history.

(56) References Cited

U.S. PATENT DOCUMENTS

| | | | |
|---|---|---|---|
| 7,652,013 B2 | 1/2010 | Gillespie et al. | |
| 2005/0119251 A1 | 6/2005 | Fu | |
| 2009/0325956 A1 | 12/2009 | Taniguchi et al. | |
| 2010/0069351 A1 | 3/2010 | Taniguchi et al. | |

FOREIGN PATENT DOCUMENTS

| | | |
|---|---|---|
| JP | 2009-19013 A | 1/2009 |
| WO | 2005/011655 A2 | 2/2005 |
| WO | 2006/014168 A1 | 2/2006 |
| WO | 2006/034279 A1 | 3/2006 |
| WO | 2006/034312 A1 | 3/2006 |
| WO | 2006/034315 A2 | 3/2006 |
| WO | 2006/034338 A1 | 3/2006 |
| WO | 2006/034341 A2 | 3/2006 |
| WO | 2006/034440 A2 | 3/2006 |
| WO | 2006/034441 A1 | 3/2006 |
| WO | 2006/034446 A2 | 3/2006 |
| WO | 2006/101521 A2 | 9/2006 |
| WO | 2006/125178 A2 | 11/2006 |
| WO | 2006/125179 A1 | 11/2006 |
| WO | 2006/125180 A1 | 11/2006 |
| WO | 2006/125181 A2 | 11/2006 |
| WO | 2006/125194 A2 | 11/2006 |
| WO | 2006/130986 A1 | 12/2006 |
| WO | 2007/009236 A1 | 1/2007 |
| WO | 2007/044085 A2 | 4/2007 |
| WO | 2007/046867 A2 | 4/2007 |
| WO | 2007/046868 A2 | 4/2007 |
| WO | 2007/050124 A1 | 5/2007 |
| WO | 2007/056846 A1 | 5/2007 |
| WO | 2007/130075 A1 | 11/2007 |
| WO | 2007/0134457 A1 | 11/2007 |
| WO | 2007/136746 A2 | 11/2007 |
| WO | 2007/143597 A2 | 12/2007 |
| WO | 2007/143823 A1 | 12/2007 |
| WO | 2007/143824 A1 | 12/2007 |
| WO | 2008/003753 A1 | 1/2008 |
| WO | 2008/017161 A1 | 2/2008 |
| WO | 2008/024390 A1 | 2/2008 |
| WO | 2008/029266 A1 | 3/2008 |
| WO | 2008/036715 A1 | 3/2008 |
| WO | 2008/043087 A2 | 4/2008 |

(Continued)

OTHER PUBLICATIONS

Miniville, "Inhibition of Stearoyl-CoA Desaturase induces cell death and activation of AMPK pathway in cancer cells" European Journal of Cancer Supplements, vol. 8, Issue 5, Jun. 2010, p. 114, No. 444.*
Mason, "SCD1 Inhibition Causes Cancer Cell Death by Depleting Mono-Unsaturated Fatty Acids", PLoS ONE, 2012, 7(3): e33823, pp. 1-8.*
International Search Report and Written Opinion for counterpart International application No. PCT/US2012/060094.
Hess et al., "Inhibition of SearoylCoA Desaturase Activity Blocks Cell Cycle Progression and Induces Programmed Cell Death in Lung Cancer Cells" PLos One 5(6):1-8 (Jun. 2010).
Beenken et al., "The FGF family: biology, pathophysiology and therapy" Nat Rev Drug Discov. 8(3):235-53 ( 2009).
Capellen et al., "Frequent activating mutations of FGFR3 in human bladder and cervix carcinomas" Nat. Genet. 23:18-20 (Sep. 1999).
Chang et al., "Immunohistochemistry accurately predicts FGFR3 aberrant expression and t(4;14) in multiple myeloma" Blood 106(1):353-355 (Jul. 1, 2005).

(Continued)

*Primary Examiner* — Sreeni Padmanabhan
*Assistant Examiner* — Sahar Javanmard
(74) *Attorney, Agent, or Firm* — Kelly B. McClellan

(57) ABSTRACT

Provided herein are therapies for the treatment of pathological conditions, such as cancer, and method of using SCD1 antagonists.

23 Claims, 21 Drawing Sheets

(56) References Cited

FOREIGN PATENT DOCUMENTS

| | | |
|---|---|---|
| WO | 2008/046226 A1 | 4/2008 |
| WO | 2008/056687 A1 | 5/2008 |
| WO | 2008/062276 A2 | 5/2008 |
| WO | 2008/064474 A1 | 6/2008 |
| WO | 2008/074824 A2 | 6/2008 |
| WO | 2008/074832 A2 | 6/2008 |
| WO | 2008/074833 A2 | 6/2008 |
| WO | 2008/074834 A2 | 6/2008 |
| WO | 2008/074835 A1 | 6/2008 |
| WO | 2008/104524 A1 | 9/2008 |
| WO | 2008/116898 A1 | 10/2008 |
| WO | 2008/120744 A1 | 10/2008 |
| WO | 2008/123469 A1 | 10/2008 |
| WO | 2008/123891 A1 | 10/2008 |
| WO | 2008/127349 A2 | 10/2008 |
| WO | 2008/127615 A1 | 10/2008 |
| WO | 2008/128335 A1 | 10/2008 |
| WO | 2008/135141 A1 | 11/2008 |
| WO | 2008/139845 A1 | 11/2008 |
| WO | 2008/141455 A1 | 11/2008 |
| WO | 2009/010560 A1 | 1/2009 |
| WO | 2009/016216 A1 | 2/2009 |
| WO | 2009/019566 A1 | 2/2009 |
| WO | 2009/056556 A1 | 5/2009 |
| WO | 2009/060452 A2 | 5/2009 |
| WO | 2010/025553 A1 | 3/2010 |
| WO | 2010/094120 A | 8/2010 |
| WO | 2010/112520 A1 | 10/2010 |
| WO | 2011/011506 A1 | 1/2011 |
| WO | 2011/011872 A1 | 2/2011 |
| WO | 2011/030312 A1 | 3/2011 |
| WO | 2011/039358 A1 | 4/2011 |
| WO | 2011/047481 A1 | 4/2011 |
| WO | 2011/011508 A1 | 11/2011 |

OTHER PUBLICATIONS

Chang et al., "KGF induces lipogenic genes through a PI3K and JNK/SREBP-1 pathway in H292 cells" J Lipid Res. 46(12):2624-35 (Dec. 2005).

Chesi et al., "Frequent translocation t(4;14)(p16.3;q32.3) in multiple myeloma is associated with increased expression and activating mutations of fibroblast growth factor receptor 3" Nat. Genet. 16:260-264 (Jul. 16, 1997).

Cortese et al., "Correlative gene expression and DNA methylation profiling in lung development nominate new biomarkers in lung" Intl. J Biochem. Cell Biol. 40:1494-1508 ( 2008).

Dailey et al., "Mechanisms underlying differential responses to FGF signaling" Cytokine & Growth Factor Reviews 16:233-247 ( 2005).

Demoulin et al., "Platelet-derived growth factor stimulates membrane lipid synthesis through activation of phosphatidylinositol 3-kinase and sterol regulatory element-binding proteins" J Biol Chem. 279(34):35392-402 (Aug. 2004).

Duvel et al., "Activation of a metabolic gene regulatory network downstream of mTOR complex 1" Mol Cell 39(2):171-83 (Jul. 2010).

Eswarakumar et al., "Cellular signaling by fibroblast growth factor receptors" Cytokine Growth Factor Rev. 16(2):139-49 (Apr. 2005).

Fritz et al., "Abrogation of de novo lipogenesis by stearoyl-CoA desaturase 1 inhibition interferes with oncogenic signaling and blocks prostate cancer progression in mice" Mol Cancer Ther. 9(6):1740-54 (Jun. 2010).

Genentech. An Open-Label, Multicenter, Phase I Dose-Escalation Trial Evaluating the Safety and Pharmacokinetics of MFGR1877S in Patients With Advanced Solid Tumors. http://clinicaltrial.gov/ct2/show/NCT01363024.

Goldstein et al., "Protein sensors for membrane sterols" Cell 124(1):35-46 (Jan. 2006).

Gomez-Roman et al., "Fibroblast growth factor receptor 3 is overexpressed in urinary tract carcinomas and modulates the neoplastic cell growth" Clin. Cancer Res. 11:459-465 (Jan. 15, 2005).

Goriely et al., "Activating mutations in FGFR3 and HRAS reveal a shared genetic origin for congenital disorders and testicular tumors" Nat Genet. 41(11):1247-52 ( 2009).

Guo et al., "EGFR signaling through an Akt-SREBP-1-dependent, rapamycin-resistant pathway sensitizes glioblastomas to antilipogenic therapy" Sci Signal 2(101):ra82 (Dec. 2009)

Horton et al., "Combined analysis of oligonucleotide microarray data from transgenic and knockout mice identifies direct Srebp target genes" Proc Natl Acad Sci U S A. 100(21):12027-32 (Oct. 2003).

Horton et al., "SREBPs: activators of the complete program of cholesterol and fatty acid synthesis in the liver" J Clin Invest. 109(9):1125-31 (May 2002).

Igal, "Stearoyl-CoA desaturase-1: a novel key player in the mechanisms of cell proliferation, programmed cell death and transformation to cancer" Carcinogenesis 31(9):1509-15 (Sep. 2010).

Jemal et al., "Cancer statistics, 2010" CA Cancer J Clin. 60(5):277-300 ( 2010).

Knowles, "Novel therapeutic targets in bladder cancer: mutation and expression of FGF receptors" Future Oncol. 4(1):71-83 ( 2008).

Koltun Do et al., "Potent, selective, and metabolically stable stearoyl-CoA desaturase (SCD) inhibitors for the potential treatment of obesity and diabetes" American Chemical Society, Division of Medicinal Chemistry Abstracts, 236th ACS National Meeting, Philadelphia, PA, Aug. 17-21, 2008, MEDI 198.

Kumar-Sinha et al., "Transcriptome analysis of HER2 reveals a molecular acid synthesis" Cancer Res. 63(1):132-9 (Jan. 2003)

Kuroso et al , "Immunohistochemical detection of fibroblast growth factor receptor 3 in human breast cancer: correlation with clinicopathological/molecular parameters and prognosis" Pathobiology 77(5):231-40 ( 2010).

Lamont et al., "Small molecule FGF receptor inhibitors block FGFR-dependent urothelial carcinoma growth in vitro and in vivo" Br J Cancer 104(1):75-82 (Jan. 2011).

Liu et al., "Discovery of potent, selective, orally bioavailable stearoyl-CoA desaturase 1 inhibitors" J Med Chem. 50(13)3086-100 (Jun. 2007).

Liu, "Stearoyl-CoA desaturase inhibitors: update on patented compounds" Expert Opin Ther Pat. 19(9):1169-91 ( 2009).

Liu, "Stearoyl-CoA desaturase-1 (SCD1) Inhibitors: Discovery and in vivo evaluation" Emerging Targets for Type 2 Diabetes Symposium, The 233th ACS National Meeting, Chicago, IL, Mar. 2007, MEDI-232.

Martinez-Torrecuadrada et al., "Targeting the extracellular domain of fibroblast growth factor receptor 3 with human single-chain Fv antibodies inhibits bladder carcinoma cell line proliferation" Clin. Cancer Res. 11(17):6280-6290 (Sep. 1, 2005).

Menendez et al., "Fatty acid synthase and the lipogenic phenotype in cancer pathogenesis" Nat Rev Cancer 7(10):763-77 (Oct. 2007).

Moreau et al., "Recurrent 14q32 translocations determine the prognosis of multiple myeloma, especially in patients receiving intensive chemotherapy" Blood 100(5):1579-1583 (Sep. 1, 2002)

Morgan-Lappe et al., "Identification of Ras-related nuclear protein, targeting protein for xenopus kinesin-like protein 2, and stearoyl-CoA desaturase 1 as promising cancer targest from an RNAi-based screen" Cancer Res. 67(9):4390-8 (May 2007).

Novartis. A dose escalation study in adult patients with advanced solid malignancies. http://clinicaltrials.gov/ct2/show/NCT01004224.

Novartis. A Phase II Multi-center, Non-randomized, Open Label Study of TKI258 in FGFR3 Mutated and FGFR3 Wild Type Advanced Urothelial Carcinoma. http://clinicaltrial.gov/ct2/show/NCT00790426.

Ornitz, "FGF signaling in the developing endochondral skeleton" Cytokine Growth Factor Rev. 16(2):205-13 (Apr. 2005).

Paton et al., "Biochemical and physiological function of stearoyl-CoA desaturase" Am J Physiol Endocrinol Metab. 297(1):E28-37 (Jul. 2009).

Porstmann et al., "PKB/Akt induces transcription of enzymes involved in cholesterol and fatty acid biosynthesis via activation of SREBP" Oncogene 24(43):6465-81 (Sep. 2005).

Porstmann et al., "SREBP activity is regulated by mTORC1 and contributes to Akt-dependent cell growth" Cell Metab. 8(3):224-36 (Sep. 2008).

(56) References Cited

OTHER PUBLICATIONS

Qing et al., "Antibody-based targeting of FGFR3 in bladder carcinoma and t(4;14)-positive multiple myeloma in mice" J. Clin. Invest. 119(5):1216-1229 (May 2009).

Qiu et al., "Over-expression of fibroblast growth factor receptor 3 in human hepatocellular carcinoma" World J Gastroenterol. 11(34):5266-5272 (2005).

Roongta et al., "Cancer cell dependence on unsaturated fatty acids implicates stearoyl-CoA desaturase as a target for cancer therapy" Mol Cancer Res. 9(11):1551-61 (Nov. 2011).

Rosty et al., "Clinical and biological characteristics of cervical neoplasias with FGFR3 mutation" Mol Cancer 4(1):15 (May 2005).

Scaglia et al, "Inhibition of Stearoyl-CoA Desaturase 1 expression in human lung adenocarcinoma cells impairs tumorigenesis" Int J Oncol. 33(4):839-50 (Oct. 2008).

Scaglia et al, "Inhibition of stearoylCoA desaturase-1 inactivates acetyl-CoA carboxylase and impairs proliferation in cancer cells: role of AMPK" PLoS One 4(8):e6812 (Aug. 2009)

Swinnen et al., "Stimulation of tumor-associated fatty acid synthase expression by growth factor activation of the sterol regulatory element-binding protein pathway" Oncogene 19(45):5173-81 (Oct. 2000).

Tomlinson et al., "FGFR3 protein expression and its relationship to mutation status and prognostic variables in bladder cancer" J. Pathol. 213:91-98 (2007).

Tomlinson et al., "Knockdown by shRNA identifies S249C mutant FGFR3 as a potential therapeutic target in bladder cancer" Oncogene 26:5889-5899 (2007).

Trudel et al, "Inhibition of fibroblast growth factor receptor 3 induces differentiation and apoptosis in t(4;14) myeloma" Blood 103(9):3521-3528 (2004).

Turner et al., "Fibroblast growth factor signalling: from development to cancer" Nat Rev Cancer; 10(2):116-29 (Feb. 2010).

van Rhijn et al., "Frequent FGFR3 mutations in utothelial papilloma" J. Pathol. 198:245-251 (2002).

Wilkie, "Bad bones, absent smell, selfish testes: the pleiotropic consequences of human FGF receptor mutations" Cytokine Growth Factor Rev. 16(2):187-203 (Apr. 2005).

Woenckhaus et al., "Smoking and cancer-related gene expression in bronchial epithelium and non-small-cell lung cancers" J. Pathol. 210:192-204 (2006).

Xin et al., "Discovery of piperidine-aryl urea-based stearoyl-CoA desturase 1 inhibitors" Bioorg Med Chem Lett. 18(15):4298-302 (Aug. 2008).

Yang et al., "Activation of fatty acid sysnthesis during neoplastic transformation: role of mitogen-activated protein kinase and phosphatidylinositol 3-kinase" Exp Cell Res. 279(1):80-90 (Sep. 2002).

Zhao et al., "Discovery of 1-(4-phenoxypiperidin-1-yl)-2-arylaminoethanone stearoyl-CoA destaturase 1 inhibitors" Bioorg Med Chem Lett. 17(12):3388-91 (Jun. 2007).

\* cited by examiner

METHODS OF USING SCD1 ANTAGONISTS

CROSS REFERENCE TO RELATED APPLICATIONS

This application claims priority under 35 USC §119 to U.S. Provisional Application No. 61/547,706, filed Oct. 15, 2011 and to U.S. Provisional Application No. 61/704,397, filed Sep. 21, 2012, the contents of which are both incorporated by reference in their entirety.

SEQUENCE LISTING

The instant application contains a Sequence Listing which has been submitted in ASCII format via EFS-Web and is hereby incorporated by reference in its entirety. Said ASCII copy, created on Oct. 11, 2012, is named P4767R1_US_Sequence_Listing.txt and is 4,365 bytes in size.

FIELD

Provided herein are therapies for the treatment of pathological conditions, such as cancer, and method of using SCD1 antagonists.

BACKGROUND

Bladder cancer is the fifth most common cancer worldwide, with an estimated 70,980 new cases and 14,330 deaths occurring in the United States in 2009 (34). The prevalence of FGFR3 activating mutations and/or overexpression in bladder cancer and the large body of preclinical loss-of-function studies have implicated FGFR3 as an important oncogenic driver and a potential therapeutic target in this disease setting (12, 21-25). Despite of recent progresses toward clinical development of therapeutic agents targeting FGFR3, critical insights into how FGFR3 signaling contributes to bladder cancer development and progression remain to be elucidated.

FGFR3 belongs to a family of four structurally and functionally related receptor tyrosine kinases, which transduce signals from many of the 22 identified FGF polypeptides in human (1-3). Upon ligand binding, FGFR3 dimerizes and becomes autophosphorylated at specific tyrosine residues. This triggers the recruitment of adaptor proteins, such as FGFR substrate 2α (FRS2α), to the receptor, resulting in the activation of multiple downstream signaling cascades, including the canonical Ras-Raf-MAPK and PI3K-Akt-mTOR pathways (1-3). FGFR3 signaling plays critical roles during embryonic development and in the maintenance of tissue homeostasis, and regulates cell proliferation, differentiation, migration and survival in a context-dependent manner (3-4).

Aberrant activation of FGFR3 has been implicated in diverse physiological and pathological conditions. Gain-of-function mutation in FGFR3 is one of the most common genetic alterations in a spectrum of human congenital skeletal and cranial disorders (5-6). Dysregulation of FGFR3 via mutations or overexpression has also been linked with a variety of human cancers, including multiple myeloma positive for t(4; 14) (p16.3; q32) chromosomal translocation (7-10), bladder cancer (11-14), breast cancer (15), cervical carcinoma (11, 16), hepatocellular carcinoma (17), squamous non-small cell lung cancer (18, 19), and testicular tumors (20). In particular, somatic activating mutations in FGFR3 have been identified in 60-70% of papillary and 16-20% of muscle-invasive bladder tumors (13-14). Moreover, FGFR3 overexpression has been documented in a significant fraction of superficial as well as advanced bladder cancers (12-13, 21). Importantly, a plethora of loss-of-function studies demonstrate that pharmacological and genetic intervention of FGFR3 function blocks bladder cancer cell proliferation in culture and inhibits tumor growth in animal models (12, 22-25). Collectively, these data indicate that a subset of bladder cancer is addictive to FGFR3 activity, underscoring the importance of this receptor as a therapeutic target in bladder cancer. Indeed, both monoclonal antibodies and small molecule inhibitors against FGFR3 have recently been developed as a potential targeted therapy in this disease setting (26-28). Despite these recent advancements toward clinical development of anti-FGFR3 agents and the characterization of canonical signaling pathways emanating from cell surface FGFR3, at present there is very little information on how FGFR3 signaling contributes to bladder carcinogenesis. The precise molecular and cellular consequences downstream of FGFR3 activation remain to be elucidated.

SUMMARY

Provided herein are therapies for the treatment of pathological conditions, such as cancer, and method of using SCD1 antagonists. In one aspect, provided herein are methods of inhibiting cell proliferation of a cancer cell comprising contacting the cancer cell with an effective amount of an SCD1 antagonist. Also provided herein are methods of inhibiting cell proliferation of a cancer cell in an individual comprising administering to the individual an effective amount of an SCD1 antagonist.

In another aspect, provided are methods of inducing cell cycle arrest of a cancer cell comprising contacting the cancer cell with an effective amount of SCD1 antagonist. Further provided herein are methods of inducing cell cycle arrest of a cancer cell in an individual comprising administering to the individual an effective amount of an SCD1 antagonist.

In one aspect, provided herein are methods of promoting apoptosis of a cancer cell comprising contacting the cancer cell with an effective amount of SCD1 antagonist. Also provided herein are methods of promoting apoptosis of a cancer cell in an individual comprising administering to the individual an effective amount of an SCD1 antagonist.

Further, in another aspect, provided herein are methods of treating a cancer cell in an individual comprising administering to the individual an effective amount of an SCD1 antagonist.

In some embodiments of any of the methods, the cancer cell is an endometrial cancer cell, a head and neck cancer cell, a kidney cancer cell, an ovarian cancer cell, a colon cancer, a pancreatic cancer cell, an urinary cancer cell, or a bladder cancer cell. In some embodiments, the cancer cell is a kidney cancer cell, pancreatic cancer cell, or bladder cancer cell. In some embodiments of any of the methods, the cancer cell expresses elevated levels of one or more biomarkers compared to a reference sample, reference cell, reference tissue, control sample, control cell, control tissue, or internal control (e.g., housekeeping gene).

In another aspect, provided herein are methods of treating cancer in an individual comprising administering to the individual an effective amount of an SCD1 antagonist. In some embodiments, the cancer in the individual expresses elevated levels of one or more biomarkers compared to a reference sample, reference cell, reference tissue, control sample, control cell, control tissue, or internal control (e.g., housekeeping gene)

In one aspect, provided herein are methods of treating cancer in an individual comprising administering to the individual an effective amount of an SCD1 antagonist, wherein treatment is based upon the individual having cancer expressing elevated levels of one or more biomarkers compared to a reference sample, reference cell, reference tissue, control sample, control cell, control tissue, or internal control (e.g., housekeeping gene).

In another aspect, provided herein are methods of treating cancer in an individual provided that the individual has been found to have cancer expressing elevated levels of one or more biomarkers compared to a reference sample, reference cell, reference tissue, control sample, control cell, control tissue, or internal control (e.g., housekeeping gene), the treatment comprising administering to the individual an effective amount of an SCD1 antagonist.

In another aspect, provided herein are methods for treating cancer in an individual, the method comprising: determining that a sample obtained from the individual expresses elevated levels of one or more biomarkers compared to a reference sample, reference cell, reference tissue, control sample, control cell, control tissue, or internal control (e.g., housekeeping gene), and administering an effective amount of an anti-cancer therapy comprising an SCD1 antagonist to the individual, whereby the cancer is treated.

Further, in another aspect, provided herein are methods of treating cancer, comprising: (a) selecting an individual having cancer, wherein the cancer expresses elevated levels of one or more biomarkers compared to a reference sample, reference cell, reference tissue, control sample, control cell, control tissue, or internal control (e.g., housekeeping gene); and (b) administering to the individual thus selected an effective amount of an SCD1 antagonist, whereby the cancer is treated.

In another aspect, provided herein are methods of identifying an individual who is more likely to benefit from treatment with an anti-cancer therapy comprising an SCD1 antagonist or less likely to benefit from treatment with an anti-cancer therapy comprising an SCD1 antagonist, the method comprising: determining expression levels of one or more biomarkers in a sample obtained from the individual, wherein elevated expression levels of one or more biomarkers in the sample as compared to a reference sample, reference cell, reference tissue, control sample, control cell, control tissue, or internal control (e.g., housekeeping gene) indicates that the individual is more likely to benefit from treatment with the anti-cancer therapy comprising the SCD1 antagonist or a reduced expression levels of one or more biomarkers in the sample as compared to a reference sample, reference cell, reference tissue, control sample, control cell, control tissue, or internal control (e.g., housekeeping gene) indicates that the individual is less likely to benefit from treatment with the anti-cancer therapy comprising the SCD1 antagonist.

In another aspect, provided herein are methods for predicting whether an individual with cancer is likely to respond effectively to treatment with an anti-cancer therapy comprising an SCD1 antagonist, the method comprising assessing one or more biomarkers, whereby elevated expression levels of one or more biomarkers as compared to a reference sample, reference cell, reference tissue, control sample, control cell, control tissue, or internal control (e.g., housekeeping gene) indicates that the individual is more likely to effectively respond to treatment with the antagonist and reduced expression levels of one or more biomarkers as compared to a reference sample, reference cell, reference tissue, control sample, control cell, control tissue, or internal control (e.g., housekeeping gene) indicates that the individual is less likely to effectively respond to treatment with the antagonist.

In one aspect, provided herein are methods of predicting the response or lack of response of an individual to an anti-cancer therapy comprising an SCD1 antagonist comprising measuring in a sample obtained from the individual expression of one or more biomarkers, wherein elevated expression levels of one or more biomarkers as compared to a reference sample, reference cell, reference tissue, control sample, control cell, control tissue, or internal control (e.g., housekeeping gene) is predictive of response of the individual to the anti-cancer therapy comprising the SCD1 antagonist and reduced expression levels of one or more biomarkers as compared to a reference sample, reference cell, reference tissue, control sample, control cell, control tissue, or internal control (e.g., housekeeping gene) is predictive of lack of response of the individual to the anti-cancer therapy comprising the SCD1 antagonist.

In another aspect, provided herein are methods for determining the likelihood that an individual with cancer will exhibit benefit from anti-cancer therapy comprising an SCD1 antagonist, the method comprising: determining expression levels of one or more biomarkers in a sample obtained from the individual, wherein elevated expression levels of one or more biomarkers in the sample as compared to a reference sample indicates that the individual has increased likelihood of benefit from the anti-cancer therapy comprising the SCD1 antagonist and reduced expression levels of one or more biomarkers in the sample as compared to a reference sample, reference cell, reference tissue, control sample, control cell, control tissue, or internal control (e.g., housekeeping gene) indicates that the individual has decreased likelihood of benefit from the anti-cancer therapy comprising the SCD1 antagonist.

In some embodiments of any of the methods, the cancer is endometrial cancer cell, head and neck cancer, a kidney cancer, an ovarian cancer, a colon cancer, a pancreatic cancer, an urinary cancer, or a bladder cancer. In some embodiments, the cancer is a kidney cancer, pancreatic cancer, or bladder cancer. In some embodiments, the cancer is bladder cancer.

In some embodiments of any of the methods, the one or more biomarkers is FGFR3. In some embodiments of any of the methods, the one or more biomarkers is phosphorylated FGFR3.

In some embodiments of any of the methods, the one or more biomarkers is one or more genes of the FGFR3-regulated lipogenic signature. In some embodiments, the one or more genes of the FGFR3-regulated lipogenic signature comprises, consists of, or consists essential of one or more genes from the group consisting of SREBF1, G6PD, ACOT7, PTPLA, PCCB, FADS1, RDH11, ACER3, PDSS1, MVD, AGPAT5, HSD17B2, ACSL4, EBP, PIGW, LBR, ALLY, ADORA2B, GPCPD1, CYP24A1, ACSL3, MVK, ACSS2, FDPS, ELOVL5, HMGCR, LIPG, ME1, DHCR7, LSS, ACAT2, FASN, CYP51A1, IDI1, FDFT1, FAR2, HMGCS1, SDR16C5, LDLR, MSMO1, INSIG1, DHRS9, LRP8, SQLE, PCSK9, SCD1, FABP4, and combinations thereof. In some embodiments, the one or more genes of the FGFR3-regulated lipogenic signature comprises, consists of, or consists essential of one or more genes from the group consisting of ELOVL5, HMGCR, LIPG, ME1, DHCR7, LSS, ACAT2, FASN, CYP51A1, IDI1, FDFT1, FAR2, HMGCS1, SDR16C5, LDLR, MSMO1, INSIG1, DHRS9, LRP8, SQLE, PCSK9, SCD1, FABP4, and combinations thereof. In some embodiments, the one or more genes of the FGFR3-regulated lipogenic signature comprises, consists of, or consists essential of one or more genes from the group consisting of CYP51A1, IDI1, FDFT1, FAR2, HMGCS1, SDR16C5, LDLR, MSMO1, INSIG1, DHRS9, LRP8, SQLE, PCSK9, SCD1, FABP4, and combinations thereof. In some embodiments, the one or more genes of the FGFR3-regulated lipogenic signature comprises, consists of, or consists essential of one or more genes from the group consisting of LDLR, MSMO1, INSIG1, DHRS9, LRP8, SQLE, PCSK9, SCD1, FABP4, and combinations thereof. In some embodiments, the one or more genes of the FGFR3-regulated lipogenic signature comprises, consists of, or consists essential of one or more genes from the group consisting of SQLE, PCSK9, SCD1, FABP4, and combinations thereof. In some embodiments, the one or more genes of the FGFR3-regulated lipogenic signature comprises, consists of, or consists essential of SC4MOL.

In some embodiments of any of the methods, the one or more biomarkers is mature SREBP1. In some embodiments of any of the methods, the one or more biomarkers is Δ9 monounsaturaturated fatty acids. In some embodiments of any of the methods, the one or more biomarkers is ratio of Δ9 monounsaturaturated fatty acids:saturated fatty acids.

In some embodiments of any of the methods, the one or more biomarkers is PI3K signaling, mTOR signaling, MEK signaling. In some embodiments of any of the methods, the one or biomarkers is one or more polymorphism in genes selected from the group consisting of PI3K, PTEN, p85, TSC1/2, and AKT. In some embodiments of any of the methods, the one or more biomarkers is phosphorylated AKT.

In some embodiments of any of the methods, the expression level of the one or more biomarkers is elevated by greater than about 1.5 fold, about 1.75 fold, about 2 fold, about 2.25 fold, about 2.5 fold, about 2.75 fold, about 3.0 fold, or about 3.25 fold as compared to a reference sample, reference cell, reference tissue, control sample, control cell, control tissue, or internal control (e.g., housekeeping gene).

In some embodiments of any of the methods, the SCD1 antagonist is an antibody, binding polypeptide, binding small molecule, or polynucleotide. In some embodiments, the SCD1 antagonist is a small molecule. In some embodiments, the small molecule is G01522403 (A37062), G02447171, or derivatives thereof. In some embodiments, the small molecule is RG1, RG3, RG8, or derivatives thereof.

In some embodiments of any of the methods, the method further comprises an additional therapeutic agent.

DETAILED DESCRIPTION

I. Definitions

Figure 1:
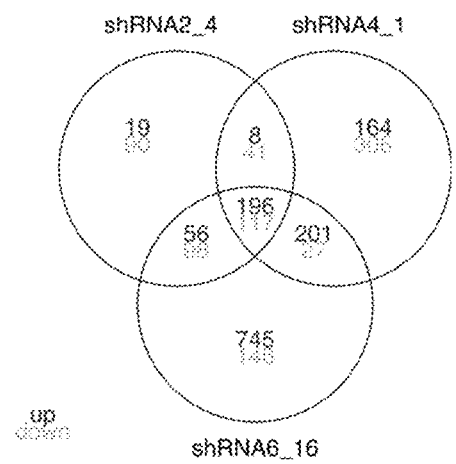
FIG. 1. Identification of FGFR3-regulated genes. A Venn-Diagram outlining overlap of genes with significant expression changes upon induction of three FGFR3 shRNAs. Red numbers represent up-regulated genes, and green ones for down-regulated genes.

The terms "stearoyl-CoA desaturase 1" and "SCD1" refer herein to a native sequence SCD1 polypeptide, polypeptide variants and fragments of a native sequence polypeptide and polypeptide variants (which are further defined herein). The SCD1 polypeptide described herein may be that which is isolated from a variety of sources, such as from human tissue types or from another source, or prepared by recombinant or synthetic methods.

A "native sequence SCD1 polypeptide" comprises a polypeptide having the same amino acid sequence as the corresponding SCD1 polypeptide derived from nature. In one embodiment, a native sequence SCD1 polypeptide comprises the amino acid sequence of SEQ ID NO:1.

```
                                         SEQ ID NO: 1
MPAHLLQDDISSSYTTTTTITAPPSRVLQNGGDKLETMPLYLEDDIRP

DIKDDIYDPTYKDKEGPSPKVEYVWRNIILMSLLHLGALYGITLIPTC

KFYTWLWGVFYYFVSALGITAGAHRLWSHRSYKARLPLRLFLIIANTM

AFQNDVYEWARDHRAHHKFSETHADPHNSRRGFFFSHVGWLLVRKHPA

VKEKGSTLDLSDLEAEKLVMFQRRYYKPGLLMMCFILPTLVPWYFWGE

TFQNSVFVATFLRYAVVLNATWLVNSAAHLFGYRPYDKNISPRENILV

SLGAVGEGFHNYHHSFPYDYSASEYRWHINFTTFFIDCMAALGLAYDR

KKVSKAAILARIKRTGDGNYKSG
```

"SCD1 polypeptide variant", or variations thereof, means a SCD1 polypeptide, generally an active SCD1 polypeptide, as defined herein having at least about 80% amino acid sequence identity with any of the native sequence SCD1 polypeptide sequences as disclosed herein. Such SCD1 polypeptide variants include, for instance, SCD1 polypeptides wherein one or more amino acid residues are added, or deleted, at the N- or C-terminus of a native amino acid sequence. Ordinarily, a SCD1 polypeptide variant will have at least about 80% amino acid sequence identity, alternatively at least about 81%, 82%, 83%, 84%, 85%, 86%, 87%, 88%, 89%, 90%, 91%, 92%, 93%, 94%, 95%, 96%, 97%, 98%, or 99% amino acid sequence identity, to a native sequence SCD1 polypeptide sequence as disclosed herein. Ordinarily, SCD1 variant polypeptides are at least about 10 amino acids in length, alternatively at least about 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600 amino acids in length, or more. Optionally, SCD1 variant polypeptides will have no more than one conservative amino acid substitution as compared to a native SCD1 polypeptide sequence, alternatively no more than 2, 3, 4, 5, 6, 7, 8, 9, or 10 conservative amino acid substitution as compared to the native SCD1 polypeptide sequence.

The term "SCD1 antagonist" as defined herein is any molecule that partially or fully blocks, inhibits, or neutralizes a biological activity mediated by a native sequence SCD1. In certain embodiments such antagonist binds to SCD1. According to one embodiment, the antagonist is a polypeptide. According to another embodiment, the antagonist is an anti-SCD1 antibody. According to another embodiment, the antagonist is a small molecule antagonist. According to another embodiment, the antagonist is a polynucleotide antagonist.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after synthesis, such as by conjugation with a label. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S("thioate"), P(S)S ("dithioate"), "(O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

"Oligonucleotide," as used herein, refers to short, single stranded polynucleotides that are at least about seven nucleotides in length and less than about 250 nucleotides in length. Oligonucleotides may be synthetic. The terms "oligonucleotide" and "polynucleotide" are not mutually exclusive. The description above for polynucleotides is equally and fully applicable to oligonucleotides.

The term "primer" refers to a single stranded polynucleotide that is capable of hybridizing to a nucleic acid and allowing the polymerization of a complementary nucleic acid, generally by providing a free 3'-OH group.

The term "small molecule" refers to any molecule with a molecular weight of about 2000 daltons or less, preferably of about 500 daltons or less.

The term "array" or "microarray" refers to an ordered arrangement of hybridizable array elements, preferably polynucleotide probes (e.g., oligonucleotides), on a substrate. The substrate can be a solid substrate, such as a glass slide, or a semi-solid substrate, such as nitrocellulose membrane.

The term "amplification" refers to the process of producing one or more copies of a reference nucleic acid sequence or its complement. Amplification may be linear or exponential (e.g., PCR). A "copy" does not necessarily mean perfect sequence complementarity or identity relative to the template sequence. For example, copies can include nucleotide analogs such as deoxyinosine, intentional sequence alterations (such as sequence alterations introduced through a primer comprising a sequence that is hybridizable, but not fully complementary, to the template), and/or sequence errors that occur during amplification.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

The terms "anti-SCD1 antibody" and "an antibody that binds to SCD1" refer to an antibody that is capable of binding SCD1 with sufficient affinity such that the antibody is useful as a diagnostic and/or therapeutic agent in targeting SCD1. In one embodiment, the extent of binding of an anti-SCD1 antibody to an unrelated, non-SCD1 protein is less than about 10% of the binding of the antibody to SCD1 as measured, e.g., by a radioimmunoassay (RIA). In certain embodiments, an anti-SCD1 antibody binds to an epitope of SCD1 that is conserved among SCD1 from different species.

A "blocking" antibody or an "antagonist" antibody is one which inhibits or reduces biological activity of the antigen it binds. Preferred blocking antibodies or antagonist antibodies substantially or completely inhibit the biological activity of the antigen.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g., scFv); and multispecific antibodies formed from antibody fragments.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called $\alpha$, $\delta$, $\epsilon$, $\gamma$, and $\mu$, respectively.

The terms "full length antibody," "intact antibody," and "whole antibody" are used herein interchangeably to refer to an antibody having a structure substantially similar to a native antibody structure or having heavy chains that contain an Fc region as defined herein.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

An "immunoconjugate" is an antibody conjugated to one or more heterologous molecule(s), including but not limited to a cytotoxic agent.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 Times the Fraction $X/Y$ where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "detection" includes any means of detecting, including direct and indirect detection.

The term "biomarker" as used herein refers to an indicator, e.g., predictive, diagnostic, and/or prognostic, which can be detected in a sample. The biomarker may serve as an indicator of a particular subtype of a disease or disorder (e.g., cancer) characterized by certain, molecular, pathological, histological, and/or clinical features. In some embodiments, a biomarker is a gene. Biomarkers include, but are not limited to, polynucleotides (e.g., DNA, and/or RNA), polypeptides, polypeptide and polynucleotide modifications (e.g. post-translational modifications), carbohydrates, and/or glycolipid-based molecular markers.

The terms "biomarker signature," "signature," "biomarker expression signature," or "expression signature" are used interchangeably herein and refer to one or a combination of biomarkers whose expression is an indicator, e.g., predictive, diagnostic, and/or prognostic. The biomarker signature may serve as an indictor of a particular subtype of a disease or disorder (e.g., cancer) characterized by certain molecular, pathological, histological, and/or clinical features. In some embodiments, the biomarker signature is a "gene signature." The term "gene signature" is used interchangeably with "gene expression signature" and refers to one or a combination of polynucleotides whose expression is an indicator, e.g., predictive, diagnostic, and/or prognostic. In some embodiments, the biomarker signature is a "protein signature." The term "protein signature" is used interchangeably with "protein expression signature" and refers to one or a combination of polypeptides whose expression is an indicator, e.g., predictive, diagnostic, and/or prognostic.

The "amount" or "level" of a biomarker associated with an increased clinical benefit to an individual is a detectable level in a biological sample. These can be measured by methods known to one skilled in the art and also disclosed herein. The expression level or amount of biomarker assessed can be used to determine the response to the treatment.

The terms "level of expression" or "expression level" in general are used interchangeably and generally refer to the amount of a biomarker in a biological sample. "Expression" generally refers to the process by which information (e.g., gene-encoded and/or epigenetic) is converted into the structures present and operating in the cell. Therefore, as used herein, "expression" may refer to transcription into a polynucleotide, translation into a polypeptide, or even polynucleotide and/or polypeptide modifications (e.g., posttranslational modification of a polypeptide). Fragments of the transcribed polynucleotide, the translated polypeptide, or polynucleotide and/or polypeptide modifications (e.g., post-translational modification of a polypeptide) shall also be regarded as expressed whether they originate from a transcript generated by alternative splicing or a degraded transcript, or from a post-translational processing of the polypeptide, e.g., by proteolysis. "Expressed genes" include those that are transcribed into a polynucleotide as mRNA and then translated into a polypeptide, and also those that are transcribed into RNA but not translated into a polypeptide (for example, transfer and ribosomal RNAs).

"Elevated expression," "elevated expression levels," or "elevated levels" refers to an increased expression or increased levels of a biomarker in an individual relative to a control, such as an individual or individuals who are not suffering from the disease or disorder (e.g., cancer) or an internal control (e.g., housekeeping biomarker).

"Reduced expression," "reduced expression levels," or "reduced levels" refers to a decrease expression or decreased levels of a biomarker in an individual relative to a control, such as an individual or individuals who are not suffering from the disease or disorder (e.g., cancer) or an internal control (e.g., housekeeping biomarker).

The term "housekeeping biomarker" refers to a biomarker or group of biomarkers (e.g., polynucleotides and/or polypeptides) which are typically similarly present in all cell types. In some embodiments, the housekeeping biomarker is a "housekeeping gene." A "housekeeping gene" refers herein to a gene or group of genes which encode proteins whose activities are essential for the maintenance of cell function and which are typically similarly present in all cell types.

"Amplification," as used herein generally refers to the process of producing multiple copies of a desired sequence. "Multiple copies" mean at least two copies. A "copy" does not necessarily mean perfect sequence complementarity or identity to the template sequence. For example, copies can include nucleotide analogs such as deoxyinosine, intentional sequence alterations (such as sequence alterations introduced through a primer comprising a sequence that is hybridizable, but not complementary, to the template), and/or sequence errors that occur during amplification.

The term "multiplex-PCR" refers to a single PCR reaction carried out on nucleic acid obtained from a single source (e.g., an individual) using more than one primer set for the purpose of amplifying two or more DNA sequences in a single reaction.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers, (1995).

"Stringent conditions" or "high stringency conditions", as defined herein, can be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) overnight hybridization in a solution that employs 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with a 10 minute wash at 42° C. in 0.2×SSC (sodium chloride/sodium citrate) followed by a 10 minute high-stringency wash consisting of 0.1×SSC containing EDTA at 55° C.

"Moderately stringent conditions" can be identified as described by Sambrook et al., Molecular Cloning: A Laboratory Manual, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

The term "diagnosis" is used herein to refer to the identification or classification of a molecular or pathological state, disease or condition (e.g., cancer). For example, "diagnosis" may refer to identification of a particular type of cancer. "Diagnosis" may also refer to the classification of a particular subtype of cancer, e.g., by histopathological criteria, or by molecular features (e.g., a subtype characterized by expression of one or a combination of biomarkers (e.g., particular genes or proteins encoded by said genes)).

The term "aiding diagnosis" is used herein to refer to methods that assist in making a clinical determination regarding the presence, or nature, of a particular type of symptom or condition of a disease or disorder (e.g., cancer). For example, a method of aiding diagnosis of a disease or condition (e.g., cancer) can comprise measuring certain biomarkers in a biological sample from an individual.

The term "sample," as used herein, refers to a composition that is obtained or derived from a subject and/or individual of interest that contains a cellular and/or other molecular entity that is to be characterized and/or identified, for example based on physical, biochemical, chemical and/or physiological characteristics. For example, the phrase "disease sample" and variations thereof refers to any sample obtained from a subject of interest that would be expected or is known to contain the cellular and/or molecular entity that is to be characterized. Samples include, but are not limited to, primary or cultured cells or cell lines, cell supernatants, cell lysates, platelets, serum, plasma, vitreous fluid, lymph fluid, synovial fluid, follicular fluid, seminal fluid, amniotic fluid, milk, whole blood, blood-derived cells, urine, cerebro-spinal fluid, saliva, sputum, tears, perspiration, mucus, tumor lysates, and tissue culture medium, tissue extracts such as homogenized tissue, tumor tissue, cellular extracts, and combinations thereof.

By "tissue sample" or "cell sample" is meant a collection of similar cells obtained from a tissue of a subject or individual. The source of the tissue or cell sample may be solid tissue as from a fresh, frozen and/or preserved organ, tissue sample, biopsy, and/or aspirate; blood or any blood constituents such as plasma; bodily fluids such as cerebral spinal fluid, amniotic fluid, peritoneal fluid, or interstitial fluid; cells from any time in gestation or development of the subject. The tissue sample may also be primary or cultured cells or cell lines. Optionally, the tissue or cell sample is obtained from a disease tissue/organ. The tissue sample may contain compounds which are not naturally intermixed with the tissue in nature such as preservatives, anticoagulants, buffers, fixatives, nutrients, antibiotics, or the like.

A "reference sample", "reference cell", "reference tissue", "control sample", "control cell", or "control tissue", as used herein, refers to a sample, cell, tissue, standard, or level that is used for comparison purposes. In one embodiment, a reference sample, reference cell, reference tissue, control sample, control cell, or control tissue is obtained from a healthy and/or non-diseased part of the body (e.g., tissue or cells) of the same subject or individual. For example, healthy and/or non-diseased cells or tissue adjacent to the diseased cells or tissue (e.g., cells or tissue adjacent to a tumor). In another embodiment, a reference sample is obtained from an untreated tissue and/or cell of the body of the same subject or individual. In yet another embodiment, a reference sample, reference cell, reference tissue, control sample, control cell, or control tissue is obtained from a healthy and/or non-diseased part of the body (e.g., tissues or cells) of an individual who is not the subject or individual. In even another embodiment, a reference sample, reference cell, reference tissue, control sample, control cell, or control tissue is obtained from an untreated tissue and/or cell of the body of an individual who is not the subject or individual.

For the purposes herein a "section" of a tissue sample is meant a single part or piece of a tissue sample, e.g. a thin slice of tissue or cells cut from a tissue sample. It is understood that multiple sections of tissue samples may be taken and subjected to analysis, provided that it is understood that the same section of tissue sample may be analyzed at both morphological and molecular levels, or analyzed with respect to both polypeptides and polynucleotides.

By "correlate" or "correlating" is meant comparing, in any way, the performance and/or results of a first analysis or protocol with the performance and/or results of a second analysis or protocol. For example, one may use the results of a first analysis or protocol in carrying out a second protocols and/or one may use the results of a first analysis or protocol to determine whether a second analysis or protocol should be performed. With respect to the embodiment of polynucleotide analysis or protocol, one may use the results of the polynucleotide expression analysis or protocol to determine whether a specific therapeutic regimen should be performed.

"Individual response" or "response" can be assessed using any endpoint indicating a benefit to the individual, including, without limitation, (1) inhibition, to some extent, of disease progression (e.g., cancer progression), including slowing down and complete arrest; (2) a reduction in tumor size; (3) inhibition (i.e., reduction, slowing down or complete stopping) of cancer cell infiltration into adjacent peripheral organs and/or tissues; (4) inhibition (i.e. reduction, slowing down or complete stopping) of metasisis; (5) relief, to some extent, of one or more symptoms associated with the disease or disorder (e.g., cancer); (6) increase in the length of progression free survival; and/or (9) decreased mortality at a given point of time following treatment.

The term "substantially the same," as used herein, denotes a sufficiently high degree of similarity between two numeric values, such that one of skill in the art would consider the difference between the two values to be of little or no biological and/or statistical significance within the context of the biological characteristic measured by said values (e.g., Kd values or expression). The difference between said two values is, for example, less than about 50%, less than about 40%, less than about 30%, less than about 20%, and/or less than about 10% as a function of the reference/comparator value.

The phrase "substantially different," as used herein, denotes a sufficiently high degree of difference between two numeric values such that one of skill in the art would consider the difference between the two values to be of statistical significance within the context of the biological characteristic measured by said values (e.g., Kd values). The difference between said two values is, for example, greater than about 10%, greater than about 20%, greater than about 30%, greater than about 40%, and/or greater than about 50% as a function of the value for the reference/comparator molecule.

The word "label" when used herein refers to a detectable compound or composition. The label is typically conjugated or fused directly or indirectly to a reagent, such as a polynucleotide probe or an antibody, and facilitates detection of the reagent to which it is conjugated or fused. The label may itself be detectable (e.g., radioisotope labels or fluorescent labels) or, in the case of an enzymatic label, may catalyze chemical alteration of a substrate compound or composition which results in a detectable product.

An "effective amount" of an agent refers to an amount effective, at dosages and for periods of time necessary, to achieve the desired therapeutic or prophylactic result.

A "therapeutically effective amount" of a substance/molecule of the invention, agonist or antagonist may vary according to factors such as the disease state, age, sex, and weight of the individual, and the ability of the substance/molecule, agonist or antagonist to elicit a desired response in the individual. A therapeutically effective amount is also one in which any toxic or detrimental effects of the substance/molecule, agonist or antagonist are outweighed by the therapeutically beneficial effects. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "anti-cancer therapy" refers to a therapy useful in treating cancer. Examples of anti-cancer therapeutic agents include, but are limited to, e.g., chemotherapeutic agents, growth inhibitory agents, cytotoxic agents, agents used in radiation therapy, anti-angiogenesis agents, apoptotic agents, anti-tubulin agents, and other agents to treat cancer, anti-CD20 antibodies, platelet derived growth factor inhibitors (e.g., Gleevec™ (Imatinib Mesylate)), a COX-2 inhibitor (e.g., celecoxib), interferons, cytokines, antagonists (e.g., neutralizing antibodies) that bind to one or more of the following targets PDGFR-beta, BlyS, APRIL, BCMA receptor(s), TRAIL/Apo2, and other bioactive and organic chemical agents, etc. Combinations thereof are also included in the invention.

The term "cytotoxic agent" as used herein refers to a substance that inhibits or prevents the function of cells and/or causes destruction of cells. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents e.g., methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below. A tumoricidal agent causes destruction of tumor cells.

A "chemotherapeutic agent" refers to a chemical compound useful in the treatment of cancer. Examples of chemotherapeutic agents include alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Nicolaou et al., Angew. Chem. Intl. Ed. Engl., 33: 183-186 (1994)); CDP323, an oral alpha-4 integrin inhibitor; dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®), liposomal doxorubicin TLC D-99 (MYOCET®), peglylated liposomal doxorubicin (CAELYX®), and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XE-LODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2'-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoid, e.g., paclitaxel (TAXOL®), albumin-engineered nanoparticle formulation of paclitaxel (ABRAXANE™), and docetaxel (TAXOTERE®); chlorambucil; 6-thioguanine; mercaptopurine; methotrexate; platinum agents such as cisplatin, oxaliplatin (e.g., ELOXATIN®), and carboplatin; vincas, which prevent tubulin polymerization from forming microtubules, including vinblastine (VELBAN®), vincristine (ONCOVIN®), vindesine (ELDISINE®, FILDESIN®), and vinorelbine (NAVELBINE®); etoposide (VP-16); ifosfamide; mitoxantrone; leucovorin; novantrone; edatrexate; daunomycin; aminopterin; ibandronate; topoisomerase inhibitor RFS 2000; difluoromethylornithine (DMFO); retinoids such as retinoic acid, including bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); rmRH (e.g., ABARELIX®); BAY439006 (sorafenib; Bayer); SU-11248 (sunitinib, SUTENT®, Pfizer); perifosine, COX-2 inhibitor (e.g., celecoxib or etoricoxib), proteosome inhibitor (e.g., PS341); bortezomib (VELCADE®); CCI-779; tipifarnib (R11577); orafenib, ABT510; Bcl-2 inhibitor such as oblimersen sodium (GENASENSE®); pixantrone; EGFR inhibitors (see definition below); tyrosine kinase inhibitors (see definition below); serine-threonine kinase inhibitors such as rapamycin (sirolimus, RAPAMUNE®); farnesyltransferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin.

Chemotherapeutic agents as defined herein include "antihormonal agents" or "endocrine therapeutics" which act to regulate, reduce, block, or inhibit the effects of hormones that can promote the growth of cancer. They may be hormones themselves, including, but not limited to: anti-estrogens with mixed agonist/antagonist profile, including, tamoxifen (NOLVADEX®), 4-hydroxytamoxifen, toremifene (FARESTON®), idoxifene, droloxifene, raloxifene (EVISTA®), trioxifene, keoxifene, and selective estrogen receptor modulators (SERMs) such as SERM3; pure anti-estrogens without agonist properties, such as fulvestrant (FASLODEX®), and EM800 (such agents may block estrogen receptor (ER) dimerization, inhibit DNA binding, increase ER turnover, and/or suppress ER levels); aromatase inhibitors, including steroidal aromatase inhibitors such as formestane and exemestane (AROMASIN®), and nonsteroidal aromatase inhibitors such as anastrazole (ARIMIDEX®), letrozole (FEMARA®) and aminoglutethimide, and other aromatase inhibitors include vorozole (RIVISOR®), megestrol acetate (MEGASE®), fadrozole, and 4(5)-imidazoles; lutenizing hormone-releaseing hormone agonists, including leuprolide (LUPRON® and ELIGARD®), goserelin, buserelin, and tripterelin; sex steroids, including progestines such as megestrol acetate and medroxyprogesterone acetate, estrogens such as diethylstilbestrol and premarin, and androgens/retinoids such as fluoxymesterone, all transretionic acid and fenretinide; onapristone; anti-progesterones; estrogen receptor down-regulators (ERDs); anti-androgens such as flutamide, nilutamide and bicalutamide; and pharmaceutically acceptable salts, acids or derivatives of any of the above; as well as combinations of two or more of the above.

The term "prodrug" as used in this application refers to a precursor or derivative form of a pharmaceutically active substance that is less cytotoxic to tumor cells compared to the parent drug and is capable of being enzymatically activated or converted into the more active parent form. See, e.g., Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," Directed Drug Delivery, Borchardt et al., (ed.), pp. 247-267, Humana Press (1985). The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described above.

A "growth inhibitory agent" when used herein refers to a compound or composition which inhibits growth of a cell (e.g., a cell whose growth is dependent upon SCD1 expression either in vitro or in vivo). Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in The Molecular Basis of Cancer, Mendelsohn and Israel, eds., Chapter 1, entitled "Cell cycle regulation, oncogenes, and antineoplastic drugs" by Murakami et al. (W B Saunders: Philadelphia, 1995), especially p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

By "radiation therapy" is meant the use of directed gamma rays or beta rays to induce sufficient damage to a cell so as to limit its ability to function normally or to destroy the cell altogether. It will be appreciated that there will be many ways known in the art to determine the dosage and duration of treatment. Typical treatments are given as a one time administration and typical dosages range from 10 to 200 units (Grays) per day.

A "patient," an "individual," or a "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the patient, individual, or subject is a human.

The term "concurrently" is used herein to refer to administration of two or more therapeutic agents, where at least part of the administration overlaps in time. Accordingly, concurrent administration includes a dosing regimen when the administration of one or more agent(s) continues after discontinuing the administration of one or more other agent(s).

By "reduce or inhibit" is meant the ability to cause an overall decrease of 20%, 30%, 40%, 50%, 60%, 70%, 75%, 80%, 85%, 90%, 95%, or greater. Reduce or inhibit can refer to the symptoms of the disorder being treated, the presence or size of metastases, or the size of the primary tumor.

A "package insert" is used to refer to instructions customarily included in commercial packages of therapeutic products or medicaments, that contain information about the indications, usage, dosage, administration, contraindications, other therapeutic products to be combined with the packaged product, and/or warnings concerning the use of such therapeutic products or medicaments and the like.

An "article of manufacture" is any manufacture (e.g., a package or container) or kit comprising at least one reagent, e.g., a medicament for treatment of a disease or disorder (e.g., cancer), or a probe for specifically detecting a biomarker described herein. In certain embodiments, the manufacture or kit is promoted, distributed, or sold as a unit for performing the methods described herein.

A "target audience" is a group of people or an institution to whom or to which a particular medicament is being promoted or intended to be promoted, as by marketing or advertising, especially for particular uses, treatments, or indications, such as individuals, populations, readers of newspapers, medical literature, and magazines, television or internet viewers, radio or internet listeners, physicians, drug companies, etc.

As is understood by one skilled in the art, reference to "about" a value or parameter herein includes (and describes) embodiments that are directed to that value or parameter per se. For example, description referring to "about X" includes description of "X".

It is understood that aspect and embodiments of the invention described herein include "consisting" and/or "consisting essentially of" aspects and embodiments. As used herein, the singular form "a", "an", and "the" includes plural references unless indicated otherwise.

II. Methods and Uses

Provided herein are uses of SCD1 antagonists as part of a specific treatment regimen intended to provide a beneficial effect. Any of the SCD1 antagonists provided herein may be used in therapeutic methods. In a further aspect, the invention provides for the use of an SCD1 antagonist in the manufacture or preparation of a medicament. In one embodiment, the medicament is for treatment of cancer. In a further aspect, the invention provides a method for treating a cancer. Further, provided herein methods and compositions for identifying individuals who may benefit from treatment with an anticancer therapy comprising an SCD1 antagonist. An "individual" according to any of the above embodiments is preferably a human.

Provided herein are methods of inhibiting cell proliferation of a cancer cell comprising contacting the cancer cell with an effective amount of an SCD1 antagonist. Further provided herein are methods of inhibiting cell proliferation of a cancer cell in an individual comprising administering to the individual an effective amount of an SCD1 antagonist. In some embodiments, cell proliferation is inhibited by greater than about any of 40%, 50%, 60%, 70%, 80%, or 90%. In some embodiments, the cancer cell expresses elevated levels of one or more biomarkers compared to a reference sample, reference cell, reference tissue, control sample, control cell, control tissue, or internal control (e.g., housekeeping gene). In some embodiments, the SCD1 antagonist is a small molecule, an anti-SCD1 antibody, a binding polypeptide, or polynucleotide. In some embodiments, the SCD1 antagonist is a small molecule. In some embodiments, the small molecule is SMI37062 (G01522403), G02447171, RG1, RG3, RG8 or derivative thereof. An "individual" according to any of the above embodiments is preferably a human.

Further provided herein are methods of inducing cell cycle arrest of a cancer cell comprising contacting the cancer cell with an effective amount of an SCD1 antagonist. Also provided herein are methods of inducing cell cycle arrest of a cancer cell in an individual comprising administering to the individual an effective amount of an SCD1 antagonist. In some embodiments, the cell cycle arrest is G1 cell cycle arrest. In some embodiments, the cancer cell expresses elevated levels of one or more biomarkers compared to a reference sample, reference cell, reference tissue, control sample, control cell, control tissue, or internal control (e.g., housekeeping gene). In some embodiments, the SCD1 antagonist is a small molecule, an anti-SCD1 antibody, a binding polypeptide, or polynucleotide. In some embodiments, the SCD1 antagonist is a small molecule. In some embodiments, the small molecule is SMI37062 (G01522403), G02447171, RG1, RG3, RG8 or derivative thereof. An "individual" according to any of the above embodiments is preferably a human.

Provided herein are methods of promoting cell death of a cancer cell comprising contacting the cancer cell with an effective amount of an SCD1 antagonist. Also provided herein are methods of promoting cell death of a cancer cell in an individual comprising administering to the individual an effective amount of an SCD1 antagonist. In some embodiments, the cell death is neucrosis. In some embodiments, the cell death is apoptosis. In some embodiments, the apoptosis is caspase-dependent apoptosis. In some embodiments, the apoptosis is caspase-independent apoptosis. In some embodiments, promotion of apoptosis is indicated by an increase in active caspases, for example, caspase 3 and caspase 7. In some embodiments, the cancer cell expresses elevated levels of one or more biomarkers compared to a reference sample, reference cell, reference tissue, control sample, control cell, control tissue, or internal control (e.g., housekeeping gene). In some embodiments, the SCD1 antagonist is a small molecule, an anti-SCD1 antibody, a binding polypeptide, or polynucleotide. In some embodiments, the SCD1 antagonist is a small molecule. In some embodiments, the small molecule is SMI37062 (G01522403), G02447171, RG1, RG3, RG8 or derivative thereof. An "individual" according to any of the above embodiments is preferably a human.

In another aspect, provided herein are methods of treating a cancer cell in an individual comprising administering to the individual an effective amount of an SCD1 antagonist. In some embodiments, the cancer cell expresses elevated levels of one or more biomarkers compared to a reference sample, reference cell, reference tissue, control sample, control cell, control tissue, or internal control (e.g., housekeeping gene). In some embodiments, the SCD1 antagonist is a small molecule, an anti-SCD1 antibody, a binding polypeptide, or polynucleotide. In some embodiments, the SCD1 antagonist is a small molecule. In some embodiments, the small molecule is SMI37062 (G01522403), G02447171, RG1, RG3, RG8 or derivative thereof. An "individual" according to any of the above embodiments is preferably a human.

In another aspect, provided herein are methods of treating cancer in an individual comprising administering to the individual an effective amount of an SCD1 antagonist. In some embodiments, the cancer in the individual expresses elevated levels of one or more biomarkers compared to a reference sample, reference cell, reference tissue, control sample, control cell, control tissue, or internal control (e.g., housekeeping gene). In some embodiments, the SCD1 antagonist is a small molecule, an anti-SCD1 antibody, a binding polypeptide, or polynucleotide. In some embodiments, the SCD1 antagonist is a small molecule. In some embodiments, the small molecule is SMI37062 (G01522403), G02447171, RG1, RG3, RG8 or derivative thereof. An "individual" according to any of the above embodiments is preferably a human.

Further provided herein are methods of treating cancer in an individual comprising administering to the individual an effective amount of an SCD1 antagonist, wherein treatment is based upon the individual having cancer expressing elevated levels and/or reduced expression levels of one or more biomarkers compared to a reference sample, reference cell, reference tissue, control sample, control cell, control tissue, or internal control (e.g., housekeeping gene). Provided herein are also methods of treating cancer in an individual provided that the individual has been found to have cancer expressing elevated levels of one or more biomarkers compared to a reference sample, reference cell, reference tissue, control sample, control cell, control tissue, or internal control (e.g., housekeeping gene), the treatment comprising administering to the individual an effective amount of an SCD1 antagonist. In some embodiments, the SCD1 antagonist is a small molecule, an anti-SCD1 antibody, a binding polypeptide, or polynucleotide. In some embodiments, the SCD1 antagonist is a small molecule. In some embodiments, the small molecule is SMI37062 (G01522403), G02447171, RG1, RG3, RG8 or derivative thereof. An "individual" according to any of the above embodiments is preferably a human.

In another aspect, provided herein are methods for treating cancer in an individual, the method comprising: (a) determining that a sample obtained from the individual expressing elevated levels of one or more biomarkers compared to a reference sample, reference cell, reference tissue, control sample, control cell, control tissue, or internal control (e.g., housekeeping gene), and (b) administering an effective amount of an anti-cancer therapy comprising an SCD1 antagonist to the individual, whereby the cancer is treated. In some embodiments, the SCD1 antagonist is a small molecule, an anti-SCD1 antibody, a binding polypeptide, or polynucleotide. In some embodiments, the SCD1 antagonist is a small molecule. In some embodiments, the small molecule is SMI37062 (G01522403), G02447171, RG1, RG3, RG8 or derivative thereof. An "individual" according to any of the above embodiments is preferably a human.

Provided herein are methods of treating cancer, comprising: (a) selecting an individual having cancer, wherein the cancer expresses elevated levels of one or more biomarkers compared to a reference sample, reference cell, reference tissue, control sample, control cell, control tissue, or internal control (e.g., housekeeping gene); and (b) administering to the individual thus selected an effective amount of an SCD1 antagonist, whereby the cancer is treated. In some embodiments, the SCD1 antagonist is a small molecule, an anti-SCD1 antibody, a binding polypeptide, or polynucleotide. In some embodiments, the SCD1 antagonist is a small molecule. In some embodiments, the small molecule is SMI37062 (G01522403), G02447171, or derivative thereof. An "individual" according to any of the above embodiments is preferably a human.

Provided herein are methods of identifying an individual who is more likely to benefit from treatment with an anti-cancer therapy comprising an SCD1 antagonist or less likely to benefit from treatment with an anti-cancer therapy comprising an SCD1 antagonist, the method comprising: determining expression levels of one or more biomarkers in a sample obtained from the individual, wherein elevated expression levels of one or more biomarkers in the sample as compared to a reference sample, reference cell, reference tissue, control sample, control cell, control tissue, or internal control (e.g., housekeeping gene) indicates that the individual is more likely to benefit from treatment with the anti-cancer therapy comprising the SCD1 antagonist or reduced expression levels of one or more biomarkers in the sample as compared to a reference sample, reference cell, reference tissue, control sample, control cell, control tissue, or internal control (e.g., housekeeping gene) indicates that the individual is less likely to benefit from treatment with the anti-cancer therapy comprising the SCD1 antagonist. In some embodiments, elevated expression levels of one or more biomarkers in the sample as compared to a reference sample, reference cell, reference tissue, control sample, control cell, control tissue, or internal control (e.g., housekeeping gene) indicates that the individual is more likely to benefit from treatment with the anti-cancer therapy comprising the SCD1 antagonist. In some embodiments, reduced expression levels of one or more biomarkers in the sample as compared to a reference sample, reference cell, reference tissue, control sample, control cell, control tissue, or internal control (e.g., housekeeping gene) indicates that the individual is less likely to benefit from treatment with the anti-cancer therapy comprising the SCD1 antagonist. In some embodiments, the SCD1 antagonist is a small molecule, an anti-SCD1 antibody, a binding polypeptide, or polynucleotide. In some embodiments, the SCD1 antagonist is a small molecule. In some embodiments, the small molecule is SMI37062 (G01522403), G02447171, RG1, RG3, RG8 or derivative thereof. An "individual" according to any of the above embodiments is preferably a human.

In another aspect, provided herein are methods for predicting the likelihood that an individual with cancer will respond effectively to treatment with an anti-cancer therapy comprising an SCD1 antagonist, the method comprising assessing one or more biomarkers, whereby elevated expression levels of one or more biomarkers as compared to a reference sample, reference cell, reference tissue, control sample, control cell, control tissue, or internal control (e.g., housekeeping gene) indicates that the individual is more likely to effectively respond to treatment with the SCD1 antagonist and reduced expression levels of one or more biomarkers as compared to a reference sample, reference cell, reference tissue, control sample, control cell, control tissue, or internal control (e.g., housekeeping gene) indicates that the individual is less likely to effectively respond to treatment with the antagonist. In some embodiments, elevated expression levels of one or more biomarkers as compared to a reference sample, reference cell, reference tissue, control sample, control cell, control tissue, or internal control (e.g., housekeeping gene) indicates that the individual is more likely to effectively respond to treatment with the SCD1 antagonist. In some embodiments, reduced expression levels of one or more biomarkers as compared to a reference sample, reference cell, reference tissue, control sample, control cell, control tissue, or internal control (e.g., housekeeping gene) indicates that the individual is less likely to effectively respond to treatment with the antagonist. In some embodiments, the SCD1 antagonist is a small molecule, an anti-SCD1 antibody, a binding polypeptide, or polynucleotide. In some embodiments, the SCD1 antagonist is a small molecule. In some embodiments, the small molecule is SMI37062 (G01522403), G02447171, RG1, RG3, RG8 or derivative thereof. An "individual" according to any of the above embodiments is preferably a human.

Provided herein are also methods of predicting response or lack of response of an individual to an anti-cancer therapy comprising an SCD1 antagonist comprising measuring in a sample obtained from the individual expression of one or more biomarkers, wherein elevated expression levels of one or more biomarkers as compared to a reference sample, reference cell, reference tissue, control sample, control cell, control tissue, or internal control (e.g., housekeeping gene) is predictive of response of the individual to the anti-cancer therapy comprising the SCD1 antagonist and reduced expression levels of one or more biomarkers as compared to a reference sample, reference cell, reference tissue, control sample, control cell, control tissue, or internal control (e.g., housekeeping gene) is predictive of lack of response of the individual to the anti-cancer therapy comprising the SCD1 antagonist. In some embodiments, elevated expression levels of one or more biomarkers as compared to a reference sample, reference cell, reference tissue, control sample, control cell, control tissue, or internal control (e.g., housekeeping gene) is predictive of response of the individual to the anti-cancer therapy comprising the SCD1 antagonist. In some embodiments, reduced expression levels of one or more biomarkers as compared to a reference sample, reference cell, reference tissue, control sample, control cell, control tissue, or internal control (e.g., housekeeping gene) is predictive of lack of response of the individual to the anti-cancer therapy comprising the SCD1 antagonist. In some embodiments, the SCD1 antagonist is a small molecule, an anti-SCD1 antibody, a binding polypeptide, or polynucleotide. In some embodiments, the SCD1 antagonist is a small molecule. In some embodiments, the small molecule is SMI37062 (G01522403), G02447171, RG1, RG3, RG8 or derivative thereof. An "individual" according to any of the above embodiments is preferably a human.

In another aspect, provided herein are methods for determining the likelihood that an individual with cancer will exhibit benefit from anti-cancer therapy comprising an SCD1 antagonist, the method comprising: determining expression levels of one or more biomarkers in a sample obtained from the individual, wherein elevated expression levels of one or more biomarkers in the sample as compared to a reference sample indicates that the individual has increased likelihood of benefit from the anti-cancer therapy comprising the SCD1 antagonist and reduced expression levels of one or more biomarkers in the sample as compared to a reference sample, reference cell, reference tissue, control sample, control cell, control tissue, or internal control (e.g., housekeeping gene) indicates that the individual has decreased likelihood of benefit from the anti-cancer therapy comprising the SCD1 antagonist. In some embodiments, elevated expression levels of one or more biomarkers in the sample as compared to a reference sample indicates that the individual has increased likelihood of benefit from the anti-cancer therapy comprising the SCD1 antagonist. In some embodiments, reduced expression levels of one or more biomarkers in the sample as compared to a reference sample, reference cell, reference tissue, control sample, control cell, control tissue, or internal control (e.g., housekeeping gene) indicates that the individual has decreased likelihood of benefit from the anti-cancer therapy comprising the SCD1 antagonist. In some embodiments, the SCD1 antagonist is a small molecule, an anti-SCD1 antibody, a binding polypeptide, or polynucleotide. In some embodiments, the SCD1 antagonist is a small molecule. In some embodiments, the small molecule is SMI37062 (G01522403), G02447171, RG1, RG3, RG8 or derivative thereof. An "individual" according to any of the above embodiments is preferably a human.

In some embodiments of any of the uses and methods, the cancer and/or cancer cell is a solid tumor. Examples of solid tumors include, but are not limited to, bladder cancer, pancreatic cancer, lung cancer, breast cancer, colon cancer, colorectal cancer, endometrial cancer, head & neck cancer, kidney cancer, ovarian cancer, hypopharyngeal, prostate cancer, esophageal, hepatocellular carcinoma, and/or urinary cancer. In some embodiments of any of the uses and methods, the cancer and/or cancer cell is a cancer selected from the group of bladder cancer, pancreatic cancer, lung cancer, breast cancer, colon cancer, colorectal cancer, endometrial cancer, head & neck cancer, kidney cancer, ovarian cancer, and/or urinary cancer. In some embodiments of any of the uses and methods, the cancer and/or cancer cell is a cancer selected from the group of bladder cancer, pancreatic cancer, colon cancer, colorectal cancer, kidney cancer, and/or urinary cancer. In some embodiments, the cancer and/or cancer cell is from a cancer selected from the group of bladder cancer, pancreatic cancer, endometrial cancer, head & neck cancer, kidney cancer, ovarian cancer, and/or urinary cancer. In some embodiments, the cancer and/or cancer cell is kidney cancer. In some embodiments, the cancer and/or cancer cell is pancreatic cancer. In some embodiments, the cancer and/or cancer cell is bladder cancer. In some embodiments, the cancer and/or cancer cell is stage I, stage II, stage III, and/or stage IV. In some embodiments, the cancer and/or cancer cell is localized. In some embodiments, the cancer and/or cancer cell is metastatic.

In some embodiments of any of the uses and methods, the one or more biomarkers is FGFR3. In some embodiments of any of the uses and methods, a sample from the individual, the cancer and/or the cancer cell has elevated levels of FGFR3 compared to a reference sample, reference cell, reference tissue, control sample, control cell, control tissue, or internal control (e.g., housekeeping gene). For example, provided herein are methods of treating cancer in an individual comprising administering to the individual an effective amount of an SCD1 antagonist, wherein the cancer in the individual expresses elevated levels of one or more biomarkers compared to a reference sample, reference cell, reference tissue, control sample, control cell, control tissue, or internal control (e.g., housekeeping gene) and the one or more biomarkers is FGFR3. In some embodiments, a sample from the individual, the cancer and/or the cancer cell has expresses substantially the same levels of FGFR3 as a reference sample, reference cell, reference tissue, control sample, control cell, control tissue, or internal control (e.g., housekeeping gene). In some embodiments of any of the uses and methods, the one or more biomarkers is phosphorylated FGFR3. In some embodiments of any of the uses and methods, a sample from the individual, the cancer and/or the cancer cell expresses phosphorylated FGFR3. For example, provided herein are methods of treating cancer in an individual comprising administering to the individual an effective amount of an SCD1 antagonist, wherein the cancer in the individual expresses elevated levels of one or more biomarkers compared to a reference sample, reference cell, reference tissue, control sample, control cell, control tissue, or internal control (e.g., housekeeping gene) and the one or more biomarkers is phosphorylated FGFR3. In some embodiments, a sample from the individual, the cancer and/or the cancer cell expresses elevated levels of phosphorylated FGFR3 compared to a reference sample, reference cell, reference tissue, control sample, control cell, control tissue, or internal control (e.g., housekeeping gene). In some embodiments, elevated expression refers to an overall increase of about any of 5%, 10%, 20%, 25%, 30%, 40%, 50%, 60%, 70%, 80%, 85%, 90%, 95%, 96%, 97%, 98%, 99% or greater, in the level of biomarker (e.g., protein or nucleic acid (e.g., gene or mRNA)), detected by standard art known methods such as those described herein, as compared to a reference sample, reference cell, reference tissue, control sample, control cell, or control tissue. In certain embodiments, the elevated expression refers to the increase in expression level/amount of a biomarker wherein the increase is at least about any of 1.5×, 1.75×, 2×, 3×, 4×, 5×, 6×, 7×, 8×, 9×, 10×, 25×, 50×, 75×, or 100× the expression level/amount of the respective biomarker in a reference sample, reference cell, reference tissue, control sample, control cell, or control tissue. In some embodiments, a sample from the individual, the cancer and/or the cancer cell expresses substantially the same levels of phosphorylated FGFR3 as a reference sample, reference cell, reference tissue, control sample, control cell, control tissue, or internal control (e.g., housekeeping gene). In some embodiments, the reference sample, reference cell, reference tissue, control sample, control cell, or control tissue is a non-cancerous with or without a known level of expression of FGFR3. In some embodiments, the reference sample, reference cell, reference tissue, control sample, control cell, or control tissue is a cancerous with or without a known level of expression of FGFR3. In some embodiments, the expression of FGFR3 in a sample from the individual, the cancer and/or the cancer cell is cell surface expression. In some embodiments, the FGFR3 pathway in a sample from the individual, the cancer and/or the cancer cell is constitutively active. In some embodiments, the FGFR3 pathway in a sample from the individual, the cancer and/or the cancer cell is ligand dependent. In some embodiments, a sample from the individual, the cancer and/or the cancer cell comprises a mutation in FGFR3. Examples of constitutively active mutations in FGFR3 include, but are not limited to, FGFR3 S249C, FGFR3 R248C, FGFR3 G372C, FGFR3 Y375C, FGFR3 K652E, FGFR3 K652Q, and/or FGFR3 K652M. In some embodiments, a sample from the individual, the cancer and/or the cancer cell is wild-type for FGFR3.

In some embodiments of any of the uses and methods, the one or more biomarkers is one or more genes of the FGFR3-regulated lipogenic signature. In some embodiments of any of the uses and methods, a sample from the individual, the cancer and/or the cancer cell expresses of one or more genes of the FGFR3-regulated lipogenic signature. In some embodiment, a sample from the individual, the cancer and/or the cancer cell expresses elevated levels of one or more genes of the FGFR3-regulated lipogenic signature compared to a reference sample, reference cell, reference tissue, control sample, control cell, control tissue, or internal control (e.g., housekeeping gene). For example, provided herein are methods of treating cancer in an individual comprising administering to the individual an effective amount of an SCD1 antagonist, wherein the cancer in the individual expresses elevated levels of one or more biomarkers compared to a reference sample, reference cell, reference tissue, control sample, control cell, control tissue, or internal control (e.g., housekeeping gene) and the one or more biomarkers is FGFR3-regulated lipogenic signature. In some embodiments, elevated expression refers to an overall increase of about any of 5%, 10%, 20%, 25%, 30%, 40%, 50%, 60%, 70%, 80%, 85%, 90%, 95%, 96%, 97%, 98%, 99% or greater, in the level of biomarker (e.g., protein or nucleic acid (e.g., gene or mRNA)), detected by standard art known methods such as those described herein, as compared to a reference sample, reference cell, reference tissue, control sample, control cell, or control tissue. In certain embodiments, the elevated expression refers to the increase in expression level/amount of a biomarker wherein the increase is at least about any of 1.5×, 1.75×, 2×, 3×, 4×, 5×, 6×, 7×, 8×, 9×, 10×, 25×, 50×, 75×, or 100× the expression level/amount of the respective biomarker in a reference sample, reference cell, reference tissue, control sample, control cell, or control tissue. In some embodiments, a sample from the individual, the cancer and/or the cancer cell expresses substantially the same levels of FGFR3-regulated lipogenic signature as a reference sample, reference cell, reference tissue, control sample, control cell, control tissue, or internal control (e.g., housekeeping gene). In some embodiments, the reference sample, reference cell, reference tissue, control sample, control cell, or control tissue is a non-cancerous with or without a known level of expression of one or more genes of the FGFR3-regulated lipogenic signature. In some embodiments, the reference sample, reference cell, reference tissue, control sample, control cell, or control tissue is a cancerous with or without a known level of expression of one or more genes of the FGFR3-regulated lipogenic signature.

In some embodiments, the one or more genes of the FGFR3-regulated lipogenic signature comprises, consists of, or consists essential of one or more genes from the group consisting of SREBF1, G6PD, ACOT7, PTPLA, PCCB, FADS1, RDH11, ACER3, PDSS1, MVD, AGPAT5, HSD17B2, ACSL4, EBP, PIGW, LBR, ALLY, ADORA2B, GPCPD1, CYP24A1, ACSL3, MVK, ACSS2, FDPS, ELOVL5, HMGCR, LIPG, MEL DHCR7, LSS, ACAT2, FASN, CYP51A1, IDI1, FDFT1, FAR2, HMGCS1, SDR16C5, LDLR, MSMO1, INSIG1, DHRS9, LRP8, SQLE, PCSK9, SCD1, FABP4, and combinations thereof. In some embodiments, the one or more genes of the FGFR3-regulated lipogenic signature comprises, consists of, or consists essential of SC4MOL. In some embodiments, elevated expression refers to an overall increase of about any of 5%, 10%, 20%, 25%, 30%, 40%, 50%, 60%, 70%, 80%, 85%, 90%, 95%, 96%, 97%, 98%, 99% or greater, in the level of biomarker (e.g., protein or nucleic acid (e.g., gene or mRNA)), detected by standard art known methods such as those described herein, as compared to a reference sample, reference cell, reference tissue, control sample, control cell, or control tissue. In certain embodiments, the elevated expression refers to the increase in expression level/amount of a biomarker wherein the increase is at least about any of 1.5×, 1.75×, 2×, 3×, 4×, 5×, 6×, 7×, 8×, 9×, 10×, 25×, 50×, 75×, or 100× the expression level/amount of the respective biomarker in a reference sample, reference cell, reference tissue, control sample, control cell, or control tissue. In some embodiments, elevated expression refers to an overall increase of about any of 1.4, 1.5, 1.6, or 1.7 fold or greater, in the level of biomarker (e.g., protein or nucleic acid (e.g., gene or mRNA)), detected by standard art known methods such as those described herein, as compared to a reference sample, reference cell, reference tissue, control sample, control cell, or control tissue. In some embodiments, elevated expression refers to an overall increase mean log 2 fold change of about any of −0.5, −0.6, −0.7, or −0.8 or greater, in the level of biomarker (e.g., protein or nucleic acid (e.g., gene or mRNA)), detected by standard art known methods such as those described herein, as compared to a reference sample, reference cell, reference tissue, control sample, control cell, or control tissue.

In some embodiments, the one or more genes of the FGFR3-regulated lipogenic signature comprises, consists of, or consists essential of one or more genes from the group consisting of ELOVL5, HMGCR, LIPG, MEL DHCR7, LSS, ACAT2, FASN, CYP51A1, IDI1, FDFT1, FAR2, HMGCS1, SDR16C5, LDLR, MSMO1, INSIG1, DHRS9, LRP8, SQLE, PCSK9, SCD1, FABP4, and combinations thereof. In some embodiments, the one or more genes of the FGFR3-regulated lipogenic signature comprises, consists of, or consists essential of SC4MOL. In some embodiments, elevated expression refers to an overall increase of about any of 1.8, 1.9, 2.0, or 2.1 fold or greater, in the level of biomarker (e.g., protein or nucleic acid (e.g., gene or mRNA)), detected by standard art known methods such as those described herein, as compared to a reference sample, reference cell, reference tissue, control sample, control cell, or control tissue. In some embodiments, elevated expression refers to an overall increase mean log 2 fold change of about any of −0.9, −1.0, −1.1, or −1.2 or greater, in the level of biomarker (e.g., protein or nucleic acid (e.g., gene or mRNA)), detected by standard art known methods such as those described herein, as compared to a reference sample, reference cell, reference tissue, control sample, control cell, or control tissue. In some embodiments, the one or more genes of the FGFR3-regulated lipogenic signature comprises, consists of, or consists essential of one or more genes from the group consisting of CYP51A1, IDI1, FDFT1, FAR2, HMGCS1, SDR16C5, LDLR, MSMO1, INSIG1, DHRS9, LRP8, SQLE, PCSK9, SCD1, FABP4, and combinations thereof. In some embodiments, the one or more genes of the FGFR3-regulated lipogenic signature comprises, consists of, or consists essential of SC4MOL. In some embodiments, elevated expression refers to an overall increase of about any of 2.2, 2.3, 2.4, 2.5, 2.6, or 2.7 fold or greater, in the level of biomarker (e.g., protein or nucleic acid (e.g., gene or mRNA)), detected by standard art known methods such as those described herein, as compared to a reference sample, reference cell, reference tissue, control sample, control cell, or control tissue. In some embodiments, elevated expression refers to an overall increase mean log 2 fold change of about any of −1.0, −1.1, or −1.2 or greater, in the level of biomarker (e.g., protein or nucleic acid (e.g., gene or mRNA)), detected by standard art known methods such as those described herein, as compared to a reference sample, reference cell, reference tissue, control sample, control cell, or control tissue.

In some embodiments, the one or more genes of the FGFR3-regulated lipogenic signature comprises, consists of, or consists essential of one or more genes from the group consisting of LDLR, MSMO1, INSIG1, DHRS9, LRP8, SQLE, PCSK9, SCD1, FABP4, and combinations thereof. In some embodiments, the one or more genes of the FGFR3-regulated lipogenic signature comprises, consists of, or consists essential of SC4MOL. In some embodiments, elevated expression refers to an overall increase of about any of 2.6, 2.7, 2.8, 2.9, 3.0, 3.1, or 3.2 fold or greater, in the level of biomarker (e.g., protein or nucleic acid (e.g., gene or mRNA)), detected by standard art known methods such as those described herein, as compared to a reference sample, reference cell, reference tissue, control sample, control cell, or control tissue. In some embodiments, elevated expression refers to an overall increase mean log 2 fold change of about any of −1.4, −1.5, −1.6 or −1.7 or greater, in the level of biomarker (e.g., protein or nucleic acid (e.g., gene or mRNA)), detected by standard art known methods such as those described herein, as compared to a reference sample, reference cell, reference tissue, control sample, control cell, or control tissue.

In some embodiments, the one or more genes of the FGFR3-regulated lipogenic signature comprises, consists of, or consists essential of one or more genes from the group consisting of SQLE, PCSK9, SCD1, FABP4, and combinations thereof. In some embodiments, the one or more genes of the FGFR3-regulated lipogenic signature comprises, consists of, or consists essential of SQLE. In some embodiments, the one or more genes of the FGFR3-regulated lipogenic signature comprises, consists of, or consists essential of PCSK9. In some embodiments, the one or more genes of the FGFR3-regulated lipogenic signature comprises, consists of, or consists essential of SCD1. In some embodiments, the one or more genes of the FGFR3-regulated lipogenic signature comprises, consists of, or consists essential of FABP4. In some embodiments, elevated expression refers to an overall increase of about any of 3.2, 3.3, 3.4, 3.5, 3.6, 3.7, or 3.8 fold or greater, in the level of biomarker (e.g., protein or nucleic acid (e.g., gene or mRNA)), detected by standard art known methods such as those described herein, as compared to a reference sample, reference cell, reference tissue, control sample, control cell, or control tissue. In some embodiments, elevated expression refers to an overall increase mean log 2 fold change of about any of −1.6, −1.7, −1.8, −1.9, or −2.0 or greater, in the level of biomarker (e.g., protein or nucleic acid (e.g., gene or mRNA)), detected by standard art known methods such as those described herein, as compared to a reference sample, reference cell, reference tissue, control sample, control cell, or control tissue.

In some embodiments of any of the uses and methods, the one or more biomarkers is cleaved mature SREBP1. In some embodiments, full-length protein SREBP1a is 1-1147 aa of UNIPROT amino acid sequence P36956-1 and cleaved mature form: 1-490 aa of UNIPROT amino acid sequence P36956-1. In some embodiments, full-length protein SREBP1c is 1-1123 aa of UNIPROT amino acid sequence P36956-3 and cleaved mature form: 1-466 aa of UNIPROT amino acid sequence P36956-3. In some embodiments of any of the uses and methods, a sample from the individual, the cancer and/or the cancer cell expresses elevated levels of mature SREBP1 compared to a reference sample, reference cell, reference tissue, control sample, control cell, control tissue, or internal control (e.g., housekeeping gene). For example, provided herein are methods of treating cancer in an individual comprising administering to the individual an effective amount of an SCD1 antagonist, wherein the cancer in the individual expresses elevated levels of one or more biomarkers compared to a reference sample, reference cell, reference tissue, control sample, control cell, control tissue, or internal control (e.g., housekeeping gene) and the one or more biomarkers is mature SREBP1. In some embodiments of any of the uses and methods, a sample from the individual, the cancer and/or the cancer cell expresses elevated levels of mature SREBP1 and the levels of mature SREBP2 are not substantially elevated (i.e., substantially the same level of expression) compared to a reference sample, reference cell, reference tissue, control sample, control cell, control tissue, or internal control (e.g., housekeeping gene). In some embodiments, elevated expression refers to an overall increase of about any of 5%, 10%, 20%, 25%, 30%, 40%, 50%, 60%, 70%, 80%, 85%, 90%, 95%, 96%, 97%, 98%, 99% or greater, in the level of biomarker (e.g., protein or nucleic acid (e.g., gene or mRNA)), detected by standard art known methods such as those described herein, as compared to a reference sample, reference cell, reference tissue, control sample, control cell, or control tissue. In some embodiments, SREBP1 is SREBP1 isoform a. In some embodiments, SREBP1 is SREBP1 isoform c. In certain embodiments, the elevated expression refers to the increase in expression level/amount of a biomarker wherein the increase is at least about any of 1.5×, 1.75×, 2×, 3×, 4×, 5×, 6×, 7×, 8×, 9×, 10×, 25×, 50×, 75×, or 100× the expression level/amount of the respective biomarker in a reference sample, reference cell, reference tissue, control sample, control cell, or control tissue. In some embodiments, a sample from the individual, the cancer and/or the cancer cell is a non-cancerous with or without a known level of expression of mature SREBP1 and/or mature SREBP2. In some embodiments, the reference sample, reference cell, reference tissue, control sample, control cell, or control tissue is a cancerous with or without a known level of expression of mature SREBP1 and/or mature SREBP2.

In some embodiments of any of the uses and methods, the one or more biomarkers is Δ9 monounsaturaturated fatty acids. In some embodiments of any of the uses and methods, a sample from the individual, the cancer and/or the cancer cell expresses elevated levels of Δ9 monounsaturaturated fatty acids compared to a reference sample, reference cell, reference tissue, control sample, control cell, control tissue, or internal control (e.g., housekeeping gene). In some embodiments of any of the uses and methods, the one or more biomarkers is ratio of Δ9 monounsaturaturated fatty acids:saturated fatty acids. In some embodiments of any of the uses and methods, a sample from the individual, the cancer and/or the cancer cell expresses elevated ratio of Δ9 monounsaturaturated fatty acids:saturated fatty acids compared to a reference sample, reference cell, reference tissue, control sample, control cell, control tissue, or internal control (e.g., housekeeping gene). For example, provided herein are methods of treating cancer in an individual comprising administering to the individual an effective amount of an SCD1 antagonist, wherein the cancer in the individual expresses elevated levels of one or more biomarkers compared to a reference sample, reference cell, reference tissue, control sample, control cell, control tissue, or internal control (e.g., housekeeping gene) and the one or more biomarkers is the ratio of Δ9 monounsaturaturated fatty acids:saturated fatty acids. In some embodiments, elevated expression refers to an overall increase of about any of 5%, 10%, 20%, 25%, 30%, 40%, 50%, 60%, 70%, 80%, 85%, 90%, 95%, 96%, 97%, 98%, 99% or greater, in the level of biomarker (e.g., protein or nucleic acid (e.g., gene or mRNA)), detected by standard art known methods such as those described herein, as compared to a reference sample, reference cell, reference tissue, control sample, control cell, or control tissue. In certain embodiments, the elevated expression refers to the increase in expression level/amount of a biomarker wherein the increase is at least about any of 1.5×, 1.75×, 2×, 3×, 4×, 5×, 6×, 7×, 8×, 9×, 10×, 25×, 50×, 75×, or 100× the expression level/amount of the respective biomarker in a reference sample, reference cell, reference tissue, control sample, control cell, or control tissue. In some embodiments, the reference sample, reference cell, reference tissue, control sample, control cell, or control tissue is a non-cancerous with or without a known level of expression of Δ9 monounsaturaturated fatty acids and/or saturated fatty acids. In some embodiments, the reference sample, reference cell, reference tissue, control sample, control cell, or control tissue is a cancerous with or without a known level of expression of Δ9 monounsaturaturated fatty acids and/or saturated fatty acids. Example of Δ9 monounsaturaturated fatty acids include, but are not limited to, palmitoleic acid (C16:1) and oleic acid (C18:1). Examples of saturated fatty acids include, but are not limited to, stearic acid (C18:0) and palmitic acid (C16:0). Methods of measuring Δ9 monounsaturaturated fatty acids and saturated fatty acids are known in the art including, but not limited to mass spectrometry, gas chromatography, and thin layer chromatography.

In some embodiments of any of the uses and methods, the one or more biomarkers is PI3K signaling, mTOR signaling, MEK signaling. In some embodiments of any of the uses and methods, the one or more biomarkers is one or more polymorphisms in genes selected from the group consisting of PI3K, PTEN, p85, TSC1/2, and AKT. In some embodiments of any of the uses and methods, the one or more biomarkers is phosphorylated AKT. In some embodiments of any of the uses and methods, a sample from the individual, the cancer and/or the cancer cell comprises activated PI3K signaling (e.g., elevated PI3K signaling), activated mTOR signaling (e.g., elevated mTOR signaling), and/or activated MEK signaling (e.g., elevated MEK signaling). In some embodiments of any of the methods and/or uses, a sample from the individual, the cancer and/or the cancer cell comprises PI3K activating mutations. In some embodiments of any of the methods and/or uses, a sample from the individual, the cancer and/or the cancer cell comprises PTEN loss and/or mutations. In some embodiments of any of the methods and/or uses, a sample from the individual, the cancer and/or the cancer cell comprises p85 mutations. In some embodiments of any of the methods and/or uses, a sample from the individual, the cancer and/or the cancer cell comprises AKT activating mutations. In some embodiments of any of the methods and/or uses, a sample from the individual, the cancer and/or the cancer cell comprises elevated levels of phosphorylated AKT (e.g., pAKT $S^{473}$). In some embodiments of any of the methods and/or uses, a sample from the individual, the cancer and/or the cancer cell comprises TSC1/2 loss of function mutations.

In some embodiments, elevated expression refers to an overall increase of about any of 5%, 10%, 20%, 25%, 30%, 40%, 50%, 60%, 70%, 80%, 85%, 90%, 95%, 96%, 97%, 98%, 99% or greater, in the level of biomarker (e.g., protein or nucleic acid (e.g., gene or mRNA)), detected by standard art known methods such as those described herein, as compared to a reference sample, reference cell, reference tissue, control sample, control cell, or control tissue. In certain embodiments, the elevated expression refers to the increase in expression level/amount of a biomarker wherein the increase is at least about any of 1.5×, 1.75×, 2×, 3×, 4×, 5×, 6×, 7×, 8×, 9×, 10×, 25×, 50×, 75×, or 100× the expression level/amount of the respective biomarker in a reference sample, reference cell, reference tissue, control sample, control cell, or control tissue. In some embodiments, elevated expression refers to an overall increase of greater than about 1.5 fold, about 1.75 fold, about 2 fold, about 2.25 fold, about 2.5 fold, about 2.75 fold, about 3.0 fold, or about 3.25 fold as compared to a reference sample, reference cell, reference tissue, control sample, control cell, control tissue, or internal control (e.g., housekeeping gene).

In some embodiments, reduced expression refers to an overall reduction of about any of 5%, 10%, 20%, 25%, 30%, 40%, 50%, 60%, 70%, 80%, 85%, 90%, 95%, 96%, 97%, 98%, 99% or greater, in the level of biomarker (e.g., protein or nucleic acid (e.g., gene or mRNA)), detected by standard art known methods such as those described herein, as compared to a reference sample, reference cell, reference tissue, control sample, control cell, or control tissue. In certain embodiments, reduced expression refers to the decrease in expression level/amount of a biomarker wherein the decrease is at least about any of 0.9×, 0.8×, 0.7×, 0.6×, 0.5×, 0.4×, 0.3×, 0.2×, 0.1×, 0.05×, or 0.01× the expression level/amount of the respective biomarker in a reference sample, reference cell, reference tissue, control sample, control cell, or control tissue.

In some embodiments of any of the uses and/or methods, the SCD1 antagonist is any antibody, binding polypeptide, binding small molecule, or polynucleotide described herein. In some embodiments, the SCD1 antagonist is a small molecule. In some embodiments, the small molecule is SMI37062 (G01522403), G02447171, or derivative thereof. In some embodiments, the SCD1 antagonist is an antibody. In some embodiments, the antibody is a monoclonal antibody. In some embodiments, the antibody is a human, humanized, or chimeric antibody. In some embodiments, the antibody is an antibody fragment and the antibody fragment binds SCD1.

In some embodiments of any of the methods, the individual according to any of the above embodiments may be a human.

Expression levels/amount of a biomarker can be determined qualitatively and/or quantitatively based on any suitable criterion known in the art, including but not limited to mRNA, cDNA, proteins, protein fragments and/or gene copy number. In certain embodiments, expression/amount of a biomarker in a first sample is increased as compared to expression/amount in a second sample. In certain embodiments, expression/amount of a biomarker in a first sample is decreased as compared to expression/amount in a second sample. In certain embodiments, the second sample is a reference sample, reference cell, reference tissue, control sample, control cell, or control tissue. Additional disclosures for determining expression level/amount of a gene are described herein.

SCD1 antagonists described herein can be used either alone or in combination with other agents in a therapy. For instance, an SCD1 antagonist described herein may be co-administered with at least one additional therapeutic agent. In certain embodiments, an additional therapeutic agent is a chemotherapeutic agent. In some embodiments, the additional therapeutic agent is a mTOR inhibitor. In some embodiments, the additional therapeutic agent is a PI3K inhibitor. In some embodiments, the additional therapeutic agent is a MEK inhibitor. In some embodiments, the additional therapeutic agent is an FGFR3 inhibitor.

Such combination therapies noted above encompass combined administration (where two or more therapeutic agents are included in the same or separate formulations), and separate administration, in which case, administration of the SCD1 antagonist of the invention can occur prior to, simultaneously, and/or following, administration of the additional therapeutic agent and/or adjuvant. SCD1 antagonists described herein can also be used in combination with radiation therapy.

An SCD1 antagonist (e.g., an antibody, binding polypeptides, and/or small molecules) described herein (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g., by injections, such as intravenous or subcutaneous injections, depending in part on whether the administration is brief or chronic. Various dosing schedules including but not limited to single or multiple administrations over various time-points, bolus administration, and pulse infusion are contemplated herein.

SCD1 antagonists (e.g., antibodies, binding polypeptides, and/or small molecules) described herein may be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The SCD1 antagonist need not be, but is optionally formulated with one or more agents currently used to prevent or treat the disorder in question. The effective amount of such other agents depends on the amount of the SCD1 antagonist present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an SCD1 antagonist described herein (when used alone or in combination with one or more other additional therapeutic agents) will depend on the type of disease to be treated, the severity and course of the disease, whether the SCD1 antagonist is administered for preventive or therapeutic purposes, previous therapy, the patient's clinical history and response to the SCD1 antagonist, and the discretion of the attending physician. The SCD1 antagonist is suitably administered to the patient at one time or over a series of treatments. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. Such doses may be administered intermittently, e.g., every week or every three weeks (e.g., such that the patient receives from about two to about twenty, or e.g., about six doses of the SCD1 antagonist described herein). An initial higher loading dose, followed by one or more lower doses may be administered. An exemplary dosing regimen comprises administering. However, other dosage regimens may be useful. The progress of this therapy is easily monitored by conventional techniques and assays.

It is understood that any of the above formulations or therapeutic methods may be carried out using an immunoconjugate in place of or in addition to the SCD1 antagonist.

Expression levels/amount of a biomarker can be determined qualitatively and/or quantitatively based on any suitable criterion known in the art, including but not limited to mRNA, cDNA, proteins, protein fragments and/or gene copy number. In certain embodiments, expression is protein expression. In certain embodiments, expression is polynucleotide expression. In certain embodiments, the polynucleotide is DNA. In certain embodiments, the polynucleotide is RNA. In certain embodiments, expression/amount of a biomarker in a first sample is increased as compared to expression/amount in a second sample. In certain embodiments, expression/amount of a biomarker in a first sample is decreased as compared to expression/amount in a second sample. In certain embodiments, the second sample is a reference sample, reference cell, reference tissue, control sample, control cell, or control tissue. Additional disclosures for determining expression level/amount of a gene are described herein.

Expression of various biomarkers in a sample can be analyzed by a number of methodologies, many of which are known in the art and understood by the skilled artisan, including, but not limited to, immunohistochemical (IHC), Western blot analysis, immunoprecipitation, molecular binding assays, ELISA, ELIFA, fluorescence activated cell sorting (FACS), MassARRAY, proteomics, quantitative blood based assays (as for example Serum ELISA), biochemical enzymatic activity assays, in situ hybridization, Northern analysis, polymerase chain reaction (PCR) including quantitative real time PCR (qRT-PCR) and other amplification type detection methods, such as, for example, branched DNA, SISBA, TMA and the like), RNA-Seq, FISH, microarray analysis, gene expression profiling, and/or serial analysis of gene expression (SAGE), as well as any one of the wide variety of assays that can be performed by protein, gene, and/or tissue array analysis. Typical protocols for evaluating the status of genes and gene products are found, for example in Ausubel et al. eds., 1995, Current Protocols In Molecular Biology, Units 2 (Northern Blotting), 4 (Southern Blotting), 15 (Immunoblotting) and 18 (PCR Analysis). Multiplexed immunoassays such as those available from Rules Based Medicine or Meso Scale Discovery (MSD) may also be used.

In some embodiments, expression level of a biomarker is determined using a method comprising: (a) performing gene expression profiling, PCR (such as rtPCR), RNA-seq, microarray analysis, SAGE, MassARRAY technique, or FISH on a sample (such as a patient cancer sample); and b) determining expression level of a biomarker in the sample. In one aspect, expression level of biomarker is determined using a method comprising: (a) performing IHC analysis of a sample (such as a patient cancer sample) with an antibody; and b) determining expression level of a biomarker in the sample. In some embodiments, IHC staining intensity is determined relative to a reference value.

According in some embodiments, gene expression is measured by observing protein expression levels of an aforementioned gene. In some embodiments, the gene expression level is measured by a method selected from a PCR method, a microarray method, or an immunoassay method. In some embodiments, the microarray method comprises the use of a microarray chip having one or more nucleic acid molecules that can hybridize under stringent conditions to a nucleic acid molecule encoding a gene mentioned above or having one or more polypeptides (such as peptides or antibodies) that can bind to one or more of the proteins encoded by the genes mentioned above. In one embodiment, the PCR method is qPCR. In one embodiment, the PCR method is multiplex-PCR. In some embodiments, gene expression is measured by microarray. In some embodiments, gene expression is measured by real-time quantitative polymerase chain reaction (qPCR). In some embodiments, expression is measured by multiplex-PCR.

In certain embodiments, the method comprises contacting the biological sample with antibodies to a biomarker described herein under conditions permissive for binding of the biomarker, and detecting whether a complex is formed between the antibodies and biomarker. Such method may be an in vitro or in vivo method. In one embodiment, an antibody is used to select subjects eligible for therapy with SCD1 antagonist, e.g., a biomarker for selection of patients.

In certain embodiments, the samples are normalized for both differences in the amount of the biomarker assayed and variability in the quality of the samples used, and variability between assay runs. Such normalization may be accomplished by measuring and incorporating the expression of certain normalizing biomarkers, including well known housekeeping genes, such as ACTB. Alternatively, normalization can be based on the mean or median signal of all of the assayed genes or a large subset thereof (global normalization approach). On a gene-by-gene basis, measured normalized amount of a patient tumor mRNA or protein is compared to the amount found in a reference set. Normalized expression levels for each mRNA or protein per tested tumor per patient can be expressed as a percentage of the expression level measured in the reference set. The expression level measured in a particular patient sample to be analyzed will fall at some percentile within this range, which can be determined by methods well known in the art.

In certain embodiments, relative expression level of a gene is determined as follows:

Relative expression gene1 sample1=2 exp (Ct housekeeping gene−Ct gene1) with Ct determined in a sample.

Relative expression gene1 reference RNA=2 exp (Ct housekeeping gene−Ct gene1) with Ct determined in the reference sample.

Normalized relative expression gene1 sample1=(relative expression gene1 sample1/relative expression gene1 reference RNA)×100

Ct is the threshold cycle. The Ct is the cycle number at which the fluorescence generated within a reaction crosses the threshold line.

All experiments are normalized to a reference RNA, which is a comprehensive mix of RNA from various tissue sources (e.g., reference RNA #636538 from Clontech, Mountain View, Calif.). Identical reference RNA is included in each qRT-PCR run, allowing comparison of results between different experimental runs.

In one embodiment, the sample is a clinical sample. In another embodiment, the sample is used in a diagnostic assay. In some embodiments, the sample is obtained from a primary or metastatic tumor. Tissue biopsy is often used to obtain a representative piece of tumor tissue. Alternatively, tumor cells can be obtained indirectly in the form of tissues or fluids that are known or thought to contain the tumor cells of interest. For instance, samples of lung cancer lesions may be obtained by resection, bronchoscopy, fine needle aspiration, bronchial brushings, or from sputum, pleural fluid or blood. Genes or gene products can be detected from cancer or tumor tissue or from other body samples such as urine, sputum, serum or plasma. The same techniques discussed above for detection of target genes or gene products in cancerous samples can be applied to other body samples. Cancer cells may be sloughed off from cancer lesions and appear in such body samples. By screening such body samples, a simple early diagnosis can be achieved for these cancers. In addition, the progress of therapy can be monitored more easily by testing such body samples for target genes or gene products.

In certain embodiments, a reference sample, reference cell, reference tissue, control sample, control cell, or control tissue is a single sample or combined multiple samples from the same subject or individual that are obtained at one or more different time points than when the test sample is obtained. For example, a reference sample, reference cell, reference tissue, control sample, control cell, or control tissue is obtained at an earlier time point from the same subject or individual than when the test sample is obtained. Such reference sample, reference cell, reference tissue, control sample, control cell, or control tissue may be useful if the reference sample is obtained during initial diagnosis of cancer and the test sample is later obtained when the cancer becomes metastatic.

In certain embodiments, a reference sample, reference cell, reference tissue, control sample, control cell, or control tissue is a combined multiple samples from one or more healthy individuals who are not the subject or patient. In certain embodiments, a reference sample, reference cell, reference tissue, control sample, control cell, or control tissue is a combined multiple samples from one or more individuals with a disease or disorder (e.g., cancer) who are not the subject or patient. In certain embodiments, a reference sample, reference cell, reference tissue, control sample, control cell, or control tissue is pooled RNA samples from normal tissues or pooled plasma or serum samples from one or more individuals who are not the subject or patient. In certain embodiments, a reference sample, reference cell, reference tissue, control sample, control cell, or control tissue is pooled RNA samples from tumor tissues or pooled plasma or serum samples from one or more individuals with a disease or disorder (e.g., cancer) who are not the subject or patient.

In certain embodiments, the expression of proteins in a sample is examined using immunohistochemistry ("IHC") and staining protocols. Immunohistochemical staining of tissue sections has been shown to be a reliable method of assessing or detecting presence of proteins in a sample.

IHC may be performed in combination with additional techniques such as morphological staining and/or fluorescence in-situ hybridization. Two general methods of IHC are available; direct and indirect assays. According to the first assay, binding of antibody to the target antigen is determined directly. This direct assay uses a labeled reagent, such as a fluorescent tag or an enzyme-labeled primary antibody, which can be visualized without further antibody interaction. In a typical indirect assay, unconjugated primary antibody binds to the antigen and then a labeled secondary antibody binds to the primary antibody. Where the secondary antibody is conjugated to an enzymatic label, a chromogenic or fluorogenic substrate is added to provide visualization of the antigen. Signal amplification occurs because several secondary antibodies may react with different epitopes on the primary antibody.

The primary and/or secondary antibody used for immunohistochemistry typically will be labeled with a detectable moiety. Numerous labels are available which can be generally grouped into the following categories: (a) Radioisotopes, such as $^{35}S$, $^{14}C$, $^{125}I$, $^{3}H$, and $^{131}I$; (b) colloidal gold particles; (c) fluorescent labels including, but are not limited to, rare earth chelates (europium chelates), Texas Red, rhodamine, fluorescein, dansyl, Lissamine, umbelliferone, phycocrytherin, phycocyanin, or commercially available fluorophores such SPECTRUM ORANGE7 and SPECTRUM GREEN7 and/or derivatives of any one or more of the above; (d) various enzyme-substrate labels are available and U.S. Pat. No. 4,275,149 provides a review of some of these. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like.

Examples of enzyme-substrate combinations include, for example, horseradish peroxidase (HRPO) with hydrogen peroxidase as a substrate; alkaline phosphatase (AP) with para-Nitrophenyl phosphate as chromogenic substrate; and β-D-galactosidase (β-D-Gal) with a chromogenic substrate (e.g., p-nitrophenyl-β-D-galactosidase) or fluorogenic substrate (e.g., 4-methylumbelliferyl-β-D-galactosidase). For a general review of these, see U.S. Pat. Nos. 4,275,149 and 4,318,980.

Specimens thus prepared may be mounted and cover-slipped. Slide evaluation is then determined, e.g., using a microscope, and staining intensity criteria, routinely used in the art, may be employed. In some embodiments, a staining pattern score of about 1+ or higher is diagnostic and/or prognostic. In certain embodiments, a staining pattern score of about 2+ or higher in an IHC assay is diagnostic and/or prognostic. In other embodiments, a staining pattern score of about 3 or higher is diagnostic and/or prognostic. In one embodiment, it is understood that when cells and/or tissue from a tumor or colon adenoma are examined using IHC, staining is generally determined or assessed in tumor cell and/or tissue (as opposed to stromal or surrounding tissue that may be present in the sample).

In alternative methods, the sample may be contacted with an antibody specific for said biomarker under conditions sufficient for an antibody-biomarker complex to form, and then detecting said complex. The presence of the biomarker may be detected in a number of ways, such as by Western blotting and ELISA procedures for assaying a wide variety of tissues and samples, including plasma or serum. A wide range of immunoassay techniques using such an assay format are available, see, e.g., U.S. Pat. Nos. 4,016,043, 4,424,279 and 4,018,653. These include both single-site and two-site or "sandwich" assays of the non-competitive types, as well as in the traditional competitive binding assays. These assays also include direct binding of a labeled antibody to a target biomarker.

Methods for the evaluation of mRNAs in cells are well known and include, for example, hybridization assays using complementary DNA probes (such as in situ hybridization using labeled riboprobes specific for the one or more genes, Northern blot and related techniques) and various nucleic acid amplification assays (such as RT-PCR using complementary primers specific for one or more of the genes, and other amplification type detection methods, such as, for example, branched DNA, SISBA, TMA and the like).

Samples from mammals can be conveniently assayed for mRNAs using Northern, dot blot or PCR analysis. In addition, such methods can include one or more steps that allow one to determine the levels of target mRNA in a biological sample (e.g., by simultaneously examining the levels a comparative control mRNA sequence of a "housekeeping" gene such as an actin family member). Optionally, the sequence of the amplified target cDNA can be determined.

Optional methods of the invention include protocols which examine or detect mRNAs, such as target mRNAs, in a tissue or cell sample by microarray technologies. Using nucleic acid microarrays, test and control mRNA samples from test and control tissue samples are reverse transcribed and labeled to generate cDNA probes. The probes are then hybridized to an array of nucleic acids immobilized on a solid support. The array is configured such that the sequence and position of each member of the array is known. For example, a selection of genes whose expression correlate with increased or reduced clinical benefit of anti-angiogenic therapy may be arrayed on a solid support. Hybridization of a labeled probe with a particular array member indicates that the sample from which the probe was derived expresses that gene.

Expression of a selected biomarker in a tissue or cell sample may also be examined by way of functional or activity-based assays. For instance, if the biomarker is an enzyme, one may conduct assays known in the art to determine or detect the presence of the given enzymatic activity in the tissue or cell sample.

III. Therapeutic Compositions

Provided herein are SCD1 antagonists useful in the methods described herein. In some embodiments, the SCD1 antagonists are an antibody, binding polypeptide, binding small molecule, and/or polynucleotide.

A. Antibodies

In one aspect, provided herein isolated antibodies that bind to SCD1. In any of the above embodiments, an antibody is humanized. In a further aspect of the invention, an anti-SCD1 antibody according to any of the above embodiments is a monoclonal antibody, including a chimeric, humanized or human antibody. In one embodiment, an anti-SCD1 antibody is an antibody fragment, e.g., a Fv, Fab, Fab', scFv, diabody, or F(ab')$_2$ fragment. In another embodiment, the antibody is a full length antibody, e.g., an intact IgG1" antibody or other antibody class or isotype as defined herein.

In a further aspect, an anti-SCD1 antibody according to any of the above embodiments may incorporate any of the features, singly or in combination, as described in Sections below:

1. Antibody Affinity

In certain embodiments, an antibody provided herein has a dissociation constant (Kd) of ≤1 μM. In one embodiment, Kd is measured by a radiolabeled antigen binding assay (RIA) performed with the Fab version of an antibody of interest and its antigen as described by the following assay. Solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881 (1999)). To establish conditions for the assay, MICROTITER® multi-well plates (Thermo Scientific) are coated overnight with 5 μg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 μl/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, Kd is measured using surface plasmon resonance assays using a BIACORE®-2000 or a BIACORE®-3000 (BIAcore, Inc., Piscataway, N.J.) at 25° C. with immobilized antigen CM5 chips at ~10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen et al., *J. Mol. Biol.* 293:865-881 (1999). If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm bandpass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al. *Nat. Med.* 9:129-134 (2003). For a review of scFv fragments, see, e.g., Pluckthün, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g., *E. coli* or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison et al., *Proc. Natl. Acad. Sci. USA,* 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing SDR (a-CDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et cd., *J. Biol. Chem.* 272:10678-10684 (1997) and Rosok et cd., *J. Biol. Chem.* 271:22611-22618 (1996)).

4. Human Antibodies

In certain embodiments, an antibody provided herein is a human antibody. Human antibodies can be produced using various techniques known in the art. Human antibodies are described generally in van Dijk and van de Winkel, Curr. Opin. Pharmacol. 5: 368-74 (2001) and Lonberg, Curr. Opin. Immunol. 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENOMOUSE™ technology; U.S. Pat. No. 5,770,429 describing HuMab® technology; U.S. Pat. No. 7,041,870 describing K-M MOUSE® technology, and U.S. Patent Application Publication No. US 2007/0061900, describing VelociMouse® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.,* 133: 3001 (1984); Brodeur et al., Monoclonal Antibody Production Techniques and Applications, pp. 51-63 (Marcel Dekker, Inc., New York, 1987); and Boerner et al., *J. Immunol.,* 147: 86 (1991).) Human antibodies generated via human B-cell hybridoma technology are also described in Li et al., *Proc. Natl. Acad. Sci. USA,* 103:3557-3562 (2006). Additional methods include those described, for example, in U.S. Pat. No. 7,189,826 (describing production of monoclonal human IgM antibodies from hybridoma cell lines) and Ni, Xiandai Mianyixue, 26(4):265-268 (2006) (describing human-human hybridomas). Human hybridoma technology (Trioma technology) is also described in Vollmers and Brandlein, *Histol. Histopathol.,* 20(3):927-937 (2005) and Vollmers and Brandlein, *Methods Find Exp. Clin. Pharmacol.,* 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in Methods in Molecular Biology 178:1-37 (O'Brien et al., ed., Human Press, Totowa, N.J., 2001) and further described, e.g., in the McCafferty et al., *Nature* 348: 552-554; Clackson et al., *Nature* 352: 624-628 (1991); Marks et al., *J. Mol. Biol.* 222:581-597 (1992); Marks and Bradbury, in Methods in Molecular Biology 248:161-175 (Lo, ed., Human Press, Totowa, N.J., 2003); Sidhu et al., *J. Mol. Biol.* 338(2):299-310 (2004); Lee et al., *J. Mol. Biol.* 340(5):1073-1093 (2004); Fellouse, *Proc. Natl. Acad. Sci. USA* 101(34): 12467-12472 (2004); and Lee et al., *J. Immunol. Methods* 284(1-2): 119-132 (2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.,* 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J,* 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.,* 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In certain embodiments, an antibody provided herein is a multispecific antibody, e.g., a bispecific antibody. Multispecific antibodies are monoclonal antibodies that have binding specificities for at least two different sites. In certain embodiments, one of the binding specificities is for SCD1 and the other is for any other antigen. In certain embodiments, bispecific antibodies may bind to two different epitopes of SCD1. Bispecific antibodies may also be used to localize cytotoxic agents to cells which express SCD1. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, Nature 305: 537 (1983)), WO 93/08829, and Traunecker et al., EMBO J. 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., Science, 229: 81 (1985)); using leucine zippers to produce bi-specific antibodies (see, e.g., Kostelny et al., J. Immunol., 148(5):1547-1553 (1992)); using "diabody" technology for making bispecific antibody fragments (see, e.g., Hollinger et al., Proc. Natl. Acad. Sci. USA, 90:6444-6448 (1993)); and using single-chain Fv (sFv) dimers (see, e.g., Gruber et al., J. Immunol., 152:5368 (1994)); and preparing trispecific antibodies as described, e.g., in Tutt et al. J. Immunol. 147: 60 (1991).

Engineered antibodies with three or more functional antigen binding sites, including "Octopus antibodies," are also included herein (see, e.g., US 2006/0025576A1).

The antibody or fragment herein also includes a "Dual Acting FAb" or "DAF" comprising an antigen binding site that binds to SCD1 as well as another, different antigen (see, US 2008/0069820, for example).

7. Antibody Variants a) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. TIBTECH 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. J. Mol. Biol. 336:1239-1249 (2004); Yamane-Ohnuki et al., Biotech. Bioeng. 87: 614 (2004). Examples of cell lines capable of producing defucosylated antibodies include Lec13 CHO cells deficient in protein fucosylation (Ripka et al. Arch. Biochem. Biophys. 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. Biotech. Bioeng. 87: 614 (2004); Kanda, Y. et al., Biotechnol. Bioeng., 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

b) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g., a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/ depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc(RIII only, whereas monocytes express Fc(RI, Fc(RII and Fc(RIII. FcR expression on hematopoietic cells is summarized in Table 3 on page 464 of Ravetch and Kinet, Annu. Rev. Immunol. 9:457-492 (1991). Non-limiting examples of in vitro assays to assess ADCC activity of a molecule of interest is described in U.S. Pat. No. 5,500,362 (see, e.g., Hellstrom, I. et al. Proc. Nat'l Acad. Sci. USA 83:7059-7063 (1986)) and Hellstrom, I et al., Proc. Nat'l Acad. Sci. USA 82:1499-1502 (1985); 5,821,337 (see Bruggemann, M. et al., J. Exp. Med. 166: 1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. Proc. Nat'l Acad. Sci. USA 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., J. Immunol. Methods 202:163 (1996); Cragg, M. S. et al., Blood 101:1045-1052 (2003); and Cragg, M. S, and M. J. Glennie, Blood 103:2738-2743 (2004)). FcRn binding and in vivo clearance/half life determinations can also be performed using methods known in the art (see, e.g., Petkova, S. B. et al., Int'l. Immunol. 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737, 056; WO 2004/056312, and Shields et al., J. Biol. Chem. 9(2): 6591-6604 (2001).) In certain embodiments, an antibody variant comprises an Fc region with one or more amino acid substitutions which improve ADCC, e.g., substitutions at positions 298, 333, and/or 334 of the Fc region (EU numbering of residues). In some embodiments, alterations are made in the Fc region that result in altered (i.e., either improved or diminished) C1q binding and/or Complement Dependent Cytotoxicity (CDC), e.g., as described in U.S. Pat. No. 6,194, 551, WO 99/51642, and Idusogie et al. J. Immunol. 164: 4178-4184 (2000).

Antibodies with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826). See also Duncan & Winter, *Nature* 322:738-40 (1988); U.S. Pat. No. 5,648,260; U.S. Pat. No. 5,624,821; and WO 94/29351 concerning other examples of Fc region variants.

c) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

B. Immunoconjugates

Further provided herein are immunoconjugates comprising an anti-SCD1 antibody herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., *Cancer Res.* 53:3336-3342 (1993); and Lode et al., *Cancer Res.* 58:2925-2928 (1998)); an anthracycline such as daunomycin or doxorubicin (see Kratz et al., *Current Med. Chem.* 13:477-523 (2006); Jeffrey et al., *Bioorganic & Med. Chem. Letters* 16:358-362 (2006); Torgov et al., *Bioconj. Chem.* 16:717-721 (2005); Nagy et al., *Proc. Natl. Acad. Sci. USA* 97:829-834 (2000); Dubowchik et al., *Bioorg. & Med. Chem. Letters* 12:1529-1532 (2002); King et al., *J. Med. Chem.* 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, Aleurites fordii proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin, and the tricothecenes.

In another embodiment, an immunoconjugate comprises an antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example $tc^{99}$ or $I^{123}$, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., *Cancer Res.* 52:127-131 (1992); U.S. Pat. No. 5,208,020) may be used.

The immunuoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

C. Binding Polypeptides

Binding polypeptides are polypeptides that bind, preferably specifically, to SCD1 as described herein. In some embodiments, the binding polypeptides are SCD1 antagonists. Binding polypeptides may be chemically synthesized using known polypeptide synthesis methodology or may be prepared and purified using recombinant technology. Binding polypeptides are usually at least about 5 amino acids in length, alternatively at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids in length or more, wherein such binding polypeptides that are capable of binding, preferably specifically, to a target, SCD1, as described herein. Binding polypeptides may be identified without undue experimentation using well known techniques. In this regard, it is noted that techniques for screening polypeptide libraries for binding polypeptides that are capable of specifically binding to a polypeptide target are well known in the art (see, e.g., U.S. Pat. Nos. 5,556,762, 5,750,373, 4,708,871, 4,833,092, 5,223, 409, 5,403,484, 5,571,689, 5,663,143; PCT Publication Nos. WO 84/03506 and WO84/03564; Geysen et al., *Proc. Natl. Acad. Sci. U.S.A.*, 81:3998-4002 (1984); Geysen et al., *Proc. Natl. Acad. Sci. U.S.A.*, 82:178-182 (1985); Geysen et al., in Synthetic Peptides as Antigens, 130-149 (1986); Geysen et al., *J. Immunol. Meth*, 102:259-274 (1987); Schoofs et al., *J. Immunol.*, 140:611-616 (1988), Cwirla, S. E. et al. (1990) *Proc. Natl. Acad. Sci. USA*, 87:6378; Lowman, H. B. et al. (1991) *Biochemistry*, 30:10832; Clackson, T. et al. (1991) *Nature*, 352: 624; Marks, J. D. et al. (1991), *J. Mol. Biol.*, 222:581; Kang, A. S. et al. (1991) *Proc. Natl. Acad. Sci. USA*, 88:8363, and Smith, G. P. (1991) *Current Opin. Biotechnol.*, 2:668).

In this regard, bacteriophage (phage) display is one well known technique which allows one to screen large polypeptide libraries to identify member(s) of those libraries which are capable of specifically binding to a target polypeptide, SCD1. Phage display is a technique by which variant polypeptides are displayed as fusion proteins to the coat protein on the surface of bacteriophage particles (Scott, J. K. and Smith, G. P. (1990) Science, 249: 386). The utility of phage display lies in the fact that large libraries of selectively randomized protein variants (or randomly cloned cDNAs) can be rapidly and efficiently sorted for those sequences that bind to a target molecule with high affinity. Display of peptide (Cwirla, S. E. et al. (1990) *Proc. Natl. Acad. Sci. USA*, 87:6378) or protein (Lowman, H. B. et al. (1991) *Biochemistry*, 30:10832; Clackson, T. et al. (1991) *Nature*, 352: 624; Marks, J. D. et al. (1991), *J. Mol. Biol.*, 222:581; Kang, A. S. et al. (1991) *Proc. Natl. Acad. Sci. USA*, 88:8363) libraries on phage have been used for screening millions of polypeptides or oligopeptides for ones with specific binding properties (Smith, G. P. (1991) *Current Opin. Biotechnol.*, 2:668). Sorting phage libraries of random mutants requires a strategy for constructing and propagating a large number of variants, a procedure for affinity purification using the target receptor, and a means of evaluating the results of binding enrichments. U.S. Pat. Nos. 5,223,409, 5,403,484, 5,571,689, and 5,663, 143.

Although most phage display methods have used filamentous phage, lambdoid phage display systems (WO 95/34683; U.S. Pat. No. 5,627,024), T4 phage display systems (Ren et al., *Gene*, 215: 439 (1998); Zhu et al., *Cancer Research*, 58(15): 3209-3214 (1998); Jiang et al., *Infection & Immunity*, 65(11): 4770-4777 (1997); Ren et al., *Gene*, 195(2):303-311 (1997); Ren, *Protein Sci.*, 5: 1833 (1996); Efimov et al., *Virus Genes*, 10: 173 (1995)) and T7 phage display systems (Smith and Scott, *Methods in Enzymology*, 217: 228-257 (1993); U.S. Pat. No. 5,766,905) are also known.

Additional improvements enhance the ability of display systems to screen peptide libraries for binding to selected target molecules and to display functional proteins with the potential of screening these proteins for desired properties. Combinatorial reaction devices for phage display reactions have been developed (WO 98/14277) and phage display libraries have been used to analyze and control bimolecular interactions (WO 98/20169; WO 98/20159) and properties of constrained helical peptides (WO 98/20036). WO 97/35196 describes a method of isolating an affinity ligand in which a phage display library is contacted with one solution in which the ligand will bind to a target molecule and a second solution in which the affinity ligand will not bind to the target molecule, to selectively isolate binding ligands. WO 97/46251 describes a method of biopanning a random phage display library with an affinity purified antibody and then isolating binding phage, followed by a micropanning process using microplate wells to isolate high affinity binding phage. The use of *Staphlylococcus aureus* protein A as an affinity tag has also been reported (Li et al. (1998) *Mol. Biotech.*, 9:187). WO 97/47314 describes the use of substrate subtraction libraries to distinguish enzyme specificities using a combinatorial library which may be a phage display library. A method for selecting enzymes suitable for use in detergents using phage display is described in WO 97/09446. Additional methods of selecting specific binding proteins are described in U.S. Pat. Nos. 5,498,538, 5,432,018, and WO 98/15833.

Methods of generating peptide libraries and screening these libraries are also disclosed in U.S. Pat. Nos. 5,723,286, 5,432,018, 5,580,717, 5,427,908, 5,498,530, 5,770,434, 5,734,018, 5,698,426, 5,763,192, and 5,723,323.

D. Binding Small Molecules

Provided herein are binding small molecules for use as a SCD1 small molecule antagonist.

Binding small molecules are preferably organic molecules other than binding polypeptides or antibodies as defined herein that bind, preferably specifically, to SCD1 as described herein. Binding organic small molecules may be identified and chemically synthesized using known methodology (see, e.g., PCT Publication Nos. WO 00/00823 and WO 00/39585). Binding organic small molecules are usually less than about 2000 daltons in size, alternatively less than about 1500, 750, 500, 250 or 200 daltons in size, wherein such organic small molecules that are capable of binding, preferably specifically, to a polypeptide as described herein may be identified without undue experimentation using well known techniques. In this regard, it is noted that techniques for screening organic small molecule libraries for molecules that are capable of binding to a polypeptide target are well known in the art (see, e.g., PCT Publication Nos. WO00/00823 and WO00/39585). Binding organic small molecules may be, for example, aldehydes, ketones, oximes, hydrazones, semicarbazones, carbazides, primary amines, secondary amines, tertiary amines, N-substituted hydrazines, hydrazides, alcohols, ethers, thiols, thioethers, disulfides, carboxylic acids, esters, amides, ureas, carbamates, carbonates, ketals, thioketals, acetals, thioacetals, aryl halides, aryl sulfonates, alkyl halides, alkyl sulfonates, aromatic compounds, heterocyclic compounds, anilines, alkenes, alkynes, diols, amino alcohols, oxazolidines, oxazolines, thiazolidines, thiazolines, enamines, sulfonamides, epoxides, aziridines, isocyanates, sulfonyl chlorides, diazo compounds, acid chlorides, or the like.

In some embodiments, the SCD1 small molecule antagonist is a compound described in WO 2005/011655 and/or US 2005/0119251, which are incorporated by reference in their entirety. In some embodiments, the SCD1 small molecule antagonist is a compound of formula (I):

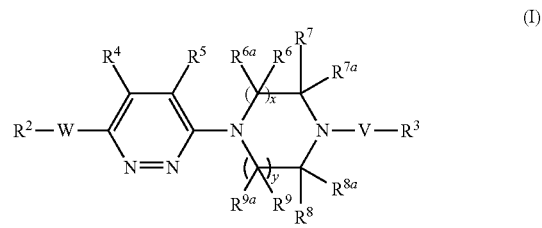

(I)

wherein: x and y are each independently 1, 2 or 3; W is —C(O)N(R$^1$)—; —C(O)N[C(O)R$^{1a}$]—, —N(R$^1$)C(O)N ($R^1$)— or —N($R^1$)C(O)—; V is —C(O)—, —C(S)—, or —C($R^{10}$)H; each $R^1$ is independently selected from the group consisting of hydrogen; $C_1$-$C_6$ alkyl optionally substituted with one or more substituents selected from the group consisting of halo, methyl or trifluoromethyl; and $C_2$-$C_6$alkyl optionally substituted with one or more substituents selected from the group consisting of methoxy and hydroxyl; $R^{1a}$ is selected from the group consisting of hydrogen, $C_1$-$C_6$ alkyl and cycloalkyl; $R^2$ is selected from the group consisting of $C_1$-$C_{12}$ alkyl, $C_2$-$C_{12}$alkenyl, $C_2$-$C_{12}$hydroxyalkyl, $C_2$-$C_{12}$ hydroxyalkenyl, $C_1$-$C_{12}$ alkoxy, $C_2$-$C_{12}$ alkoxyalkyl, $C_3$-$C_{12}$cycloalkyl, $C_4$-$C_{12}$cycloalkylalkyl, aryl, $C_2$-$C_{12}$aralkyl, $C_3$-$C_{12}$ heterocyclyl, $C_3$-$C_{12}$heterocyclylalkyl, $C_1$-$C_{12}$heteroaryl, and $C_3$-$C_{12}$heteroarylalkyl; or $R^2$ is a multi-ring structure having 2 to 4 rings wherein the rings are independently selected from the group consisting of cycloalkyl, heterocyclyl, aryl and heteroaryl and where some or all of the rings may be fused to each other; $R^3$ is selected from the group consisting of $C_1$-$C_{12}$ alkyl, $C_2$-$C_{12}$ alkenyl, $C_2$-$C_{12}$hydroxyalkyl, $C_2$-$C_{12}$hydroxyalkenyl, $C_1$-$C_{12}$alkoxy, $C_2$-$C_{12}$alkoxyalkyl, $C_3$-$C_{12}$cycloalkyl, $C_4$-$C_{12}$cycloalkylalkyl, aryl, $C_7$-$C_{12}$aralkyl, $C_3$-$C_{12}$heterocyclyl, $C_3$-$C_{12}$heterocyclylalkyl, $C_1$-$C_{12}$heteroaryl and $C_3$-$C_{12}$heteroarylalkyl; or $R^3$ is a multi-ring structure having 2 to 4 rings wherein the rings are independently selected from the group consisting of cycloalkyl, heterocyclyl, aryl and heteroaryl and where some or all of the rings may be fused to each other; $R^4$ and $R^5$ are each independently selected from hydrogen, fluoro, chloro, methyl, methoxy, trifluoromethyl, cyano, nitro or —N($R^{12}$)$_2$; $R^6$, $R^{6a}$, $R^7$, $R^{7a}$, $R^8$, $R^{8a}$, $R^9$, and $R^{9a}$ are each independently selected from hydrogen or $C_1$-$C_3$ alkyl; or $R^6$ and $R^{6a}$ together, or $R^7$ and $R^{7a}$ together, or $R^8$ and $R^{8a}$ together, or $R^9$ and $R^{9a}$ together are an oxo group, provided that when V is —C(O)—, $R^7$ and $R^{7a}$ together or $R^8$ and $R^{8a}$ together do not form an oxo group, while the remaining $R^6$, $R^{6a}$, $R^7$, $R^{7a}$, $R^8$, $R^{8a}$, $R^9$, and $R^{9a}$ are each independently selected from hydrogen or $C_1$-$C_3$ alkyl; or one of $R^6$, $R^{6a}$, $R^7$, and $R^{7a}$ together with one of $R^8$, $R^{8a}$, $R^9$ and $R^{9a}$ form an alkylene bridge, while the remaining $R^6$, $R^{6a}$, $R^7$, $R^{7a}$, $R^8$, $R^{8a}$, $R^9$, and $R^{9a}$ are each independently selected from hydrogen or $C_1$-$C_3$ alkyl; $R^{10}$ is hydrogen or $C_1$-$C_3$ alkyl; and each $R^{12}$ is independently selected from hydrogen or $C_1$-$C_6$ alkyl; a stereoisomer, enantiomer or tautomer thereof, a pharmaceutically acceptable salt thereof, a pharmaceutical composition thereof or a prodrug thereof.

In some embodiments, the SCD1 small molecule antagonist is a compound of formula (II):

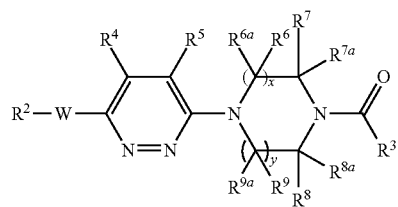

(II)

wherein: x and y are each independently 1, 2 or 3; W is selected from —C(O)N($R^1$)— and —N($R^1$)C(O)—; each $R^1$ is independently selected from the group consisting of hydrogen; $C_1$-$C_6$ alkyl optionally substituted with one or more substituents selected from the group consisting of halo, methyl or trifluoromethyl; and $C_2$-$C_6$ alkyl optionally substituted with one or more substituents selected from the group consisting of methoxy and hydroxy; $R^2$ is selected from the group consisting of $C_7$-$C_{12}$ alkyl, $C_3$-$C_{12}$ alkenyl, $C_7$-$C_{12}$hydroxyalkyl, $C_2$-$C_{12}$ alkoxyalkyl, $C_3$-$C_{12}$ hydroxyalkenyl, $C_3$-$C_{12}$ cycloalkyl, $C_4$-$C_{12}$ cycloalkylalkyl, $C_{13}$-$C_{19}$ aralkyl, $C_3$-$C_{12}$ heterocyclylalkyl, and $C_3$-$C_{12}$ heteroarylalkyl; or $R^2$ is a multi-ring structure having 2 to 4 rings wherein the rings are independently selected from the group consisting of cycloalkyl, heterocyclyl, aryl and heteroaryl, where some or all of the rings may be fused to each other; $R^3$ is selected from the group consisting of $C_3$-$C_{12}$ alkyl, $C_3$-$C_{12}$ alkenyl, $C_3$-$C_{12}$ hydroxyalkyl, $C_3$-$C_{12}$ hydroxyalkenyl, $C_3$-$C_{12}$ alkoxy, $C_3$-$C_{12}$ alkoxyalkyl, $C_3$-$C_{12}$ cycloalkyl, $C_4$-$C_{12}$cycloalkylalkyl, aryl, $C_7$-$C_{12}$ aralkyl, $C_3$-$C_{12}$heterocyclyl, $C_3$-$C_{12}$ heterocyclylalkyl, $C_5$-$C_{12}$ heteroaryl and $C_3$-$C_{12}$heteroarylalkyl; or $R^3$ is a multi-ring structure having 2 to 4 rings wherein the rings are independently selected from the group consisting of cycloalkyl, heterocyclyl, aryl and heteroaryl and where some or all of the rings may be fused to each other; $R^4$ and $R^5$ are each independently selected from hydrogen, fluoro, chloro, methyl, methoxy and trifluoromethyl; and $R^6$, $R^{6a}$, $R^7$, $R^{7a}$, $R^8$, $R^{8a}$, $R^9$, and $R^{9a}$ are each independently selected from hydrogen or $C_1$-$C_3$ alkyl; or $R^6$ and $R^{6a}$ together, or $R^7$ and $R^{7a}$ together, or $R^8$ and $R^{8a}$ together, or $R^9$ and $R^{9a}$ together are an oxo group, provided that when V is —C(O)—, $R^7$ and $R^{7a}$ together or $R^8$ and $R^{8a}$ together do not form an oxo group, while the remaining $R^6$, $R^{6a}$, $R^7$, $R^{7a}$, $R^8$, $R^{8a}$, $R^9$, and $R^{9a}$ are each independently selected from hydrogen or $C_1$-$C_3$ alkyl; or one of $R^6$, $R^{6a}$, $R^7$, and $R^{7a}$ together with one of $R^8$, $R^{8a}$, $R^9$ and $R^{9a}$ form an alkylene bridge, while the remaining $R^6$, $R^{6a}$, $R^7$, $R^{7a}$, $R^8$, $R^{8a}$, $R^9$, and $R^{9a}$ are each independently selected from hydrogen or $C_1$-$C_3$ alkyl; including a stereoisomer, enantiomer or tautomer thereof, a pharmaceutically acceptable salt thereof, a pharmaceutical composition thereof or a prodrug thereof.

In some embodiments, the SCD1 small molecule antagonist is a compound of formula (III):

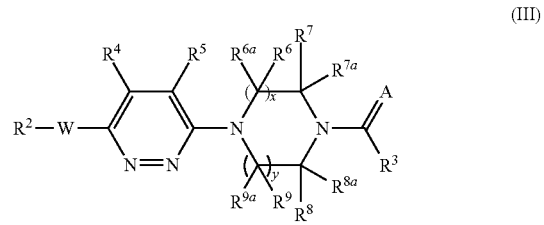

(III)

wherein: x and y are each independently 1, 2 or 3; A is oxygen or sulfur; W is selected from —C(O)N($R^1$)— and —N($R^1$)C(O)—; each $R^1$ is independently selected from the group consisting of hydrogen; $C_1$-$C_6$ alkyl optionally substituted with one or more substituents selected from the group consisting of halo, methyl or trifluoromethyl; and $C_2$-$C_6$alkyl optionally substituted with one or more substituents selected from the group consisting of methoxy and hydroxy; $R^2$ is selected from the group consisting of $C_1$-$C_{12}$ alkyl, $C_2$-$C_{12}$ alkenyl, $C_2$-$C_{12}$ hydroxyalkyl, $C_2$-$C_{12}$ hydroxyalkenyl, $C_1$-$C_6$ alkoxy, $C_3$-$C_{12}$ alkoxyalkyl, $C_3$-$C_{12}$cycloalkyl, $C_4$-$C_{12}$ cycloalkylalkyl, aryl, $C_7$-$C_{12}$ aralkyl, $C_3$-$C_{12}$ heterocyclyl, $C_3$-$C_{12}$heterocyclylalkyl, C $C_{12}$heteroaryl and $C_3$-$C_{12}$heteroarylalkyl; or $R^2$ is a multi-ring structure having 2 to 4 rings wherein the rings are independently selected from the group consisting of cycloalkyl, heterocyclyl, aryl and heteroaryl, where some or all of the rings may be fused to each other; $R^3$ is phenyl optionally substituted by one or more substituents selected from the group consisting of halo, cyano, nitro, hydroxy, $C_1$-$C_6$ alkyl, $C_1$-$C_6$ trihaloalkyl, $C_1$-$C_6$ trihaloalkoxy $C_1$-$C_6$ alkylsulfonyl, —N($R^{11}$)$_2$, —OC(O)$R^{11}$, —C(O)O$R^{11}$, —S(O)$_2$N($R^{11}$)$_2$ cycloalkyl, heterocyclyl, heteroaryl and heteroarylcycloalkyl, provided that $R^3$ is not phenyl substituted with optionally substituted thienyl; $R^4$ and $R^5$ are each independently selected from hydrogen, fluoro, chloro, methyl, methoxy and trifluoromethyl; $R^6$, $R^{6a}$, $R^7$, $R^{7a}$, $R^8$, $R^{8a}$, $R^9$, and $R^{9a}$ are each independently selected from hydrogen or $C_1$-$C_3$ alkyl; or $R^6$ and $R^{6a}$ together, or $R^7$ and $R^{7a}$ together, or $R^8$ and $R^{8a}$ together, or $R^9$ and $R^{9a}$ together are an oxo group, provided that when V is —C(O)—, $R^7$ and $R^{7a}$ together or $R^8$ and $R^{8a}$ together do not form an oxo group, while the remaining $R^6$, $R^{6a}$, $R^7$, $R^{7a}$, $R^8$, $R^{8a}$, $R^9$, and $R^{9a}$ are each independently selected from hydrogen or $C_1$-$C_3$ alkyl; or one of $R^6$, $R^{6a}$, $R^7$, and $R^{7a}$ together with one of $R^8$, $R^{8a}$, $R^9$ and $R^{9a}$ form an alkylene bridge, while the remaining $R^6$, $R^{6a}$, $R^7$, $R^{7a}$, $R^8$, $R^{8a}$, $R^9$, and $R^{9a}$ are each independently selected from hydrogen or $C_1$-$C_3$ alkyl; and each $R^{11}$ is independently selected from hydrogen, $C_1$-$C_6$ alkyl, $C_3$-$C_6$ cycloalkyl, aryl or aralkyl; a stereoisomer, enantiomer or tautomer thereof, a pharmaceutically acceptable salt thereof, a pharmaceutical composition thereof or a prodrug thereof.

In some embodiments, the SCD1 small molecule antagonist is a compound of formula (IV):

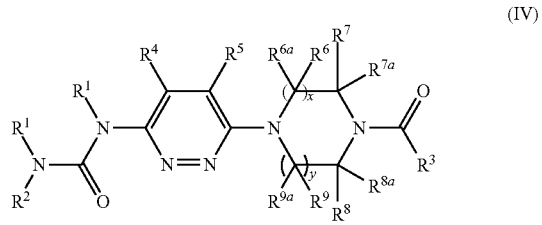

(IV)

wherein: x and y are each independently 1, 2 or 3; each $R^1$ is independently selected from the group consisting of hydrogen; $C_1$-$C_6$ alkyl optionally substituted with one or more substituents selected from the group consisting of halo, methyl or trifluoromethyl; and $C_2$-$C_6$ alkyl optionally substituted with one or more substituents selected from the group consisting of methoxy and hydroxy; $R^2$ is selected from the group consisting of $C_1$-$C_{12}$ alkyl, $C_2$-$C_{12}$ alkenyl, $C_2$-$C_{12}$hydroxyalkyl, $C_2$-$C_{12}$hydroxyalkenyl, $C_2$-$C_{12}$alkoxyalkyl, $C_3$-$C_{12}$ cycloalkyl, $C_4$-$C_{12}$ cycloalkylalkyl, $C_3$-$C_{12}$heterocyclyl, $C_3$-$C_{12}$ heterocyclylalkyl, aryl, $C_7$-$C_{12}$ aralkyl, $C_1$-$C_{12}$ heteroaryl, and $C_3$-$C_{12}$ heteroarylalkyl; or $R^2$ is a multi-ring structure having 2 to 4 rings wherein the rings are independently selected from the group consisting of cycloalkyl, heterocyclyl, aryl and heteroaryl and where some or all of the rings may be fused to each other; $R^3$ is selected from the group consisting of $C_1$-$C_{12}$ alkyl, $C_2$-$C_{12}$alkenyl, $C_2$-$C_{12}$hydroxyalkyl, $C_2$-$C_{12}$ hydroxyalkenyl, $C_1$-$C_{12}$ alkoxy, $C_2$-$C_{12}$alkoxyalkyl, $C_3$-$C_{12}$ cycloalkyl, $C_4$-$C_{12}$ cycloalkylalkyl, aryl, $C_2$-$C_{12}$aralkyl, $C_3$-$C_{12}$ heterocyclyl, $C_3$-$C_{12}$ heterocyclylalkyl, $C_1$-$C_{12}$ heteroaryl and $C_3$-$C_{12}$ heteroarylalkyl; or $R^3$ is a multi-ring structure having 2 to 4 rings wherein the rings are independently selected from the group consisting of cycloalkyl, heterocyclyl, aryl and heteroaryl and where some or all of the rings may be fused to each other; $R^4$ and $R^5$ are each independently selected from hydrogen, fluoro, chloro, methyl, methoxy and trifluoromethyl; and $R^6$, $R^{6a}$, $R^7$, $R^{7a}$, $R^8$, $R^{8a}$, $R^9$, and $R^{9a}$ are each independently selected from hydrogen or $C_1$-$C_3$ alkyl; or $R^6$ and $R^{6a}$ together, or $R^7$ and $R^{7a}$ together, or $R^8$ and $R^{8a}$ together, or $R^9$ and $R^{9a}$ together are an oxo group, provided that when V is —C(O)—, $R^7$ and $R^{7a}$ together or $R^8$ and $R^{8a}$ together do not form an oxo group, while the remaining $R^6$, $R^{6a}$, $R^7$, $R^{7a}$, $R^8$, $R^{8a}$, $R^9$, and $R^{9a}$ are each independently selected from hydrogen or $C_1$-$C_3$ alkyl; or one of $R^6$, $R^{6a}$, $R^7$, and $R^{7a}$ together with one of $R^8$, $R^{8a}$, $R^9$ and $R^{9a}$ form an alkylene bridge, while the remaining $R^6$, $R^{6a}$, $R^7$, $R^{7a}$, $R^8$, $R^{8a}$, $R^9$, and $R^{9a}$ are each independently selected from hydrogen or $C_1$-$C_3$ alkyl; a stereoisomer, enantiomer or tautomer thereof, a pharmaceutically acceptable salt thereof, a pharmaceutical composition thereof or a prodrug thereof.

In some embodiments, the SCD1 small molecule antagonist is a compound of formula (Va):

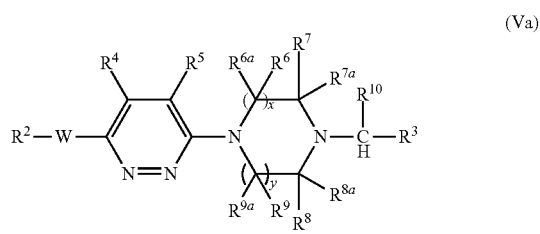

(Va)

wherein: x and y are each independently 1, 2 or 3; W is —C(O)N($R^1$)—; —N($R^1$)C(O)N($R^1$)— or —N($R^1$)C(O)—; each $R^1$ is independently selected from the group consisting of hydrogen; $C_1$-$C_6$alkyl optionally substituted with one or more substituents selected from the group consisting of halo, methyl or trifluoromethyl; and $C_2$-$C_6$ alkyl optionally substituted with one or more substituents selected from the group consisting of methoxy and hydroxy; $R^2$ is selected from the group consisting of $C_7$-$C_{12}$ alkyl, $C_2$-$C_{12}$ alkenyl, $C_7$-$C_{12}$ hydroxyalkyl, $C_2$-$C_{12}$ hydroxyalkenyl, $C_1$-$C_{12}$ alkoxy, $C_2$-$C_{12}$alkoxyalkyl, $C_3$-$C_{12}$ cycloalkyl, $C_1$-$C_{12}$ cycloalkylalkyl, $C_{13}$-$C_{19}$ aralkyl, $C_1$-$C_{12}$ heterocyclyl, $C_3$-$C_{12}$ heterocyclylalkyl, $C_1$-$C_{12}$ heteroaryl, and $C_3$-$C_{12}$ heteroarylalkyl; $R^3$ is selected from the group consisting of $C_1$-$C_{12}$ alkyl, $C_2$-$C_{12}$ alkenyl, $C_2$-$C_{12}$ hydroxyalkyl, $C_2$-$C_{12}$ hydroxyalkenyl, $C_1$-$C_{12}$ alkoxy, $C_2$-$C_{12}$ alkoxyalkyl, $C_3$-$C_{12}$ cycloalkyl, $C_4$-$C_{12}$cycloalkylalkyl, aryl, $C_7$-$C_{12}$aralkyl, $C_3$-$C_{12}$heterocyclyl, $C_3$-$C_{12}$heterocyclylalkyl, $C_1$-$C_{12}$ heteroaryl and $C_3$-$C_{12}$heteroarylalkyl; $R^4$ and $R^5$ are each independently selected from hydrogen, fluoro, chloro, methyl, methoxy, trifluoromethyl, cyano, nitro or —N($R^2$)$_2$; $R^6$, $R^{6a}$, $R^7$, $R^{7a}$, $R^8$, $R^{8a}$, $R^9$, and $R^{9a}$ are each independently selected from hydrogen or $C_1$-$C_3$ alkyl; or $R^6$ and $R^{6a}$ together, or $R^7$ and $R^{7a}$ together, or $R^8$ and $R^{8a}$ together, or $R^9$ and $R^{9a}$ together are an oxo group, provided that when V is —C(O)—, $R^7$ and $R^{7a}$ together or $R^8$ and $R^{8a}$ together do not form an oxo group, while the remaining $R^6$, $R^{6a}$, $R^7$, $R^{7a}$, $R^8$, $R^{8a}$, $R^9$, and $R^{9a}$ are each independently selected from hydrogen or $C_1$-$C_3$ alkyl; or one of $R^6$, $R^{6a}$, $R^7$, and $R^{7a}$ together with one of $R^8$, $R^{8a}$, $R^9$ and $R^{9a}$ form an alkylene bridge, while the remaining $R^6$, $R^{6a}$, $R^7$, $R^{7a}$, $R^8$, $R^{8a}$, $R^9$, and $R^{9a}$ are each independently selected from hydrogen or $C_1$-$C_3$ alkyl; $R^{10}$ is hydrogen or $C_1$-$C_3$ alkyl; and each $R^{12}$ is independently selected from hydrogen or $C_1$-$C_6$ alkyl; provided, however, that $R^2$ can not be pyrazinyl, pyridinonyl, pyrrolidinonyl or imidazolyl; a stereoisomer, enantiomer or tautomer thereof, a pharmaceutically acceptable salt thereof, a pharmaceutical composition thereof or a prodrug thereof.

In some embodiments, the SCD1 small molecule antagonist is a compound of formula (Vb):

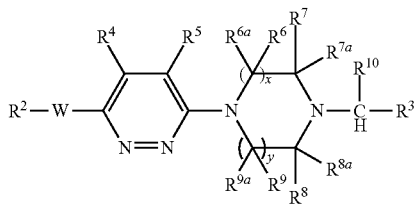

wherein: x and y are each independently 1, 2 or 3; W is
—C(O)N($R^1$)—; —N($R^1$)C(O)N($R^1$)— or —N($R^1$)C(O)—;
each $R^1$ is independently selected from the group consisting
of hydrogen; $C_1$-$C_6$ alkyl optionally substituted with one or
more substituents selected from the group consisting of halo,
methyl or trifluoromethyl; and $C_2$-$C_6$ alkyl optionally substituted with one or more substituents selected from the group
consisting of methoxy and hydroxy; $R^2$ is selected from the
group consisting of $C_1$-$C_{12}$ alkyl, $C_2$-$C_{12}$ alkenyl, $C_2$-$C_{12}$hydroxyalkyl, $C_2$-$C_{12}$hydroxyalkenyl, $C_1$-$C_{12}$ alkoxy, $C_2$-$C_{12}$ alkoxyalkyl, $C_3$-$C_{12}$cycloalkyl, $C_4$-$C_{12}$ cycloalkylalkyl, aryl, $C_7$-$C_{12}$ aralkyl, $C_3$-$C_{12}$ heterocyclyl, $C_3$-$C_{12}$ heterocyclylalkyl, $C_1$-$C_{12}$ heteroaryl, and $C_3$-$C_{12}$heteroarylalkyl;
$R^3$ is selected from the group consisting of $C_2$-$C_{12}$ alkyl, $C_2$-$C_{12}$ alkenyl, $C_2$-$C_{12}$ hydroxyalkyl, $C_2$-$C_{12}$ hydroxyalkenyl, $C_1$-$C_{12}$ alkoxy or $C_2$-$C_{12}$alkoxyalkyl; $R^4$ and $R^5$ are each independently selected from hydrogen, fluoro, chloro, methyl, methoxy, trifluoromethyl, cyano, nitro or —N($R^{12}$)$_2$;
$R^6$, $R^{6a}$, $R^7$, $R^{7a}$, $R^8$, $R^{8a}$, $R^9$, and $R^{9a}$ are each independently selected from hydrogen or $C_1$-$C_3$ alkyl; or $R^6$ and $R^{6a}$ together, or $R^7$ and $R^{7a}$ together, or $R^8$ and $R^{8a}$ together, or $R^9$ and $R^{9a}$ together are an oxo group, provided that when V is —C(O)—, $R^7$ and $R^{7a}$ together or $R^8$ and $R^{8a}$ together do not form an oxo group, while the remaining $R^6$, $R^{6a}$, $R^7$, $R^{7a}$, $R^8$, $R^{8a}$, $R^9$, and $R^{9a}$ are each independently selected from hydrogen or $C_1$-$C_3$-alkyl; or one of $R^6$, $R^{6a}$, $R^7$, and $R^{7a}$ together with one of $R^8$, $R^{8a}$, $R^9$ and $R^{9a}$ form an alkylene bridge, while the remaining $R^6$, $R^{6a}$, $R^7$, $R^{7a}$, $R^8$, $R^{8a}$, $R^9$, and $R^{9a}$ are each independently selected from hydrogen or $C_1$-$C_3$ alkyl; $R^{10}$ is hydrogen or $C_1$-$C_3$ alkyl; and each $R^{12}$ is independently selected from hydrogen or $C_1$-$C_6$ alkyl; as a stereoisomer, enantiomer or tautomer thereof, a pharmaceutically acceptable salt thereof, a pharmaceutical composition thereof or a prodrug thereof.

In some embodiments, the SCD1 antagonist small molecule is a SCD1 antagonist small molecule described in US20050119251, WO2006014168, WO2006034441, WO2006034312, WO2006034315, WO2006125194, WO2007046868, WO2007050124, WO2006034279, WO2006034338, WO2006125181, WO2007044085, WO2007046867, WO2006034341, WO2006101521, WO2006125179, WO2006034440, WO2006034446, WO2006125178, WO2006125180, WO2007136746, WO2007130075, WO2007143597, WO2008024390, WO2008036715, WO2008074835, WO2008127349, which are incorporated by reference in its entirety.

In some embodiments, the SCD1 small molecule antagonist comprises a central pyridazine/pyridine substituted by functionalized piperazine benzamide on the one end, and a carboxamide on the other end. In some embodiments, the SCD1 small molecule antagonist is Compound 1. In some embodiments, the SCD1 small molecule antagonist is Compound 2.

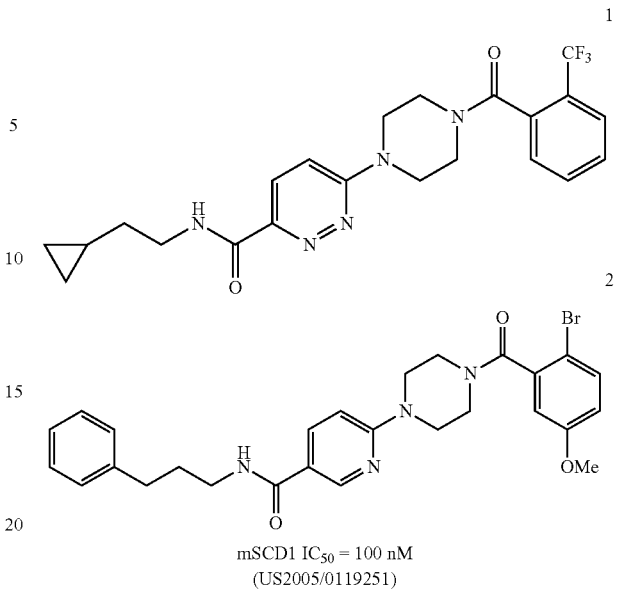

mSCD1 $IC_{50}$ = 100 nM
(US2005/0119251)

In some embodiments, the pyridazine/pyridine core has been replaced with other monocyclic and bicyclic rings, including pyrimidine (both regioisomers) and pyrazine, pyridinone, phenyl ring, imidazolopyridazine and benzimidazole, as shown below.

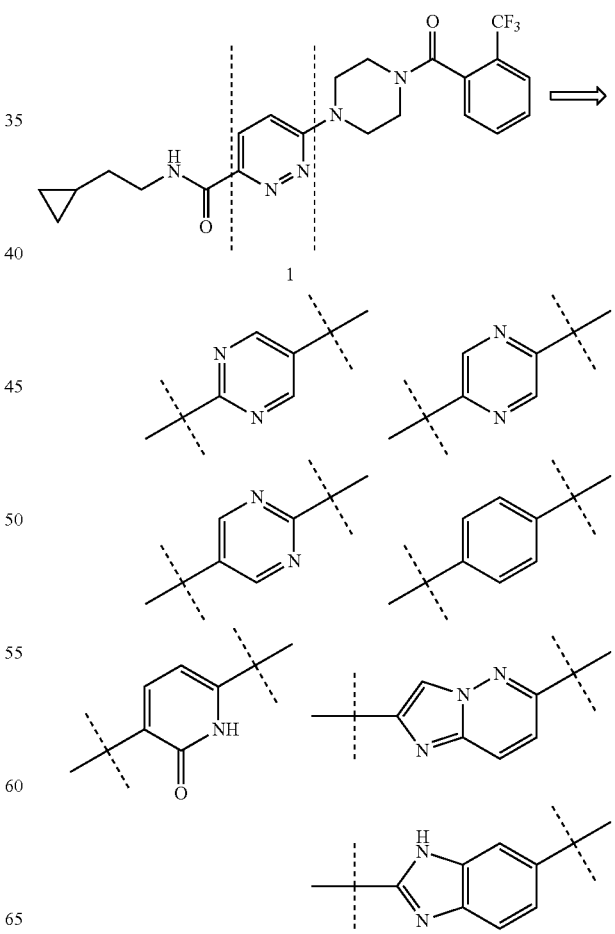

In some embodiments, the six-membered heteroaryl ring can be replaced with the five-membered rings, such as [1,2,4]thiadiazole, pyrazole, and thiazole, as pyridazine surrogates. In some embodiments, the SCD1 antagonist small molecule is Compound 3. In some embodiments, the SCD1 antagonist small molecule is Compound 4. In some embodiments, the SCD1 antagonist small molecule is Compound 5.

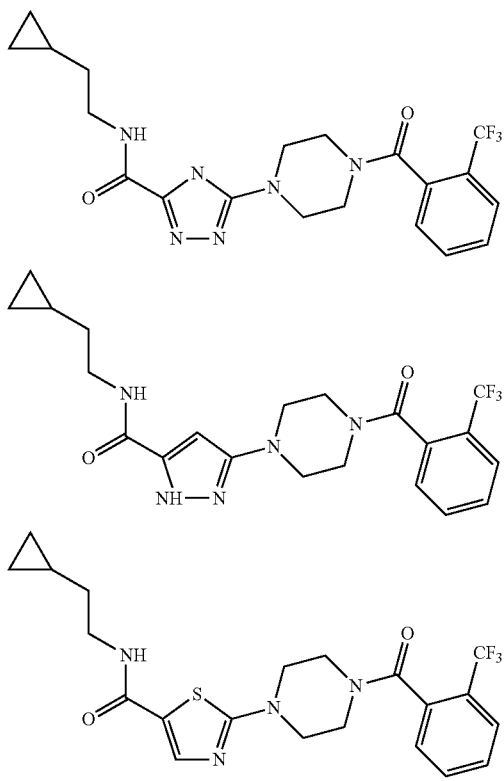

In some embodiments, the pyridazine ring is changed to an acyclic amidine structure. In some embodiments, the SCD1 antagonist small molecule is Compound 6. In some embodiments, the SCD1 antagonist small molecule is a non-aromatic thiazolidinedione piperidine derivative. In some embodiments, the SCD1 antagonist small molecule is Compound 7. In some embodiments, the SCD1 antagonist small molecule is fused tetrahydro-1,6-naphthyridine. In some embodiments, the SCD1 antagonist small molecule is tetrahydrofuro[2,3-c]pyridine. In some embodiments, the SCD1 antagonist small molecule is Compound 8. In some embodiments, the SCD1 antagonist small molecule is Compound 9.

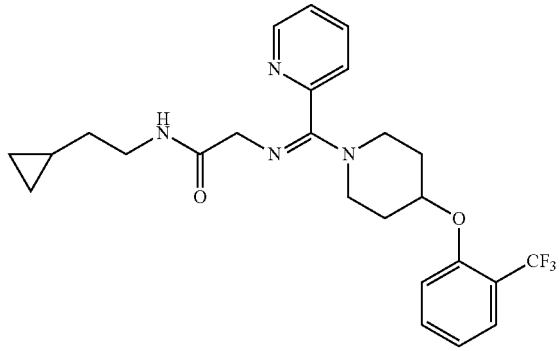

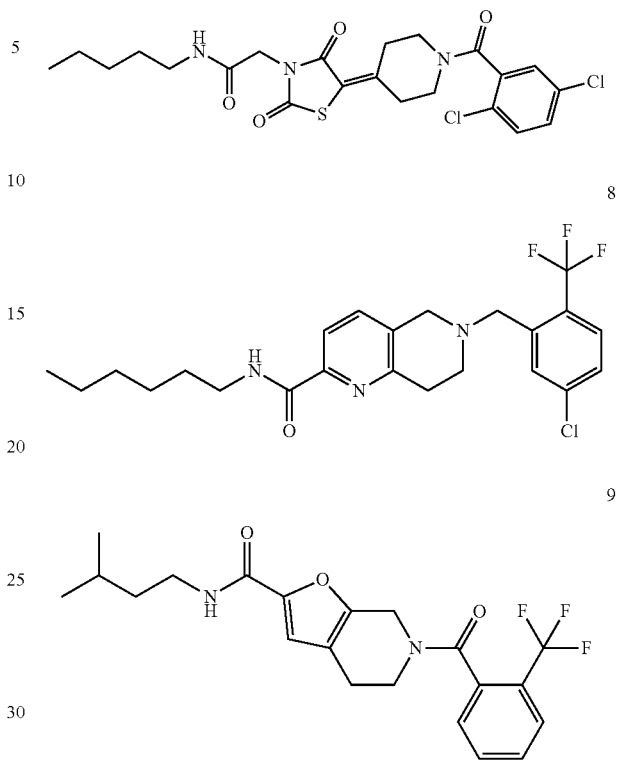

In some embodiments, the SCD1 antagonist small molecule comprises a piperazine benzamide. In some embodiments, the piperazine benzamide is modified to a piperidine benzamide. In some embodiments, the piperazine benzamide is modified to an aniline piperidine (nitrogen on the other side) and a bicyclic 3-azabicyclo[3.1.0]hexan-6-amine. In some embodiments, the SCD1 antagonist small molecule comprises a double bond linker between piperidine and phenyl ring. In some embodiments, the SCD1 antagonist small molecule is the piperazine is modified to cyclohexane or tetrahydropyrimidine. In some embodiments, the SCD1 antagonist small molecule comprises a domain shown below.

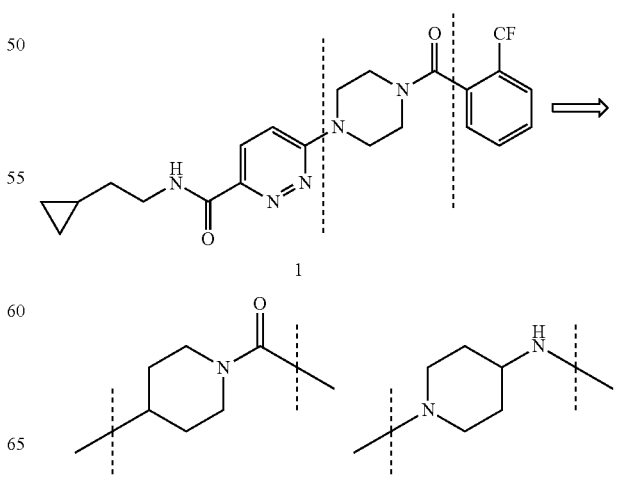

-continued

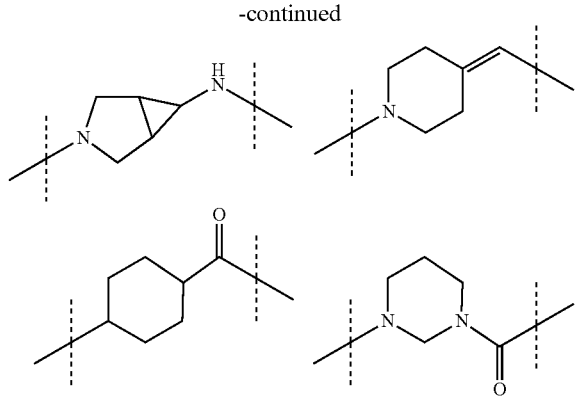

In some embodiments, the SCD1 antagonist small molecule comprises a linker, such as oxygen, amino and/or carbonyl group, inserted between the pyridazine and the piperidine ring. In some embodiments, the SCD1 antagonist small molecule is Compound 10. In some embodiments, the SCD1 antagonist small molecule is a directly-connected heteroarylpiperazine derivative. In some embodiments, the SCD1 antagonist small molecule is Compound 11. In some embodiments, the SCD1 antagonist small molecule is a tricyclic SCD1 inhibitor. In some embodiments, the SCD1 antagonist small molecule is Compound 12.

10

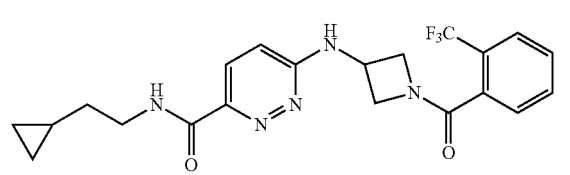

11

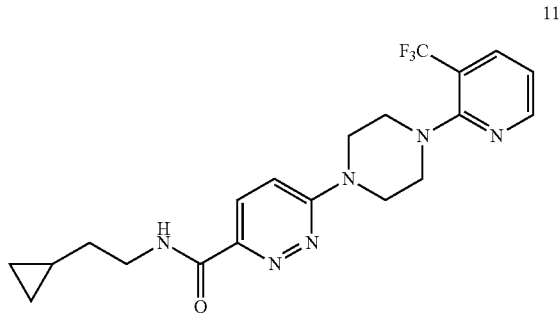

12

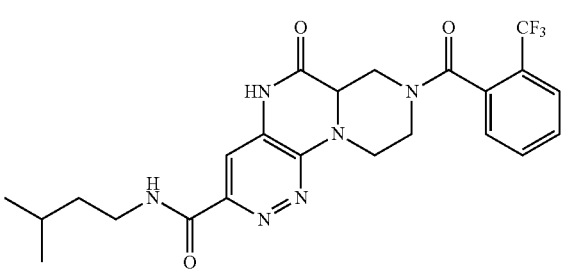

In some embodiments, the SCD1 antagonist small molecule is an imidazoline. In some embodiments, the SCD1 antagonist small molecule is an oxadiazole (three different regioisomers). In some embodiments, the SCD1 antagonist small molecule is an imidazopyridine. In some embodiments, the SCD1 antagonist small molecule is a cyclic urea. In some embodiments, the SCD1 antagonist small molecule comprises a domain shown below.

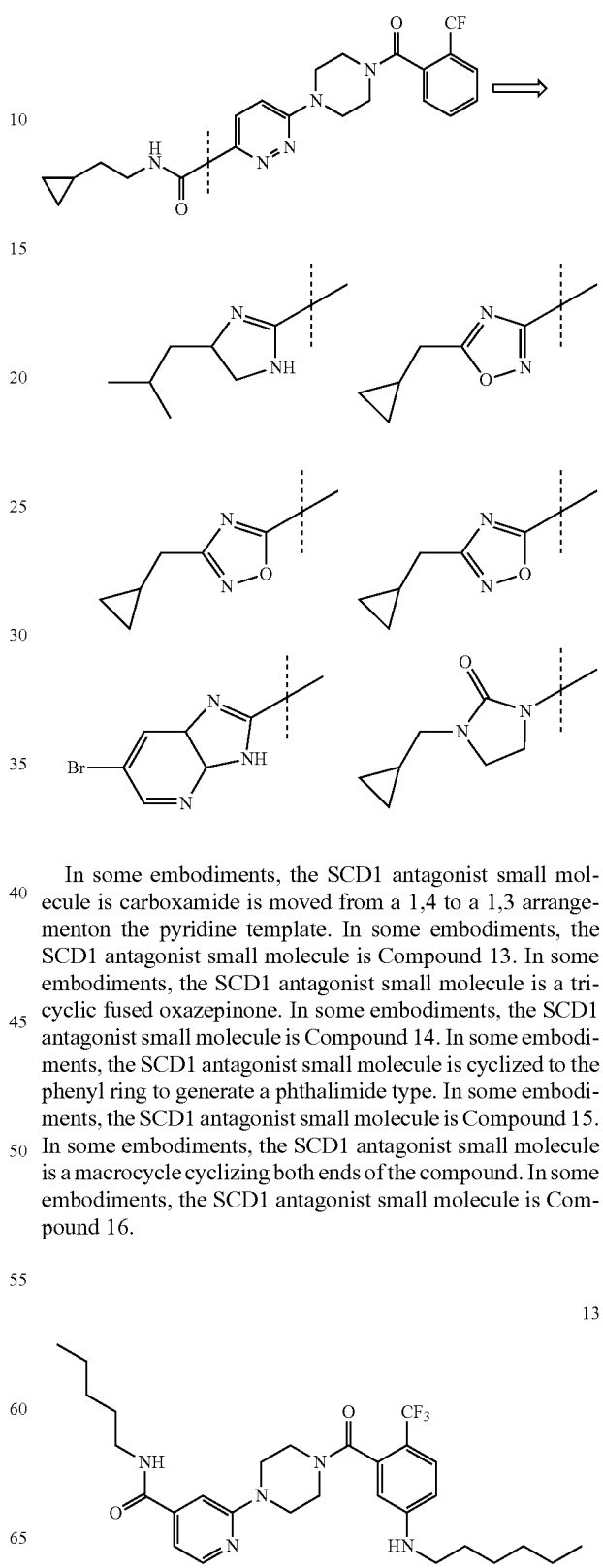

In some embodiments, the SCD1 antagonist small molecule is carboxamide is moved from a 1,4 to a 1,3 arrangementon the pyridine template. In some embodiments, the SCD1 antagonist small molecule is Compound 13. In some embodiments, the SCD1 antagonist small molecule is a tricyclic fused oxazepinone. In some embodiments, the SCD1 antagonist small molecule is Compound 14. In some embodiments, the SCD1 antagonist small molecule is cyclized to the phenyl ring to generate a phthalimide type. In some embodiments, the SCD1 antagonist small molecule is Compound 15. In some embodiments, the SCD1 antagonist small molecule is a macrocycle cyclizing both ends of the compound. In some embodiments, the SCD1 antagonist small molecule is Compound 16.

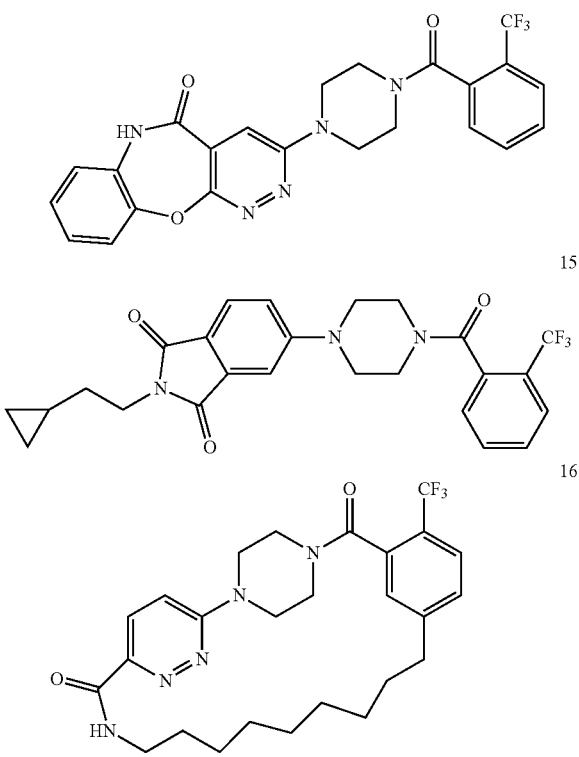

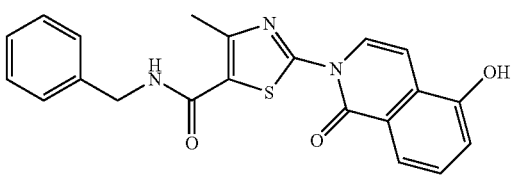

In some embodiments, the SCD1 antagonist small molecule is a thiazole carboxamide. In some embodiments, the SCD1 antagonist small molecule is Compound 17. In some embodiments, the SCD1 antagonist small molecule is a 2-oxopyridin-1(2H)-yl thiazole carboxamide derivative. In some embodiments, the SCD1 antagonist small molecule is Compound 18. In some embodiments, the SCD1 antagonist small molecule has an $IC_{50}$ value of 50 nM. In some embodiments, the SCD1 antagonist small molecule is Compound 19. In some embodiments, the SCD1 antagonist small molecule has an $IC_{50}$ value of 30 nM.

In some embodiments, the SCD1 antagonist small molecule is a 2-(pyrazin-2-yl)-thiazole derivative. In some embodiments, the SCD1 antagonist small molecule is a 2-(1H-pyrazol-3-yl)-thiazole derivative. In some embodiments, the SCD1 antagonist small molecule is Compound 21. In some embodiments, the SCD1 antagonist small molecule has an $IC_{50}$ value of 42 nM. In some embodiments, the SCD1 antagonist small molecule is Compound 22. In some embodiments, the SCD1 antagonist small molecule has an $IC_{50}$ value of 49 nM. In some embodiments, the SCD1 antagonist small molecule is a thiazolyl pyrrolidinone and piperidinone-based SCD1 inhibitor. In some embodiments, the SCD1 antagonist small molecule is a triazolyl thiazole-based SCD1 inhibitor. In some embodiments, the SCD1 antagonist small molecule is Compound 22. In some embodiments, the SCD1 antagonist small molecule has an $IC_{50}$ value of 120 nM. In some embodiments, the SCD1 antagonist small molecule is Compound 23. In some embodiments, the SCD1 antagonist small molecule has an $IC_{50}$ value of 10 nM. In some embodiments, the SCD1 antagonist small molecule is a dihydroimidazolinone. In some embodiments, the SCD1 antagonist small molecule is an imidazolidinone. In some embodiments, the SCD1 antagonist small molecule is Compound 26. In some embodiments, the SCD1 antagonist small molecule is Compound 27.

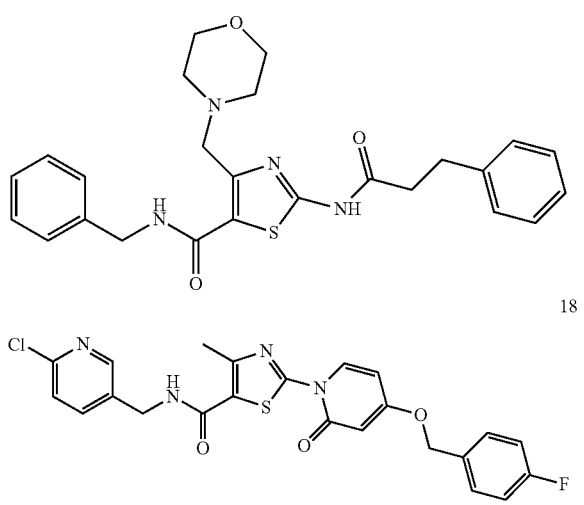

-continued

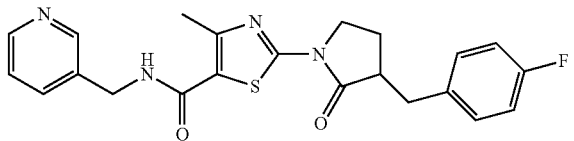

23

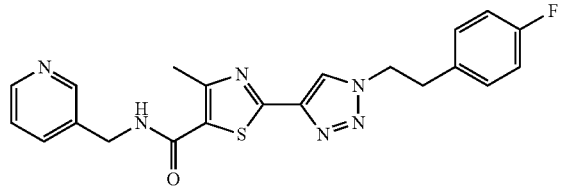

24

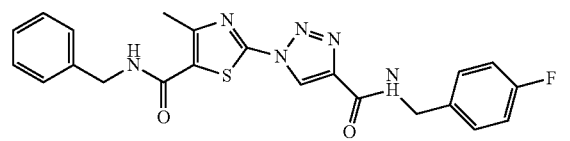

25

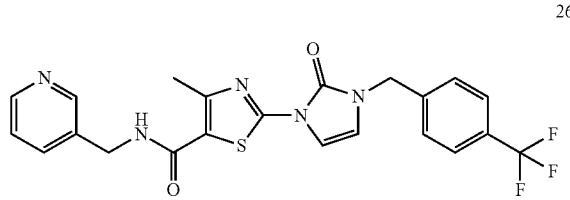

26

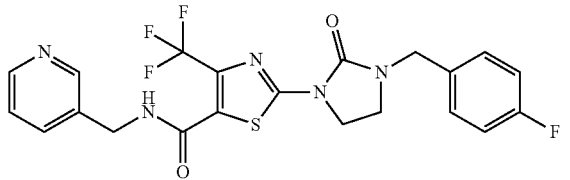

27

In some embodiments, the SCD1 antagonist small molecule is a SCD1 antagonist small molecule described in WO2006130986, WO2007009236, WO2007056846, WO2008017161 WO2008141455, WO2007134457, WO2007143823, WO2007143824, WO2008046226, WO2008064474, and/or WO2008128335, which are incorporated by reference in its entirety. In some embodiments, the SCD1 antagonist small molecule is an azacyclohexane derivative.

In some embodiments, the SCD1 antagonist small molecule is a thiazolyl oxadiazole compound. In some embodiments, the SCD1 antagonist small molecule is Compound 26. In some embodiments, the SCD1 antagonist small molecule is Compound 27.

In some embodiments, the SCD1 antagonist small molecule is a pyridazine derivative with different carboxamide bioisosteres. In some embodiments, the SCD1 antagonist small molecule is Compound 28. In some embodiments, the SCD1 antagonist small molecule is Compound 29.

In some embodiments, the SCD1 antagonist small molecule is a compound with fused bicyclic heteroaryls. In some embodiments, the SCD1 antagonist small molecule is a thiazolopyrimidinone with fused bicyclic heteroaryls. In some embodiments, the SCD1 antagonist small molecule is a thiazolopyrimidine with fused bicyclic heteroaryls. In some embodiments, the SCD1 antagonist small molecule is a purine with fused bicyclic heteroaryls. In some embodiments, the SCD1 antagonist small molecule is 1H-imidazo[4,5-c]pyridin-4-amine (e.g., replacing the pyridazine core) with fused bicyclic heteroaryls. In some embodiments, the SCD1 antagonist small molecule is Compound 30. In some embodiments, the SCD1 antagonist small molecule is Compound 31. In some embodiments, the SCD1 antagonist small molecule is Compound 32. In some embodiments, the SCD1 antagonist small molecule is Compound 33.

In some embodiments, the SCD1 antagonist small molecule is bycyclic. In some embodiments, the SCD1 antagonist small molecule is Compound 34. In some embodiments, the SCD1 antagonist small molecule is Compound 35. In some embodiments, the SCD1 antagonist small molecule comprises a pyridazine ring in some embodiments, the SCD1 antagonist small molecule does not comprises a pyridazine ring. In some embodiments, the SCD1 antagonist small molecule is Compound 36. In some embodiments, the SCD1 antagonist small molecule is Compound 37.

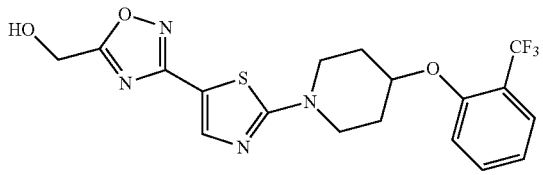

28

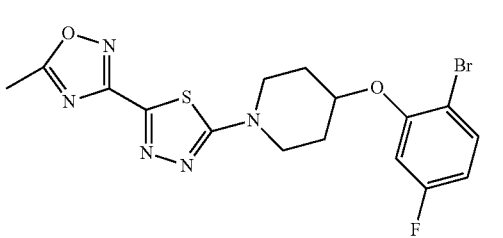

29

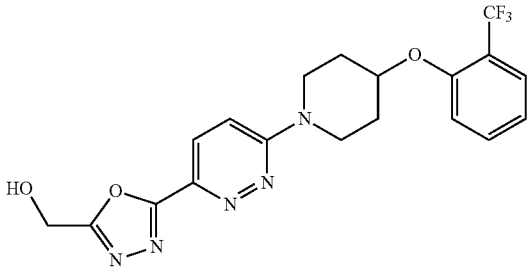

30

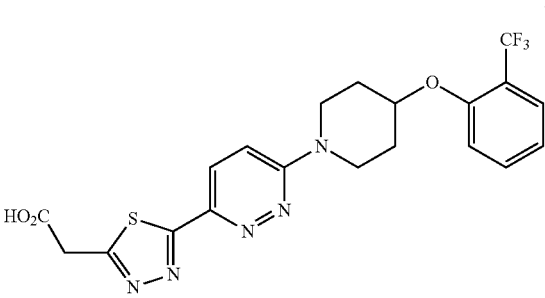

31

-continued

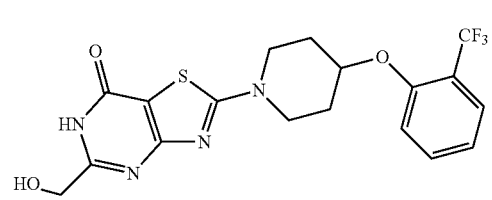
32

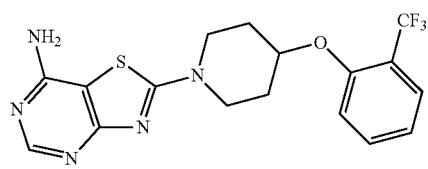
33

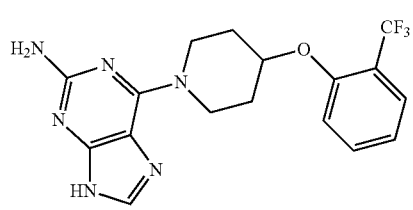
34

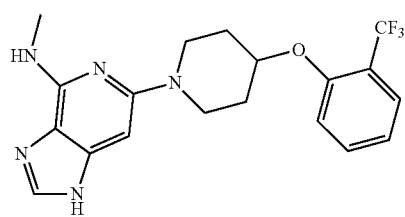
35

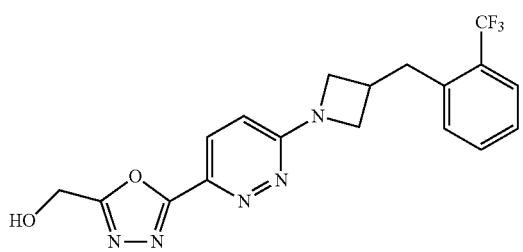
38

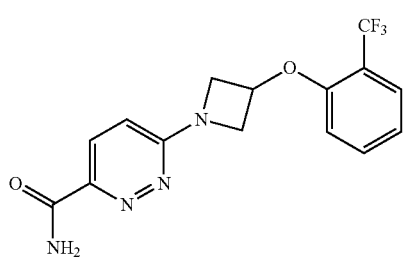
39

In some embodiments, the SCD1 antagonist small molecule comprises a 5-membered pyrrolidine ring. In some embodiments, the SCD1 antagonist small molecule is Compound 40. In some embodiments, the SCD1 antagonist small molecule is Compound 41. In some embodiments, the SCD1 antagonist small molecule is Compound 42.

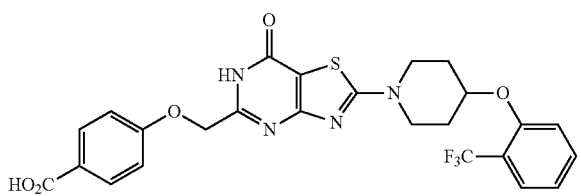
36

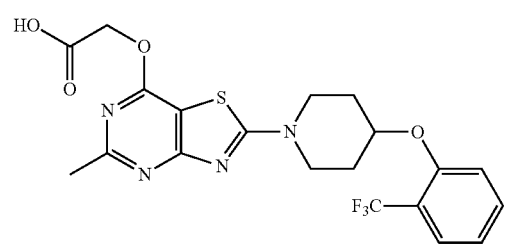
37

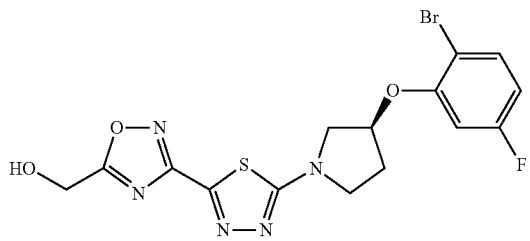
40, 41, 42

In some embodiments, the SCD1 antagonist small molecule comprises a six-membered piperidine. In some embodiments, the SCD1 antagonist small molecule comprises a four membered azetidine. In some embodiments, the SCD1 antagonist small molecule is Compound 38. In some embodiments, the SCD1 antagonist small molecule is Compound 39.

In some embodiments, the SCD1 antagonist small molecule is Compound 43. In some embodiments, the SCD1 antagonist small molecule is Compound 44. In some embodiments, the SCD1 antagonist small molecule comprises a tetrazole acetic acid. In some embodiments, the SCD1 antagonist small molecule comprising a tetrazole acetiic acid further comprises an aliphatic portion. In some embodiments, the SCD1 antagonist small molecule is Compound 45. In some embodiments, the SCD1 antagonist small molecule is Compound 46.

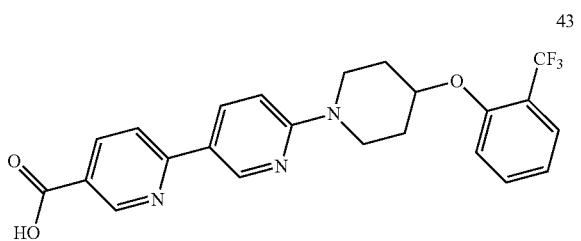

43

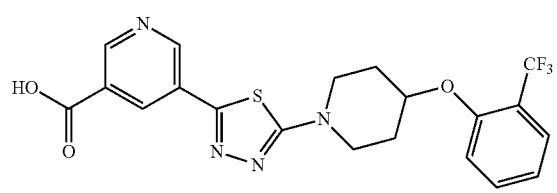

44

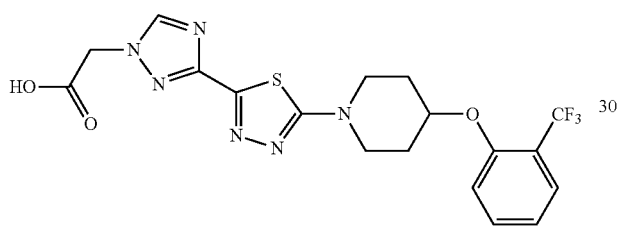

45

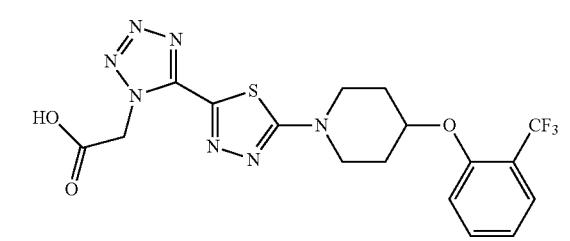

46

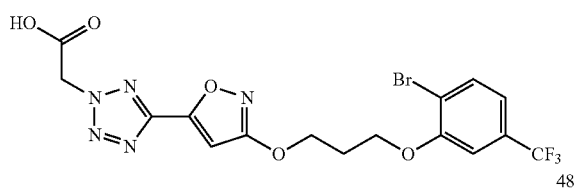

47

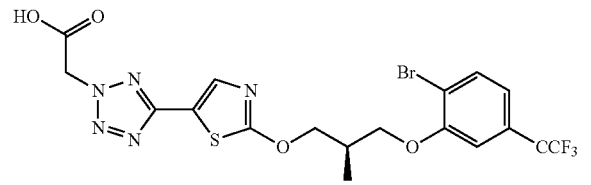

48

In some embodiments, the SCD1 antagonist small molecule is a SCD1 antagonist small molecule described in Liu G. et al., *J Med Chem* (2007); 50:3086-100, Zhao H. et al., *Bioorg Med Chem Lett* (2007); 17:3388-91, Xin Z. et al., *Bioorg Med Chem Lett* (2008); 18:4298-302, and/or Liu G. Stearoyl-CoA desaturase-1 (SCD1) Inhibitors: Discovery and in vivo evaluation. Emerging Targets for Type 2 Diabetes Symposium, The 233th ACS National Meeting, Chicago, Ill., March 2007, MEDI-382, which are incorporated by reference in its entirety. In some embodiments, the SCD1 antagonist small molecule is Compound 46. In some embodiments, the SCD1 antagonist small molecule is orally bioavailable. In some embodiments, the SCD1 antagonist small molecule has $IC_{50}$ values of 4.5 and 26 nM in mouse and human, respectively. In some embodiments, the SCD1 antagonist small molecule is inhibits the long-chain fatty acid-CoA desaturation in HepG2 cell with an $IC_{50}$ value of 6.8 nM as measured by $[^{13}C]$-C16:1/$[^{13}C]$-C16:0. In some embodiments, the SCD1 antagonist small molecule is in vivo PK of (CL=0.28 (1 h)/kg, Vss=0.71 l/kg, AUC=10.66 (μg h)/ml and F=59%).

In some embodiments, the SCD1 antagonist small moleculecomprises a glycine amide pyridine. In some embodiments, the SCD1 antagonist small molecule is Compound 48. In some embodiments, the SCD1 antagonist small molecule inhibits human SCD1 with an $IC_{50}$ value of 90 nM. In some embodiments, the SCD1 antagonist small molecule is a pyrazine compound. In some embodiments, the SCD1 antagonist small molecule is Compound 49. In some embodiments, the SCD1 antagonist small molecule has an $IC_{50}$ value of 37 nM against human SCD1.

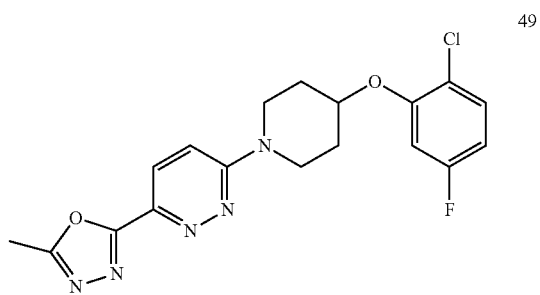 [SMILES: Cc1nnc(-c2ccc(N3CCC(Oc4cc(F)ccc4Cl)CC3)nn2)o1]

49

In some embodiments, the SCD1 antagonist small molecule is a piperidine urea. In some embodiments, the SCD1 antagonist small molecule is Compound 50. In some embodiments, the SCD1 antagonist small molecule has an $IC_{50}$<4 nM versus mSCD1, 37 nM versus hSCD1) and PK properties (CL=0.4 (1 h)/kg, Vss=0.4 l/kg, oral AUC=13.3 (μg h)/ml, oral F=102%).

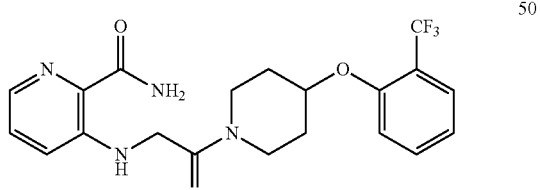

50

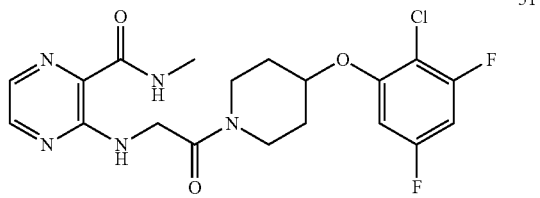

51

-continued

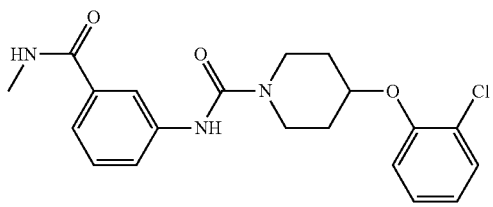

In some embodiments, the SCD1 antagonist small molecule is a SCD1 antagonist small molecule described in WO2008123891, WO2008043087, WO2008127615, and/or Koltun D O et al. Potent, selective, and metabolically stable stearoyl-CoA desaturase (SCD) inhibitors for the potential treatment of obesity and diabetes. The 236th ACS National Meeting, Philadelphia, Pa., August 2008, MEDI-198, which are incorporated by reference in its entirety. In some embodiments, the SCD1 antagonist small molecule is a pteridinone derivative. In some embodiments, the SCD1 antagonist small molecule is a pteridinone derivative comprising a systematic modification of the core template led to improvement in both potency and in vitro ADME profiles as shown in WO2008043087 and/or WO2008127615. In some embodiments, the SCD1 antagonist small molecule is Compound 51. In some embodiments, the SCD1 antagonist small molecule is a pteridone analogue. In some embodiments, the SCD1 antagonist small molecule has $IC_{50}$ values of 250 and 280 nM against rat and human SCD1, respectively. In some embodiments, the SCD1 antagonist small molecule is a 3-oxopyrido [3,2-b]pyrazine. In some embodiments, the SCD1 antagonist small molecule is Compound 52. Compound 52 is A37602 (G01522403) used in the Examples. In some embodiments, the SCD1 antagonist small molecule has a hSCD1 $IC_{50}$ of 37 nM. In some embodiments, the SCD1 antagonist small molecule has an $IC_{50}$ in rat of 7.8 nM. In some embodiments, the SCD1 antagonist small molecule is a the 2-oxopyrido[3,4-b]pyrazine analogue. In some embodiments, the SCD1 antagonist small molecule is Compound 53. In some embodiments, the SCD1 antagonist small molecule is a 2-oxoquinoxaline-based SCD1 inhibitors. In some embodiments, the SCD1 antagonist small molecule is Compound 54. In some embodiments, the SCD1 antagonist small molecule has a subnanomolar $IC_{50}$s, to be selective against Δ5 and Δ6 desaturases, and to have greater than 50% stability in HLM and RLM (30 min incubation).

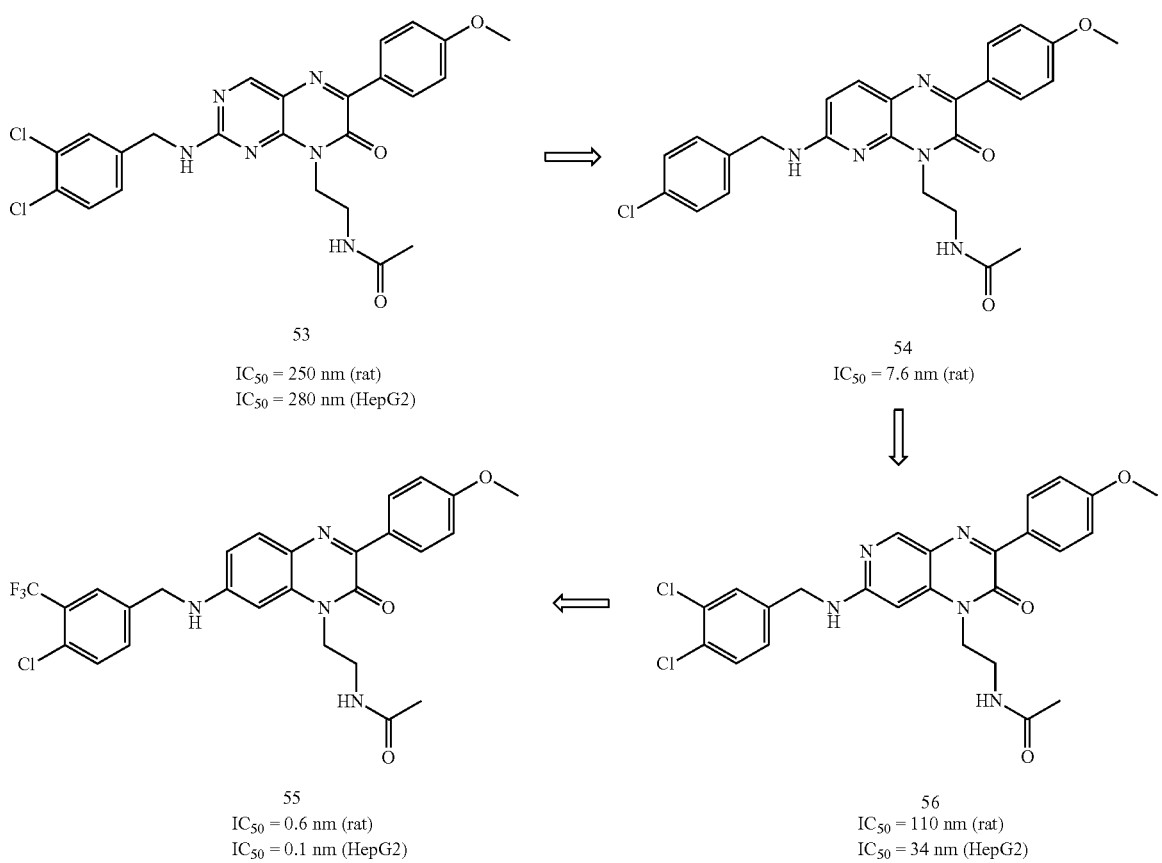

In some embodiments, the SCD1 antagonist small molecule is a SCD1 antagonist small molecule described in WO2008074824, W020080074832, W02008074833, WO2008074834, WO2008104524, and/or WO2009010560, which are incorporated by reference in their entirety. GSK published a number of patent applications regarding SCD1 inhibitors. In some embodiments, the SCD1 antagonist small molecule is a pyrazolyl 4-amide. In some embodiments, the SCD1 antagonist small molecule is Compound 55. In some embodiments, the SCD1 antagonist small molecule has an $pIC_{50}$ (-log $IC_{50}$) Value<5.5 against rat SCD1.

In some embodiments, the SCD1 antagonist small molecule is a pyrazolyl 3-amide. In some embodiments, the SCD1 antagonist small molecule is Compound 56. In some embodiments, the SCD1 antagonist small molecule inhibits rat SCD1 with pIC$_{50}$ greater than 5.5. In some embodiments, the pyrazole is modified to thiadiazole. In some embodiments, the SCD1 antagonist small molecule is Compound 57. In some embodiments, the SCD1 antagonist small molecule inhibits rat SCD1 with pIC$_{50}$ greater than 5.5. In some embodiments, the SCD1 antagonist small molecule is Compound 58. In some embodiments, the SCD1 antagonist small molecule has in vitro and cellular potency (pIC$_{50}$ between 7.00 and 7.25, respectively).

57

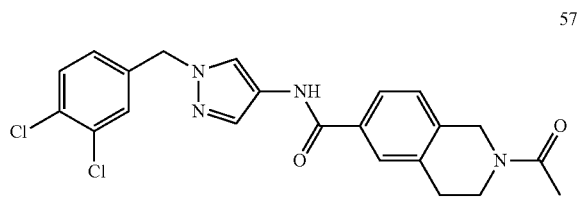

58

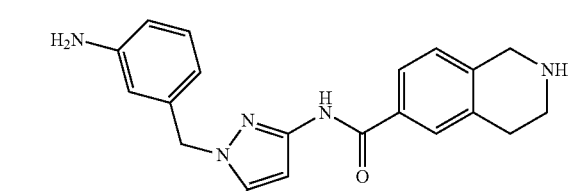

59

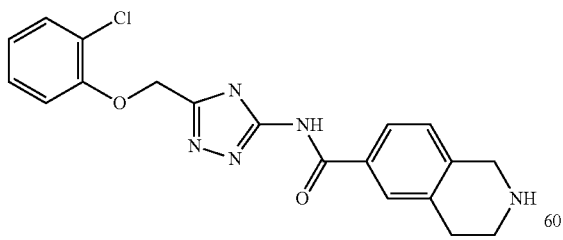

60

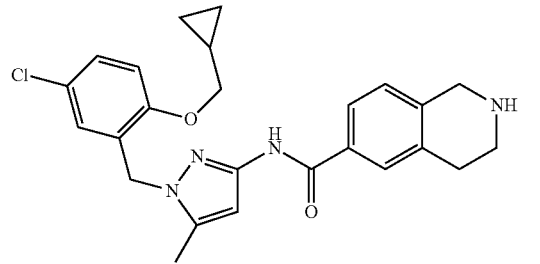

In some embodiments, the SCD1 antagonist small molecule is a SCD1 antagonist small molecule described in WO2008044767 and/or WO2008096746, which are incorporated by reference in their entirety. In some embodiments, the SCD1 antagonist small molecule is an aromatic amine derivative. In some embodiments, the SCD1 antagonist small molecule is Compound 59. In some embodiments, the SCD1 antagonist small molecule at 10 µM inhibits 100% of the microsomal SCD1 activity. In some embodiments, the SCD1 antagonist small molecule is a pyridazine template. In some embodiments, the SCD1 antagonist small molecule is Compound 60. In some embodiments, the SCD1 antagonist small molecule reduces DI (C18:1/C18:0) in DIO mice.

In some embodiments, the SCD1 antagonist small molecule is a SCD1 antagonist small molecule described in WO2008056687, JP2009019013, and/or WO2008139845, which are incorporated by reference in their entirety. In some embodiments, the SCD1 antagonist small molecule is a spiropiperidine derivative. In some embodiments, the SCD1 antagonist small molecule is Compound 61. In some embodiments, the SCD1 antagonist small molecule has an IC$_{50}$ values below 0.2 µM against human SCD1 transfected in HEK293 cells. In some embodiments, the SCD1 antagonist small molecule is Compound 62. In some embodiments, the SCD1 antagonist small molecule is an azole amide. In some embodiments, the SCD1 antagonist small molecule is Compound 63. In some embodiments, the SCD1 antagonist small molecule inhibits human SCD1 with an IC$_{50}$ value<1 µM.

61

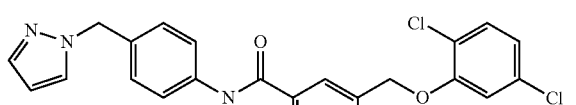

62

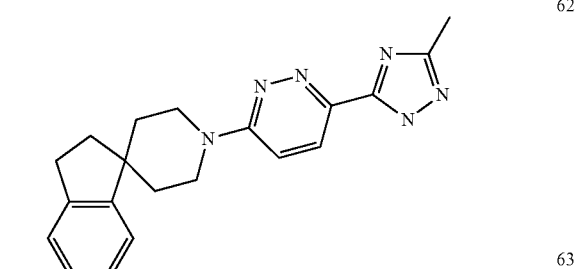

63

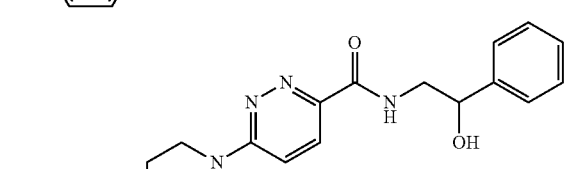

64

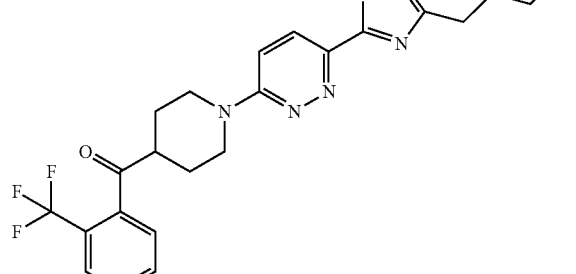

65

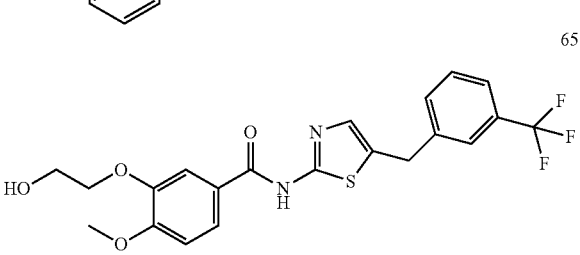

In some embodiments, the SCD1 antagonist small molecule is a SCD1 antagonist small molecule described in WO2008120744, WO2008123469, and/or WO2008029266, which are incorporated by reference in their entirety. In some embodiments, the SCD1 antagonist small molecule is a 2,5-disubstituted thiophene/furan derivatives. In some embodiments, the SCD1 antagonist small molecule is Compound 64. In some embodiments, the SCD1 antagonist small molecule has an $IC_{50}$ value below 0.1 µM. In some embodiments, the SCD1 antagonist small molecule is a modified to six-membered aryl ring. In some embodiments, the SCD1 antagonist small molecule is a benzamide analogue. In some embodiments, the SCD1 antagonist small molecule is Compound 65. In some embodiments, the SCD1 antagonist small molecule has an $IC_{50}$ value below 0.1 µM against rat SCD1. In some embodiments, the SCD1 antagonist small molecule has modified to piperidine. In some embodiments, the SCD1 antagonist small molecule is a urea derivative. In some embodiments, the SCD1 antagonist small molecule is Compound 66. In some embodiments, the SCD1 antagonist small molecule has an $IC_{50}$ value below 0.1 µM against rat SCD1.

66

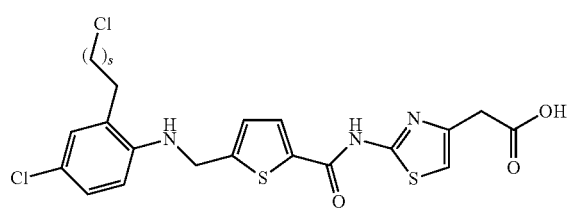

67

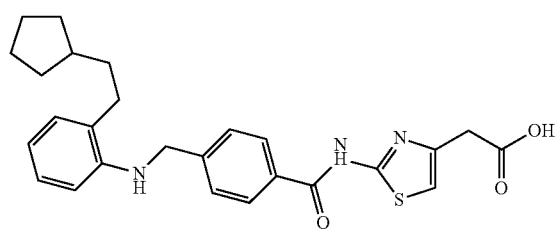

68

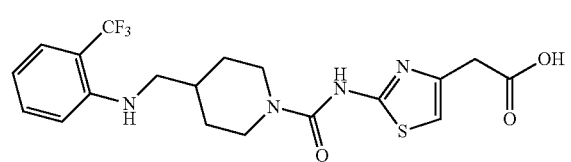

In some embodiments, the SCD1 antagonist small molecule is a SCD1 antagonist small molecule described in WO2008029266 and/or WO2008062276, which are incorporated by reference in their entirety. In some embodiments, the SCD1 antagonist small molecule is pyridinyloxazolanones. In some embodiments, the SCD1 antagonist small molecule is Compound 67. In some embodiments, the SCD1 antagonist small molecule inhibits human SCD1 99% at 10 µM. In some embodiments, the SCD1 antagonist small molecule is acetylene containing pyridazines/pyridines. In some embodiments, the SCD1 antagonist small molecule is Compound 68. In some embodiments, the SCD1 antagonist small molecule inhibits human SCD1 100% at 10 µM.

69

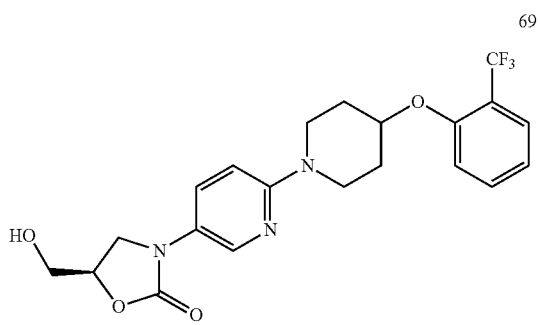

70

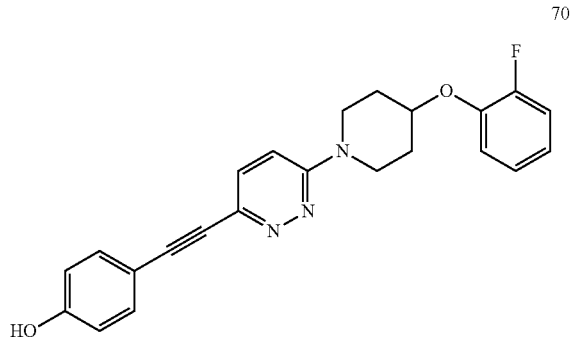

In some embodiments, the SCD1 antagonist small molecule is a SCD1 antagonist small molecule described in WO2008003753 and/or WO2008116898, which are incorporated by reference in their entirety. In some embodiments, the SCD1 antagonist small molecule is a pyrazolo[1,5-a]pyrimidine derivatives. In some embodiments, the SCD1 antagonist small molecule is Compound 69. In some embodiments, the SCD1 antagonist small molecule has an $IC_{50}$ value of 140 nM. In some embodiments, the SCD1 antagonist small molecule is compound 70. In some embodiments, the SCD1 antagonist small molecule has an $IC_{50}$ value of 22 nM.

In some embodiments, the SCD1 antagonist small molecule is a SCD1 antagonist small molecule described in WO2008157844, which is incorporated by reference in its entirety. In some embodiments, the SCD1 antagonist small molecule is piperazine-based SCD1 inhibitors. In some embodiments, the SCD1 antagonist small molecule is Compound 71. In some embodiments, the SCD1 antagonist small molecule is Compound 72. In some embodiments, the SCD1 antagonist small molecule inhibits rat SCD1 with $IC_{50}$ values<10 mM.

71

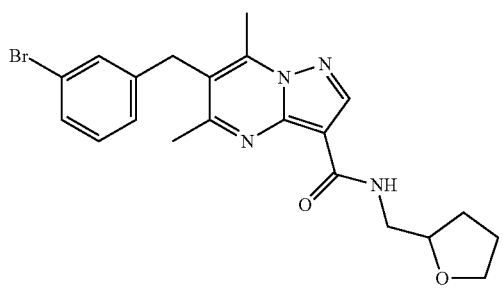

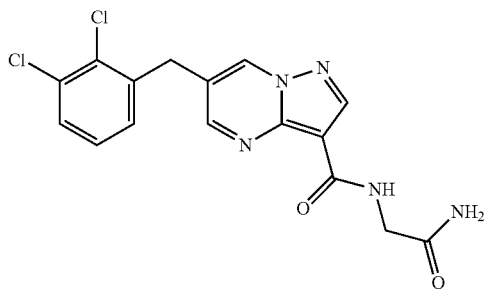

72

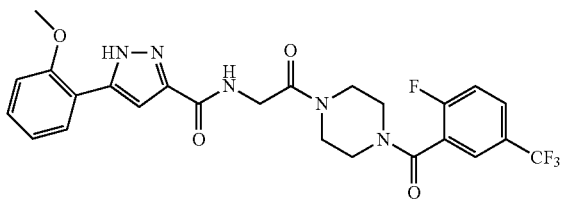

74

In some embodiments, the SCD1 antagonist small molecule is a SCD1 antagonist small molecule described in WO2008135141, which is incorporated by reference in its entirety. In some embodiments, the SCD1 antagonist small molecule is a bicyclic pyrrolo[3,4-c]pyrrolo diamine core scaffold. In some embodiments, the SCD1 antagonist small molecule is Compound 73. In some embodiments, the SCD1 antagonist small molecule is Compound 74. In some embodiments, the SCD1 antagonist small molecule inhibits rat SCD1 100% at 10 µM. In some embodiments, the SCD1 antagonist small molecule is Compound 75. In some embodiments, the SCD1 antagonist small molecule is Compound 76.

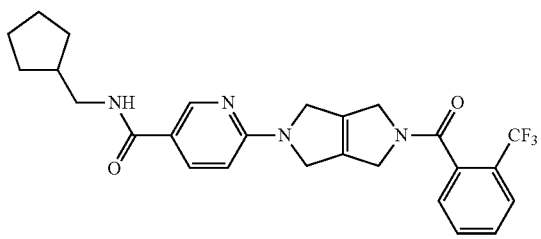

75

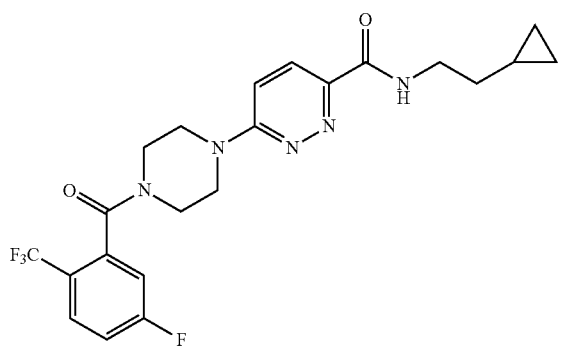

76

73

In some embodiments, the SCD1 antagonist small molecule is Compound 19b. In some embodiments, the SCD1 antagonist small molecule is Compound 24b. Compound 24b is 602447171.1 (G02447171) used in the Examples.

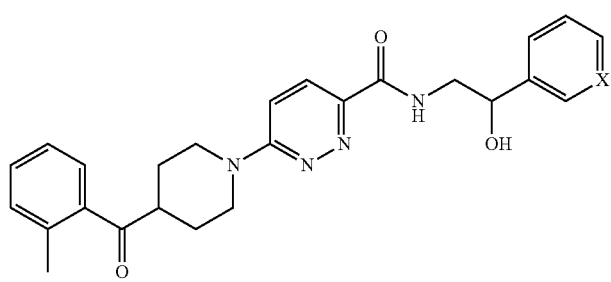

| | ADME and Pharmacokinetic Profiles of 19b and 24b | | | | | | | | | | |
|---|---|---|---|---|---|---|---|---|---|---|---|
| | Solubility* | | | Murine liver S9 Stability | PK$^e$(iv, S mg/kg) | | | PK$^e$ (pe, 20 mg/kg) | | | |
| No. | JP-1 (µM) pH 1.2 | JP-2 (µM) pH 6.8 | cLog P$^c$ | N$^2$ at 30 min | $t_{1/2}$ (h) | Cl (mL/min/kg) | $V_o$ (L/kg) | $C_{max}$ (µg/mL) | $t_{1/2}$ (h) | AUC$_{o, xk3}$ (µg h/mL) | F (S) |
| 19b | 88 | 3 | 2.6 | 58 | 0.6 | 42 | 0.9 | 0.3 | 0.8 | 0.5 | 6 |
| 24b | >100 | 29 | 1.1 | 78 | 1.3 | 29 | 2.4 | 6.3 | 0.9 | 7.8 | 65 |

X = CH; 19b
X = N; 24b

In some embodiments, the SCD1 antagonist small molecule is a SCD1 antagonist small molecule described in WO2011011872, WO2011011506, WO2011047481, WO2011011508, WO2011039358, WO2011030312, WO2010025553, WO2010094120, WO2010112520, WO2009060452, WO2009019566, WO2009010560, WO2009016216, and/or WO2009056556, which are incorporated by reference in its entirety. In some embodiments, the SCD1 antagonist small molecule is a spirocyclic compound. In some embodiments, the SCD1 antagonist small molecule is Spiro compound. In some embodiments, the SCD1 antagonist small molecule is a benzo-fused oxazepine compound. In some embodiments, the SCD1 antagonist small molecule is a pyrazole derivative. In some embodiments, the SCD1 antagonist small molecule is a triazole dertivative. In some embodiments, the SCD1 antagonist small molecule is a N-thiazolyl-1,2,3,4-tetrahydro-6-isoquinolinecarboxamide derivative. In some embodiments, the SCD1 antagonist small molecule is A939572 (4-(2-chlorophenoxy)-N-(3-(methylcarbamoyl)-phenyl)piperidine-1-carboxamide). In some embodiments, the SCD1 antagonist small molecule is CVT-11,127. In some embodiments, the SCD1 antagonist small molecule is MF-438. In some embodiments, the SCD1 antagonist small molecule is a quinoxalinone. In some embodiments, the SCD1 antagonist small molecule is CVT-13,036. In some embodiments, the SCD1 antagonist small molecule is 11,563. In some embodiments, the SCD1 antagonist small molecule is CVT-12,012. In some embodiments, the SCD1 antagonist small molecule is CVT-12,805. In some embodiments, the SCD1 antagonist small molecule is a SCD1 antagonist small molecule in http://caocao.myipcn.org/science?_ob=MImg&_cid=273013&_user=4861547&_pii=S0065774310450071&_zone=rslt_list_item&_coverDate=12%2F31%2F2010&wchp=dGLzVlt-zSkWz&_valck=1&md5=117298fb3b239424e814148d8b4bae32&ie=/sdarticle.pdf, which is incorporated by reference in its entirety.

In some embodiments, the SCD1 antagonist small molecule is a compound of formula (I):

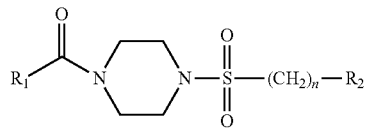

(IIa)

wherein: $R_1$ represents an alkyl, a cycloalkyl, an aryl or a heteroaryl group in $C_5$ to $C_{14}$, in particular in $C_6$, said aryl or heteroaryl being optionally substituted with one or more groups $R_a$; —$R_a$ represents an halogen atom, an hydroxyl group, —$NO_2$, —CN, —$NH_2$, —$N(C_{1-6}alkyl)_2$, a $C_{1-6}$alkyl, a $C_{1-6}$alkoxy, a —C(O)—$C_{1-6}$alkyl, $C_{2-6}$alkenyl, $C_{3-6}$cycloalkyl, aryl, $C_{3-6}$ heterocyclyl or heteroaryl, said alkyl, alkoxy, alkenyl, cycloalkyl, aryl, heterocyclyl or heteroaryl being optionally substituted with one or more halogen atom, $C_{1-6}$ alkyl, $C_{1-6}$ alkoxy, —C(0)-$C_{1-6}$ alkyl, —$NO_2$, —$CF_3$, —$OCF_3$, —CN, —$NH_2$, and/or —$N(C_{1-6}alkyl)_2$; —n represents 0, 1, 2, or 3;—$R_2$ represents an alkyl, a cycloalkyl, an aryl or a heteroaryl group in $C_5$ to $C_{14}$, in particular in $C_6$, said aryl or heteroaryl being optionally substituted with one or more groups $R_b$;—$R_b$ represents an halogen atom, an hydroxyl group, $NO_2$, —CN, —$CF_3$, —$OCF_3$, a $C_{1-6}$ alkyl, $C_{1-6}$ alkoxy, —C(O)—$C_{1-6}$ alkyl, —$NH_2$, —$N(C_{1-6}alkyl)_2$, $C_{3-6}$ cycloalkyl, $C_{3-6}$ heterocyclyl, aryl, heteroaryl, said alkyl, alkoxy, cycloalkyl, heterocyclyl, aryl, heteroaryl being optionally substituted with one or more hydroxyl group, —$CF_3$, —$OCF_3$, —$NH_2$, —$NO_2$, and/or —CN, or one of its salts or enantiomer forms.

In some embodiments, the SCD1 antagonist small molecule is a SCD1 antagonist small molecule described in U.S. Pat. No. 7,652,013, which is incorporated by reference in its entirety. In some embodiments, the SCD1 antagonist small molecule is a compound of formula (II):

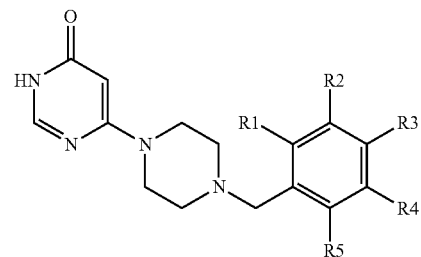

wherein: R1 and R5, independently of each other, are hydrogen, unsubstituted lower alkyl, halogen, trifluoromethyl, hydroxy, aryl, alkoxy or $NO_2$; R1 and R2, optionally, together with the carbon atoms to which they are attached, form a 9-membered ring having 1 or 2 heteroatoms; R2 and R4, independently of each other, are hydrogen, unsubstituted lower alkyl, lower alkyenyl, alkoxy, halogen, cyano, trifluoromethyl, O-trifluoromethyl or $NO_2$; and R3 is hydrogen, unsubstituted lower alkyl, alkoxy or halogen; wherein at least one of R1, R2, R3, R4 or R5 is hydrogen, and pharmaceutically acceptable salts thereof. In some embodiments, R1 is halogen, R4 is alkoxy and R5 is hydroxy. In some embodiments, R1, R4 and R5 are each hydrogen. In some embodiments, R2 is halogen, R4 is halogen and R5 is hydroxy. In some embodiments, both R2 and R3 are unsubstituted lower alkyl. In some embodiments, both R2 and R5 are trifluoromethyl. In some embodiments, both R3 and R4 are halogen. In some embodiments, both R4 and R5 are halogen. In some embodiments, R2 is halogen and R3 is hydroxy. In some embodiments, R2 is halogen and R5 is $NO_2$. In some embodiments, R2 is —O-trifluoromethyl and R5 is hydroxy. In some embodiments, R3 is halogen. In some embodiments, R4 is unsubstituted lower alkyl. In some embodiments, R5 is unsubstituted lower alkyl. In some embodiments, R5 is trifluoromethyl. In some embodiments, R5 is halogen. In some embodiments, R5 is $NO_2$. In some embodiments, the compound is 6-[4-(3-Bromo-benzyl)-piperazin-1-yl]-3H-pyrimidin-4-one; 6-[4-(5-Bromo-2-hydroxy-benzyl)-piperazin-1-yl]-3H-pyrimidin-4-one; 6-[4-(3-Chloro-benzyl)-piperazin-1-yl]-3H-pyrimidin-4-one; 6-[4-(5-Chloro-2-nitro-benzyl)-piperazin-1-yl]-3H-pyrimidin-4-one; 6-[4-(2,3-Dichloro-benzyl)-piperazin-1-yl]-3H-pyrimidin-4-one; 6-[4-(3,5-Dichloro-2-hydroxy-benzyl)-piperazin-1-yl]-3H-pyrimidin-4-one; 6-[4-(2,6-Dimethyl-benzyl)-piperazin-1-yl]-3H-pyrimidin-4-one; 6-[4-(2-Hydroxy-5-trifluoromethoxy-benzyl)-piperazin-1-yl]-3H-pyrimidin-4-one; 6-[4-(2-Nitro-benzyl)-piperazin-1-yl]-3H-pyrimidin-4-one; or 6-[4-(2-Trifluoromethyl-benzyl)-piperazin-1-yl]-3H-pyrimidin-4-one.

In some embodiments, the SCD1 antagonist small molecule is Compound 77 (RG1 of the Examples; Example 24 in U.S. Pat. No. 7,652,013). In some embodiments, the SCD1 antagonist small molecule is Compound 78 (RG2 of the Examples; Example 51 in U.S. Pat. No. 7,652,013). In some embodiments, the SCD1 antagonist small molecule is Compound 79 (RG3 of the Examples; Example 50 in U.S. Pat. No. 7,652,013). In some embodiments, the SCD1 antagonist small molecule is Compound 80 (RG4 of the Examples; Example 44 in U.S. Pat. No. 7,652,013). In some embodiments, the SCD1 antagonist small molecule is Compound 81 (RG5 of the Examples; Example 45 in U.S. Pat. No. 7,652,013). In some embodiments, the SCD1 antagonist small molecule is Compound 82 (RG6 of the Examples; Example 46 in U.S. Pat. No. 7,652,013). In some embodiments, the SCD1 antagonist small molecule is Compound 83 (RG7 of the Examples; Example 28 in U.S. Pat. No. 7,652,013). In some embodiments, the SCD1 antagonist small molecule is Compound 84 (RG8 of the Examples; Example 49 in U.S. Pat. No. 7,652,013). In some embodiments, the SCD1 antagonist small molecule is Compound 85 (RG9 of the Examples; Example 48 in U.S. Pat. No. 7,652,013). In some embodiments, the SCD1 antagonist small molecule is Compound 86 (RG10 of the Examples; Example 25 in U.S. Pat. No. 7,652,013). In some embodiments, the SCD1 antagonist small molecule is Compound 87 (RG11 of the Examples; Example 38 in U.S. Pat. No. 7,652,013). In some embodiments, the SCD1 antagonist small molecule is Compound 88 (RG12 of the Examples; Example 47 in U.S. Pat. No. 7,652,013). In some embodiments, the SCD1 antagonist small molecule is Compound 89 (RG13 of the Examples; Example 35 in U.S. Pat. No. 7,652,013). In some embodiments, the SCD1 antagonist small molecule is Compound 90 (RG14 of the Examples; Example 31 in U.S. Pat. No. 7,652,013).

77

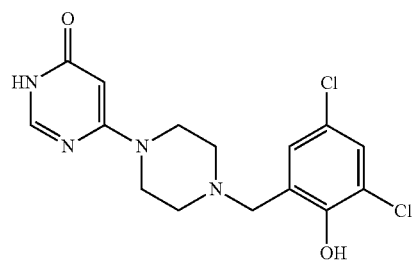

78

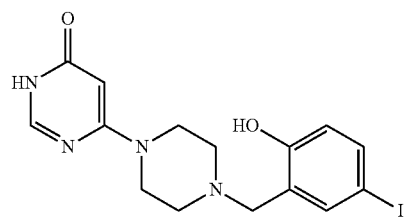

79

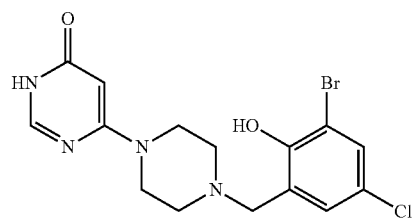

80

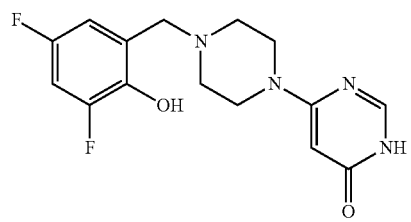

-continued

81

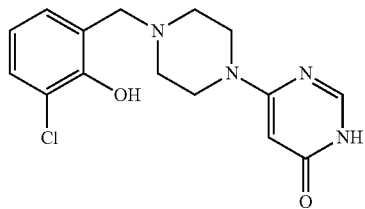

82

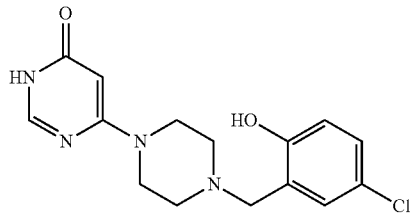

83

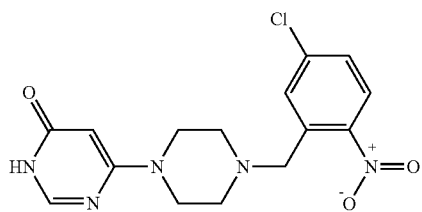

84

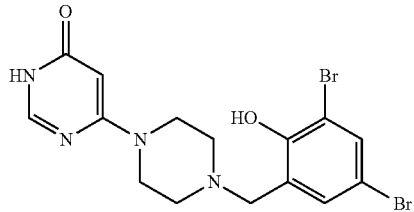

85

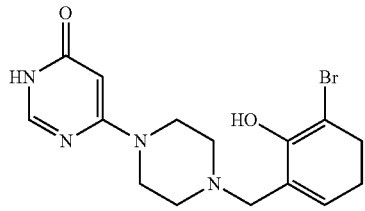

86

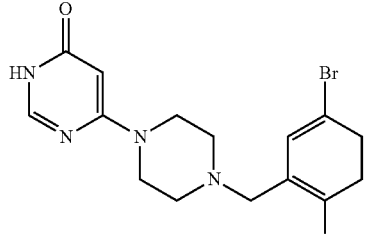

87

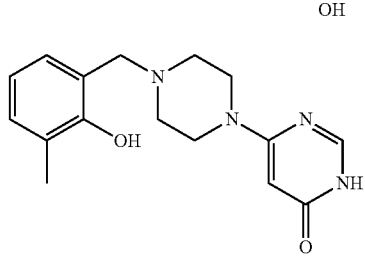

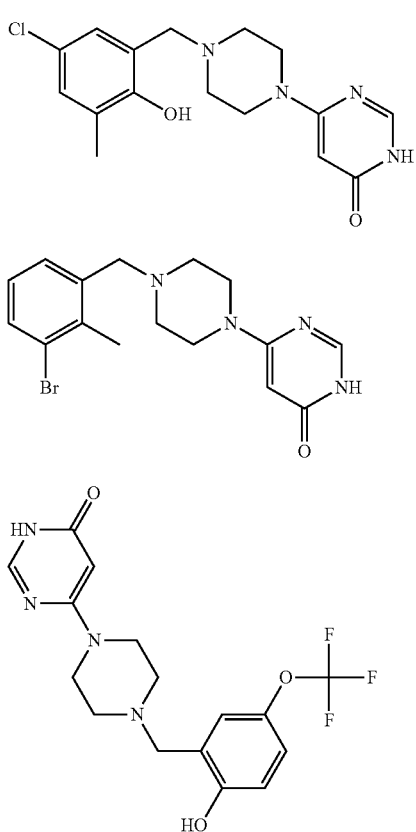

E. Antagonist Polynucleotides

Provided herein are polynucleotide antagonists. The polynucleotide may be an antisense nucleic acid and/or a ribozyme. The antisense nucleic acids comprise a sequence complementary to at least a portion of an RNA transcript of a SCD1 gene. However, absolute complementarity, although preferred, is not required.

A sequence "complementary to at least a portion of an RNA," referred to herein, means a sequence having sufficient complementarity to be able to hybridize with the RNA, forming a stable duplex; in the case of double stranded SCD1 antisense nucleic acids, a single strand of the duplex DNA may thus be tested, or triplex formation may be assayed. The ability to hybridize will depend on both the degree of complementarity and the length of the antisense nucleic acid. Generally, the larger the hybridizing nucleic acid, the more base mismatches with an SCD1 RNA it may contain and still form a stable duplex (or triplex as the case may be). One skilled in the art can ascertain a tolerable degree of mismatch by use of standard procedures to determine the melting point of the hybridized complex.

In some embodiments the polynucleotide antagonists comprises 5'-GATCCCCCTACAAGAGTG GCT-GAGTTTTCAAGAGAAACTCAGCCACTCT-TGTAGTTTTTTGGAAA-3' (SEQ ID NO:2); 5'-GA TCCCCCTACGGCTCTTTCTGATCAT-TCAAGAGATGATCAGAAAGAGCCG-TAGTTTTTTGGA AA-3' (SEQ ID NO:3); or 5'-GATC-CCCGCACATCAACTTCACCACATTCAAGAGATGTG GTGAAGTTG ATGTGCTTTTTTGGAAA-3' (SEQ ID NO:4).

Polynucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. See generally, Wagner, R., 1994. Nature 372:333-335. Thus, oligonucleotides complementary to either the 5'- or 3'-nontranslated, non-coding regions of the SCD1 gene, could be used in an antisense approach to inhibit translation of endogenous SCD1 mRNA. Polynucleotides complementary to the 5' untranslated region of the mRNA should include the complement of the AUG start codon. Antisense polynucleotides complementary to mRNA coding regions are less efficient inhibitors of translation but could be used in accordance with the invention. Whether designed to hybridize to the 5'-, 3'- or coding region of SCD1 mRNA, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

In one embodiment, the SCD1 antisense nucleic acid of the invention is produced intracellularly by transcription from an exogenous sequence. For example, a vector or a portion thereof, is transcribed, producing an antisense nucleic acid (RNA) of the SCD1 gene. Such a vector would contain a sequence encoding the SCD1 antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others know in the art, used for replication and expression in vertebrate cells. Expression of the sequence encoding SCD1, or fragments thereof, can be by any promoter known in the art to act in vertebrate, preferably human cells. Such promoters can be inducible or constitutive. Such promoters include, but are not limited to, the SV40 early promoter region (Bernoist and Chambon, Nature 29:304-310 (1981), the promoter contained in the 3' long terminal repeat of Rous sarcoma virus (Yamamoto et al., Cell 22:787-797 (1980), the herpes thymidine promoter (Wagner et al., Proc. Natl. Acad. Sci. U.S.A. 78:1441-1445 (1981), the regulatory sequences of the metallothionein gene (Brinster, et al., Nature 296:39-42 (1982)), etc.

F. Antibody and Binding Polypeptide Variants

In certain embodiments, amino acid sequence variants of the antibodies and/or the binding polypeptides provided herein are contemplated. For example, it may be desirable to improve the binding affinity and/or other biological properties of the antibody and/or binding polypeptide. Amino acid sequence variants of an antibody and/or binding polypeptides may be prepared by introducing appropriate modifications into the nucleotide sequence encoding the antibody and/or binding polypeptide, or by peptide synthesis. Such modifications include, for example, deletions from, and/or insertions into and/or substitutions of residues within the amino acid sequences of the antibody and/or binding polypeptide. Any combination of deletion, insertion, and substitution can be made to arrive at the final construct, provided that the final construct possesses the desired characteristics, e.g., target-binding.

In certain embodiments, antibody variants and/or binding polypeptide variants having one or more amino acid substitutions are provided. Sites of interest for substitutional mutagenesis include the HVRs and FRs. Conservative substitutions are shown in Table 1 under the heading of "conservative substitutions." More substantial changes are provided in Table 1 under the heading of "exemplary substitutions," and as further described below in reference to amino acid side chain classes. Amino acid substitutions may be introduced into an antibody and/or binding polypeptide of interest and the products screened for a desired activity, e.g., retained/improved antigen binding, decreased immunogenicity, or improved ADCC or CDC.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g., a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g., binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or SDRs (a-CDRs), with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligo-nucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions.

A useful method for identification of residues or regions of the antibody and/or the binding polypeptide that may be targeted for mutagenesis is called "alanine scanning mutagenesis" as described by Cunningham and Wells (1989) *Science,* 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT) or a polypeptide which increases the serum half-life of the antibody.

G. Antibody and Binding Polypeptide Derivatives

In certain embodiments, an antibody and/or binding polypeptide provided herein may be further modified to contain additional nonproteinaceous moieties that are known in the art and readily available. The moieties suitable for derivatization of the antibody and/or binding polypeptide include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody and/or binding polypeptide may vary, and if more than one polymer are attached, they can be the same or different molecules. In general, the number and/or type of polymers used for derivatization can be determined based on considerations including, but not limited to, the particular properties or functions of the antibody and/or binding polypeptide to be improved, whether the antibody derivative and/or binding polypeptide derivative will be used in a therapy under defined conditions, etc.

In another embodiment, conjugates of an antibody and/or binding polypeptide to nonproteinaceous moiety that may be selectively heated by exposure to radiation are provided. In one embodiment, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody and/or binding polypeptide-nonproteinaceous moiety are killed.

IV. Recombinant Methods and Compositions

Antibodies and/or binding polypeptides may be produced using recombinant methods and compositions, e.g., as described in U.S. Pat. No. 4,816,567. In one embodiment, isolated nucleic acid encoding an anti-SCD1 antibody. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid encoding the antibody and/or binding polypeptide are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g., a Chinese Hamster Ovary (CHO) cell or lymphoid cell (e.g., Y0, NS0, Sp20 cell). In one embodiment, a method of making an anti-SCD1 antibody and/or binding polypeptide is provided, wherein the method comprises culturing a host cell comprising a nucleic acid encoding the antibody and/or binding polypeptide, as provided above, under conditions suitable for expression of the antibody and/or binding polypeptide, and optionally recovering the antibody and/or polypeptide from the host cell (or host cell culture medium).

For recombinant production of an anti-SCD1 antibody and/or a binding polypeptide, nucleic acid encoding the antibody and/or the binding polypeptide, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789, 199, and 5,840,523. (See also Charlton, *Methods in Molecular Biology*, Vol. 248 (B. K. C. Lo, ed., Humana Press, Totowa, N.J., 2003), pp. 245-254, describing expression of antibody fragments in *E. coli*.) After expression, the antibody and/or binding polypeptides may be isolated from the bacterial cell paste in a soluble fraction and can be further purified.

In addition to prokaryotes, eukaryotic microbes such as filamentous fungi or yeast are suitable cloning or expression hosts for vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated antibody and/or glycosylated binding polypeptides are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK); buffalo rat liver cells (BRL 3A); human lung cells (W138); human liver cells (Hep G2); mouse mammary tumor (MMT 060562); TR1 cells, as described, e.g., in Mather et al., *Annals N.Y. Acad. Sci.* 383: 44-68 (1982); MRC 5 cells; and FS4 cells. Other useful mammalian host cell lines include Chinese hamster ovary (CHO) cells, including DHFR$^-$ CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production and/or binding polypeptide production, see, e.g., Yazaki and Wu, *Methods in Molecular Biology*, Vol. 248 (B. K. C. Lo, ed., Humana Press, Totowa, N.J.), pp. 255-268 (2003).

While the description relates primarily to production of antibodies and/or binding polypeptides by culturing cells transformed or transfected with a vector containing antibody- and binding polypeptide-encoding nucleic acid. It is, of course, contemplated that alternative methods, which are well known in the art, may be employed to prepare antibodies and/or binding polypeptides. For instance, the appropriate amino acid sequence, or portions thereof, may be produced by direct peptide synthesis using solid-phase techniques [see, e.g., Stewart et al., *Solid-Phase Peptide Synthesis*, W.H. Freeman Co., San Francisco, Calif. (1969); Merrifield, *J. Am. Chem. Soc.*, 85:2149-2154 (1963)]. In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of the antibody and/or binding polypeptide may be chemically synthesized separately and combined using chemical or enzymatic methods to produce the desired antibody and/or binding polypeptide.

Forms of antibody and/or binding polypeptide may be recovered from culture medium or from host cell lysates. If membrane-bound, it can be released from the membrane using a suitable detergent solution (e.g., Triton-X 100) or by enzymatic cleavage. Cells employed in expression of antibody and/or binding polypeptide can be disrupted by various physical or chemical means, such as freeze-thaw cycling, sonication, mechanical disruption, or cell lysing agents.

It may be desired to purify antibody and/or binding polypeptide from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the antibody and/or binding polypeptide. Various methods of protein purification may be employed and such methods are known in the art and described for example in Deutscher, *Methods in Enzymology*, 182 (1990); Scopes, Protein Purification: Principles and Practice, Springer-Verlag, New York (1982). The purification step(s) selected will depend, for example, on the nature of the production process used and the particular antibody and/or binding polypeptide produced.

When using recombinant techniques, the antibody and/or binding polypeptide can be produced intracellularly, in the periplasmic space, or directly secreted into the medium. If the antibody and/or binding polypeptide is produced intracellularly, as a first step, the particulate debris, either host cells or lysed fragments, are removed, for example, by centrifugation or ultrafiltration. Carter et al., *Bio/Technology* 10:163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody and/or binding polypeptide is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody and/or binding polypeptide composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2 or γ4 heavy chains (Lindmark et al., *J. Immunol. Meth.* 62:1-13 (1983)). Protein G is recommended for all mouse isotypes and for human γ3 (Guss et al., *EMBO J.* 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody and/or binding polypeptide to be recovered.

Following any preliminary purification step(s), the mixture comprising the antibody and/or binding polypeptide of interest and contaminants may be subjected to low pH hydrophobic interaction chromatography using an elution buffer at a pH between about 2.5-4.5, preferably performed at low salt concentrations (e.g., from about 0-0.25M salt).

V. Methods of Screening and/or Identifying SCD1 Antagonists with Desired Function Techniques for generating SCD1 antagonists such as antibodies, binding polypeptides, and/or small molecules have been described above. Additional SCD1 antagonists such as anti-SCD1 antibodies, binding polypeptides, and/or binding small molecules provided herein may be identified, screened for, or characterized for their physical/chemical properties and/or biological activities by various assays known in the art.

Further provided herein are methods of screening for and/or identifying an SCD1 antagonist which induces cancer cell cycle arrest, inhibits cancer cell proliferation, and/or promotes cancer cell death said method comprising: (a) contacting a cancer cell, cancer tissue, and/or cancer sample with a SCD1 candidate antagonist, (b) determining the distribution of cell cycle stage, level of cell proliferation, and/or level of cancer cell death to the cancer cell, cancer tissue, and/or cancer sample in the absence of the SCD1 candidate antagonist, whereby a difference in distribution of cell cycle stage, decreased level of cell proliferation, and/or increased level of cancer cell death between the cancer cell, cancer tissue, and/or cancer sample in the presence of a SCD1 candidate antagonist and the cancer cell, cancer tissue, and/or cancer sample in the absence of a SCD1 candidate antagonist identifies the SCD1 candidate antagonist as an SCD1 antagonist which induces cancer cell cycle arrest, inhibits cancer cell proliferation, and/or promotes cancer cell cancer death. In some embodiments of any of methods of screening for and/or identifying an SCD1 antagonist, the SCD1 candidate antagonist induces cancer cell cycle arrest. In some embodiments of any of methods of screening for and/or identifying an SCD1 antagonist, the SCD1 candidate antagonist inhibits cancer cell proliferation. In some embodiments of any of methods of screening for and/or identifying an SCD1 antagonist, the SCD1 candidate antagonist promotes cancer cell death. In some embodiments, the cancer cell death is apoptosis. In some embodiments, the cancer cell death is neucrosis.

In some embodiments of any of the methods of screening for and/or identifying an SCD1 antagonist, the cancer cell, cancer tissue, or cancer sample is bladder cancer, pancreatic cancer, lung cancer, breast cancer, colon cancer, colorectal cancer, endometrial cancer, head & neck cancer, kidney cancer, ovarian cancer, hypopharyngeal, prostate cancer, esophageal, hepatocellular carcinoma, and/or urinary cancer. In some embodiments of any of the methods of screening for and/or identifying an SCD1 antagonist, the cancer cell, cancer tissue, or cancer sample is from a cancer selected from the group of bladder cancer, pancreatic cancer, lung cancer, breast cancer, colon cancer, colorectal cancer, endometrial cancer, head & neck cancer, kidney cancer, ovarian cancer, and/or urinary cancer. In some embodiments, the cancer cell, cancer tissue, or cancer sample is from a cancer selected from the group of bladder cancer, pancreatic cancer, endometrial cancer, head & neck cancer, kidney cancer, ovarian cancer, and/or urinary cancer. In some embodiments, the cancer cell, cancer tissue, or cancer sample is bladder cancer.

In some embodiments of any of the methods of screening for and/or identifying an SCD1 antagonist, the cancer cell, cancer tissue, and/or cancer sample expresses FGFR3. In some embodiments, the cancer cell, cancer tissue, and/or cancer sample expresses elevated levels of FGFR3 compared to a reference sample, reference cell, reference tissue, control sample, control cell, control tissue, or internal control (e.g., housekeeping gene). In some embodiments, the reference cancer cell expresses substantially the same levels of FGFR3 as a reference sample, reference cell, reference tissue, control sample, control cell, control tissue, or internal control (e.g., housekeeping gene). In some embodiments of any of the methods of screening for and/or identifying an SCD1 antagonist, the cancer cell, cancer tissue, and/or cancer sample expresses phosphorylated FGFR3. In some embodiments, the cancer cell, cancer tissue, and/or cancer sample expresses elevated levels of phosphorylated FGFR3 compared to a reference sample, reference cell, reference tissue, control sample, control cell, control tissue, or internal control (e.g., housekeeping gene). In some embodiments, the reference cancer cell expresses substantially the same levels of phosphorylated FGFR3 as a reference sample, reference cell, reference tissue, control sample, control cell, control tissue, or internal control (e.g., housekeeping gene). In some embodiments, the reference sample, reference cell, reference tissue, control sample, control cell, or control tissue is a non-cancerous with or without a known level of expression of FGFR3 and/or phosphorylated FGFR3. In some embodiments, the reference sample, reference cell, reference tissue, control sample, control cell, or control tissue is a cancerous with or without a known level of expression of FGFR3 and/or phosphorylated FGFR3. In some embodiments, the expression of FGFR3 in the cancer cell, cancer tissue, and/or cancer sample is cell surface expression. In some embodiments, the FGFR3 pathway in the cancer cell, cancer tissue, and/or cancer sample is constitutively active. In some embodiments, the FGFR3 pathway in the cancer cell, cancer tissue, and/or cancer sample is ligand dependent. In some embodiments, the cancer cell, cancer tissue, and/or cancer sample comprises a mutation in FGFR3. Examples of constitutively active mutations in FGFR3 include, but are not limited to, FGFR3 S249C. In some embodiments, the cancer cell, cancer tissue, and/or cancer sample is wild-type for FGFR3.

In some embodiments of any of the methods of screening for and/or identifying an SCD1 antagonist, the cancer cell, cancer tissue, and/or cancer sample expresses of one or more genes of the FGFR3-regulated lipogenic signature. In some embodiment, the cancer cell, cancer tissue, and/or cancer sample expresses elevated levels of one or more genes of the FGFR3-regulated lipogenic signature compared to a reference sample, reference cell, reference tissue, control sample, control cell, control tissue, or internal control (e.g., housekeeping gene). In some embodiments, the cancer cell, cancer tissue, and/or cancer sample expresses substantially the same levels of FGFR3-regulated lipogenic signature as a reference sample, reference cell, reference tissue, control sample, control cell, control tissue, or internal control (e.g., housekeeping gene). In some embodiments, the reference sample, reference cell, reference tissue, control sample, control cell, or control tissue is a non-cancerous with or without a known level of expression of one or more genes of the FGFR3-regulated lipogenic signature. In some embodiments, the reference sample, reference cell, reference tissue, control sample, control cell, or control tissue is a cancerous with or without a known level of expression of one or more genes of the FGFR3-regulated lipogenic signature. In some embodiments, the one or more genes of the FGFR3-regulated lipogenic signature comprises, consists of, or consists essential of one or more genes from the group consisting of SREBF1, G6PD, ACOT7, PTPLA, PCCB, FADS1, RDH11, ACER3, PDSS1, MVD, AGPAT5, HSD17B2, ACSL4, EBP, PIGW, LBR, ALLY, ADORA2B, GPCPD1, CYP24A1, ACSL3, MVK, ACSS2, FDPS, ELOVL5, HMGCR, LIPG, MEL DHCR7, LSS, ACAT2, FASN, CYP51A1, IDI1, FDFT1, FAR2, HMGCS1, SDR16C5, LDLR, MSMO1, INSIG1, DHRS9, LRP8, SQLE, PCSK9, SCD1, FABP4, and combinations thereof. In some embodiments, the one or more genes of the FGFR3-regulated lipogenic signature comprises, consists of, or consists essential of one or more genes from the group consisting of ELOVL5, HMGCR, LIPG, MEL DHCR7, LSS, ACAT2, FASN, CYP51A1, IDI1, FDFT1, FAR2, HMGCS1, SDR16C5, LDLR, MSMO1, INSIG1, DHRS9, LRP8, SQLE, PCSK9, SCD1, FABP4, and combinations thereof. In some embodiments, the one or more genes of the FGFR3-regulated lipogenic signature comprises, consists of, or consists essential of one or more genes from the group consisting of CYP51A1, IDI1, FDFT1, FAR2, HMGCS1, SDR16C5, LDLR, MSMO1, INSIG1, DHRS9, LRP8, SQLE, PCSK9, SCD1, FABP4, and combinations thereof. In some embodiments, the one or more genes of the FGFR3-regulated lipogenic signature comprises, consists of, or consists essential of one or more genes from the group consisting of LDLR, MSMO1, INSIG1, DHRS9, LRP8, SQLE, PCSK9, SCD1, FABP4, and combinations thereof. In some embodiments, the one or more genes of the FGFR3-regulated lipogenic signature comprises, consists of, or consists essential of one or more genes from the group consisting of SQLE, PCSK9, SCD1, FABP4, and combinations thereof. In some embodiments, the one or more genes of the FGFR3-regulated lipogenic signature comprises, consists of, or consists essential of SQLE. In some embodiments, the one or more genes of the FGFR3-regulated lipogenic signature comprises, consists of, or consists essential of PCSK9. In some embodiments, the one or more genes of the FGFR3-regulated lipogenic signature comprises, consists of, or consists essential of SCD1. In some embodiments, the one or more genes of the FGFR3-regulated lipogenic signature comprises, consists of, or consists essential of FABP4.

In some embodiments of any of the methods of screening for and/or identifying an SCD1 antagonist, the cancer cell, cancer tissue, or cancer sample expresses elevated levels of mature SREBP1 compared to a reference sample, reference cell, reference tissue, control sample, control cell, control tissue, or internal control (e.g., housekeeping gene). In some embodiments of any of the methods of screening for and/or identifying an SCD1 antagonist, the cancer cell, cancer tissue, or cancer sample expresses elevated levels of mature SREBP1 and the levels of mature SREBP2 are not substantially elevated (i.e., substantially the same level of expression) compared to a reference sample, reference cell, reference tissue, control sample, control cell, control tissue, or internal control (e.g., housekeeping gene). In some embodiments, the reference sample, reference cell, reference tissue, control sample, control cell, or control tissue is a non-cancerous with or without a known level of expression of mature SREBP1 and/or mature SREBP2. In some embodiments, the reference sample, reference cell, reference tissue, control sample, control cell, or control tissue is a cancerous with or without a known level of expression of mature SREBP1 and/or mature SREBP2.

In some embodiments of any of the methods of screening for and/or identifying an SCD1 antagonist, the cancer cell, cancer tissue, or cancer sample expresses elevated levels of Δ9 monounsaturaturated fatty acids compared to a reference sample, reference cell, reference tissue, control sample, control cell, control tissue, or internal control (e.g., housekeeping gene). In some embodiments of any of the methods of screening for and/or identifying an SCD1 antagonist, the cancer cell, cancer tissue, or cancer sample expresses elevated ratio of Δ9 monounsaturaturated fatty acids:saturated fatty acids compared to a reference sample, reference cell, reference tissue, control sample, control cell, control tissue, or internal control (e.g., housekeeping gene). In some embodiments, the reference sample, reference cell, reference tissue, control sample, control cell, or control tissue is a non-cancerous with or without a known level of expression of Δ9 monounsaturaturated fatty acids and/or saturated fatty acids. In some embodiments, the reference sample, reference cell, reference tissue, control sample, control cell, or control tissue is a cancerous with or without a known level of expression of Δ9 monounsaturaturated fatty acids and/or saturated fatty acids. Example of Δ9 monounsaturaturated fatty acids include, but are not limited to, palmitoleic acid (C16:1) and oleic acid (C18:1). Examples of saturated fatty acids include, but are not limited to, stearic acid (C18:0) and palmitic acid (C16:0).

In some embodiments of any of the methods of screening for and/or identifying an SCD1 antagonist, the cancer cell, cancer tissue, and/or cancer sample comprises activated PI3K signaling, activated mTOR signaling, and/or activated MEK signaling. In some embodiments of any of the methods of screening for and/or identifying an SCD1 antagonist, the cancer cell, cancer tissue, and/or cancer sample comprises PI3K activating mutations. In some embodiments of any of the methods of screening for and/or identifying an SCD1 antagonist, the cancer cell, cancer tissue, and/or cancer sample comprises PTEN loss and/or mutations. In some embodiments of any of the methods of screening for and/or identifying an SCD1 antagonist, the cancer cell, cancer tissue, and/or cancer sample comprises p85 mutations. In some embodiments of any of the methods of screening for and/or identifying an SCD1 antagonist, the cancer cell, cancer tissue, and/or cancer sample comprises AKT activating mutations. In some embodiments of any of the methods of screening for and/or identifying an SCD1 antagonist, the cancer cell, cancer tissue, and/or cancer sample comprises elevated levels of phosphorylated AKT (e.g., pAKT $S^{473}$). In some embodiments of any of the methods of screening for and/or identifying an SCD1 antagonist, the cancer cell, cancer tissue, and/or cancer sample comprises TSC1/2 loss of function mutations.

In some embodiments of any of the methods of screening for and/or identifying an SCD1 antagonist, elevated expression refers to an overall increase of about any of 5%, 10%, 20%, 25%, 30%, 40%, 50%, 60%, 70%, 80%, 85%, 90%, 95%, 96%, 97%, 98%, 99% or greater, in the level of biomarker (e.g., protein or nucleic acid (e.g., gene or mRNA)), detected by standard art known methods such as those described herein, as compared to a reference sample, reference cell, reference tissue, control sample, control cell, or control tissue. In certain embodiments, the elevated expression refers to the increase in expression level/amount of a biomarker in the sample wherein the increase is at least about any of 1.5×, 1.75×, 2×, 3×, 4×, 5×, 6×, 7×, 8×, 9×, 10×, 25×, 50×, 75×, or 100× the expression level/amount of the respective biomarker in a reference sample, reference cell, reference tissue, control sample, control cell, or control tissue. In some embodiments, elevated expression refers to an overall increase of greater than about 1.5 fold, about 1.75 fold, about 2 fold, about 2.25 fold, about 2.5 fold, about 2.75 fold, about 3.0 fold, or about 3.25 fold as compared to a reference sample, reference cell, reference tissue, control sample, control cell, control tissue, or internal control (e.g., housekeeping gene).

In some embodiments of any of the methods of screening for and/or identifying an SCD1 antagonist, reduced expression refers to an overall reduction of about any of 5%, 10%, 20%, 25%, 30%, 40%, 50%, 60%, 70%, 80%, 85%, 90%, 95%, 96%, 97%, 98%, 99% or greater, in the level of biomarker (e.g., protein or nucleic acid (e.g., gene or mRNA)), detected by standard art known methods such as those described herein, as compared to a reference sample, reference cell, reference tissue, control sample, control cell, or control tissue. In certain embodiments, reduced expression refers to the decrease in expression level/amount of a biomarker in the sample wherein the decrease is at least about any of 0.9×, 0.8×, 0.7×, 0.6×, 0.5×, 0.4×, 0.3×, 0.2×, 0.1×, 0.05×, or 0.01× the expression level/amount of the respective biomarker in a reference sample, reference cell, reference tissue, control sample, control cell, or control tissue.

The growth inhibitory effects of an SCD1 antagonist described herein may be assessed by methods known in the art, e.g., using cells which express SCD1 either endogenously or following transfection with the respective gene(s). For example, appropriate tumor cell lines, and SCD1 polypeptide-transfected cells may be treated with an SCD1 antagonist described herein at various concentrations for a few days (e.g., 2-7) days and stained with crystal violet or MTT or analyzed by some other colorimetric assay. Another method of measuring proliferation would be by comparing $^3$H-thymidine uptake by the cells treated in the presence or absence an antibody, binding polypeptide or binding small molecule of the invention. After treatment, the cells are harvested and the amount of radioactivity incorporated into the DNA quantitated in a scintillation counter. Appropriate positive controls include treatment of a selected cell line with a growth inhibitory antagonist known to inhibit growth of that cell line. Growth inhibition of tumor cells in vivo can be determined in various ways known in the art.

Methods of determining the distribution of cell cycle stage, level of cell proliferation, and/or level of cell death are known in the art and are described in the examples herein. In some embodiments, cancer cell cycle arrest is arrest in G1.

In some embodiments, the SCD1 antagonist will inhibit cancer cell proliferation of the cancer cell, cancer tissue, or cancer sample in vitro or in vivo by about 25-100% compared to the untreated cancer cell, cancer tissue, or cancer sample, more preferably, by about 30-100%, and even more preferably by about 50-100% or about 70-100%. For example, growth inhibition can be measured at an SCD1 antagonist concentration of about 0.5 to about 30 μg/ml or about 0.5 nM to about 200 nM in cell culture, where the growth inhibition is determined 1-10 days after exposure of the tumor cells to the SCD1 candidate antagonist. The SCD1 antagonist is growth inhibitory in vivo if administration of the SCD1 candidate antagonist at about 1 μg/kg to about 100 mg/kg body weight results in reduction in tumor size or reduction of tumor cell proliferation within about 5 days to 3 months from the first administration of the SCD1 candidate antagonist, preferably within about 5 to 30 days.

To select for an SCD1 antagonist which induces cancer cell death, loss of membrane integrity as indicated by, e.g., propidium iodide (PI), trypan blue or 7AAD uptake may be assessed relative to a reference. A PI uptake assay can be performed in the absence of complement and immune effector cells. SCD1-expressing tumor cells are incubated with medium alone or medium containing the appropriate SCD1 antagonist. The cells are incubated for a 3-day time period.

Following each treatment, cells are washed and aliquoted into 35 mm strainer-capped 12×75 tubes (1 ml per tube, 3 tubes per treatment group) for removal of cell clumps. Tubes then receive PI (10 µg/ml). Samples may be analyzed using a FACSCAN® flow cytometer and FACSCONVERT® CellQuest software (Becton Dickinson). Those antibodies, binding polypeptides or binding small molecules that induce statistically significant levels of cell death as determined by PI uptake may be selected as cell death-inducing antibodies, binding polypeptides or binding small molecules. In some embodiments, cancer cell apoptosis is indicated by activation of caspase 3 and/or caspase 7.

To screen for an SCD1 antagonist which bind to an epitope or interact with on a polypeptide bound by an antibody of interest, a routine cross-blocking assay such as that described in Antibodies, A Laboratory Manual, Cold Spring Harbor Laboratory, Ed Harlow and David Lane (1988), can be performed. This assay can be used to determine if a test SCD1 antagonist binds the same site or epitope as a known antibody. Alternatively, or additionally, epitope mapping can be performed by methods known in the art. For example, the antibody sequence or binding polypeptide can be mutagenized such as by alanine scanning, to identify contact residues. The mutant antibody and/or mutant binding polypeptide is initially tested for binding with polyclonal antibody or binding polypeptide to ensure proper folding. In a different method, peptides corresponding to different regions of a polypeptide can be used in competition assays with the test antibodies or test binding polypeptides or with a test antibody or a test binding polypeptide and an antibody with a characterized or known epitope.

In some embodiments of any of the methods of screening and/or identifying, the SCD1 candidate antagonist is an antibody, binding polypeptide, binding small molecule, or polynucleotide. In some embodiments, the SCD1 candidate antagonist is an antibody. In some embodiments, the SCD1 antagonist is a small molecule.

In one aspect, an SCD1 antagonist is tested for its binding activity (e.g., antigen binding activity) by known methods such as ELISA, Western blot, etc.

VI. Pharmaceutical Formulations

Pharmaceutical formulations of an SCD1 antagonist as described herein are prepared by mixing such SCD1 antagonists having the desired degree of purity with one or more optional pharmaceutically acceptable carriers (*Remington's Pharmaceutical Sciences* 16th edition, Osol, A. Ed. (1980)), in the form of lyophilized formulations or aqueous solutions. In some embodiments, the SCD1 antagonist is a binding small molecule, an antibody, binding polypeptide, and/or polynucleotide. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized formulations are described in U.S. Pat. No. 6,267,958. Aqueous formulations include those described in U.S. Pat. No. 6,171,586 and WO2006/044908, the latter formulations including a histidine-acetate buffer.

The formulation herein may also contain more than one active ingredients as necessary for the particular indication being treated, preferably those with complementary activities that do not adversely affect each other. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody and/or binding polypeptide, which matrices are in the form of shaped articles, e.g., films, or microcapsules.

The formulations to be used for in vivo administration are generally sterile. Sterility may be readily accomplished, e.g., by filtration through sterile filtration membranes.

VII. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an SCD1 antagonist of the invention. The label or package insert indicates that the composition is used for treating the condition of choice. Moreover, the article of manufacture may comprise (a) a first container with a composition contained therein, wherein the composition comprises an SCD1 antagonist; and (b) a second container with a composition contained therein, wherein the composition comprises a further cytotoxic or otherwise therapeutic agent.

In some embodiments, the article of manufacture comprises a container, a label on said container, and a composition contained within said container; wherein the composition includes one or more reagents (e.g., primary antibodies that bind to one or more biomarkers or probes and/or primers to one or more of the biomarkers described herein), the label on the container indicating that the composition can be used to evaluate the presence of one or more biomarkers in a sample, and instructions for using the reagents for evaluating the presence of one or more biomarkers in a sample. The article of manufacture can further comprise a set of instructions and materials for preparing the sample and utilizing the reagents. In some embodiments, the article of manufacture may include reagents such as both a primary and secondary antibody, wherein the secondary antibody is conjugated to a label, e.g., an enzymatic label. In some embodiments, the article of manufacture one or more probes and/or primers to one or more of the biomarkers described herein.

In some embodiments of any of the articles of manufacture, the one or more biomarkers is FGFR3. In some embodiments of any of the articles of manufacture, the one or more biomarkers is phosphorylated FGFR3.

In some embodiments of any of the articles of manufacture, the one or more biomarkers is one or more genes of the FGFR3-regulated lipogenic signature. In some embodiments, the one or more genes of the FGFR3-regulated lipogenic signature comprises, consists of, or consists essential of one or more genes from the group consisting of SREBF1, G6PD, ACOT7, PTPLA, PCCB, FADS1, RDH11, ACER3, PDSS1, MVD, AGPAT5, HSD17B2, ACSL4, EBP, PIGW, LBR, ALLY, ADORA2B, GPCPD1, CYP24A1, ACSL3, MVK, ACSS2, FDPS, ELOVL5, HMGCR, LIPG, MEL DHCR7, LSS, ACAT2, FASN, CYP51A1, IDI1, FDFT1, FAR2, HMGCS1, SDR16C5, LDLR, MSMO1, INSIG1, DHRS9, LRP8, SQLE, PCSK9, SCD1, FABP4, and combinations thereof. In some embodiments, the one or more genes of the FGFR3-regulated lipogenic signature comprises, consists of, or consists essential of one or more genes from the group consisting of ELOVL5, HMGCR, LIPG, MEL DHCR7, LSS, ACAT2, FASN, CYP51A1, IDI1, FDFT1, FAR2, HMGCS1, SDR16C5, LDLR, MSMO1, INSIG1, DHRS9, LRP8, SQLE, PCSK9, SCD1, FABP4, and combinations thereof. In some embodiments, the one or more genes of the FGFR3-regulated lipogenic signature comprises, consists of, or consists essential of one or more genes from the group consisting of CYP51A1, IDI1, FDFT1, FAR2, HMGCS1, SDR16C5, LDLR, MSMO1, INSIG1, DHRS9, LRP8, SQLE, PCSK9, SCD1, FABP4, and combinations thereof. In some embodiments, the one or more genes of the FGFR3-regulated lipogenic signature comprises, consists of, or consists essential of one or more genes from the group consisting of LDLR, MSMO1, INSIG1, DHRS9, LRP8, SQLE, PCSK9, SCD1, FABP4, and combinations thereof. In some embodiments, the one or more genes of the FGFR3-regulated lipogenic signature comprises, consists of, or consists essential of one or more genes from the group consisting of SQLE, PCSK9, SCD1, FABP4, and combinations thereof. In some embodiments, the one or more genes of the FGFR3-regulated lipogenic signature comprises, consists of, or consists essential of SC4MOL.

In some embodiments of any of the articles of manufacture, the one or more biomarkers is mature SREBP1. In some embodiments of any of the articles of manufacture, the one or more biomarkers is Δ9 monounsaturaturated fatty acids. In some embodiments of any of the articles of manufacture, the one or more biomarkers is ratio of Δ9 monounsaturaturated fatty acids:saturated fatty acids. In some embodiments of any of the articles of manufacture, the one or more biomarkers is PI3K signaling, mTOR signaling, MEK signaling. In some embodiments of any of the articles of manufacture, the one or more biomarkers is one or more polymorphism in genes selected from the group consisting of PI3K, PTEN, p85, TSC1/2, and AKT. In some embodiments of any of the articles of manufacture, the one or more biomarkers is phosphorylated AKT.

Other optional components in the article of manufacture include one or more buffers (e.g., block buffer, wash buffer, substrate buffer, etc), other reagents such as substrate (e.g., chromogen) which is chemically altered by an enzymatic label, epitope retrieval solution, control samples (positive and/or negative controls), control slide(s) etc.

In some embodiments of any of the article of manufacture, the SCD1 antagonist is an antibody, binding polypeptide, binding small molecule, or polynucleotide. In some embodiments, the SCD1 antagonist is a small molecule. In some embodiments, the SCD1 antagonist is an antibody. In some embodiments, the antibody is a monoclonal antibody. In some embodiments, the antibody is a human, humanized, or chimeric antibody. In some embodiments, the antibody is an antibody fragment and the antibody fragment binds SCD1.

The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate described herein in place of or in addition to an SCD1 antagonist.

EXAMPLES

The following are examples of methods and compositions of the invention. It is understood that various other embodiments may be practiced, given the general description provided above.

Materials and Methods for Examples

Cell Culture, siRNA Transfection and Reagents

The human bladder cancer cell lines SW780, BFTC-905 and Ca129 were obtained from ATCC. RT112 cells were purchased from German Collection of Microorganisms and Cell Cultures (DSMZ, Germany). RT112 cells stably expressing doxycycline-inducible shRNAs targeting FGFR3 or EGFP were previously described in (24). Bladder cancer cell line UMUC-14 was obtained from Dr. H. B. Grossman (Currently at University of Texas M. D. Anderson Cancer Center, TX) from the University of Michigan. Bladder cancer cell line TCC-97-7 was a gift from Dr. Margret Knowles of St. James's University Hospital (Leeds, United Kingdom). The cells were maintained with RPMI medium supplemented with 10% fetal bovine serum (FBS) (Sigma), 100 U/ml penicillin, 0.1 mg/ml streptomycin and L-glutamine under conditions of 5% $CO_2$ at 37° C.

Rapamycin and PI3K inhibitor LY294002 were obtained from Cell Signaling Technology (Danvers, Mass.). A potent and selective MEK1/2 inhibitor PD0325901 (Pfizer) was purchased from Synthesis Med Chem (San Diego, Calif.). SCD1 small molecule inhibitor A37062 was purchased from BioFine International (Vancouver, Canada).

All RNA interferenec experiments were carried out with ON-TARGETplus siRNAs (50 nM, Dharmacon, Lafayette, Colo.). Cells were transfected with Lipofectamine RNAiMax (Invitrogen, Carlsbad, Calif.), and cell proliferation or apoptosis were assessed 48 hr or 72 hr after transfection.

Gene Expression Array and Analyses

RT112 cells expressing doxycline-inducible shRNAs targeting FGFR3 or EGFP were grown in 10 cm plates in the presence or absence of doxycycline (1 μg/ml) for 48 hr. Total RNA from sub-confluent cell cultures was isolated using RNAeasy kit (Qiagen). RNA quality was verified by running samples on an Agilent Bioanalyzer 2100, and samples of sufficient quality were profiled on Affymetrix HGU133-Plus_2.0 chips. Microarray studies were performed using triplicate RNA samples. Preparation of complementary RNA, array hybridizations, scanning, and subsequent array image data analysis were done following manufacturer's protocols. Expression summary values for all probe sets were calculated using the RMA algorithm as implemented in the affy package from Bioconductor. Statistical analyses of differentially expressed genes were performed using linear models and empirical Bayes moderated statistics as implemented in the limma package from Bioconductor. To obtain the biological processes that are over-represented by the differentially expressed genes, hypergeometric tests for association of Gene Ontology (G0) biological process categories and genes were performed using the GOstats and Category packages. Hierarchical clustering of the expression profile was performed using (1-Pearson's correlation) as the distance measure and Ward's minimum-variance method as the agglomeration method.

Quantitative RT-PCR Analyses of mRNA Expression Level

To detect transcripts of SREBP1, SREBP2, FASN, SCD1, SQLE, and HMGCoA synthase, quantitative RT-PCR was performed with pre-designed Taqman gene Expression assays (Applied Biosystems). All reactions were performed at least in duplicates. The relative amount of all mRNAs was calculated using the comparative CT method after normalization to human RPL19.

Analyses of Total Fatty Acid Synthesis

Lipogenic activity was determined by monitoring the incorporation of $[1,2-^{14}C]$ acetate (Perkin Elmer, Waltham, Mass.) into fatty acids as reported (39). $[1,2-^{14}C]$ acetate (0.5 μCi/mL in DMEM medium with 0.1% BSA) was added to cells and incubated at 37° C. for 4 hr. Cells were washed twice with ice cold PBS, scraped, and lysed in 2% KOH. Lysates were transferred to a test tube, and saponified overnight at 80° C. Sterol and other neutral lipids were extracted twice with diethyl ether. The lower phase was then neutralized with 6N HCl, and mixed with hexane twice to extract fatty acids. The fatty acids fractions were collected, dried under a steam of nitrogen, and analyzed by scintillation counting. The $[^{14}C]$ radioactivity was normalized to sample protein content.

SCD1 Activity Assay

SCD1 activity was determined by monitoring the desaturation of $[1-^{14}C]$ 18:0 stearate (American Radiolabeled Chemicals, St. Louis, Mo.) or the incorporation of $[1,2-^{14}C]$ acetate into monounsaturated fatty acid. Cells were incubated with the labeled substrates for 6-8 hr. Total lipids were isolated as described above, dissolved in 1 ml of 14% boron trifluoride in methanol, and incubated at 64° C. for 6 hr. After addition of 1 mL of water, methyl esters were extracted with 2 mL of hexane and separated by thin-layer chromatography (TLC) on a 10% argent impregnated silica gel plate using a solvent phase consisting of hexane/diethyl ether (85:15, v/v) following the procedure of Wilson and Sergeant. After separation, air-dried plates were exposed to x-ray film, and fatty acid spots on TLC were scrapped off and counted for radioactivity using a liquid scintillation spectrometer. SCD1 activity was expressed as the ratio of oleic on stearic methyl ester acids or palmitoleic on palmitic methyl ester acids.

Preparation of BSA-Complexed Oleate and Palmitate

A 50 mM oleate or palmitate stock solution was prepared in 4 mM NaOH using the sodium salt of oleate or palmtate (Sigma-Aldrich). Fatty acid-free BSA (Sigma-Aldrich) was prepared in distilled $H_2O$ at a final concentration of 4 mM. One volume of 50 mM stock of oleate or palmitate was combined with 1.5 volume of 4 mM BSA and heated to 55° C. for 1 hr to obtain a 20 mM stock solution of BSA-complexed oleate or palmitate at a fatty acid/BSA ratio of ~8.3:1.

Generation of SW780 Stable Cells Expressing SCD1 shRNA

Three independent SCD1 shRNAs were cloned into pG-pHUSH lentiviral vector Genentech developed. Detailed information of the vector would be provided upon request. The sequence for SCD1 shRNAs used in the studies is as follows: shRNA1: 5'-GATCCCCCTACAAGAGTGGCTG AGTTTTCAAGAGAAACTCAGCCACTCT-TGTAGTTTTTTGGAAA-3' (SEQ ID NO:2); shRNA2: 5'-GATCCCCCTACGGCTCTTTCTGATCAT-TCAAGAGATGATCAGAAAGAGCCGTAGTTTTT TGGAAA-3' (SEQ ID NO:3); shRNA3: 5'-GATCCCCGCA-CATCAACTTCACCACATTCAAGAGA TGTGGT-GAAGTTGATGTGCTTTTTTGGAAA-3' (SEQ ID NO:4). All constructs were confirmed by sequencing. EGFP control shRNA was described previously (24). The shRNA-containing lentivirus was produced by co-transfecting GNE293T cells with packaging plasmid delta 8.9, envelope plasmid VSV-G and pG-pHUSH-shRNA constructs. Viral supernatants were harvested 48 and 72 hr after transfection, and cleared of cell debris by filtering through a 0.45 μm syringe filter. Lentiviral transduction and stable cell selection were performed as described (24).

Cell Proliferation and Apoptosis Studies

For small interfering RNA experiments, at 72 hr after transfection, cells were processed for [Methyl-$^3$H] thymidine incorporation. For doxycycline-inducible shRNA experiments, cells were treated with or without 1 ng/mL doxycyline for 72 hr before further incubation with [$^3$H] thymidine for 16 hr. For SCD1 small molecule inhibitor experiment, cells were treated with indicated concentration of A37062 in DMSO or DMSO alone for 48 hr. Cell viability was assessed with CellTiter-Glo (Promega). Activation of caspase 3 and caspase 7 was measured with the Caspase-Glo 3/7 assay kit (Promega). Values are presented as mean+/−SD of quadruplets. Data are representative of at least three independent experiments.

For cell cycle analysis, cell suspensions were fixed in 70% ethanol and stained with 0.5 mL of propidium iodide and RNase staining buffer (BD Pharmingen) for 15 minutes at room temperature. For flow cytometry analysis of apoptosis, MitoTracker Red and Alexa Fluor 488-conjugated Annexin V were used to stain cells following manufacturer's instructions (Invitrogen). Flow cytometric data analysis and visualization were conducted using FlowJo v8.4 software (Tree Star, Inc.).

Protein Analyses

Cells were treated as described in the figure legends. For total cell lysates, cells were washed twice with ice-cold PBS and extracted in RIPA buffer (Millapore, Billerica, Mass.) supplemented with phosphatase inhibitor cocktail PhosSTOP and Complete protease inhibitor cocktail (Roche Applied Science, Indianapolis, Ind.). The lysates were cleared of insoluble materials by centrifugation. For analysis of protein expression in tumor xenografts, lysate from tumor tissues was extracted with lysis buffer (consisted of 150 mM sodium chloride, 20 mM Tris (pH 7.5), 2 M EDTA, 1% Triton X-100, 10 mM sodium fluoride, supplemented with protease inhibitors and phosphatase inhibitors) by pulverizing the frozen tissues using FastPrep-24 homogenizer as described by the manufacturer (MP Biomedicals, Irvine, Calif.).

To detect pFGFR3, FGFR3 was immunoprecipitated using a rabbit polyclonal antibody (sc-123, Santa Cruz Biotechnology, Santa Cruz, Calif.) and analyzed by sodium dodecyl-polyacrylamide gel electrophoresis (SDS-PAGE) and Western blot. Phosphorylated FGFR3 was assessed with a monoclonal antibody against phospho-tyrosine (4G10, Millipore) or pFGFR$^{Y653/645}$ (#3476, Cell Signaling Technology, Danvers, Mass.). To detect SCD1 in tumor tissues, SCD1 was immunoprecipitated from equal amount of lysates using a mouse monoclonal antibody (GTX19862, GeneTex, Irvine, Calif.) and probed with a rabbit SCD1 antibody (#2438, Cell Signaling Technology).

Primary blotting antibodies used are FGFR3 (sc-13121, Santa Cruz Biotechnology), SREBP1 (sc-13551, Santa Cruz Biotechnology), SREBP2 (557037, BD Pharmingen), total FRS2 (sc-8318, Santa Cruz Biotechnology), pAKT$^{T308}$ (#2214-1, Epitomics). The following primary antibodies were purchased from Cell Signaling Technology: pFRS2$^{Y196}$ (#3864), FASN (#3189), pAKT$^{S473}$ (#4060), total AKT (#9272), pMAPK (#9101), total MAPK (#4695), pS6 (#2211), cleaved caspase 3 (#9664), total caspase 3 (#9665), cleaved caspase 7 (#9491), total caspase 7 (#9492), and PARP (#9542). The blots were visualized using a chemiluminescent substrate (ECL Plus, Amersham Pharmacia Biotech, Piscataway, N.J.).

Xenograft Studies

Figure 18:
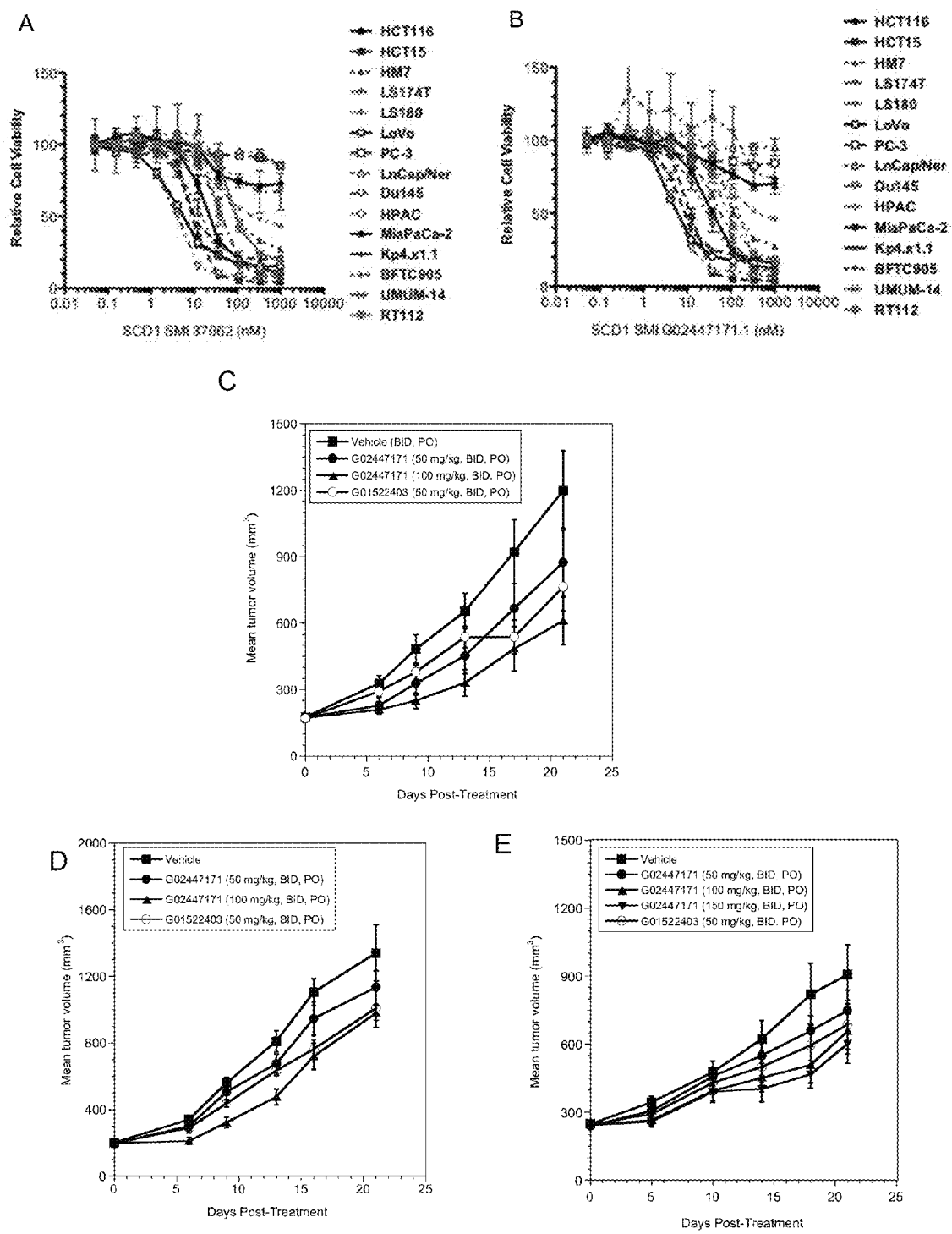
FIG. 18. Pharmacological inhibition of SCD1 reduces cell viability and increases caspases 3/7 activity in a panel of human cancer cell lines, including colon, prostate, pancreatic, and bladder cancers and attenuates tumor growth in mice. (A) SCD1 small molecule inhibitor A37062 reduces cell viability of human cancer cells. (B) SCD1 small molecule inhibitor G02447171.1 reduces cell viability of human cancer cells. (C) SCD1 small molecule inhibitors delay xenograft growth of pre-established HCT15 colon tumors. (D) SCD1 small molecule inhibitors delay xenograft growth of pre-established SW780 bladder tumors. (E) SCD1 small molecule inhibitors delay xenograft growth of pre-established HPAC pancreatic tumors.

Female CB17 severe combined immunodeficiency (SCID) mice, 6-8 weeks of age, were purchased from Charles River Laboratory (Hollister, Calif.). Female athymic nude mice were obtained from Harlan Laboratory (Hayward, Calif.). Mice were maintained under specific pathogen-free conditions. SW780 shRNA stable cells ($7\times10^6$) were implanted subcutaneously into the flank of CB17.SCID mice in a volume of 0.2 ml in HBSS/matrigel (1:1 v/v, BD Biosciences). UMUC-14 cells ($5\times10^6$) and HCT-15 cells ($5\times10^6$) were implanted into athymic nude mice without matrigel. For efficacy studies, mice with tumors of a mean volume of 150 to 200 mm$^3$ were randomly grouped into treatment cohorts of 8 or 10. For shRNA studies, mice were given sucrose H$_2$O alone or supplemented with 1 mg/mL doxycycline. SCD1 inhibitor A37062 (75 mg/kg) or the vehicle control was administered twice daily by oral gavage for 21 days. For the experiments of FIG. 18, different doses of SCD1 inhibitors G02447171 and A37062, or the vehicle control was administered twice daily by oral gavage for 21 days. Tumor volume results are presented as mean tumor volume+/−SEM and data were analyzed by Student's t test. Body weights and caliper measurement were taken twice weekly, and tumor volume was calculated using the formula: $V=0.5\ a\times b^2$, where a and b are the length and width of the tumor, respectively. Tumor volume results are presented as mean tumor volume+/−SEM and data were analyzed by Student's t test.

To analyze fatty acid desaturation in tumor tissues and mouse plasma and liver, samples were collected at the end of the efficacy study (2 hr after the last dose) and snap frozen. Fatty acid profiling was performed by Microbial ID, Inc (Newark, Del.) using a standard sample preparation method for saponification and methylation. The fatty acid methyl esters were extracted and loaded onto the gas chromatograph for analysis. Desaturation index was expressed as the ratio of oleic on stearic methyl ester acids or palmitoleic on palmitic methyl ester acids.

Statistics

Pooled data were expressed as mean+/−SEM. Unpaired Student's t tests (2-tailed) were used for comparison between two groups. A value of P<0.05 was considered statistically significant in all experiments.

Cell Viability and Caspase 3/7 Activity Assays

For SCD1 small molecule inhibitor experiment, cells were treated with indicated concentration of A37062 (Abbott compound 4c) or G02447171.1 (Daichii compound 24) in DMSO or DMSO alone for 48-72 hr. Cell viability was assessed with CellTiter-Glo at 72 hr post treatment (Promega). Activation of caspase 3 and caspase 7 was measured with the Caspase-Glo 3/7 assay kit at 48 hr after treatment (Promega). Values are presented as mean+/−SD of quadruplets. Data are representative of at least three independent experiments.

Example 1

Figure 2:
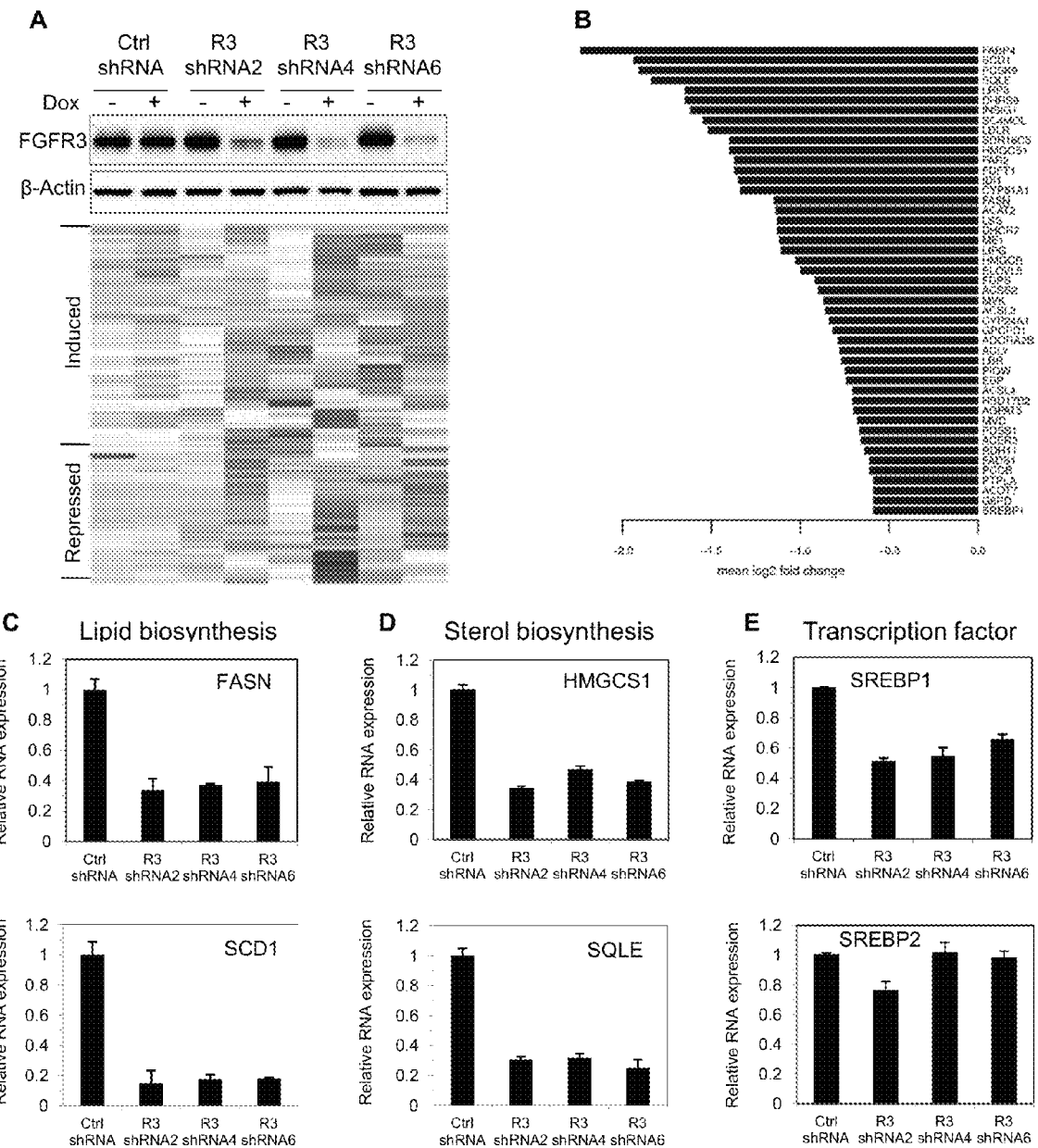
FIG. 2. FGFR3 knockdown reduces the expression of genes involved in sterol and fatty acid biosynthesis and metabolism. (A) Heat map of the probes found to be regulated by FGFR3 knockdown. RT112 bladder cancer cells expressing three independent doxycycline-inducible FGFR3 shRNAs or a control shRNA (Ctrl) were cultured with or without 1 μg/mL doxycycline for 2 days prior to RNA extraction. Total RNA was subjected to microarray studies. Genes that are regulated by all three FGFR3 shRNAs were shown in the heat map. Top panel shows FGFR3 protein level. (B) A cohort of genes involved in cholesterol and lipid biosynthesis are repressed in FGFR3 knockdown cell. (C, D) Confirmation of FGFR3-regulated lipogenic genes by qRT-PCR. The mRNA level of representative genes from lipid (C) and sterol biosynthesis pathways (D) was measured by qRT-PCR. Data are presented as mean+/−SD. (E) FGFR3 knockdown reduces SREBP1 expression modestly, but not SREBP2. SREBP1 and SREBP2 mRNA level was analyzed by qRT-PCR. Data are presented as mean+/−SD.

FGFR3 Knockdown Suppresses the Expression of Genes Involved in Sterol and Fatty Acid Biosynthesis and Metabolism Using doxycycline-inducible shRNA, knockdown of FGFR3 in bladder cancer cell line RT112 significantly attenuated tumor growth in vitro and in vivo as previously shown in Qing et al. J. Clin. Invest. 119(5):1216-1229 (2009). To identify potential FGFR3-downstream targets, the transcriptional profile of RT112-derived cell lines that express either the control shRNA or three independent FGFR3 shRNAs was compared. The use of three RT112-derived cell lines expressing different FGFR3 shRNAs provided a control for non-specific difference in these independently established cell lines. All cell lines were treated with or without doxycycline for 48 hours to deplete FGFR3 protein prior to the isolation of mRNA for microarray analysis (FIG. 2A). Genes that were differentially expressed (false discovery rate<0.1, fold change>2) upon doxycycline induction in all three FGFR3 shRNA cell lines but not in the control shRNA cells were considered potential FGFR3-regulated genes (FIG. 1). Among the 19,701 genes represented on the array, 313 genes showed consistent differential expression in response to FGFR3 knockdown, with 196 unregulated and 117 down-regulated (FIG. 2A and FIG. 1; see also Table 2).

Figure 3:
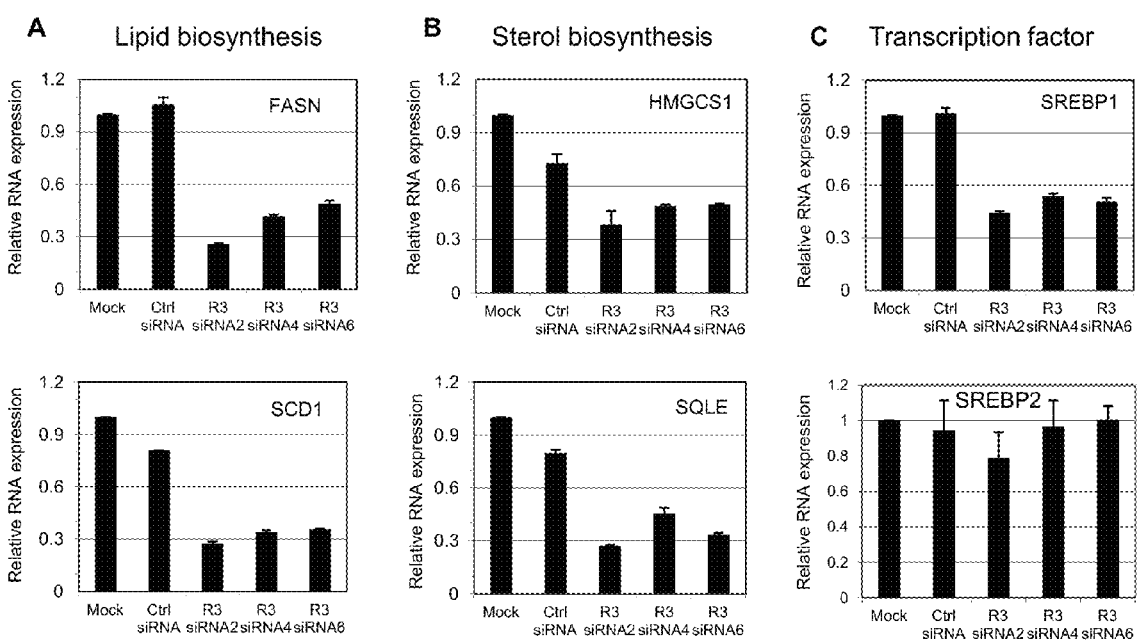
FIG. 3. FGFR3 siRNAs reduce the expression of genes involved in sterol and fatty acid biosynthesis and metabolism in UMUC-14 cells. UMUC-14 bladder cancer cells were transfected with FGFR3 siRNA or a non-targeting control siRNA (Ctrl), and total RNA was extracted 48 hr after transfection. The mRNA level of representative genes from lipid (A) and sterol biosynthesis pathways (B) was measured by qRT-PCR. Data are presented as mean+/−SD. (C) FGFR3 knockdown reduces SREBP1 expression modestly, but not SREBP2. SREBP1 and SREBP2 mRNA level was analyzed by qRT-PCR. Data are presented as mean+/−SD.

Functional classification of these FGFR3-modulated genes revealed that a large fraction of the significantly downregulated genes (with a p value <0.01) encode a cohort of enzymes and proteins that are involved in fatty acid and sterol biosynthesis and metabolism (FIG. 2B). SCD1, a rate-limiting enzyme catalyzing the conversion of saturated fatty acids into monounsaturated fatty acids, was among the genes showing the greatest decline (down by 3.85 fold, FIG. 2B). This cluster also included fatty acid synthase (FASN), hydroxymethylglutaryl-coenzyme A synthase 1 (HMGCS1), and squalene epoxidase (SQLE) (FIG. 2B). The microarray results were further confirmed using quantitative RT-PCR (qRT-PCR) analysis of the mRNA abundance level of representative genes (FIGS. 2C and D). In addition, the FGFR3-dependent regulation of these lipogenic genes was also verified in bladder cancer cell line UMUC-14 with short-interfering RNA (siRNA)-mediated FGFR3 knockdown (FIGS. 3A and B). Together, these data suggest a major effect of FGFR3 signaling on sterol and lipid biosynthesis and metabolism pathways.

In addition, a specific anti-FGFR3 antibody, R3Mab, reduced the expression of lipogenic genes in UMUC-14 tumor xenograft. UMUC-14 xenograft tumors were treated with a control antibody (Ctrl Ab) or R3Mab, and tumor tissues were harvested at Day 5. Total RNA was isolated from tumor tissues for microarray analysis. Genes shown significant modulation by R3Mab compared with Ctrl Ab were further analyzed. All the genes and further including SC4MOL were similarly downregulated as using si-RNA-mediated FGFR3 knockdown.

Since a large number of these lipogenesis genes identified in our expression array study are regulated by the SREBP family of master transcriptional factors, SREBP1 and SREBP2 mRNA level were examined using qRT-PCR and found that FGFR3 knockdown in RT112 cells modestly reduced SREBP1 mRNA level by about 50%, and had no effect on SREBP2 level (FIG. 2E). Similar results were observed in UMUC-14 cells transfected with FGFR3 siRNA (FIG. 3C). These data raised the possibility that FGFR3 signaling may regulate de novo lipogenesis in part through SREBP1.

Example 2

FGFR3 Knockdown Inhibits Fatty Acid Synthesis and Desaturation

Figure 4:
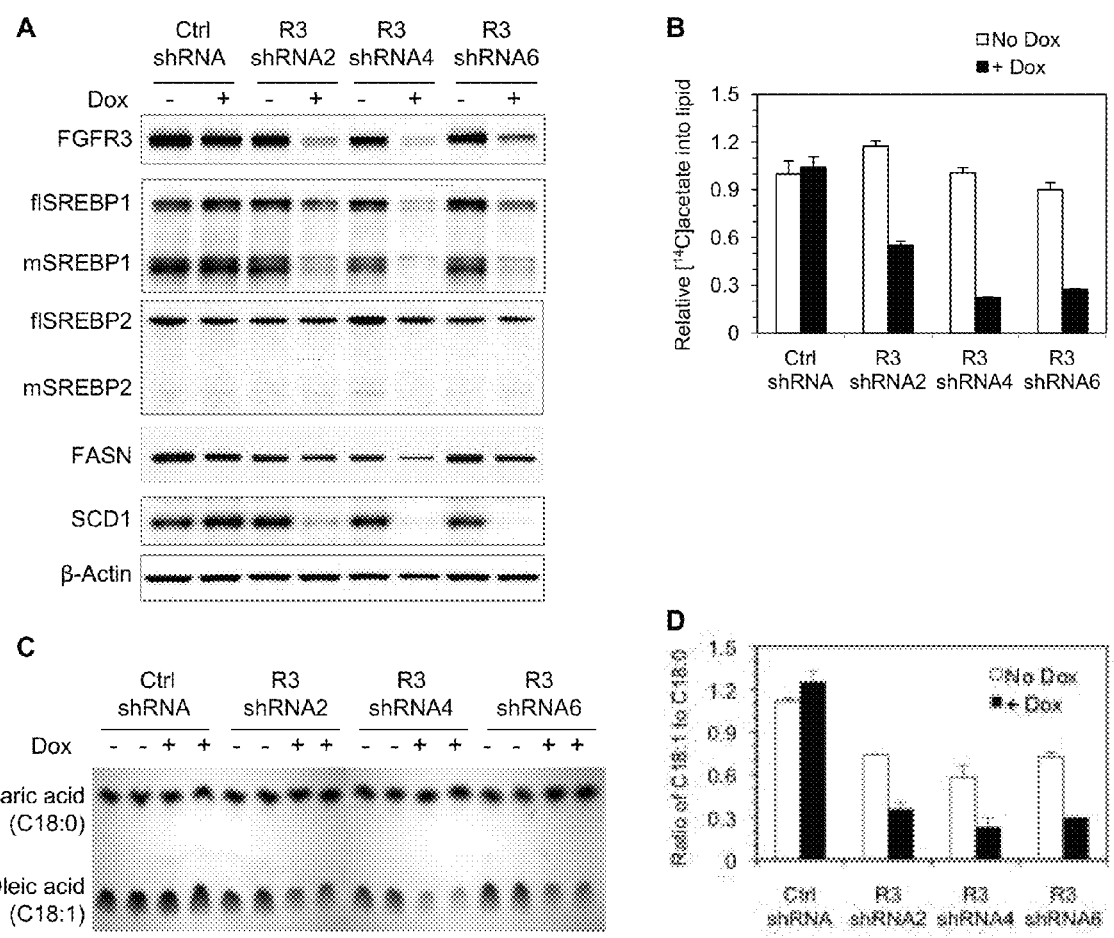
FIG. 4. Reduced expression of SREBP1, FASN and SCD1 in FGFR3 knockdown cells correlates with decreased fatty acid synthesis and desaturation. (A) FGFR3 knockdown reduces the expression of SREBP1, FASN and SCD1. RT112 bladder cancer cells expressing doxycycline-inducible FGFR3 shRNAs or a control shRNA (Ctrl) were cultured with or without 1 μg/mL doxycycline for 3 days prior to harvest. Cell lysates were subjected to immunoblot analyses. (B) FGFR3 knockdown suppresses lipid biosynthesis. RT112 cells were cultured with or without 1 μg/mL doxycycline for 3 days prior to 4 hr incubation with [$^{14}$C]acetate. The lipid fraction was extracted and [$^{14}$C]acetate incorporated into lipids was measured by scintillation counting. Data were normalized to sample protein content, and presented as mean+/−SD. (C, D) FGFR3 knockdown blocks stearic acid desaturation. RT112 cells were cultured with or without 1 μg/mL doxycycline for 3 days prior to 6 hr incubation with [$^{14}$C]stearic acid. [$^{14}$C]stearic acid desaturation was analyzed by argentation thin-layer chromatography (C) and measured by scintillation counting (D). Data are presented as mean+/−SD, and representative of three independent experiments.
Figure 5:
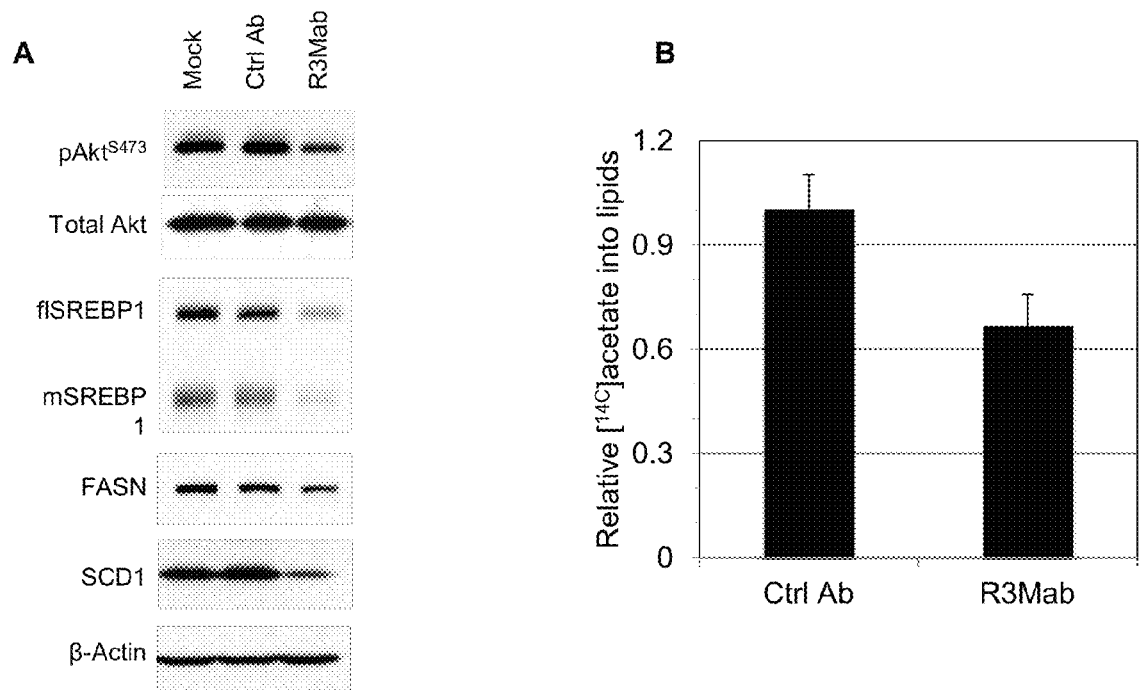
FIG. 5. Anti-FGFR3 monoclonal antibody, R3Mab, reduces expression of SREBP1, FASN and SCD1 and fatty acid synthesis in UMUC-14 cells. (A) UMUC-14 bladder cancer cells were cultured in 1% FBS medium and treated with 15 ug/mL anti-FGFR3 antibody, R3Mab, or a control antibody (Ctrl Ab) for 48 hr. Cell lysates were subjected to Western blot analysis. (B) UMUC-14 cells were cultured in 1% FBS medium containing 15 μg/mL R3Mab or the Ctrl Ab for 48 hr, with [$^{14}$C]acetate added at the final four hr. [$^{14}$C] acetate incorporation into the lipid fraction was extracted and measured by scintillation counting. Data were normalized to total protein level in each sample, and presented as mean+/−SD.

Based on the microarray and qRT-PCR results, the role of FGFR3 signaling in regulating lipogenesis and the cellular consequence was investigated. First SREBP1 expression and activation upon FGFR3 knockdown was examined. It is known that in response to cholesterol and fatty acid deprivation, SREBP1 undergoes N-terminal proteolytic cleavage and subsequent nuclear translocation to elicit the transcriptional induction of lipogenic enzymes. Induction of FGFR3 shRNAs by doxycycline diminished FGFR3 protein level (FIG. 4A). Doxycycline treatment also reduced the full-length as well as the cleaved mature form of SREBP1, but had no effect on full-length or processed SREBP2 (FIG. 4A). A modest reduction in FASN and a pronounced decrease in SCD1 level were observed in cells expressing FGFR3 shRNA, but not in control shRNA cells (FIG. 4A). Further analysis of RT112 cells incubated with $[1,2-^{14}C]$ acetate revealed that FGFR3 knockdown markedly reduced fatty acid synthesis (FIG. 4B). Consistent with this observation, a 24 hour-treatment of UMUC-14 cells with an anti-FGFR3 specific antibody, R3Mab (see WO 2010/111367, which is incorporated by reference in its entirety), also decreased the level of the full-length and processed active form of SREBP1, as well as the expression of FASN and SCD1 (FIG. 5A). Similarly, total fatty acid synthesis was reduced by R3Mab in UMUC-14 cells (FIG. 5B).

Since FGFR3 knockdown almost abolished SCD1 expression, and SCD1 is the rate-limiting enzyme in the biosynthesis of monounsaturated fatty acid, the effect of FGFR3 shRNA on fatty acid desaturation was examined using [14C]-labeled stearic acid. FGFR3 shRNA blocked the production of unsaturated oleic acid from the saturated stearic acid precursor, whereas the control shRNA had no effect (FIGS. 4C and D). Together, these results suggest that FGFR3 inhibition caused a marked reduction of de novo fatty acid synthesis and desaturation, accompanied by decreased SREBP1 expression and/or cleavage as well as a reduction of key lipogenic enzymes, including FASN and SCD1.

Example 3

FGFR3 Signaling Activates SREBP1 and Promotes De Novo Fatty Acid Synthesis Through PI3K-mTORC1

Figure 6:
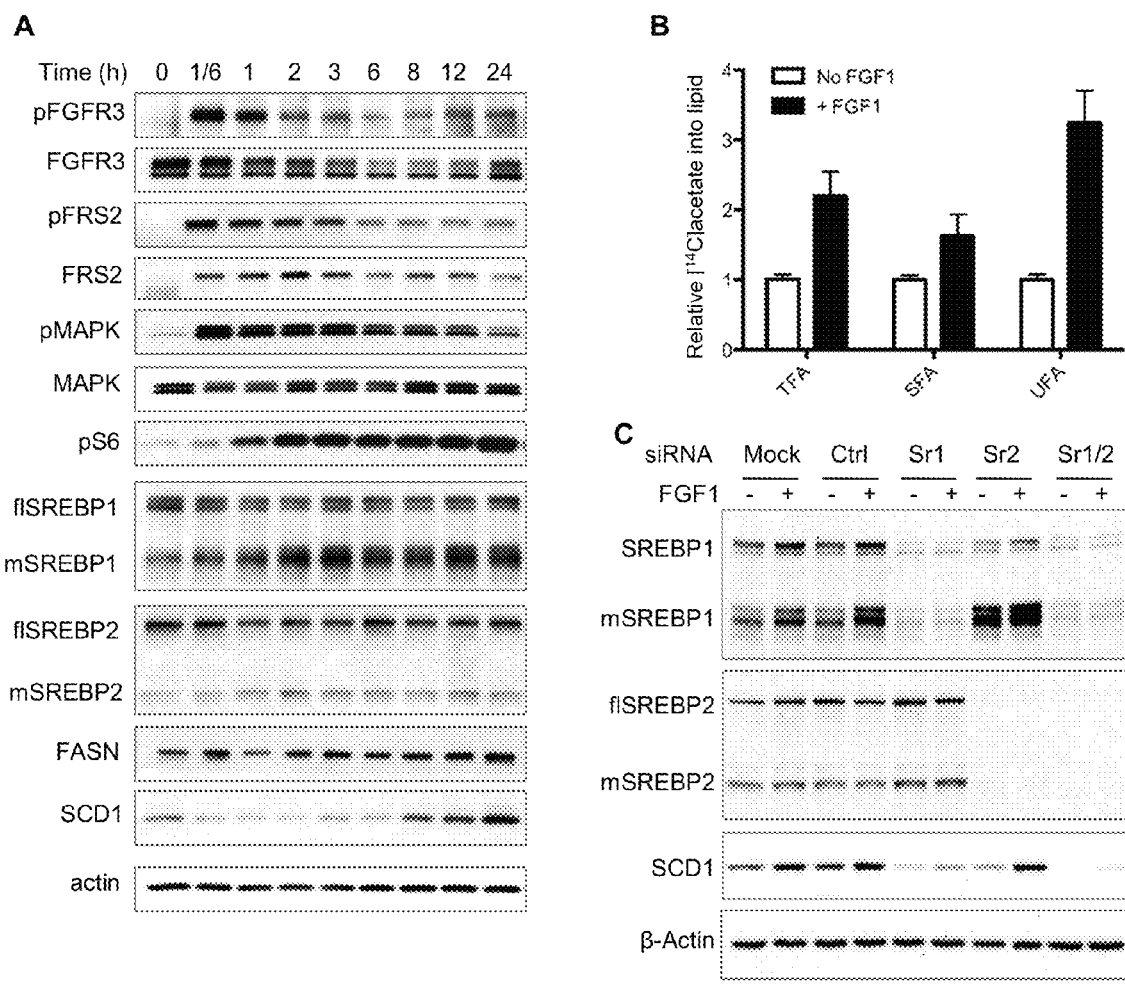
FIG. 6. FGFR3 signalling promotes lipogenesis in an SREBP1-dependent manner. (A) FGF1-FGFR3 axis stimulates the accumulation of matured SREBP1 and the expression of FASN and SCD1. Ca129 bladder cancer cells were serum starved for 20 hr, then treated with FGF1 (25 ng/mL) and heparin (10 μg/mL) for indicated time. Cell lysates were immunoprecipitated with anti-FGFR3 antibody and assessed for FGFR3 phosphorylation with an anti-phospho-tyrosine antibody (4G10). Lysates were also immunoblotted to detect indicated proteins as described in Methods. (B) FGF1 stimulates fatty acid synthesis in Ca129 cells. Ca129 cells were serum starved for 20 hr, then incubated with 25 ng/mL of FGF1 and 10 μg/mL of heparin for 24 hr. [$^{14}$C]acetate was added for another 16 hr incubation. $^{14}$C incorporation into total fatty acid (TFA), saturated (SFA) and unsaturated fatty acids (UFA) was measured by scintillation counting. Data are normalized to sample protein content and presented as mean+/−SD relative to no FGF1 treatment, and are representative of three independent experiments. (C) FGF1 stimulates SCD1 expression mainly through SREBP1. RT112 cells were transfected with siRNA targeting SREBP1 (Sr1), SREBP2 (Sr2), or a non-targeting control siRNA (Ctrl). At 24 hr after transfection, cells were serum starved for 20 hr, then treated with FGF1 (25 ng/mL) and heparin (10 μg/mL) for 24 hr. Total cell lysates were subjected to immunoblot analyses.
Figure 7:
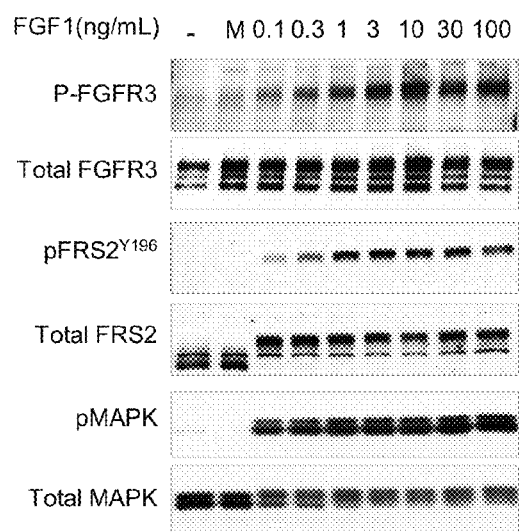
FIG. 7. FGF1 stimulates SREBP1 activation and lipogenesis in bladder cancer cells. (A, B) Dose response of FGF1-induced FGFR3 activation in Ca129 (A) and RT112 (B) bladder cancer cells. Ca129 and RT112 cells were serum starved for 20 hr, then treated with different doses of FGF1 plus 10 μg/ml heparin for 10 minutes. Cell lysates were subjected to immunoblot analyses with indicated antibodies. FGFR3 phosphorylation was analyzed as described in Methods. Note that in Ca129 cells, phosphorylated FRS2 displays apparent mobility shift. (C) FGF1 stimulates SREBP1 expression and maturation, and FASN and SCD1 expression. RT112 bladder cancer cells were serum starved for 20 hr, then treated with 30 ng/mL FGF1 plus 10 μg/ml heparin for indicated time. Total cell lysates were subjected to Western blot analyses. (D) FGF1 stimulates fatty acid synthesis. RT112 cells were serum-starved for 20 hr, then incubated with 30 ng/mL of FGF1 plus 10 μg/ml of heparin for 24 hr. [$^{14}$C]acetate was added for the final 16 hr. [$^{14}$C]acetate incorporation into saturated (SFA) and unsaturated fatty acids (UFA) was measured by scintillation counting. Data are normalized to total protein level and presented as mean+/−SD relative to no FGF1 treatment, and are representative of two independent experiments.
Figure 7:
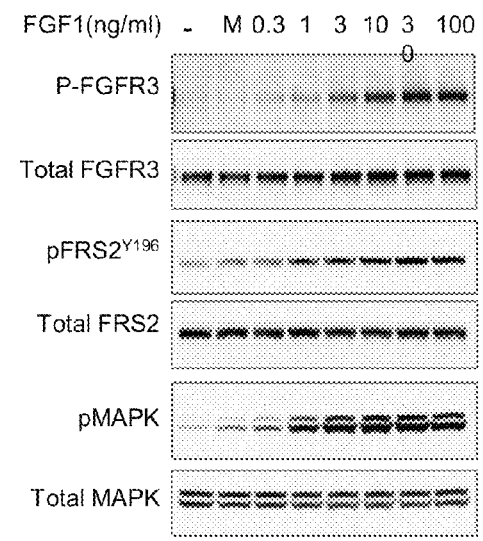
Figure 7:
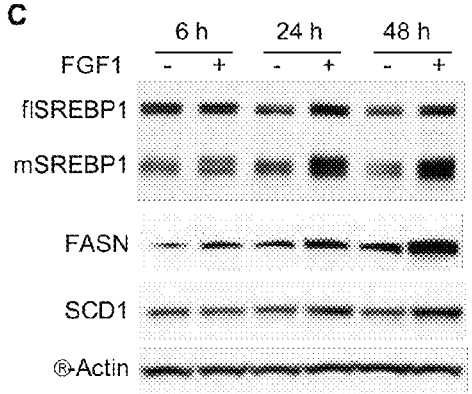
Figure 7:
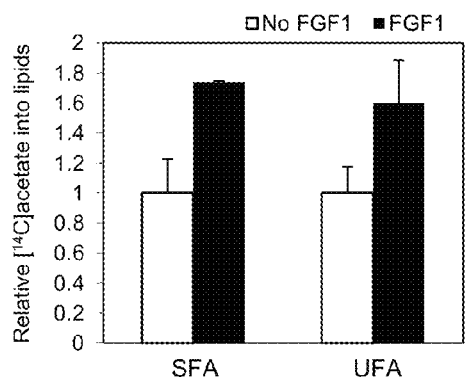

To dissect out the molecular circuitry underlying the FGFR3 regulation of de novo lipogenesis, FGFR3 signaling in bladder cancer cells was activated with FGF1, and SREBP1 expression and cleavage was analyzed. Ca129 bladder cancer cell line expresses high level of FGFR3 endogenously, and FGF1 treatment induced a robust phosphorylation and activation of FGFR3 and downstream signaling effectors in a time- and dose-dependent manner (FIG. 6A and FIG. 7A). While FGF1 did not affect full-length inactive SREBP1 protein level, the cleaved active form of SREBP1 was substantially higher after 2 hr treatment and the accumulation sustained for the entire course of the experiment at 24 hr (FIG. 6A). By contrast, neither full-length nor the processed SREBP2 was affected. Similarly, SCD1 protein level, and FASN to a lesser extent, were induced by FGF1 (FIG. 6A). Consistent with these changes, FGF1 increased the synthesis of total fatty acid after 24-hour incubation (FIG. 6B). Fractionation analysis revealed that both saturated and unsaturated fatty acids were induced by FGF1 (FIG. 6B). Similar results were observed in RT112 cells with a slower kinetics, with modest increase in full-length SREBP1, and the accumulation of active SREBP1 peaked around 24 hr post-treatment (FIG. 7B, C and D).

To determine whether the induction of lipogenic enzymes such as SCD1 by FGF1 stimulation depends on the processed active SREBP1, SREBP1 or SREBP2 expression was depleted using siRNAs in RT112 cells. siRNAs targeting SREBP1 markedly reduced both basal and FGF1-induced SCD1 expression, whereas knockdown of SREBP2 alone had no effect (FIG. 6C). Of interest, targeting both SREBP1 and SREBP2 almost completely abolished SCD1 expression (FIG. 6C), suggesting that although SREBP1 plays a dominant role in regulating SCD1 expression, both SREBP1 and SREBP2 contribute to maximal induction of SCD1 upon FGF1 stimulation. Similarly, the induction of FASN also depends on both SREBP1 and SREBP2, with SREBP1 playing a more prominent role (Data not shown).

Figure 8:
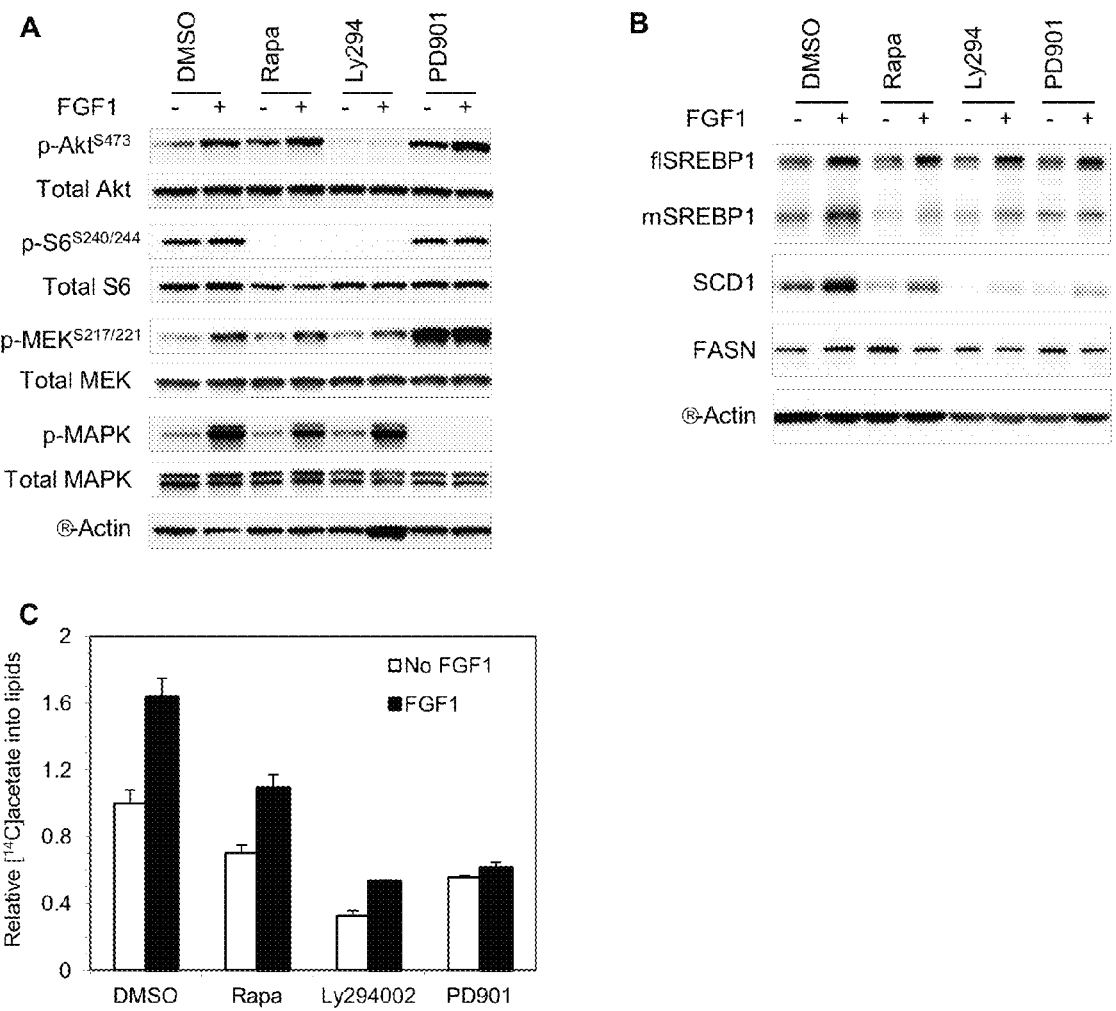
FIG. 8. FGFR3 signalling promotes the accumulation of matured SREBP1 and lipogenesis via PI3K-mTORC1 pathway. (A) Pharmacological inhibition of FGFR3 signalling. RT112 cells were serum starved for 20 hr, then treated with rapamycin (50 nM), Ly294002 (Ly294, 20 μM) and PD325901(PD901, 100 nM) for 2 hr, followed by stimulation with 30 ng/ml FGF1 plus 10 μg/mL of heparin for 10 min. Cell lysates were subjected to immunoblot analyses with indicated antibodies. Note the increased phosphorylation of MEK upon PD901 treatment, presumably due to a relief of feedback inhibition. (B) PI3K-mTORC1 and MEK inhibitors block FGF1 induction of SREBP1 and SCD1 in RT112 cells. RT112 cells were serum starved for 20 hr, treated with kinase inhibitors for 4 hr, followed by 24 hr incubation in medium supplemented with 30 ng/ml FGF1. Cell lysates were immunoblotted to detect SREBP1 maturation, SCD1 and FASN expression. (C) PI3K-mTORC1 and MEK inhibitors block FGF1-stimulated lipid synthesis. RT112 cells were treated the same as described in (B). [$^{14}$C]acetate was added for the final 4 hr incubation. The lipid fraction was extracted and [$^{14}$C]acetate incorporated into lipids was measured by scintillation counting. Data were normalized to sample protein content, and presented as mean+/−SD. These data are representative of two independent experiments.
Figure 9:
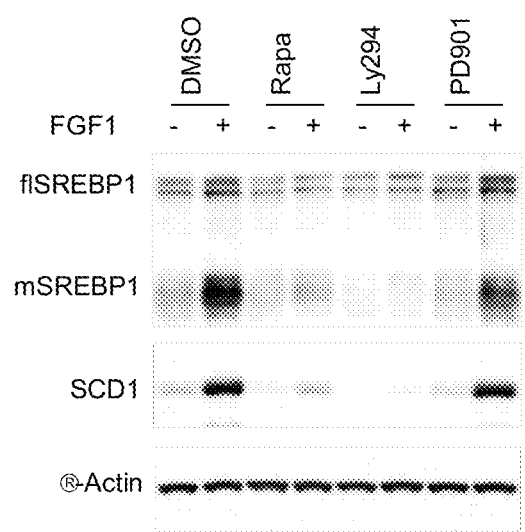
FIG. 9. FGFR3 signalling promotes the accumulation of matured SREBP1 and SCD1 expression via PI3K-mTORC1 pathway but not MEK-MAPK pathway in Ca129 cells. Ca129 cells were serum starved for 20 hr, treated for 4 hr with vehicle (DMSO), 50 nM rapamycin (Rapa), Ly294002 (Ly294, 20 μM) and PD325901(PD901, 100 nM). Then cells were cultured in medium supplemented with 30 ng/ml FGF1 for 24 hr. Cell lysates were analyzed by Western blot.

To assess the involvement of FGFR3 downstream signaling cascades in the regulation of lipogenesis, the canonical FGFR3 signaling was pharmacologically blocked at multiple nodes with the PI3K inhibitor Ly294002, mTORC1 inhibitor rapamycin, and a potent and selective MEK1/2 inhibitor PD325901. In RT112 bladder cancer cells, each inhibitor blunted FGF1-induced activation of their intended target, as assessed by the phosphorylation of AKT, S6, and MAPK respectively (FIG. 8A). While the inhibitors elicited minimal effect on the expression of full-length SREBP1 protein, they all substantially reduced both basal and FGF1-induced level of the cleaved active SREBP1 (FIG. 8B). Coordinately, SCD1 expression was diminished significantly by each of the inhibitors, with PI3K inhibitor Ly294002 showing strongest inhibition. FASN expression was reduced only modestly by each of the inhibitor (FIG. 8B). Treatment of RT112 cells with the inhibitors markedly suppressed total fatty acid synthesis stimulated by FGF1, with Ly294002 and PD325901 showing most potent inhibitory effect (FIG. 8C). It's worth noting that in Ca129 bladder cancer cells, rapamycin and Ly294002 blocked the accumulation of active SREBP1 and the expression of SCD1, consistent with the results observed in RT112 cells (FIG. 9). However, in Ca129 cells, the selective MEK1/2 inhibitor PD325901 only partially reduced FGF1-induced accumulation of active SREBP1, and did not have much effect on SCD1 induction (FIG. 9). Thus, in bladder cancer cells, FGFR3 mainly signals through PI3K-mTORC1 axis to promote SREBP1 cleavage and activation, resulting in elevated de novo lipogenesis and fatty acid desaturation. The contribution of MEK-MAPK pathway may be cell line- and/or context-dependent.

Example 4 siRNA-Mediated Knockdown of SCD1 Blocks Cell Cycle Progression and Induces Apoptosis in Bladder Cancer Cells with Active FGFR3 Signaling De novo lipogenesis is necessary for rapidly proliferating cells to form new membranes and organelles, a prerequisite for cell growth and proliferation. Lipids and their metabolic intermediate can also regulate signal transduction through lipidation of signaling molecules, modulation of subcellular localization of proteins, or serving as second messengers. Thus, it has been postulated that certain cancer types, including breast, prostate and glioblastomas, rely on de novo fatty acid synthesis for uncontrolled cell proliferation and survival (33). To examine the importance of FGFR3-stimulated lipogenesis in bladder tumor growth and to explore the potential of lipogenic pathway as a therapeutic target, cell proliferation following siRNA-mediated knockdown of SREBP1, FASN and SCD1 was accessed. Our initial studies revealed that SCD1 siRNAs elicited the strongest anti-proliferative effect and therefore, SCD1 was further investigated (data not shown).

Figure 10:
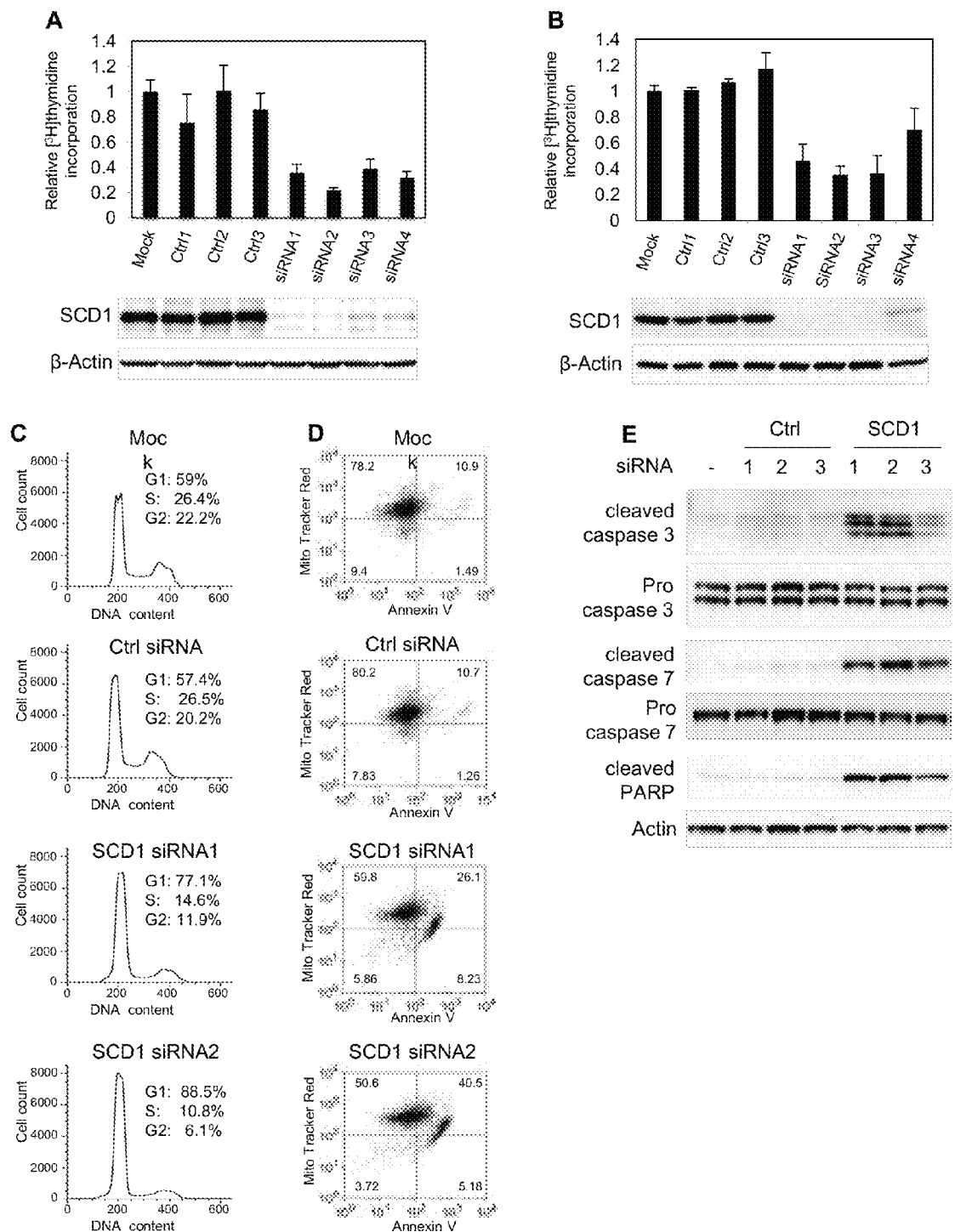
FIG. 10. SCD1 knockdown inhibits cell proliferation and induces apoptosis. SW780 (A) and UMUC-14 (B) cells were transfected with SCD1 siRNAs or three non-targeting control siRNAs (Ctrl), and cell proliferation was measured by [$^3$H] thymidine incorporation at 72 hr after transfection. Data are presented as mean+/−SD relative to cells transfected with RNAiMax alone (Mock), and are representative of three independent experiments. Lower panel: Representative Western blots showing SCD1 level in siRNA transfected cells. (C, D) SCD1 knockdown leads to G1 cell cycle arrest (C) and apoptosis (D) in SW780 cells. Cells were analyzed at 48 hr after transfection as described in Methods. (E) SCD1 knockdown induces caspases 3/7 cleavage and activation. UMUC-14 cells were transfected with SCD1 siRNAs or three non-targeting control siRNAs (Ctrl), and cell lysates were subjected to immunoblot analysis.
Figure 11:
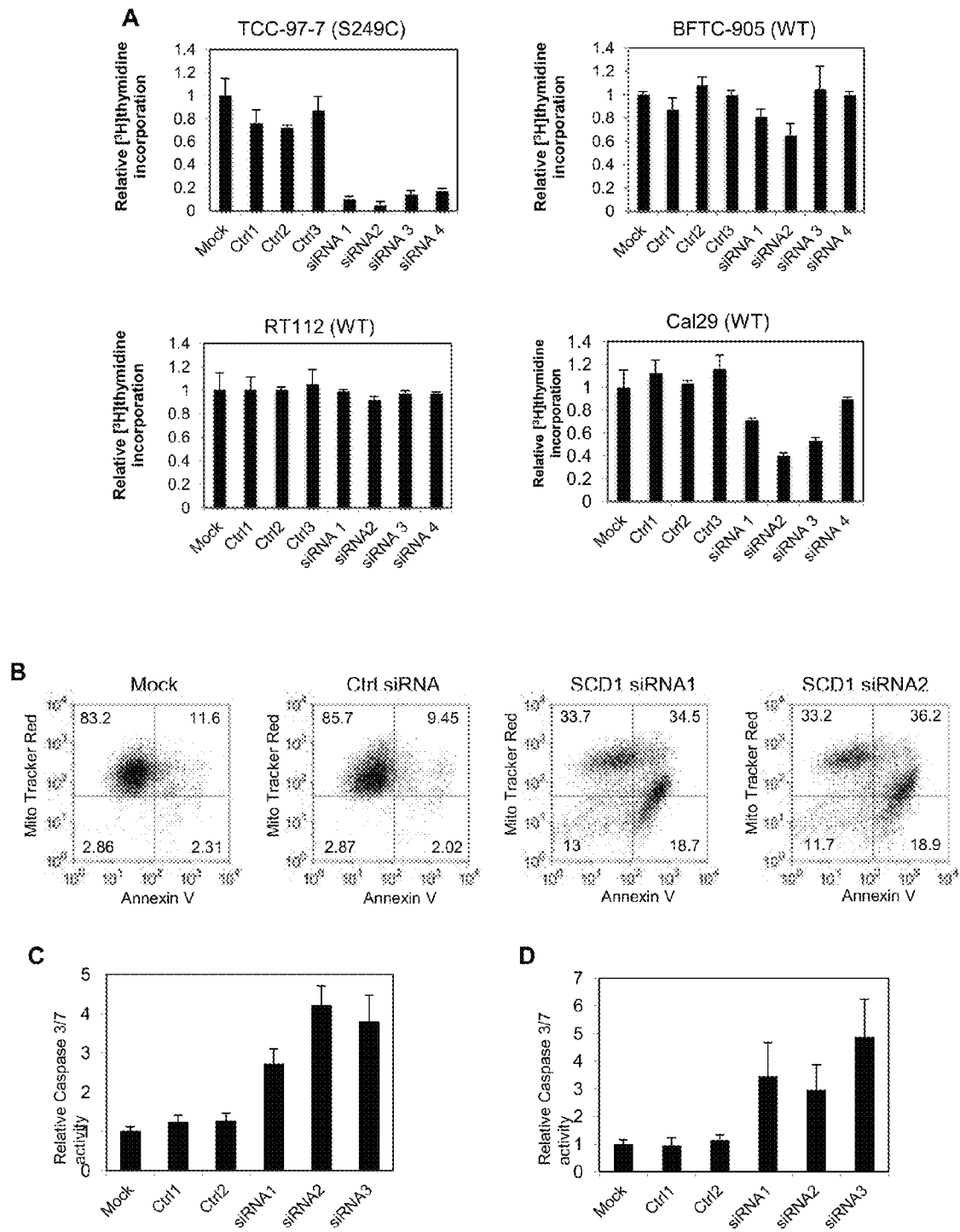
FIG. 11. SCD1 knockdown induces apoptosis in bladder cancer cells. (A) Effect of SCD1 siRNAs on bladder cancer cell proliferation. Cells were transfected with SCD1 siRNAs or three non-targeting control siRNAs (Ctrl), and cell proliferation was measured by [$^3$H]thymidine incorporation at 72 hr after transfection. Data are presented as mean+/−SD relative to cells transfected with RNAiMax alone (Mock). (B) UMUC-14 cells cultured in 1% FBS medium were transfected with SCD1 siRNAs or a control siRNA (Ctrl). FACS analyses were performed at 48 hr after transfection as described in Methods. Data are representative of three independent experiments. (C, D) SCD1 knockdown induces caspases 3/7 activation. UMUC-14 cells (C) and SW780 cells (D) were transfected with SCD1 siRNAs or two non-targeting control siRNAs (Ctrl). At 48 hr post transfection, activities of caspases 3 and 7 were measured with Caspase-Glo 3/7 assay kit (Promega). Data are presented as mean+/−SD, and are representative of two independent experiments.

A panel of bladder cancer cells lines was used in this study (Table 3). UMUC-14 and TCC-97-7 cells harbor $FGFR3^{S249C}$, the most frequent activating mutation in FGFR3 (24). Though SW780 cell line contains wild type FGFR3, it shows constitutive FGFR3-FRS2-AKT activation (data not shown). Multiple SCD1 siRNAs reduced SCD1 protein level, with siRNA4 being less effective (FIGS. 10A and B). SCD1 knockdown markedly suppressed [$^3$H]thymidine incorporation by cells with constitutively activated FGFR3, including SW780, UMUC-14 and TCC-97-7 cells (FIGS. 10A and B; FIG. 11A). By contrast, RT112 and BFTC-905 cells contain wild type FGFR3, and SCD1 siRNAs did not have apparent effect on their proliferation (FIG. 11A). These results suggested that cells with constitutively active FGFR3 signaling may rely more on SCD1 activity for proliferation and survival.

TABLE 3

Mutational status of FGFR3 in bladder cancer cell lines and response to SCD1 knockdown

| Cell line | FGFR3 status | FGFR3 pathway activity | Inhibition of [3H]thymidine incorporation by SCD1 siRNA |
|---|---|---|---|
| UMUC-14 | S249C | Constitutive active | Yes (60%) |
| TCC-97-7 | S249C | Constitutive active | Yes (80-90%) |
| SW780 | WT | Constitutive active | Yes (60-70%) |
| RT112 | WT | Ligand-dependent | No |
| BFTC-905 | WT | Ligand-dependent | No |
| Cal29 | WT | Ligand-dependent | 40-50% |

Further analyses of exponentially growing SW780 cells revealed that at 48-hour post SCD1 knockdown, the percentage of cells in G2 and S phase of the cell cycle was substantially and specifically reduced, with concomitant increase of cells in G1 phase (FIG. 10C). Since a sub-diploid population started to appear at 72 hr post SCD1 knockdown (data not shown), the effect of SCD1 siRNAs on apoptosis was analyzed. SCD1 knockdown significantly increased the cell populations stained positive for Annexin-V in SW780 cells (FIG. 10D) and UMUC-14 cells (FIG. 11B). Further studies of effector caspase revealed that SCD1 knockdown resulted in the cleavage and activation caspases 3 and 7, as well as their downstream target PARP (FIG. 10E). Consistent with this observation, SCD1 siRNAs caused higher enzymatic activity of caspases 3 and 7 in these cells (FIGS. 11C and D). Hence, the inhibitory effect of SCD1 knockdown on the bladder cancer cells with activated FGFR3 signaling is due to both the blockade of cell cycle progression and the induction of apoptosis.

Example 5

Figure 12:
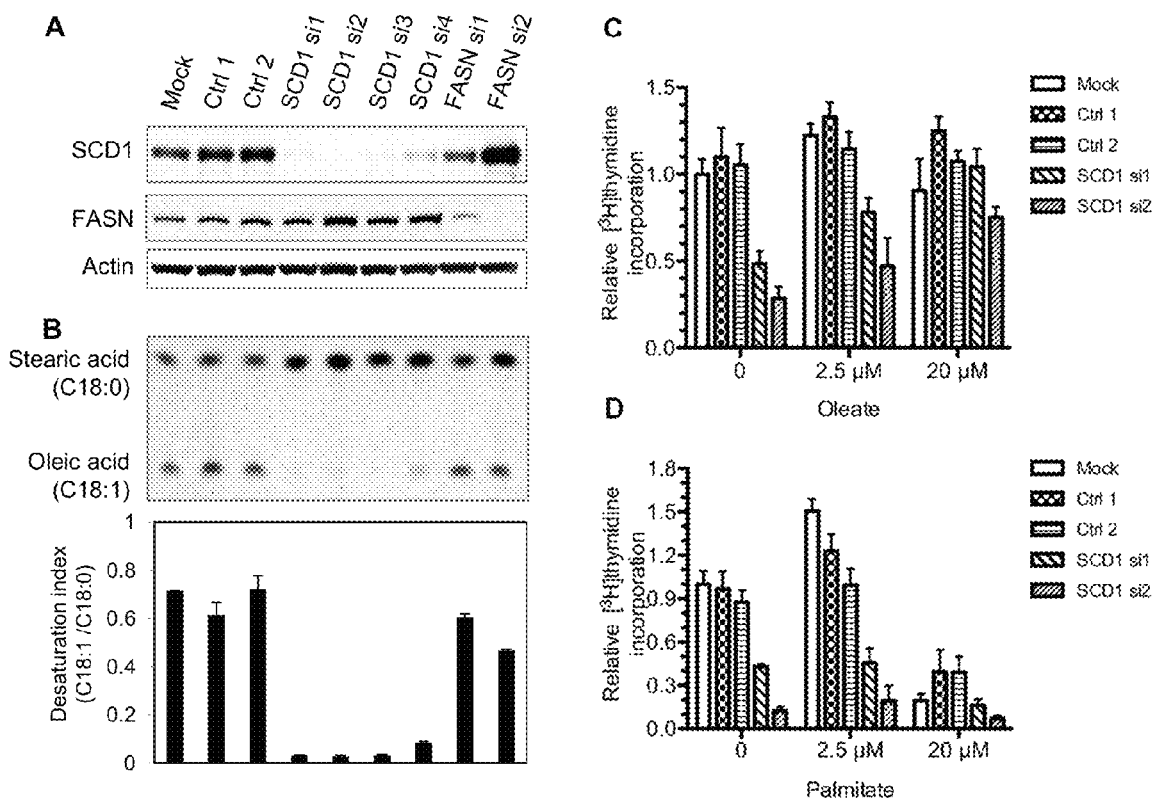
FIG. 12. SCD1 knockdown inhibits cell proliferation in a fatty acid desaturation-dependent manner. (A) Downregulation of SCD1 protein level by SCD1 siRNA. SW780 cells were transfected with siRNAs targeting SCD1, FASN, or two non-targeting control siRNAs (Ctrl). Cell lysates were immunoblotted to assess SCD1 and FASN expression. (B) SCD1 knockdown blocks stearic acid desaturation. SW780 cells were transfected as described in (A). At 48 hr post transfection, [$^{14}$C]stearic acid was added for 6 hr further incubation. [$^{14}$C]stearic acid desaturation was analyzed by argentation thin-layer chromatography and measured by scintillation counting. Data are presented as mean+/−SD. (C) Monounsaturated oleate rescues SW780 cells from SCD1 knockdown. SW780 cells grown in medium containing 1% FBS were transfected with SCD1 siRNAs or two non-targeting control siRNAs (Ctrl). At 6 hr after transfection, BSA-complexed oleate acid was added to the culture medium at indicated concentration. Cell proliferation was measured by [$^3$H]thymidine incorporation at 72 hr post treatment. Data are presented as mean+/−SD relative to cells transfected with RNAiMax alone (Mock) and grown in medium supplemented with BSA only. These data are representative of three independent experiments. (D) Saturated palmitate is unable to reverse the effect of SCD1 siRNAs. Cells were treated similarly as described in (C), except that BSA-complexed palmitate was supplemented at 6 hr post siRNA transfection.
Figure 13:
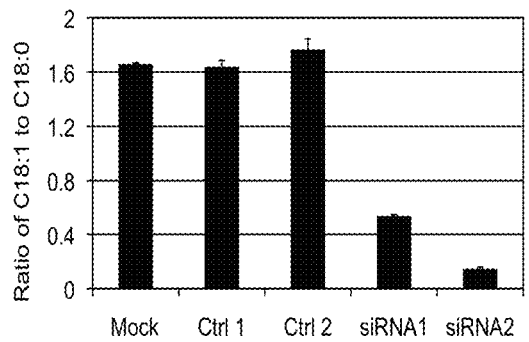
FIG. 13. SCD1 knockdown inhibits cell proliferation in a fatty acid desaturation-dependent manner in UMUC-14 cells. (A) SCD1 knockdown blocks stearic acid desaturation. UMUC-14 cells were transfected with SCD1 siRNAs or two non-targeting control siRNAs (Ctrl). At 48 hr post transfection, [$^{14}$C]stearic acid was added for 6 hr further incubation. [$^{14}$C]stearic acid desaturation was analyzed by thin-layer chromatography and measured by scintillation counting. Data are presented as mean+/−SD, and are representative of two independent experiments. (B) Monounsaturated oleate rescues UMUC-14 cells from SCD1 knockdown. UMUC-14 cells grown in medium containing 1% FBS were transfected with SCD1 siRNAs or two non-targeting control siRNAs (Ctrl). At 6 hr after transfection, BSA-conjugated oleate acid was added to the culture medium as indicated. Cell proliferation was measured by [3H]thymidine incorporation at 72 hr post treatment. Data are presented as mean+/−SD relative to cells transfected with RNAiMax alone (Mock) and grown in medium supplemented with BSA only. These data are representative of three independent experiments. (C) Saturated palmitate is unable to reverse the effect of SCD1 siRNAs. Cells were treated similarly as described in (B), except that BSA-conjugated palmitate was supplemented at 6 hr post siRNA transfection. Note that high dose of palmitate reduced cell proliferation significantly.
Figure 13:
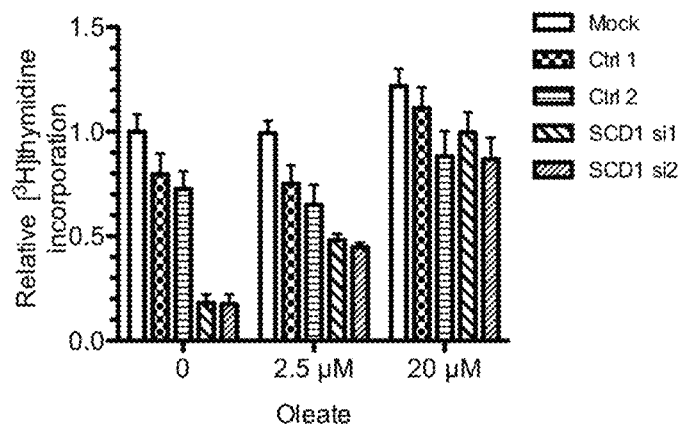
Figure 13:
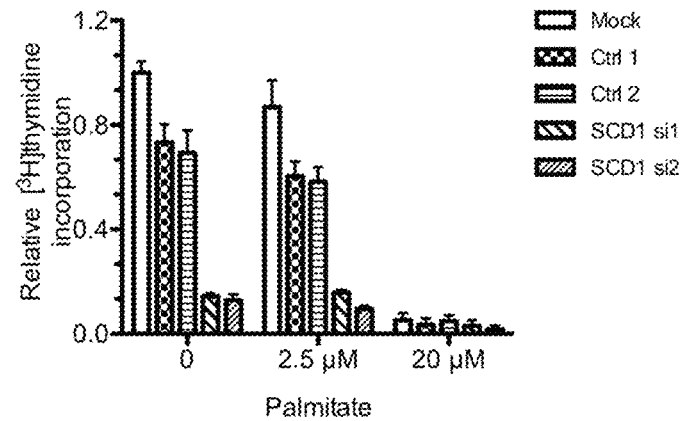

SCD1 siRNAs Inhibit Cell Proliferation in a Fatty Acid Desaturation-Dependent Manner Since SCD1 is the rate-limiting enzyme in the biosynthesis of monounsaturated fatty acid, the effect of SCD1 siRNAs on fatty acid desaturation was accessed. Using argentation thin-layer chromatography, SCD1 knockdown was found to markedly blocked the conversion of [$^{14}$C]-stearate into oleate (FIGS. 12A and B), whereas the non-specific control siRNAs or FASN siRNAs had no effect. The inhibition on cell proliferation may be due to the deficiency of the production of monounsaturated fatty acid, exogenously provided oleate may be able to rescue the cells. Indeed, oleate supplements reversed SCD1 siRNA-mediated growth inhibition in a dose-dependent manner in both SW780 and UMUC-14 cells, whereas adding back palmitate failed to rescue (FIGS. 12C and D; FIG. 13). It's worth noting that high concentration of palmitate (20 µM) is detrimental to the viability of these cells (FIG. 12D; FIG. 13C). Hence, fatty acid desaturation mediated by SCD1 is essential for bladder cancer cell proliferation and survival.

Example 6

Doxycycline-Inducible Knockdown of SCD1 Attenuated Tumor Growth In Vivo

Figure 14:
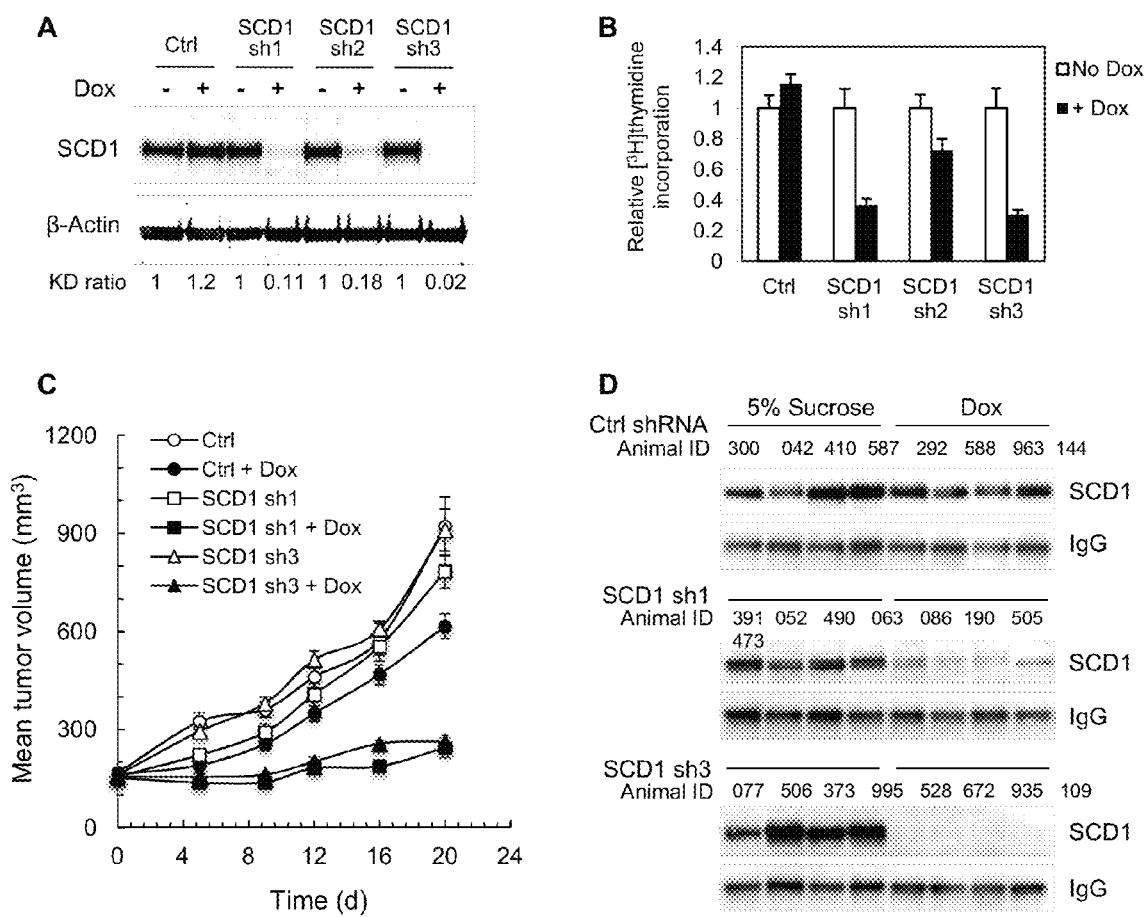
FIG. 14. Doxycycline-inducible knockdown of SCD1 in SW780 bladder caner cells suppresses tumor growth in vivo. Three different SCD1 shRNAs were cloned into a Tet-inducible lentiviral expression vector. SW780 cells stably expressing doxycycline-inducible SCD1 shRNA or a control shRNA (Ctrl) were established with puromycin selection. (A) Representative blots showing SCD1 expression in stable cells treated with or without 1 μg/mL doxycycline for 3 days. KD ratio indicates the efficiency of SCD1 knockdown relative to cells without doxycycline treatment. (B) SCD1 knockdown reduces [$^3$H]thymidine incorporation. SW780 cells were cultured with or without 1 μg/mL doxycycline for 3 days prior to 16 hr incubation with [$^3$H]thymidine. Counts of incorporated [$^3$H]thymidine were presented as mean+/−SD relative to cells without doxycycline treatment. (C) SCD1 knockdown attenuates tumor growth in mice. SW780 cells expressing SCD1 shRNA1 and 3 or a control shRNA (Ctrl) were inoculated into CB.17 SCID mice, and grouped out into cohorts of 10 for treatment. Mice were given 5% sucrose alone or supplemented with 1 mg/mL doxycycline, and tumor size was measured twice a week. Tumor volume is presented as mean+/−SD. At day 20, for SCD1 shRNA1: p<0.0001; for SCD1 shRNA3, p<0.0001. (D) Expression of SCD1 protein in tumor lysates extracted from control or SCD1 shRNA xenograft tissues. Tumor lysates were immunoprecipitated with anti-SCD1 antibody and evaluated for SCD1 protein level by immunoblot.

In order to evaluate the effect of SCD1 on tumor growth in animal models, stable SW780 cells expressing doxycycline-inducible SCD1 shRNA were established. Induction of three independent SCD1 shRNAs by doxycycline diminished SCD1 expression, whereas expression of a control shRNA targeting EGFP had no effect (FIG. 14A). Doxycycline treatment reduced [$^3$H]thymidine incorporation by cells expressing SCD1 shRNAs, but not control shRNA (FIG. 14B), confirming that SCD1 knockdown inhibits cell proliferation.

The effect of SCD1 shRNAs on the growth of pre-established SW780 tumor xenografts in mice was evaluated. SCD1 knockdown substantially and specifically suppressed tumor growth as compared with cells expressing the control shRNA (FIG. 14C). Analysis of day 20 tumor samples confirmed effective SCD1 knockdown upon doxycycline induction of SCD1 shRNA (FIG. 14D). These results demonstrate that SCD1 is critically important both in vitro and in vivo for the growth of SW780 bladder cancer cells.

Example 7

Figure 15:
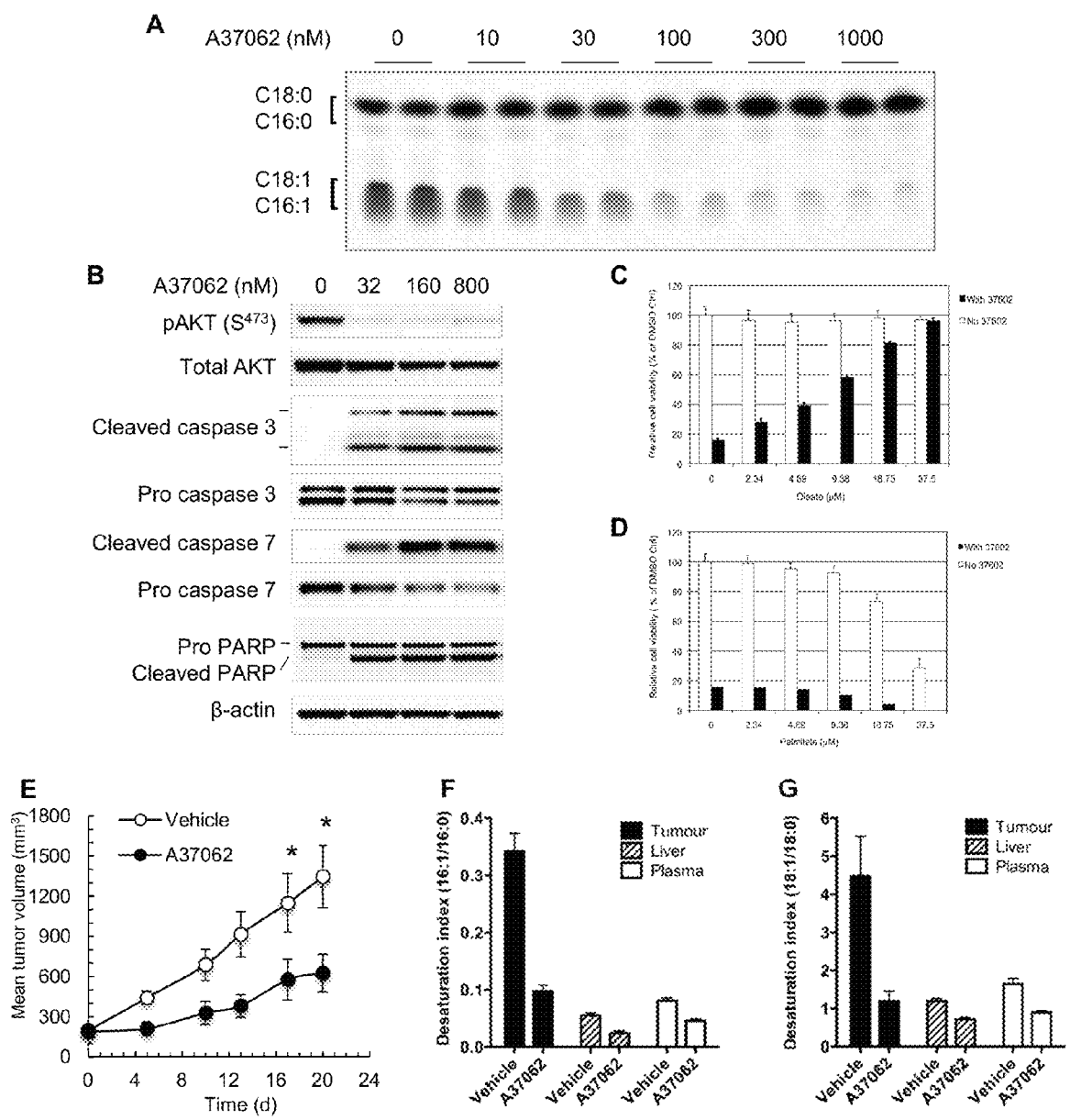
FIG. 15. Pharmacological inhibition of SCD1 attenuates tumor growth and reduces fatty acid desaturation in mice. (A) SCD1 small molecule inhibitor A37062 blocks the synthesis of monounsaturated fatty acid. UMUC-14 cells were treated with A37062 for 4 hr, then incubated with [$^{14}$C]acetate for 6 hr. Total fatty acids were extracted and separated by thin-layer chromatography. (B) A37062 abolishes AKT phosphorylation and activates caspases 3 and 7. UMUC-14 cells were serum starved for 20 hr, then treated with A37062 for 20 hr. Cell lysates were subjected to Western blot analyses. (C) Monounsaturated oleate reverses growth inhibition by A37062 (100 nM) in UMUC-14 cells. (D) Saturated palmitate fails to rescue A37062-treated UMUC-14 cells. (E) SCD1 inhibitor A37062 delays xenograft growth of pre-established UMUC-14 tumors. Mice were given vehicle or A37062 (75 mg/kg) orally, twice a day, and tumor volume was presented as mean+/−SEM. n=8 per group. At day 20, p=0.0073. (F, G) A37062 reduces desaturation of palmitate (F) and stearate (G) in xenografted tumor tissues as well as in mouse liver and plasma at the end of the study. At 2 hr post the last treatment, samples (n=5 per group) were collected and processed as described in Methods. Fatty acid methyl esters were identified by gas chromatography. Data are presented as mean+/−SD.

Pharmacological Inhibition of SCD1 Attenuated Tumor Growth and Reduced Fatty Acid Desaturation in Mice To examine further the importance of fatty acid desaturation in tumor growth, SCD1 enzymatic activity was pharmacologically blocked with a small molecule inhibitor A37062. This compound blocked the conversion of [$^{14}$C]stearic acid into oleic acid (data not shown), and suppressed the synthesis of monounsaturated fatty acid from [$^{14}$C]acetate, with an estimated $IC_{50}$ value of 30 nM (FIG. 15A). Treatment of UMUC-14 cells with the SCD1 inhibitor resulted in the reduction of phosphorylated AKT and the cleavage and activation of effector caspases 3 and 7, as well as their target PARP (FIG. 15B).

Figure 16:
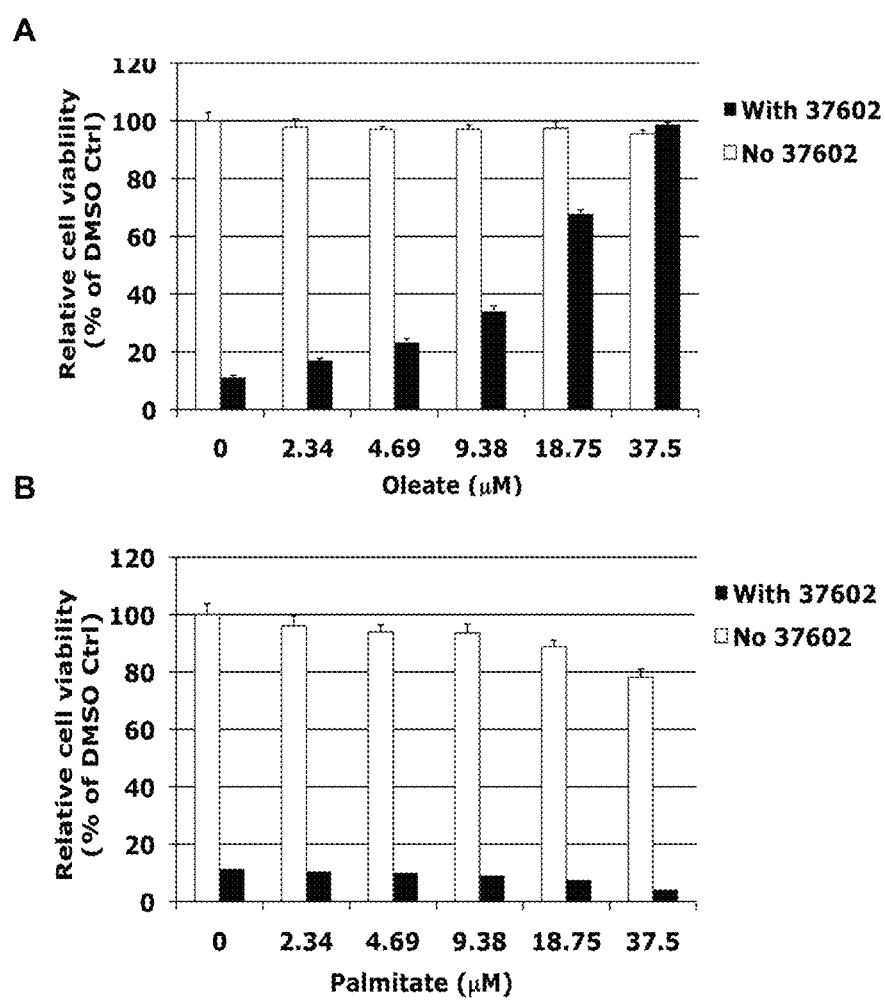
FIG. 16. SCD1 inhibitor suppresses cell proliferation in a fatty acid desaturation-dependent manner in SW780 cells. (A) Monounsaturated oleate rescues SW780 cells from SCD1 inhibitor A37062. SW780 cells grown in medium containing 1% FBS were treated with 100 nM of SCD1 inhibitor A37062 or DMSO (No 37602). BSA-conjugated oleate acid was added to the culture medium as indicated. Cell viability was measured by CellTiter Glo (Promega) at 48 hr post treatment. Data are presented as mean+/−SD relative to cells treated with DMSO alone and grown in medium supplemented with BSA only. (B) Saturated palmitate is unable to reverse the effect of SCD1 inhibitor A37062. Cells were treated similarly as described in (A), except that BSA-conjugated palmitate was supplemented.

The specificity and selectivity of A37062 was also evaluated. Under normal growth condition, A37062 suppressed proliferation of multiple bladder cancer cell lines and induced apoptosis in culture (data not shown). 100 nM A37062 reduced the viability of UMUC-14 cells by approximately 85% (FIGS. 15C and D). Exogenously supplemented oleate reversed the growth inhibitory effect in a dose-dependent fashion (FIG. 15C), whereas palmitate failed to rescue the cells (FIG. 15D). Similar results were observed in SW780 cells (FIG. 16). These data strongly suggest that the inhibitor A37062 is SCD1-specific, and its inhibitory effect on cell proliferation and survival is due to the deficiency in generating monounsaturated fatty acid.

Next, the effect of A37062 on the growth of bladder cancer cells in vivo was examined. Athymic nude mice were inoculated with UMUC-14 cells, allowed tumors to grow to a mean volume of ~150 mm³, and dosed the animals twice a day with vehicle or A37062 (75 mg/kg) for 20 days. Compared with vehicle control at day 20, A37062 suppressed tumor growth by about 60% (FIG. 15E). Analysis of tumor lysates collected at 2 hr after last treatment showed that A37062 markedly decreased the ratio of monounsaturated fatty acid to saturated fatty acid (FIGS. 15F and G). Similarly, fatty acid desaturation in mouse liver and plasma was significantly reduced too (FIGS. 15F and G). Thus, A37062 inhibits growth of UMUC-14 tumor xenografts in conjunction with a blockade in fatty acid desaturation. In the course of the experiments, no significant weight loss or other gross abnormalities in the nude mice were observed.

Example 8

In Vivo Efficacy Studies Using SCD1 Small Molecule Inhibitors

Figure 17:
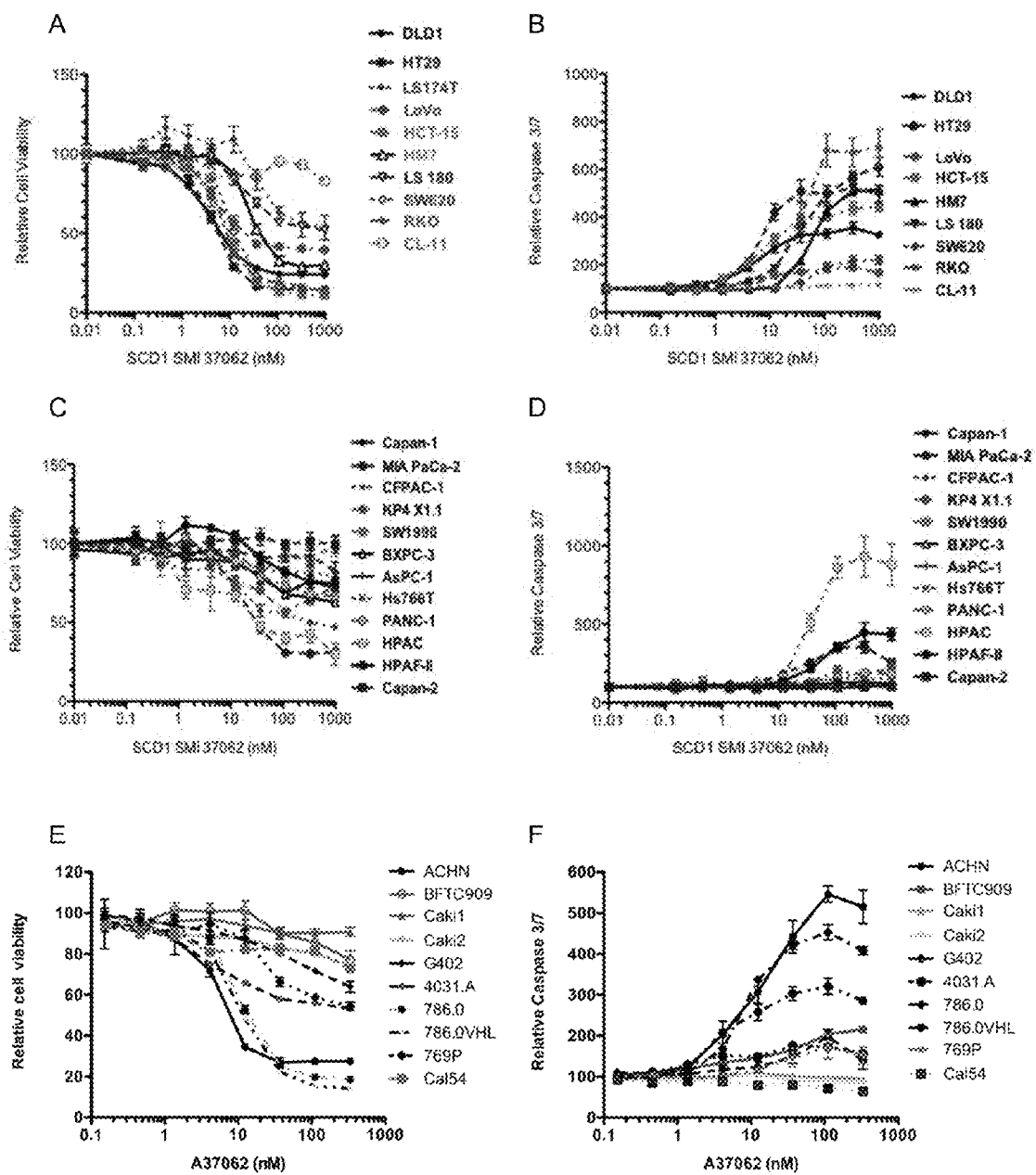
FIG. 17. Pharmacological inhibition of SCD1 reduces cell viability and increases caspases 3/7 activity in human colon cancer cell lines, human pancreatic cancer cell lines, and kidney cancer cell lines. (A) SCD1 small molecule inhibitor A37062 reduces cell viability of colon cancer cells. (B) SCD1 small molecule inhibitor A37062 activates caspases 3/7 in colon cancer cells. (C) SCD1 small molecule inhibitor A37062 reduces cell viability of pancreatic cancer cells. (D) SCD1 small molecule inhibitor A37062 activates caspases 3/7 in pancreatic cancer cells. (E) SCD1 small molecule inhibitor A37062 reduces cell viability of kidney cancer cells. (F) SCD1 small molecule inhibitor A37062 activates caspases 3/7 in kidney cancer cells.

To investigate the effect of SCD1 small molecule antagonists on colon, pancreatic, and kidney cancer, colon cancer cells lines, pancreatic cancer cell lines, and kidney cancer cell lines were treated with serially diluted A37062 for 72 hr, and cell viability was measured by CellTiter-Glo (Promega) as described above. Further, colon cancer cells lines, pancreatic cancer cell lines, and kidney cancer cell lines were treated with serially diluted A37062 for 48 hr, and caspases 3/7 activity was measured by Caspase-Glo 3/7 assay kit (Promega) as described above. Pharmacological inhibition of SCD1 reduced cell viability and increased caspases 3/7 activity in human colon cancer cell lines (FIGS. 17A and B), in human pancreatic cancer cell lines (FIGS. 17C and D), and in human kidney cancer cell lines (FIGS. 17E and F). Data was represented as mean+/−SD, and representative of two independent experiments.

To investigate the effect of additional SCD1 small molecule antagonists, human cancer cell lines, including colon, prostate, pancreatic, and bladder cancers were treated with serially diluted A37062 or G02447171.1 for 72 hr, and cell viability was measured by CellTiter-Glo (Promega). Pharmacological inhibition of SCD1 using A37062 or G02447171.1 reduced cell viability and increased caspases 3/7 activity in a panel of human cancer cell lines, including colon, prostate, pancreatic, and bladder cancers (FIGS. 18A and B, respectively). Data are represented as mean+/−SD, and representative of two independent experiments.

To investigate the effect of SCD1 small molecule antagonists on cancer cell lines were treated with serially diluted A37062 for 72 hr, and cell titer 1050 (nM) and cell viability was measured by CellTiter-Glo (Promega) as described above. See Table 4.

TABLE 4

|  | Cell Titer IC50 (nM) | Maximum Inhibition (%) |
|---|---|---|
| Colon Cancer Cell Lines Treated with A37062 (n = 2) | | |
| HT29 | 4.1 | 85.7 |
| DLD1 | 4.6 | 74.7 |
| LoVo | 6.3 | 56.5 |
| HCT-15 | 6.9 | 93.0 |
| RKO | 7.3 | 83.0 |
| SW620 | 11.7 | 83.1 |
| HT55 | 18.3 | 52.7 |
| LS 180 | 18.8 | 51.0 |
| Colo205 | 20.4 | 81.7 |
| LS174T | 31.3 | 50.9 |
| HM7 | 35.3 | 70.9 |
| HCT116 | 41.5 | 84.9 |
| CL-11 | Resistant | 11.2 |
| Pancreatic Cancer Cell Lines Treated with A37062 (n = 2-3) | | |
| KP4 X1.1 | 6.0 | 48.9 |
| Capan-1 | 10.3 | 33.4 |
| MIA PaCa-2 | 12.8 | 66.8 |
| CFPAC-1 | 14.9 | 50.5 |
| PANC-1 | 21.8 | 32.6 |
| BxPC-3 | 30.9 | 49.4 |
| HPAC | 40.5 | 56.3 |
| HPAF-II | 48.3 | 27.5 |
| Capan-2 | Resistant | None |
| Hs 766T | Resistant | 14.6 |
| AsPC-1 | Resistant | None |
| SW1990 | Resistant | None |
| Bladder Cancer Cell Lines Treated with A37062 (n = 2) | | |
| SW780 | 12.5 | 54.6 |
| UMUC-14 | 14.4 | 88.2 |
| BTFC905 | 12.6 | 82.8 |
| RCC Cancer Cell Lines Treated with A37062 (n = 1) | | |
| 4031.A | 12.7 | 46.9 |
| ACHN | 15.8 | 73.5 |
| 786.O-VHL | 32.0 | 85.8 |
| 786.O | 32.4 | 81.3 |
| 769P | 77.6 | 44.1 |
| G402 | 689.5 | 36.1 |
| BFTC909 | 766.6 | 39.0 |
| Caki 1 | Resistant | 9.6 |
| Caki 2 | Resistant | 24.0 |
| Cal 54 | Resistant | 20.0 |
| Prostate Cell Lines Treated with A37062 (n = 1) | | |
| Du145 | 7.1 | 34.4 |
| LNCap/Ner | Resistant | None |
| PC-3 | Resistant | None |

To investigate the effect of SCD1 small molecule antagonists on tumor growth in mice, mice were given vehicle or SCD1 small molecular inhibitors G01522403 (A37062) and G02447171 orally, twice a day as described above. Pharmacological inhibition of SCD1 delayed xenograft growth of pre-established HCT15 colon tumors, pre-established SW780 bladder tumors, and pre-established HPAC pancreatic tumors (FIG. 18C, D, and E, respectively). Tumor volume was presented as mean+/−SEM. See also Table 5.

TABLE 5

| Cell line | Tissue origin | SCD1 inhibitor | Max % TGI, PO |
|---|---|---|---|
| UMUC-14 | Bladder | G01522403 | 77% |
| DLD1 | Colon | G01522403 | No effect |
| HM7 | Colon | G02447171 | No effect |
| HCT15 | Colon | G02447171 | 69% |
| SW780 | Bladder | G02447171 | 54% |
| HPAC | Pancreas | G02447171 | 46% |

Example 9

Pharmacological Inhibition of SCD1 Attenuated Tumor Cell Viability

Figure 19:
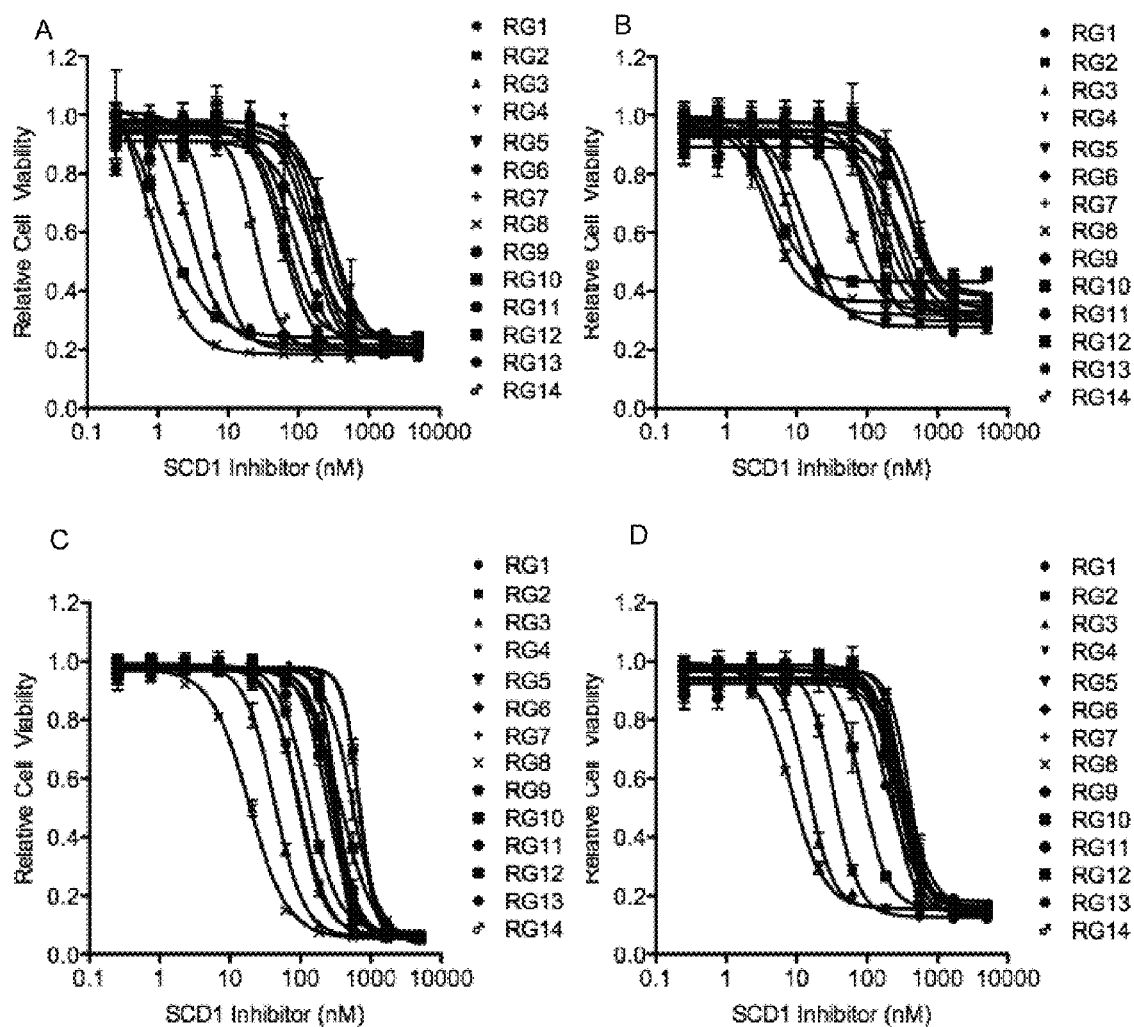
FIG. 19. Pharmacological inhibition of SCD1 by fourteen small molecule SCD1 inhibitors reduces cell viability in HCT15 (A, B) and HT29 (C, D) cancer cells.
Figure 20:
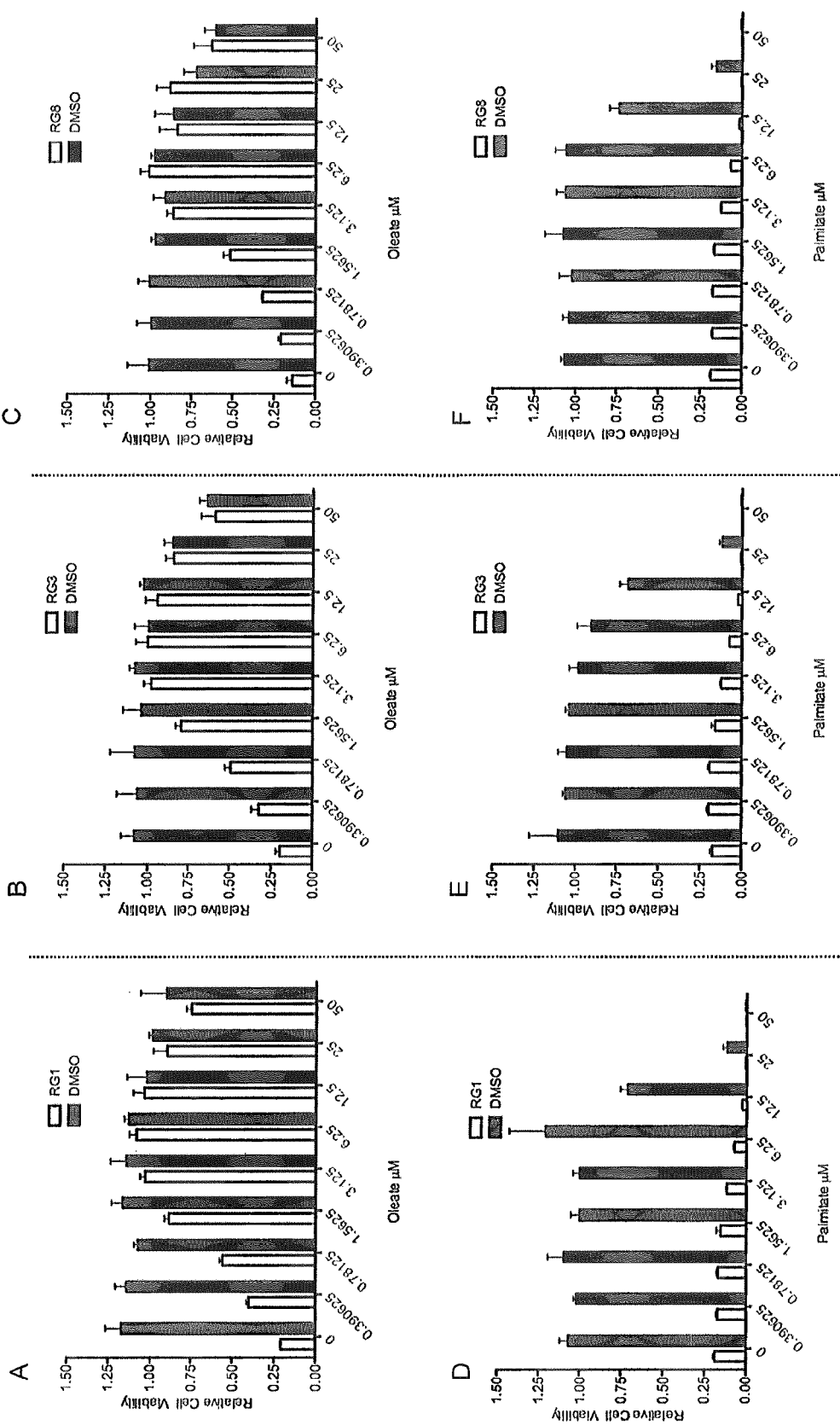
FIG. 20. SCD1 inhibitors RG1, RG3, and RG8 suppress cell proliferation in a fatty acid desaturation-dependent manner in HCT15 cells. (A-C) Monounsaturated oleate rescues HCT15 cells from SCD1 inhibitors. (D-F) Saturated palmitate is unable to reverse the effect of SCD1 inhibitors in HCT15 cells.
Figure 21:
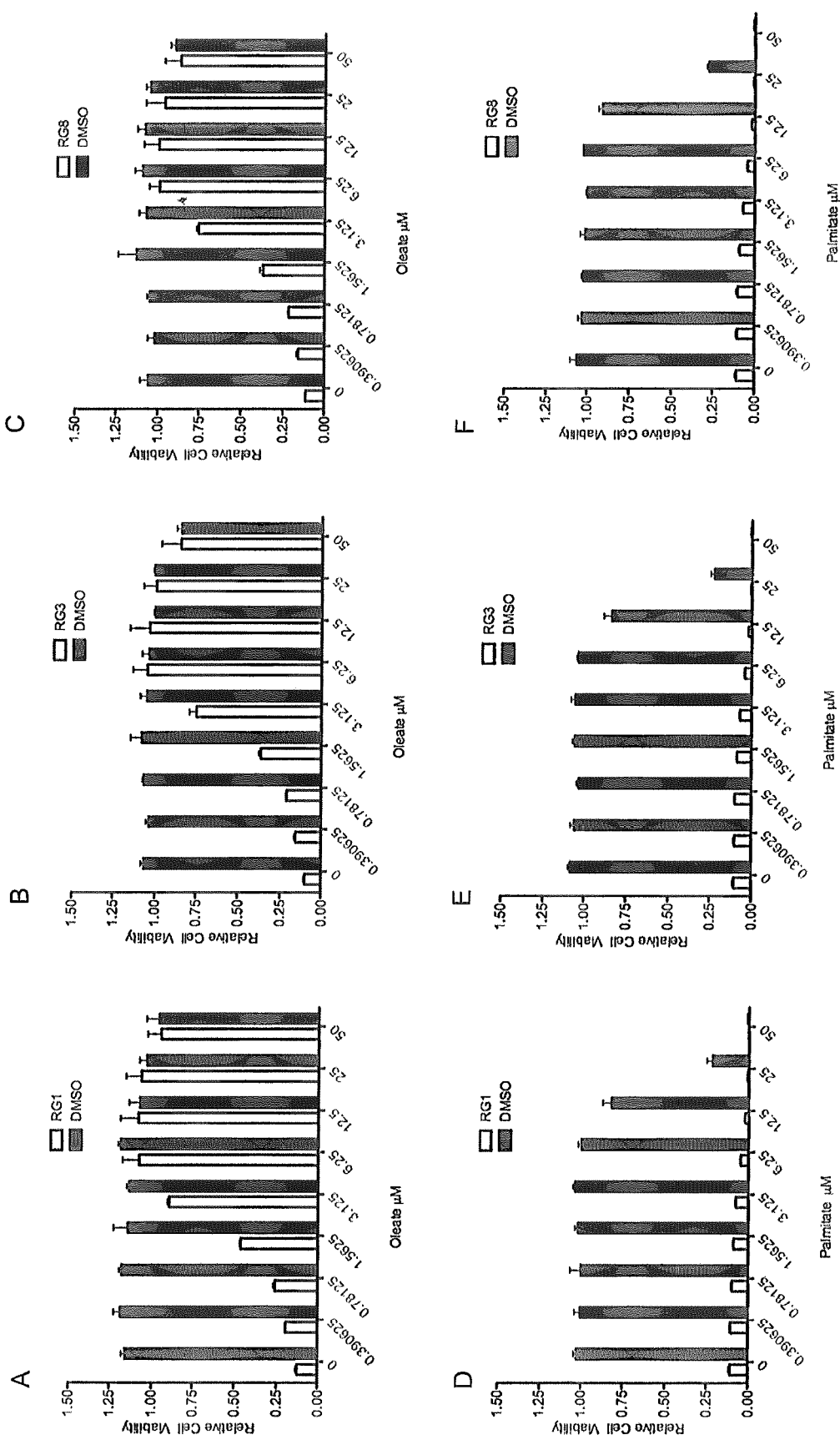
FIG. 21. SCD1 inhibitors RG1, RG3, and RG8 suppress cell proliferation in a fatty acid desaturation-dependent manner in HT29 cells. (A-C) Monounsaturated oleate rescues HT29 cells from SCD1 inhibitors. (D-F) Saturated palmitate is unable to reverse the effect of SCD1 inhibitors in HT29 cells.

To investigate the effect of additional SCD1 small molecule antagonists, HT29 and HCT15 were treated with serially diluted small molecule inhibitors RG1-14 and G02447171 (G7171) for 72 hr, and cell viability was measured by CellTiter-Glo (Promega). The specificity and selectivity of the SCD1 small molecule inhibitors was also evaluated. See Tables 6-9. Under normal growth condition, the small molecule SCD1 antagonists suppressed proliferation of HT29 and HCT15 cells (FIG. 19). Exogenously supplemented oleate reversed the growth inhibitory effect in a dose-dependent fashion (FIGS. 20A-C and 21A-C), whereas palmitate failed to rescue the cells (FIGS. 20D-F and 21D-F).

TABLE 6

Experiment 1 HCT15

| | IC50 (nM) | R square | Bottom | Top |
|---|---|---|---|---|
| RG1 | 5.838 | 0.9907 | 0.1995 | 1.01 |
| RG2 | 58.06 | 0.9953 | 0.1829 | 0.9681 |
| RG3 | 2.773 | 0.9924 | 0.2168 | 1.025 |
| RG4 | 289.2 | 0.9563 | 0.1912 | 0.982 |
| RG5 | 152.5 | 0.9841 | 0.191 | 0.9372 |
| RG6 | 86.88 | 0.9705 | 0.191 | 0.976 |
| RG7 | 176.7 | 0.9766 | 0.192 | 0.9544 |
| RG8 | 0.7843 | 0.9945 | 0.1839 | 1.13 |
| RG9 | 206.7 | 0.9754 | 0.2374 | 0.9775 |
| RG10 | 63.35 | 0.9672 | 0.2418 | 0.9502 |
| RG11 | 148.3 | 0.9055 | 0.2171 | 0.9111 |
| RG12 | 1.003 | 0.9952 | 0.2409 | 1.126 |
| RG13 | 287.8 | 0.9291 | 0.219 | 0.913 |
| RG14 | 24.61 | 0.9869 | 0.2003 | 0.9503 |

TABLE 7

Experiment 2 HCT15

| | IC50 | R square | Bottom | Top |
|---|---|---|---|---|
| RG1 | 13.44 | 0.9817 | 0.2787 | 0.9632 |
| RG2 | 121.6 | 0.9659 | 0.299 | 0.9261 |
| RG3 | 8.22 | 0.974 | 0.3197 | 0.996 |
| RG4 | 244 | 0.9385 | 0.299 | 0.9533 |
| RG5 | 382.8 | 0.9613 | 0.3466 | 0.9771 |
| RG6 | 169.1 | 0.9167 | 0.3298 | 0.9319 |
| RG7 | 495.3 | 0.9174 | 0.3853 | 0.9458 |
| RG8 | 4.139 | 0.964 | 0.3645 | 0.9664 |
| RG9 | 399.5 | 0.9477 | 0.3367 | 0.9725 |
| RG10 | 125.7 | 0.9738 | 0.3257 | 0.9825 |
| RG11 | 416.5 | 0.8575 | 0.3943 | 0.8913 |
| RG12 | 4.331 | 0.9711 | 0.4316 | 0.992 |
| RG13 | 274.4 | 0.8963 | 0.2951 | 0.9362 |
| RG14 | 53.02 | 0.9568 | 0.3318 | 0.9505 |

TABLE 8

Experiment 1 HT29

| | IC50 | R square | Bottom | Top |
|---|---|---|---|---|
| RG1 | 95.67 | 0.9962 | 0.05711 | 0.9793 |
| RG2 | 683.4 | 0.9933 | 0.05245 | 0.9737 |
| RG3 | 42.61 | 0.9933 | 0.0588 | 0.9909 |
| RG4 | 546.6 | 0.994 | 0.05143 | 0.9778 |
| RG5 | 277.1 | 0.9903 | 0.06627 | 0.9743 |
| RG6 | 329.9 | 0.997 | 0.06325 | 0.9778 |
| RG7 | 89.65 | 0.996 | 0.06893 | 0.9847 |
| RG8 | 18.69 | 0.9966 | 0.0546 | 0.9739 |
| RG9 | 311.6 | 0.9877 | 0.05633 | 0.9681 |
| RG10 | 306.9 | 0.9982 | 0.05551 | 0.9788 |
| RG11 | 242.8 | 0.9889 | 0.05832 | 0.9778 |
| RG12 | 377.5 | 0.9906 | 0.02686 | 0.9791 |
| RG13 | 129.2 | 0.9956 | 0.0767 | 0.9896 |
| RG14 | 689 | 0.9943 | 0.05572 | 0.9799 |

TABLE 9

Experiment 2 HT29

| | IC50 | R square | Bottom | Top |
|---|---|---|---|---|
| RG1 | 33.53 | 0.9914 | 0.1271 | 0.984 |
| RG2 | 397.8 | 0.9894 | 0.1294 | 0.9694 |
| RG3 | 14.49 | 0.9915 | 0.1558 | 0.9688 |
| RG4 | 345.5 | 0.9816 | 0.1579 | 0.9656 |
| RG5 | 328.1 | 0.9756 | 0.1567 | 0.9445 |
| RG6 | 280.4 | 0.9866 | 0.1384 | 0.9358 |
| RG7 | 271.6 | 0.9771 | 0.1562 | 0.9666 |
| RG8 | 8.131 | 0.9967 | 0.156 | 0.996 |
| RG9 | 300.1 | 0.9847 | 0.1545 | 0.9731 |
| RG10 | 225.1 | 0.993 | 0.1432 | 0.9884 |
| RG11 | 265.7 | 0.9742 | 0.1671 | 0.9241 |
| RG12 | 83.55 | 0.985 | 0.1535 | 0.9792 |
| RG13 | 190.6 | 0.9899 | 0.1797 | 0.9744 |
| RG14 | 322.7 | 0.9942 | 0.165 | 0.9727 |

Discussion of Examples

The Examples show that FGFR3 signals through PI3K-mTORC1 to activate SREBP1 and its downstream targets to promote de novo lipogenesis and fatty acid desaturation in human bladder cancer cells. Moreover, the genetic or pharmacological intervention to block fatty acid desaturation catalyzed by SCD1 was shown to profoundly inhibit tumor growth in cell culture and in xenografted mice. These results for the first time reveal the importance of FGFR3-regulated lipid metabolism in maintaining bladder tumor growth and survival, providing a mechanistic link between oncogenic growth factor signaling with altered cellular metabolism.

One striking finding from the unbiased expression analysis is that a large cohort of genes involved in sterol and fatty acid synthesis and metabolisms are among the most prominently downregulated genes as a result of FGFR3 knockdown in bladder cancer cells. The examples further demonstrate that activation of FGFR3 signaling increased the amount of cleaved, transcriptionally active SREBP1, which in turn induced the expression of key lipogenic enzymes and promoted the de novo synthesis of fatty acid, including both saturated and unsaturated classes. These results are reminiscent with a recent report showing that activated EGFR signaling in glioblastomas promotes lipogeneis via stimulating SREBP1 processing (35). These findings are consistent with and extend earlier studies showing that activation of EGFR and Her2 induces FASN expression in breast cancer cell lines (36-38). Given that growth factors such as EGF and PDGF are able to promote SREBP1 activation and lipogenesis in fibroblasts (39) and epithelial cells (40-41), it is conceivable that oncogenic growth factor receptor signaling-stimulated lipogenesis could be a common mechanism underlying the elevated fatty acid synthesis in many cancer types.

In response to low intracellular sterol level or insulin stimulation, SREBP1 is activated by proteolytic cleavage and the mature N-terminal fragment translocates into nucleus to activate the transcription of a cascade of lipogenic genes (32). Growth factors and their receptors potentially can activate SREBP1 through multiple mechanisms, including transcriptional upregulation, increased proteolytic processing, or stabilizing cleaved SREBP1 by inhibiting GSK3-Fbw7-mediated ubiquitination and proteasomal degradation (33). The examples demonstrate that ligand-induced FGFR3 activation only has a minor effect in the induction of the full-length inactive SREBP1, whereas the cleaved active form of SREBP1 accumulates significantly. Furthermore, acute pharmacological inhibition of canonical FGFR3 signaling by either PI3K or mTORC1 inhibitor markedly diminishes the level of matured SREBP1 without affecting that of full-length inactive SREBP1. These data suggest that FGFR3-driven activation of SREBP1 mainly hinges on the selective increase of matured SREBP1 by PI3K-mTORC1. This finding is consistent with several recent studies in cells overexpressing myr-AKT (42) or mouse embryonic fibroblasts with constitutive hyperactivation of mTORC via genetic ablation of TSC (43). Another notable observation from this study is the differential contribution of MEK-MAPK to FGF1-stimulated SREBP1 activation in different cell lines. This is in keeping with earlier studies showing seemingly contradictory results of the involvement of MEK-MAPK in SREBP1 activation by growth factor receptors, suggesting that MEK-MAPK regulation of SREBP1 could be highly context-dependent (37, 39-41). The exact mechanisms of how FGFR3 signaling regulates SREBP1 processing and/or stability await further investigations.

One important finding of our current study is that SCD1, the rate-limiting enzyme in fatty acid desaturation, is among the genes that showed most dramatic modulation by FGFR3 knockdown in bladder cancer cells. Accordingly, FGF1 induced a pronounced increase in SCD1 expression and the synthesis of unsaturated fatty acids. This regulation is mediated mainly through SREBP1, since SREBP1 siRNA markedly reduced basal and FGF1-induced SCD1 expression, whereas knockdown SREBP2 alone had no apparent effect on SCD1 expression. Furthermore, the examples indicate that SCD1 is essential to maintain the proliferation and survival of bladder cancer cells with constitutively activated FGFR3 Inhibition of SCD1 through RNA interference or pharmacological intervention blocked fatty acid desaturation, resulting in G1 cell cycle arrest and subsequent apoptosis. Moreover, exogenously supplemented oleic acid is able to rescue cells from SCD1 inhibition, confirming the importance of fatty acid desaturation in cell proliferation and survival. Finally, SCD1 inhibition markedly attenuated the growth of several bladder cancer xenografts in mice. Thus, the importance of SCD1 function in maintaining bladder tumor growth suggests it as a potential new therapeutic target in this disease setting. Although the examples with a limited cell line panel suggested that cells with constitutively activated FGFR3 are more sensitive to SCD1 inhibition, it is not yet clear whether FGFR3 activation status per se may predict response to SCD1-based therapy. Since PI3K-AKT-mTORC1 axis, and to a lesser extent, MEK-MAPK, were able to promote lipogenesis and SCD1 activity, alterations in signaling pathways downstream of FGFR3, or dysregulation in other receptor tyrosine kinases may impact the response to SCD1-targeted therapy.

Several recent studies have reported that SCD1 is overexpressed and essential for tumor growth in other malignancies, including lung cancer and prostate cancer (44-46), and the fatty acid desaturation index in prostate cancer correlates with disease progression (45). Although the underlying mechanisms of SCD1 up-regulation in these diseases have not been delineated yet (45-48), these data suggest that SCD1 may play a broader role in tumorigenesis, in part by controlling membrane biogenesis during cell division and signal transduction of diverse pathways important for cell proliferation, survival, and stress adaptation.

PARTIAL LIST OF REFERENCES

1. Eswarakumar, V. P., Lax, I., and Schlessinger, J. 2005. *Cytokine Growth Factor Rev.* 16:139-149.
2. Beenken, A., and Mohammadi, M. 2009. *Nat. Rev. Drug discovery* 8:235-253.
3. Turner, N., and Grose, R. 2010. *Nat. Rev. Cancer* 10:116-129.
4. Dailey, L. et al., 2005. *Cytokine Growth Factor Rev* 16:233-247.
5. Ornitz, D. M. 2005. *Cytokine Growth Factor Rev.* 16:205-213.
6. Wilkie, A. O. 2005. *Cytokine Growth Factor Rev.* 16:187-203.
7. Chesi, M. et al., 1997. *Nat. Genet.* 16:260-264.
8. Moreau, P. et al., 2002. *Blood* 100:1579-1583.
9. Trudel, S. et al., 2004. *Blood* 103:3521-3528.
10. Chang, H. et al., 2005. *Blood* 106:353-355.
11. Cappellen, D. et al., 1999. *Nat. Genet.* 23:18-20.
12. Gomez-Roman, J. J. et al., 2005. *Clin Cancer Res* 11:459-465.
13. Tomlinson, D. C. et al., 2007. *J Pathol* 213:91-98.
14. van Rhijn, B. W. et al., 2002. *J Pathol* 198:245-251.
15. Kuroso, K. et al. 2010. *Pathobio.: J. Immun., Mol. Cell. Biol.* 77:231-240.
16. Rosty, C. et al., 2005. *Mol Cancer* 4:15.
17. Qiu, W. H. et al., 2005. *World J Gastroenterol* 11:5266-5272.
18. Woenckhaus, M. et al., 2006. *JPathol* 210:192-204.
19. Cortese, R. et al., 2008. *Int J Biochem Cell Biol* 40:1494-1508.
20. Goriely, A. et al. 2009. *Nat. Genet.* 41:1247-1252.
21. Knowles, M. A. 2008. *Future Oncol* 4:71-83.
22. Martinez-Torrecuadrada, J. et al., 2005. *Clin Cancer Res* 11:6280-6290.
23. Tomlinson, D. C. et al., 2007. *Oncogene* 26:5889-5899.
24. Qing, J. et al., 2009. *J. Clin. Invest.* 119:1216-1229.
25. Lamont, F. R. et al., 2011. *Brit. J. Cancer* 104:75-82.
26. Novartis. A dose escalation study in adult patients with advanced solid malignancies. http://clinicaltrials.gov/ct2/show/NCT01004224.
27. Novartis. A Phase II Multi-center, Non-randomized, Open Label Study of TKI258 in FGFR3 Mutated and FGFR3 Wild Type Advanced Urothelial Carcinoma. http://clinicaltrial.gov/ct2/show/NCT00790426.
28. Genentech. An Open-Label, Multicenter, Phase I Dose-Escalation Trial Evaluating the Safety and Pharmacokinetics of MFGR1877S in Patients With Advanced Solid Tumors. http://clinicaltrial.gov/ct2/show/NCT01363024.
29. Paton, C. M., and Ntambi, J. M. 2009. *Am. J. Physiol. Endocrinol. Metab.* 297:E28-37.
30. Horton, J. D. et al., 2002. *J. Cin. Invest.* 109:1125-1131.
31. Horton, J. D. et al., 2003. *Proc. Natl. Acad. Sci. USA* 100:12027-12032.
32. Goldstein, J. L. et al., 2006. *Cell* 124:35-46.
33. Menendez, J. A., and Lupu, R. 2007. *Nat. Rev. Cancer* 7:763-777.
34. Jemal, A. et al., 2010. Cancer Statistics, 2010. *CA: a Cancer Journal for Clinicians* 60:277-300.
35. Guo, D. et al., 2009. *Sci. Signal.* 2(101):ra82.
36. Swinnen, J. V. et al., 2000. *Oncogene* 19:5173-5181.
37. Yang, Y. A. et al., 2002. *Exp. Cell Res.* 279(1):80-90.

38. Kumar-Sinha, C. et al., 2003. *Cancer Res.* 63:132-139.
39. Demoulin, J. B. et al., 2004. *J. Biol. Chem.* 279:35392-35402.
40. Porstmann, T. et al., 2005. *Oncogene* 24:6465-6481.
41. Chang, Y. et al., 2005. *J. Lipid Res.* 46:2624-2635.
42. Porstmann, T. et al., 2008. *Cell Metabol.* 8:224-236.
43. Duvel, K. et al., 2010. *Mol. Cell.* 39:171-183.
44. Morgan-Lappe, S. E. et al., 2007. *Cancer Res.* 67:4390-4398.
45. Fritz, V. et al., 2010. *Mol. Cancer. Ther.* 9:1740-1754.
46. Roongta, U. V. et al., 2011. *Mol. Cancer. Res.* doi: 10.1158/1541-7786.MCR-11-0126.
47. Igal, R. A. 2010. *Carcinogenesis* 31:1509-1515.
48. Scaglia, N. et al., 2009. *PloS One* 4:e6812.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

TABLE 3

Cohort of Genes Involved in Cholesterol and Lipid Biosynthesis Repressed In FGFR3 Knockdown Cells

| GENE | Accession Refseq | Accession Genbank |
|---|---|---|
| SREBF1 | NM_001005291.2, NM_004176.4 | AB209609.1, AB373958.1, AB373959.1, AK091131.1, AK095325.1, AK128320.1, AK293795.1, AK294800.1, AK297113.1, BC023621.2, BC026962.1, BC057388.1, BC063281.1, BE208013.1, BI906407.1, BQ025047.1, S66167.1, S66168.1, U00968.1 |
| G6PD | NM_000402.3, NM_001042351.1 | AK292304.1, AK302341.1, AL560686.3, BC000337.2, DQ892219.2, DQ895415.2, M19866.1, M21248.1, M27940.1, S58359.1, X03674.1 |
| ACOT7 | NM_007274.3, NM_181864.2, NM_181865.2, NM_181866.2, NM_181862.2, NM_181863.2 | AB074415.1, AB074416.1, AB074417.1, AB074418.1, AB074419.1, AK057168.1, AK289572.1, AK290097.1, AK291583.1, AK292202.1, AK300831.1, AL702662.1, BC017365.2, BG332214.1, BM807217.1, BQ067921.1, BT006888.1, BU594651.1, D88894.2, U91316.1 |
| PTPLA | NM_014241.3 | AF114494.1, AW022173.1, AY455942.1, BC010353.1, BC027709.2, HQ447343.1 |
| PCCB | NM_000532.4, NM_001178014.1 | AB209009.1, AF217984.1, AI191766.1, AK130359.1, AK225215.1, AK225733.1, AK295312.1, AK302522.1, AK303079.1, AL831978.2, BC005909.1, BC013768.1, BC018013.1, BC053661.1, DA090969.1, JF432277.1, M13573.1, S67325.1, X73424.1 |
| FADS1 | NM_013402.4 | AF035284.1, AF084558.1, AF199596.1, AF226273.1, AF271778.1, AI052027.1, AK027427.1, AK027522.1, AK074754.1, AK074819.1, AK096275.1, AK222906.1, AK289552.1, AK298871.1, AK314199.1, AL512760.1, AL834479.1, BC007846.2, BP253788.1, DQ890643.2, DQ893822.2 |
| RDH11 | NM_016026.3 | AB209223.1, AF151840.1, AF167438.1, AF395068.1, AK057195.1, AK074749.1, AK289427.1, AK293355.1, AK307500.1, AK314465.1, BC000112.1, BC011727.2, BC026274.1, BC037302.1, BC051291.1, CR457180.1, DC355364.1, DQ426886.1, HQ447163.1 |
| ACER3 | NM_018367.5 | AF214454.1, AF327353.1, AK002100.1, AK293800.1, AK294978.1, AK295142.1, AK295327.1, AK308856.1, AK315000.1, AK316120.1, BC049837.1, BC063034.1, BC073853.1, BG702017.1, HQ447508.1 |
| PDSS1 | NM_014317.3 | AB209763.1, AB210838.1, AF118395.1, AK024802.1, AK223414.1, AK296288.1, BC049211.1, BC063635.1 |
| MVD | NM_002461.1 | AB209229.1, AY203927.1, BC000011.2, BT006930.1, DQ890562.2, DQ893724.2, U49260.1 |
| AGPAT5 | NM_018361.3 | AF375789.1, AK002072.1, AK021722.1, AK310545.1, AL136587.1, AL514578.3, AM392899.1, AM393058.1, BC023550.2, BC068519.1, BC080537.1, BM837881.1, CA414711.1, DQ893436.2, DQ896747.2 |
| HSD17B2 | NM_002153.2 | AK223001.1, AK313109.1, AU139034.1, BC009581.1, BC059170.1, BM670647.1, BP270993.1, DQ893100.2, DQ896372.2, L11708.1 |
| ACSL4 | NM_004458.2, NM_022977.2 | AB061713.1, AB061714.1, AF030555.1, AK292070.1, AK294915.1, AK307566.1, BC034959.2, BQ016115.1, CN310691.1, DQ890835.2, DQ893990.2, DR004263.1, Y12777.1, Y13058.1 |
| EBP | NM_006579.2 | AU128761.1, BC001549.1, BC001572.1, BC046501.1, CA488777.1, CR456815.1, CR542094.1, DQ891591.2, DQ894785.2, DQ894786.2, Z37986.1 |
| PIGW | NM_178517.3 | AB097818.1, AK094752.1, BC156433.1, BC160092.1, BC172479.1 |
| LBR | NM_002296.3, NM_194442.2 | AB209514.1, AK125116.1, AK222834.1, AK303589.1, AK312258.1, AU134026.1, AW504657.1, BC020079.1, BE243907.1, DA447510.1, DB091880.1, DQ891049.2, DQ894227.2, L25931.1 |
| ACLY | NM_001096.2, NM_198830.1 | AB210035.1, AK095084.1, AK295675.1, AK304802.1, AK312315.1, BC006195.2, BG037168.1, DQ575356.1, JF432308.1, U18197.1, X64330.1 |
| ADORA2B | NM_000676.2 | AY136748.1, BC025722.1, DQ891714.2, DQ894891.2, M97759.1, X68487.1 |
| GPCPD1 | NM_019593.3 | AB037855.1, AK001947.1, AK308111.1, AL049446.1, AL833069.1, BC027588.2, BG674365.1, BI561344.1, BP421674.1, T79323.1 |
| CYP24A1 | NM_000782.4, NM_001128915.1 | AI400154.1, AW022349.1, AY858838.1, BC109083.1, BC109084.1, BI491491.1, BM928702.1, BU662901.1, CN311231.1, L13286.1, N29030.1, S67623.1 |
| ACSL3 | NM_004457.3, NM_203372.1 | AB061712.1, AF116690.1, AI378485.1, AK001471.1, AK023191.1, AK314621.1, BC012066.1, BC032144.2, BC041692.1, BF679686.1, BG772246.1, BM971377.1, BQ435549.1, BX472576.1, D89053.1, N44998.1 |
| MVK | NM_000431.2, NM_001114185.1 | AB209722.1, AF217536.1, AK023087.1, AK293130.1, AK295338.1, AK315678.1, BC016140.1, DC421549.1, DQ891089.2, DQ894271.2, M88468.1 |
| ACSS2 | NM_001076552.2, NM_001242393.1, NM_018677.3, NM_139274.1 | AF263614.1, AI674262.1, AK000162.1, AK000188.1, AK022608.1, AK025990.1, AK092281.1, AK098026.1, AK293634.1, AL359946.1, BC010141.2, BC012172.1, BC073846.1, BC098422.1, CR749716.1, DA411343.1, DA626707.1, DA628275.1, DA630609.1 |
| FDPS | NM_001135821.1, NM_001135822.1, NM_001242824.1, NM_001242825.1, NM_002004.3 | AK021828.1, AK022841.1, AK291084.1, BC010004.2, BE047993.1, BP370037.1, CD675633.1, CN346026.1, D14697.1, DA610405.1, DQ893471.2, DQ895943.2, J05262.1, M29863.1 |

TABLE 3-continued

Cohort of Genes Involved in Cholesterol and Lipid Biosynthesis Repressed In FGFR3 Knockdown Cells

| GENE | Accession Refseq | Accession Genbank |
| --- | --- | --- |
| ELOVL5 | NM_001242828.1, NM_001242830.1, NM_001242831.1, NM_021814.4 | AB209798.1, AF052129.1, AF111849.1, AF231981.1, AF338241.1, AK074748.1, AK074889.1, AK125098.1, AK299674.1, AK302948.1, AL136939.1, BC009838.2, BC017270.2, BC067123.1, BC074503.1, DC345924.1, HQ447433.1 |
| HMGCR | NM_000859.2, NM_001130996.1 | AA648735.1, AK292892.1, AK296499.1, AK299655.1, AK312437.1, AY429541.1, AY429542.1, AY429543.1, BC024180.1, BC033692.1, CN278665.1, DQ890855.2, DQ894009.2, M11058.1, M62627.1, M62633.1 |
| LIPG | NM_006033.2 | AF118767.1, AI861822.1, AK124636.1, AK125344.1, AK291799.1, AK300333.1, AK315252.1, AY358928.1, BC060825.1, HQ448045.1 |
| ME1 | NM_002395.4 | AJ420574.1, AK223417.1, AK289783.1, AK301875.1, AK302777.1, BC017403.1, BC025246.1, BX376125.2, DA520723.1, DQ892155.2, EU176687.1, L34035.1, U43944.1, X77244.1 |
| DHCR7 | NM_001163817.1, NM_001360.2 | AF034544.1, AF062481.1, AF067127.1, AF096305.1, AI888720.1, AK289497.1, AK303881.1, AK309625.1, AK312775.1, BC000054.2, BU848891.1, DA502590.1, DQ891827.2, DQ895014.2 |
| LSS | NM_001001438.2, NM_001145436.1, NM_001145437.1, NM_002340.5 | AA922470.1, AK093334.1, AK096769.1, AK098352.1, AK128839.1, AK226141.1, AK296313.1, AK312489.1, AY927524.1, BC035638.1, BM662957.1, BU728696.1, BX443698.2, D63807.1, DA333499.1, DQ891234.2, DQ894418.2, S81221.1, X87809.1 |
| ACAT2 | NM_005891.2 | AB208993.1, AF356877.1, AK055001.1, AK225089.1, AK225244.1, AK291080.1, AK294273.1, BC000408.2, BM997310.1, BP210609.1, HQ448187.1, S70154.1 |
| FASN | NM_004104.4 | AB209988.1, AY451392.1, BC007267.1, BC007305.2, BC007909.1, BC014631.2, BC014634.2, BC021544.2, BC063242.1, S80437.1, U26644.1, U29344.1 |
| CYP51A1 | NM_000786.3, NM_001146152.1 | AK295932.1, AK314205.1, BC018429.1, BC032322.1, D55653.1, DA349400.1, DC376300.1, DQ891311.2, DQ894495.2, U23942.1 |
| IDI1 | NM_004508.2 | AF271720.1, AK222875.1, AK303669.1, AK311110.1, BC005247.2, BC006999.2, BC019227.2, BC022418.2, BC025375.2, BC057827.1, BC107893.1, BE891119.1, BT006761.1, BX537663.1, BX648472.1, X17025.1 |
| FDFT1 | NM_004462.3 | AI679762.1, AK057726.1, AK098682.1, AK293545.1, AK296043.1, AK297868.1, AK300059.1, AK300245.1, AK301617.1, AK311246.1, AK311362.1, AK315993.1, AK316033.1, AK316182.1, AK316351.1, AK316531.1, AK316534.1, BC003573.1, BC009251.2, BC029641.1, BC034440.1, BT006704.1, CR457033.1, DQ890697.2, DQ893882.2, L06070.1, L06105.1, S76822.1, X69141.1 |
| FAR2 | NM_018099.3 | AK001324.1, AK001927.1, AK027756.1, AK129857.1, AK314670.1, AL136843.1, BC022267.1 |
| HMGCS1 | NM_001098272.1, NM_002130.6 | AK095492.1, AK315593.1, AL050004.1, BC000297.2, BC082234.1, BC083514.1, BT007302.1, DB078662.1, L25798.1, M15802.1, X66435.1 |
| SDR16C5 | NM_138969.2 | AB083038.1, AK057667.1, AK095159.1, AK294634.1, AY444559.1, BC037219.1, BC064525.1 |
| LDLR | NM_000527.4, NM_001195798.1, NM_001195799.1, NM_001195800.1, NM_001195802.1, NM_001195803.1 | AA292214.1, AB209409.1, AK295612.1, AK296312.1, AK299038.1, AK300313.1, AY114155.1, BC014514.1, BM785950.1, BT007361.1, BX648281.1, DA008286.1, DB081391.1, DC306821.1, DQ893879.2, M28219.1, S40543.1, S70123.1 |
| MSMO1 | NM_001017369.2, NM_006745.4 | AK292418.1, AK295432.1, AK309206.1, AV704962.1, BC010653.1, BC107879.1, BU676028.1, BU940384.1, BX441001.2, DQ891060.2, DQ894237.2, U60205.1, U93162.1 |
| INSIG1 | NM_005542.4, NM_198336.2, NM_198337.2 | AA565248.1, AF086365.1, AK095977.1, AK291675.1, AL541939.3, AY112745.1, BC001880.1, BI550548.1, BI918342.1, BM995866.1, BQ059075.1, BT007227.1, DA590854.1, DA738378.1, DN996424.1 |
| DHRS9 | NM_001142270.1, NM_001142271.1, NM_005771.4, NM_199204.1 | AF067174.1, AF240697.1, AF240698.1, AF295380.1, AF343729.1, AF529286.1, AF529287.1, AF529288.1, AK296625.1, AK313220.1, AY017349.1, AY359046.1, BC040380.1, BC051797.1, BC058883.1, CA307349.1, DB010228.1, GQ129414.1, GQ129415.1, HQ448109.1 |
| LRP8 | NM_001018054.2, NM_004631.4, NM_017522.4, NM_033300.3 | AA775280.1, AK096482.1, AK122887.1, AL119002.1, BC006443.1, BC051836.1, BE543079.1, BM477111.1, CD300289.1, CF593917.1, D50678.1, DB452432.1, DB455425.1, DR002432.1, Z75190.1 |
| SQLE | NM_003129.3 | AF098865.1, AK055357.1, AK225085.1, AK295302.1, AK301792.1, AK313384.1, AM393564.1, BC017033.1, BG772453.1, BX647400.1, BX647605.1, D78129.1, D78130.1, DQ894657.2 |
| PCSK9 | NM_174936.3 | AK075365.1, AK122717.1, AK124635.1, AK293870.1, AK297473.1, BC042095.1, BC166619.1, DA738424.1, EF692496.1 |
| SCD1 | NM_005063.4 | AB032261.1, AB208982.1, AF097514.1, AF109362.1, AF132203.1, AI740935.1, AK222862.1, AK312312.1, BC005807.2, BC062303.1, BI827092.1, BM546583.1, BU940035.1, CD245516.1, CF454075.1, S70284.1, Y13647.1 |
| FABP4 | NM_001442.2 | BC003672.1, BQ880795.1, BT006809.1, CD000452.1, CR456903.1, J02874.1, JF432859.1 |

What is claimed is:

1. A method of treating a cancer cell in an individual wherein the cancer cell is a kidney cancer cell, a pancreatic cancer cell, an urinary cancer cell, or a bladder cancer cell comprising administering to the individual an effective amount of (i) a compound of formula (I):

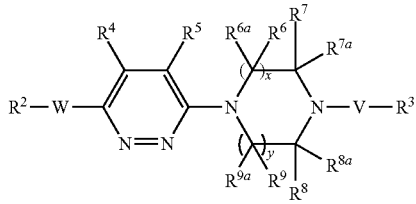

wherein: x and y are each independently 1, 2 or 3; W is —C(O)N($R^1$)—; —C(O)N[C(O)$R^{1a}$]—, —N($R^1$)C(O)N($R^1$)— or —N($R^1$)C(O)—; V is —C(O)—, —C(S)—, or —C($R^{10}$)H; each $R^1$ is independently selected from the group consisting of hydrogen; $C_1$-$C_6$alkyl optionally substituted with one or more substituents selected from the group consisting of halo, methyl or trifluoromethyl; and $C_2$-$C_6$alkyl optionally substituted with one or more substituents selected from the group consisting of methoxy and hydroxyl; $R^{1a}$ is selected from the group consisting of hydrogen, $C_1$-$C_6$alkyl and cycloalkyl; $R^2$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_1$-$C_{12}$alkoxy, $C_2$-$C_{12}$alkoxyalkyl, $C_3$-$C_{12}$cycloalkyl, $C_4$-$C_{12}$cycloalkylalkyl, aryl, $C_7$-$C_{12}$aralkyl, $C_3$-$C_{12}$heterocyclyl, $C_3$-$C_{12}$heterocyclylalkyl, $C_1$-$C_{12}$heteroaryl, and $C_3$-$C_{12}$heteroarylalkyl; or $R^2$ is a multi-ring structure having 2 to 4 rings wherein the rings are independently selected from the group consisting of cycloalkyl, heterocyclyl, aryl and heteroaryl and where some or all of the rings may be fused to each other; $R^3$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_1$$C_{12}$alkoxy, $C_2$-$C_{12}$alkoxyalkyl, $C_3$-$C_{12}$cycloalkyl, $C_4$-$C_{12}$cycloalkylalkyl, aryl, $C_7$-$C_{12}$aralkyl, $C_3$-$C_{12}$heterocyclyl, $C_3$-$C_{12}$heterocyclylalkyl, $C_1$-$C_{12}$heteroaryl and $C_3$-$C_{12}$heteroarylalkyl; or $R^3$ is a multi-ring structure having 2 to 4 rings wherein the rings are independently selected from the group consisting of cycloalkyl, heterocyclyl, aryl and heteroaryl and where some or all of the rings may be fused to each other; $R^4$ and $R^5$ are each independently selected from hydrogen, fluoro, chloro, methyl, methoxy, trifluoromethyl, cyano, nitro or —N($R^{12}$)$_2$; $R^6$, $R^{6a}$, $R^7$, $R^{7a}$, $R^8$, $R^{8a}$, $R^9$, and $R^{9a}$ are each independently selected from hydrogen or $C_1$-$C_3$ alkyl; or $R^6$ and $R^{6a}$ together, or $R^7R^{7a}$ together, or $R^8$ and $R^{8a}$ together, or $R^9$ and $R^{9a}$ together are an oxo group, provided that when V is —C(O)—, $R^7$ and $R^{7a}$ together or $R^8$ and $R^{8a}$ together do not form an oxo group, while the remaining $R^6$, $R^{6a}$, $R^7$ $R^{7a}$, $R^8$, $R^{8a}$, $R^9$, and $R^{9a}$ are each independently selected from hydrogen or $C_1$-$C_3$ alkyl; or one of $R^6$, $R^{6a}$, $R^7$ and $R^{7a}$ together with one of $R^8$, $R^{8a}$, $R^9$ and $R^{9a}$ form an alkylene bridge, while the remaining $R^6$, $R^{6a}$, $R^7$, $R^{7a}$, $R^8$, $R^{8a}$, $R^9$, and $R^{9a}$ are each independently selected from hydrogen or $C_1$-$C_3$ alkyl; $R^{10}$ is hydrogen or $C_1$-$C_3$ alkyl; and each $R^{12}$ is independently selected from hydrogen or $C_1$-$C_6$ alkyl (ii) G01522403 (A37062), (iii) G0244 7171, or a pharmaceutically acceptable salt thereof derivatives thereof.

2. The method of claim 1, wherein the cancer cell expresses elevated levels of one or more biomarkers compared to a reference sample, reference cell, reference tissue, control sample, control cell, control tissue, or internal control (e.g., housekeeping gene).

3. A method of treating cancer in an individual wherein the cancer is kidney cancer, pancreatic cancer, urinary cancer, or bladder cancer comprising administering to the individual an effective amount of (i) a compound of formula (I):

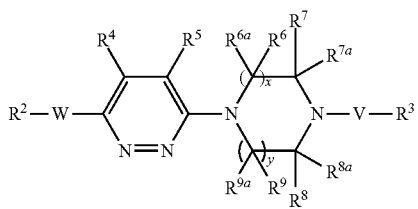

(I)

wherein: x and y are each independently 1, 2 or 3; W is —C(O)N($R^1$)—; —C(O)N[C(O)$R^{1a}$]—, —N($R^1$)C(O)N($R^1$)— or —N($R^1$)C(O)—; V is —C(O)—,—C(S)—or —C($R^{10}$)H; each $R^1$ is independently selected from the group consisting of hydrogen; $C_1$-$C_6$ alkyl optionally substituted with one or more substituents selected from the group consisting of halo, methyl or trifluoromethyl; and $C_2$-$C_6$alkyl optionally substituted with one or more substituents selected from the group consisting of methoxy and hydroxyl; $R^{1a}$ is selected from the group consisting of hydrogen, $C_1$-$C_6$ alkyl and cycloalkyl; $R^2$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkellyl, $C_1C_{12}$alkoxy, $C_2$-$C_{12}$ alkoxyalkyl, $C_3$-$C_{12}$cycloalkyl, $C_4$-$C_{12}$cycloalkylalkyl, aryl, $C_7$-$C_{12}$aralkyl, $C_3$-$C_{12}$ heterocyclyl, $C_3$-$C_{12}$heterocyclylalkyl, $C_1$-$C_{12}$heteroaryl, and $C_3$-$C_{12}$heteroarylalkyl; or $R^2$ is a multi-ring structure having 2 to 4 rings wherein the rings are independently selected from the group consisting of cycloalkyl, heterocyclyl, aryl and heteroaryl and where some or all of the rings may be fused to each other; $R^3$ is selected from the group consisting of $C_1$-$C_{12}$alkyl, $C_2$-$C_{12}$ alkenyl, $C_2$-$C_{12}$hydroxyalkyl, $C_2$-$C_{12}$hydroxyalkenyl, $C_1$-$C_{12}$alkoxy, $C_2$-$C_{12}$alkoxyalkyl, $C_3$-$C_{12}$cycloalkyl, $C_4$-$C_{12}$cycloalkylalkyl, aryl, $C_7$-$C_{12}$aralkyl, $C_3$-$C_{12}$heterocyclyl, $C_3$-$C_{12}$heterocyclylalkyl, $C_1$-$C_{12}$heteroaryl and $C_3$-$C_{12}$heteroarylalkyl; or $R^3$ is a multi-ring structure having 2 to 4 rings wherein the rings are independently selected from the group consisting of cycloalkyl, heterocyclyl, aryl and heteroaryl and where some or all of the rings may be fused to each other; $R^4$ and $R^5$ are each independently selected from hydrogen, fluoro, chloro, methyl, methoxy, trifluoromethyl, cyano, nitro or —N($R^{12}$)$_2$; $R^6$, $R^{6a}$, $R^7$, $R^{7a}$, $R^8$, $R^{8a}$, $R^9$, and $R^{9a}$ are each independently selected from hydrogen or $C_1$-$C_3$ alkyl; or $R^6$ and $R^{6a}$ together, or $R^7$ and $R^{7a}$ together, or $R^8$ and $R^{8a}$ together, or $R^9$ and $R^{9a}$ together are an oxo group, provided that when V is —C(O)—,and $R^7$ and $R^{7a}$ together or $R^8$ and $R^{8a}$ together do not form an oxo group, while the remaining $R^6$, $R^{6a}$, $R^7$, $R^{7a}$, $R^8$, $R^{8a}$, $R^9$, and $R^{9a}$ are each independently selected from hydrogen or $C_1$-$C_3$ alkyl; or one of $R^6$,$R^{6a}$, $R^7$ and $R^{7a}$ together with one of $R^8$, $R^{8a}$, $R^9$ and $R^{9a}$ form an alkylene bridge, while the remaining $R^6$, $R^{6a}$,$R^7$, $R^{7a}$, $R^8$, $R^{8a}$, $R^9$, and $R^{9a}$ are each independently selected from hydrogen or $C_1$-$C_3$ alkyl; $R^{10}$ is hydrogen or $C_1$-$C_3$ alkyl; and each $R^{12}$ is independently selected from hydrogen or $C_1$-$C_6$ alkyl (ii) G01522403(A37062), (iii) G0244 7171, or a pharmaceutically acceptable salt thereof.

4. The method of claim 3, wherein the cancer in the individual expresses elevated levels of one or more biomarkers compared to a reference sample, reference cell, reference tissue, control sample, control cell, control tissue, or internal control (e.g., housekeeping gene).

5. A method of treating cancer wherein the cancer is kidney cancer, pancreatic cancer, urinary cancer, or bladder cancer in an individual comprising administering to the individual an effective amount of (i) a compound of formula (I):

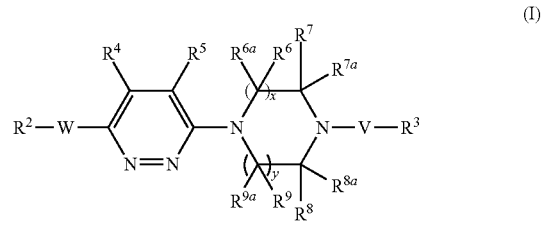

(I)

wherein: x and y are each independently 1, 2 or 3; W is —C(O)N($R^1$)—; —C(O)N[C(O)$R^{1a}$]—, —N($R^1$)C(O)N($R^1$)— or —N($R^1$)C(O)—; V is —C(O)—, —C(S)—, or —C($R^{10}$)H; each $R^1$ is independently selected from the group consisting of hydrogen; $C_1$-$C_6$alkyl optionally substituted with one or more substituents selected from the group consisting of halo, methyl or trifluoromethyl; and $C_2$-$C_6$alkyl optionally substituted with one or more substituents selected from the group consisting of methoxy and hydroxyl; $R^{1a}$ is selected from the group consisting of hydrogen, $C_1$-$C_6$ alkyl and cycloalkyl; $R^2$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_1$-$C_{12}$alkoxy, $C_2$-$C_{12}$alkoxyalkyl, $C_3$-$C_{12}$cycloalkyl, $C_4$-$C_{12}$cycloalkylalkyl, aryl, $C_7$-$C_{12}$aralkyl, $C_3$-$C_{12}$heterocyclyl, $C_3$-$C_{12}$heterocyclylalkyl, $C_1$-$C_{12}$heteroaryl, and $C_3$-$C_{12}$heteroarylalkyl; or $R^2$ is a multi-ring structure having 2 to 4 rings wherein the rings are independently selected from the group consisting of cycloalkyl, heterocyclyl, aryl and heteroaryl and where some or all of the rings may be fused to each other; $R^3$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_1$-$C_{12}$alkoxy, $C_2$-$C_{12}$alkoxyalkyl, $C_3$-$C_{12}$cycloalkyl, $C_4$-$C_{12}$cycloalkylalkyl, aryl, $C_7$-$C_{12}$aralkyl, $C_3$-$C_{12}$heterocyclyl, $C_3$-$C_{12}$heterocyclylalkyl, $C_1$-$C_{12}$heteroaryl and $C_3$-$C_{12}$heteroarylalkyl; or $R^3$ is a multi-ring structure having 2 to 4 rings wherein the rings are independently selected from the group consisting of cycloalkyl, heterocyclyl, aryl and heteroaryl and where some or all of the rings may be fused to each other; $R^4$ and $R^5$ are each independently selected from hydrogen, fluoro, chloro, methyl, methoxy, trifluoromethyl, cyano, nitro or —N($R^{12}$)$_2$; $R^6$, $R^{6a}$, $R^7$, $R^{7a}$, $R^8$. $R^{8a}$, $R^9$. and $R^{9a}$ are each independently selected from hydrogen or $C_1$-$C_3$ alkyl; or $R^6$ and $R^{6a}$ together, or $R^7$ and $R^{7a}$ together, or $R^8$ and $R^{8a}$ together, or $R^9$ and $R^{9a}$ together are an oxo group, provided that when V is —C(O)—, $R^7$ and $R^{7a}$ together or $R^8$ and $R^{8a}$ together do not form an oxo group, while the remaining $R^6$, $R^{6a}$, $R^7$, $R^{7a}$, $R^8$, $R^{8a}$, $R^9$, and $R^{9a}$ are each independently selected from hydrogen or $C_1$-$C_3$ alkyl; or one of $R^6$,$R^{6a}$, $R^7$ and $R^{7a}$ together with one of $R^8$, $R^{8a}$, $R^9$ and $R^{9a}$ form an alkylene bridge, while the remaining $R^6$, $R^{6a}$, $R^7$, $R^{7a}$, $R^8$, $R^8a$, $R^9$, and $R^{9a}$ are each independently selected from hydrogen or $C_1$-$C_3$ alkyl; $R^{10}$ is hydrogen or $C_1$-$C_3$ alkyl; and each $R^{12}$ is independently selected from hydrogen or $C_1$-$C_6$ alkyl (ii) GO 1 522403 (A37062), (iii) G0244 7171, or (iv) a stereoisomer thereof, an enantiomer thereof, a tautomer thereof, or a pharmaceutically acceptable salt thereof derivatives thereof, wherein treatment is based upon the individual having cancer expressing elevated levels of one or more biomarkers compared to a reference sample, reference cell, reference tissue, control sample, control cell, control tissue, or internal control (e.g., housekeeping gene).

6. The method of claim 5, wherein the cancer is bladder cancer.

7. The method of claim 5, wherein the biomarkers is FGFR3.

8. The method of claim 5, wherein the biomarkers is phosphorylated FGFR3.

9. The method of claim 5, wherein the biomarkers is one or more genes of the FGFR3-regulated lipogenic signature.

10. The method of claim 9, wherein the signature comprises one or more genes selected from the group consisting of SREBF1, G6PD, ACOT7, PTPLA, PCCB, FADS1, RDH11, ACER3, PDSS1, MVD, AGPAT5, HSD17B2, ACSL4, EBP, PIGW, LBR, ACLY, ADORA2B, GPCPD1, CYP24A1, ACSL3, MVK, ACSS2, FDPS, ELOVL5, HMGCR, LIPG, ME1, DHCR7, LSS, ACAT2, FASN, CYP51A1, IDI1, FDFT1, FAR2, HMGCS1, SDR16C5, LDLR, MSMO1, INSIG1, DHRS9, LRPS, SQLE, PCSK9, SCD1, and FABP4, or combinations thereof.

11. The method of claim 9, wherein the signature comprises one or more genes selected from the group consisting of ELOVL5, HMGCR, LIPG, ME1, DHCR7, LSS, ACAT2, FASN, CYP51A1, IDI1, FDFT1, FAR2, HMGCS1, SDR16C5, LDLR, MSMO1, INSIG1, DHRS9, LRPS, SQLE, PCSK9, SCD1, and FABP4, or combinations thereof.

12. The method of claim 9, wherein the signature comprises one or more genes selected from the group consisting of CYP51A1, IDI1, FDFT1, FAR2, HMGCS1, SDR16C5, LDLR, MSMO1, INSIG1, DHRS9, LRPS, SQLE, PCSK9, SCD1, and FABP4, or combinations thereof.

13. The method of claim 9, wherein the signature comprises one or more genes selected from the group consisting of LDLR, MSMO1, INSIG1, DHRS9, LRPS, SQLE, PCSK9, SCD1, and FABP4, or combinations thereof.

14. The method of claim 9, wherein the signature comprises one or more genes selected from the group consisting of SQLE, PCSK9, SCD1, and FABP4, or combinations thereof.

15. The method of claim 5, wherein the biomarkers is mature SREBP1.

16. The method of claim 5, wherein the biomarkers is $\Delta 9$ monounsaturaturated fatty acids.

17. The method of claim 5, wherein the biomarkers is ratio of $\Delta 9$ monounsaturaturated fatty acids:saturated fatty acids.

18. The method of claim 5, wherein the biomarkers is PI3K signaling, mTOR signaling, MEK signaling.

19. The method of claim 5, wherein the biomarkers is one or more polymorphism in genes selected from the group consisting of PI3K, PTEN, p85, TSC½, and AKT.

20. The method of claim 5, wherein the biomarkers is phosphorylated AKT.

21. The method of claim 5, wherein the expression level of the one or more biomarkers is elevated by greater than about 1.5 fold, about 1.75 fold, about 2 fold, about 2.25 fold, about 2.5 fold, about 2.75 fold, about 3.0 fold, or about 3.25 fold as compared to a reference sample, reference cell, reference tissue, control sample, control cell, control tissue, or internal control (e.g., housekeeping gene).

22. The method of claim 1, wherein the SCD1 antagonist is G01522403(A37062), G0244 7171, or pharmaceutically acceptable salt thereof derivatives thereof.

23. The method of claim 3, wherein the method further comprises an additional therapeutic agent.

* * * * *

SEQUENCE LISTING

<160> NUMBER OF SEQ ID NOS: 4

<210> SEQ ID NO 1
<211> LENGTH: 359
<212> TYPE: PRT

<213> ORGANISM: Homo sapiens

<400> SEQUENCE: 1

Met Pro Ala His Leu Leu Gln Asp Asp Ile Ser Ser Tyr Thr Thr
1               5                   10                  15

Thr Thr Thr Ile Thr Ala Pro Pro Ser Arg Val Leu Gln Asn Gly Gly
            20                  25                  30

Asp Lys Leu Glu Thr Met Pro Leu Tyr Leu Glu Asp Ile Arg Pro
            35                  40                  45

Asp Ile Lys Asp Asp Ile Tyr Asp Pro Thr Tyr Lys Asp Lys Glu Gly
        50                  55                  60

Pro Ser Pro Lys Val Glu Tyr Val Trp Arg Asn Ile Ile Leu Met Ser
65                  70                  75                  80

Leu Leu His Leu Gly Ala Leu Tyr Gly Ile Thr Leu Ile Pro Thr Cys
                    85                  90                  95

Lys Phe Tyr Thr Trp Leu Trp Gly Val Phe Tyr Phe Val Ser Ala
                100                 105                 110

Leu Gly Ile Thr Ala Gly Ala His Arg Leu Trp Ser His Arg Ser Tyr
                115                 120                 125

Lys Ala Arg Leu Pro Leu Arg Leu Phe Leu Ile Ile Ala Asn Thr Met
            130                 135                 140

Ala Phe Gln Asn Asp Val Tyr Glu Trp Ala Arg Asp His Arg Ala His
145                 150                 155                 160

His Lys Phe Ser Glu Thr His Ala Asp Pro His Asn Ser Arg Arg Gly
                165                 170                 175

Phe Phe Phe Ser His Val Gly Trp Leu Leu Val Arg Lys His Pro Ala
                180                 185                 190

Val Lys Glu Lys Gly Ser Thr Leu Asp Leu Ser Asp Leu Glu Ala Glu
            195                 200                 205

Lys Leu Val Met Phe Gln Arg Arg Tyr Tyr Lys Pro Gly Leu Leu Met
            210                 215                 220

Met Cys Phe Ile Leu Pro Thr Leu Val Pro Trp Tyr Phe Trp Gly Glu
225                 230                 235                 240

Thr Phe Gln Asn Ser Val Phe Val Ala Thr Phe Leu Arg Tyr Ala Val
                245                 250                 255

Val Leu Asn Ala Thr Trp Leu Val Asn Ser Ala Ala His Leu Phe Gly
                260                 265                 270

Tyr Arg Pro Tyr Asp Lys Asn Ile Ser Pro Arg Glu Asn Ile Leu Val
            275                 280                 285

Ser Leu Gly Ala Val Gly Glu Gly Phe His Asn Tyr His His Ser Phe
            290                 295                 300

Pro Tyr Asp Tyr Ser Ala Ser Glu Tyr Arg Trp His Ile Asn Phe Thr
305                 310                 315                 320

Thr Phe Phe Ile Asp Cys Met Ala Ala Leu Gly Leu Ala Tyr Asp Arg
                325                 330                 335

Lys Lys Val Ser Lys Ala Ala Ile Leu Ala Arg Ile Lys Arg Thr Gly
            340                 345                 350

Asp Gly Asn Tyr Lys Ser Gly
        355

<210> SEQ ID NO 2
<211> LENGTH: 65
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 2
gatcccccta caagagtggc tgagtttttca agagaaactc agccactctt gtagtttttt    60
ggaaa                                                                 65

<210> SEQ ID NO 3
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gatcccccta cggctctttc tgatcattca agagatgatc agaaagagcc gtagtttttt    60
ggaaa                                                                 65

<210> SEQ ID NO 4
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gatccccgca catcaacttc accacattca agagatgtgg tgaagttgat gtgctttttt    60
ggaaa                                                                 65
```